United States Patent
Taylor et al.

(10) Patent No.: US 10,590,121 B2
(45) Date of Patent: Mar. 17, 2020

(54) KINASE INHIBITORS AND METHODS FOR MAKING AND USING

(71) Applicant: Rigel Pharmaceuticals, Inc., South San Francisco, CA (US)

(72) Inventors: Vanessa Taylor, San Francisco, CA (US); Yan Chen, Foster City, CA (US); Rose Yen, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 16/022,323

(22) Filed: Jun. 28, 2018

(65) Prior Publication Data

US 2019/0002455 A1     Jan. 3, 2019

Related U.S. Application Data

(60) Provisional application No. 62/526,838, filed on Jun. 29, 2017.

(51) Int. Cl.
| | |
|---|---|
| *C07D 401/04* | (2006.01) |
| *C07D 401/14* | (2006.01) |
| *C07D 405/04* | (2006.01) |
| *C07D 405/14* | (2006.01) |
| *A61P 29/00* | (2006.01) |
| *C07D 417/14* | (2006.01) |
| *C07D 417/04* | (2006.01) |
| *C07D 413/14* | (2006.01) |

(52) U.S. Cl.
CPC ............ *C07D 417/14* (2013.01); *A61P 29/00* (2018.01); *C07D 401/04* (2013.01); *C07D 401/14* (2013.01); *C07D 405/04* (2013.01); *C07D 405/14* (2013.01); *C07D 413/14* (2013.01); *C07D 417/04* (2013.01)

(58) Field of Classification Search
CPC .. C07D 401/04; C07D 401/14; C07D 405/14; C07D 417/14
See application file for complete search history.

(56) References Cited

U.S. PATENT DOCUMENTS

2016/0068543 A1\* 3/2016 Greenwood ......... C07D 495/04
514/232.8

FOREIGN PATENT DOCUMENTS

WO    WO 2017/023941      2/2017

OTHER PUBLICATIONS

Wang et al. Current Topics in Medicinal Chemistry, vol. 9 p. 724-737. (Year: 2009).\*
Chaudhary et al. J.Med. Chem. vol. 58 p. 96-110 (Year: 2015).\*
Buckley et al., "IRAK-4 inhibitors. Part 1: A series of amides," *Bioorganic & Medicinal Chemistry Letters* 18(11):3211-3214, 2008.

\* cited by examiner

*Primary Examiner* — Emily A Bernhardt
(74) *Attorney, Agent, or Firm* — Travis Young; Klarquist Sparkman, LLP

(57) ABSTRACT

Disclosed embodiments concern kinase inhibitors having a structure according to formula 1, such as interleukin receptor associated kinases (IRAK) inhibitors, and compositions comprising such inhibitors.

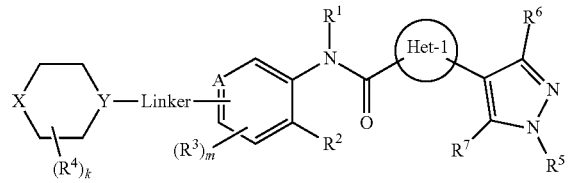

Formula 1

Also disclosed are methods of making and using the compounds and compositions. The disclosed compounds and/or compositions may be used to treat or prevent a kinase-associated disease or condition, particularly an IRAK-associated disease or condition.

37 Claims, No Drawings

KINASE INHIBITORS AND METHODS FOR MAKING AND USING

CROSS REFERENCE TO RELATED APPLICATIONS

This application claims the benefit of U.S. Provisional Application No. 62/526,838, filed Jun. 29, 2017, which is herein incorporated by reference in its entirety.

FIELD

This disclosure concerns compounds, and embodiments of a method for making and using the compounds, such as for inhibiting kinases, particularly interleukin receptor-associated kinase (IRAK), and for treating diseases and conditions related to IRAK.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Certain disclosed embodiments concern compounds having a formula 1

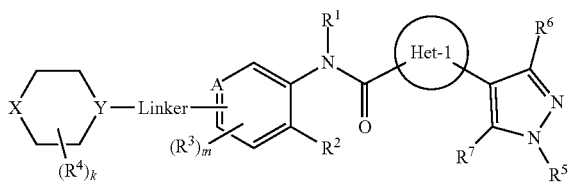

1 or a pharmaceutically acceptable salt thereof. A person of ordinary skill in the art will appreciate that compounds within formula 1 also can be hydrates, N-oxides, prodrugs, or solvates thereof. With respect to formula 1, Het-1 is heteroaryl. Het-1 may be a 5-membered heteroaryl or a 6-membered heteroaryl, such as furanyl, thiazolyl, or pyridinyl, and in certain embodiments, Het-1 is

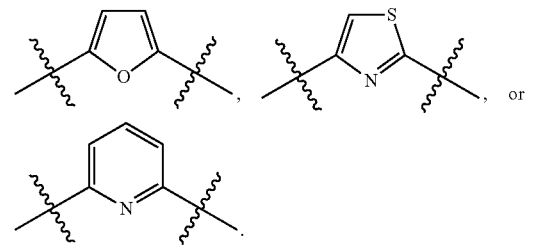

$R^1$ may be H or alkyl, such as $C_{1-6}$alkyl, and in certain particular examples, $R^1$ is H.

$R^2$ may be alkoxy, such as $C_{1-6}$alkoxy, or $—N(R^c)_2$. In some embodiments, $R^2$ is $C_{1-3}$alkoxy, typically methoxy, or $R^2$ has a formula

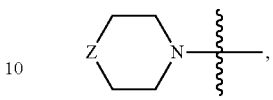

where Z is a bond, O, $—NR^a$, or $C(R^8)_2$, and each $R^8$ independently is $R^a$ or $R^b$. Each $R^8$ independently may be H, $—OH$, $C_{1-3}$alkyl, or halo, and/or Z may be a bond, O, or $C(R^8)_2$. In particular embodiments, $R^2$ is $—OCH_3$,

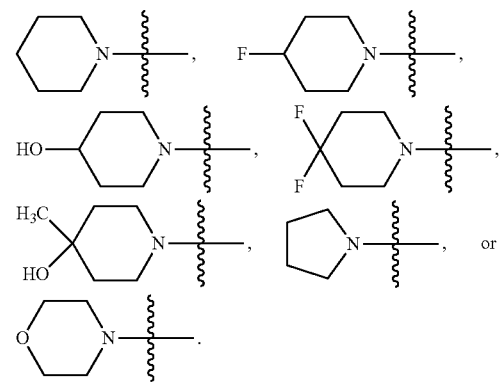

$R^a$ is independently for each occurrence H, D, $C_{1-6}$alkyl, or $C_{3-6}$cycloalkyl. $R^b$ is independently for each occurrence $—OH$, $—OR^a$, or halo. And $R^c$ is independently for each occurrence $R^a$, or two $R^c$ groups together with the nitrogen bound thereto form a $C_{3-7}$heterocyclyl optionally interrupted with one or two additional heteroatoms selected from O, N, or S.

Each $R^3$ independently is $C_{1-6}$alkyl, $C_{1-3}$haloalkyl, or halo, such as F, Cl, Br, or I. In certain examples, $R^3$ is F. And m may be 0, 1 or 2. In some examples, m is 0, and in other examples, m is 1.

X may be O or $NR^9$, where $R^9$ is $R^a$, $C(O)C_{1-6}$aliphatic, $C(O)N(R^c)_2$, or $CO_2R^a$. And Y may be N or CH, typically N. And in certain examples, the

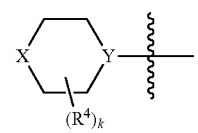

moiety is

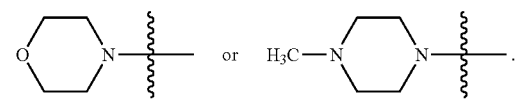

Each $R^4$ independently is $C_{1-6}$alkyl. k may be 0, 1, 2, 3, 4, 5, 6, 7, 8, or 9, typically, 0, 1, 2, 3 or 4, and in some embodiments, k is 0.

In some embodiments, Linker is a bond, —(C(R$^{10}$)$_2$)$_n$—, —(C(R$^{10}$)$_2$)$_n$—O—, —C(O)—(C(R$^{10}$)$_2$)$_p$—, or —(C(R$^{10}$)$_2$)$_p$—N(R$^a$)—, where each R$^{10}$ independently may be R$^a$ or R$^b$, typically H or halo, such as F; n may be 1, 2, 3, 4, 5, or 6, typically 1 or 2; and p is 0, 1, or 2, typically 0 or 1. In certain embodiments, Linker is a bond, —CH$_2$—, —C(O)—, —C(O)—CH$_2$—, —CH$_2$CH$_2$—, —CH$_2$CH$_2$N(CH$_3$)—, —CH$_2$CH$_2$N(H)—, —CH$_2$CH$_2$O—, or —CH$_2$CF$_2$—. And in particular examples, the

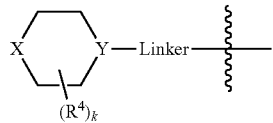

moiety is

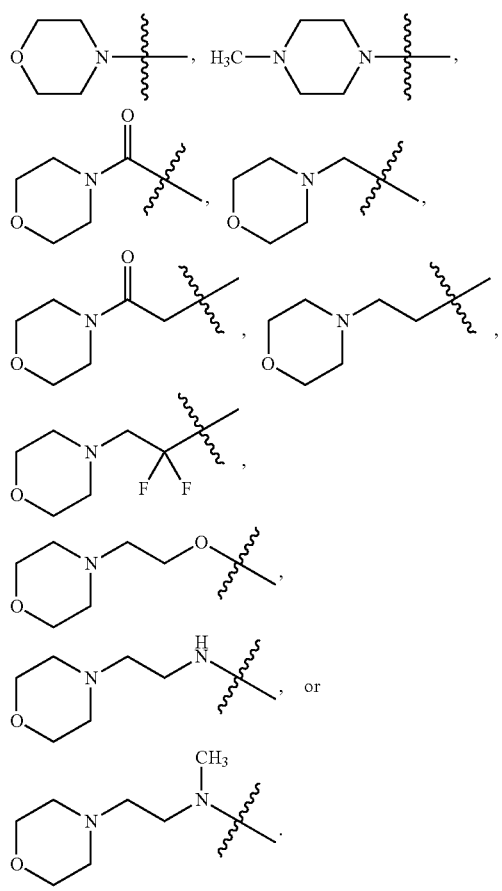

R$^5$ is H, aliphatic, phosphonooxyalkyl, phosphonoalkyl, or acyl. R$^5$ may be H, C$_{1-6}$alkyl, —CH$_2$OP(O)(R$^d$)$_2$, —CH$_2$P(O)(R$^d$)$_2$, or acyl, where each R$^d$ is independently for each occurrence —OR$^a$, —O$^-$M$^+$ where each M$^+$ independently is an alkali metal ion, such as K$^+$, Na$^+$, Li$^+$ or an ammonium ion, such as $^+$NH$_4$ or $^+$N(R$^a$)$_4$, or —O$^-$[M$^{2+}$]$_{0.5}$ where M$^{2+}$ is an alkaline metal earth ion, such as Mg$^{2+}$, Ca$^{2+}$ or Ba$^{2+}$, and in some examples, R$^5$ is H, C$_{1-6}$ alkyl, or —CH$_2$OP(O)(R$^d$)$_2$, preferably H.

Each of R$^6$ and R$^7$ independently may be H, aliphatic, or halo, such as H, halo, or C$_{1-6}$ alkyl. In some examples, each of R$^6$ and R$^7$ is H. In certain examples, each of R$^5$, R$^6$ and R$^7$ is H.

A may be N or CR$^h$, where R$^h$ is H, R$^3$ or the

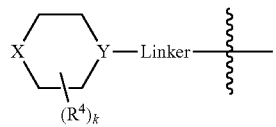

moiety. The compounds may have a formula

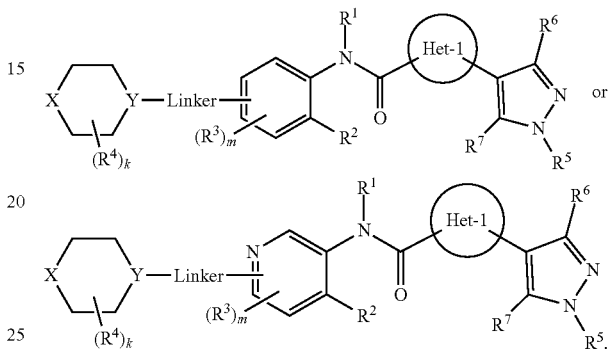

In any disclosed embodiments, the

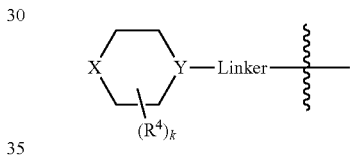

moiety may be para to R$^2$, or the

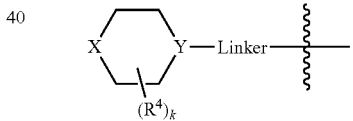

moiety may be para to the amide. In some embodiments, m is 1 and R$^3$ is para to the amide, and in other embodiments, m is 1 and R$^3$ is para to R$^2$.

Also disclosed are compounds having a formula 2

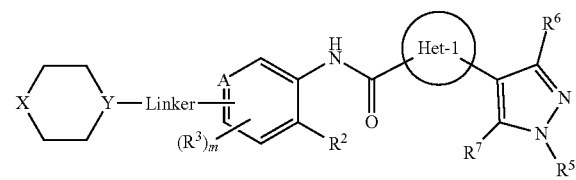

or a pharmaceutically acceptable salt, hydrates, N-oxides, prodrugs, or solvates thereof. With respect to formula 2, Het-1, A, X, Y, Linker, R$^2$, R$^3$, R$^5$, R$^6$, R$^7$, and m may be as previous defined with respect in the preceding embodiments. In certain embodiments, Het-1 is pyridinyl, furanyl or thiazolyl; R$^2$ is alkoxy or —N(R$^c$)$_2$; each R$^3$ independently is halo; m is 0 or 1; each of $R^5$, $R^6$ and $R^7$ is H; A is N or $CR^h$; X is O or $NR^9$; $R^9$ is $R^a$; Y is N or CH; Linker is a bond, $-(C(R^{10})_2)_n-$, $-(C(R^{10})_2)_n-O-$, $-C(O)-(C(R^{10})_2)_p-$, or $-(C(R^{10})_2)_p-N(R^a)-$; each $R^{10}$ independently is $R^a$ or $R^b$; n is 1 or 2; and p is 0 or 1.

In certain disclosed embodiments of formulas 1 and 2, the compound has a formula selected from

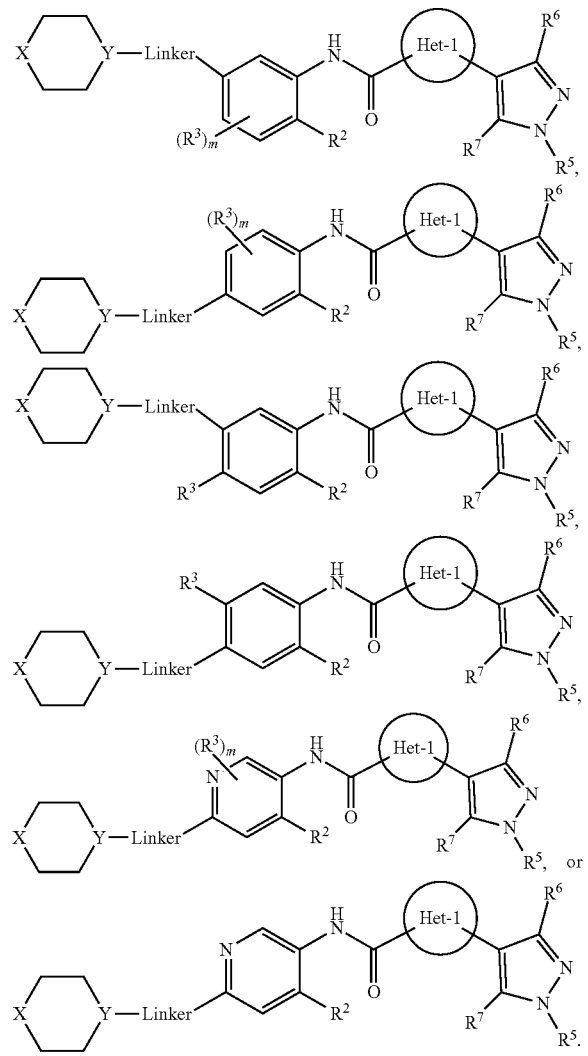

Compounds according to the present disclosure also may be formulated as compositions comprising one or more compounds according to the formulas disclosed herein, and a pharmaceutically acceptable excipient. Such compositions also may comprise an additional therapeutic agent.

Methods for making and using such compounds and compositions also are disclosed. For example, one disclosed embodiment of a method for using compounds according to the present disclosure comprises administering to a subject in need thereof an effective amount of a compound, two or more compounds, or a composition comprising at least one compound, according to the disclosed formulas. The method may be particularly suitable for treating a disease or condition for which a kinase inhibitor is indicated. For example, the method may comprise administering a compound to a subject to treat a disease or condition where an IRAK inhibitor is indicated, including an IRAK1, IRAK2, IRAK3 and/or IRAK4 inhibitor. The disease may be an autoimmune disease, inflammatory disorder, cardiovascular disease, neurodegenerative disorder, allergic disorder, multi-organ failure, kidney disease, platelet aggregation, cancer, transplantation, sperm motility, erythrocyte deficiency, graft rejection, lung injury, respiratory disease, ischemic condition, bacterial infection, viral infection, immune regulatory disorder or a combination thereof.

Additionally, or alternatively, disclosed embodiments of a method for using compounds according to the present disclosure may comprise inhibiting a kinase, such as by contacting an IRAK protein with an effective amount of a compound or compounds, or composition comprising a compound or compounds, according to any or all of the disclosed formulas, wherein the compound has an $EC_{50}$ with respect to the kinase of from greater than 0 to 5 µM, typically from 0 to 1 µM, and with many disclosed compounds having an $EC_{50}$ substantially lower than 1 µM. The kinase, such as an IRAK protein, may be in a subject, or the method may comprise contacting the kinase in vitro.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

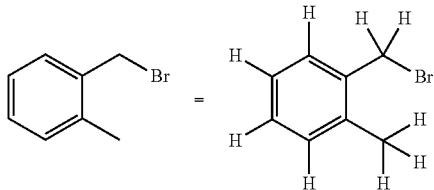

Sometimes a particular atom in a structure is described in textual formula as having a hydrogen or hydrogen atoms, for example —CH$_2$CH$_2$—. It will be understood by a person of ordinary skill in the art that the aforementioned descriptive techniques are common in the chemical arts to provide brevity and simplicity to description of organic structures.

If a group R is depicted as "floating" on a ring system, as for example in the group:

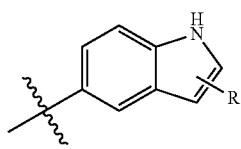

then, unless otherwise defined, a substituent R can reside on any atom of the fused bicyclic ring system, so long as a stable structure is formed that conforms to standard valence conditions as understood by a person of ordinary skill in the art. In the example depicted, the R group can reside on an atom in either the 5-membered or the 6-membered ring of the indolyl ring system, including the heteroatom by replacing the explicitly recited hydrogen, but excluding the atom carrying the bond with the "∿∿" symbol and the bridging carbon atoms.

When there are more than one such depicted "floating" groups, as for example in the formulae:

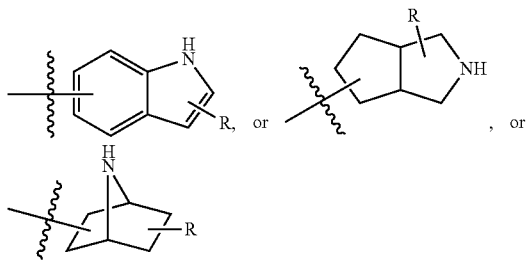

where there are two groups, namely, the R and the bond indicating attachment to a parent structure; then, unless otherwise defined, each "floating" group can reside on any atoms of the ring system, again assuming each replaces a depicted, implied, or expressly defined hydrogen on the ring system and a chemically stable compound would be formed by such an arrangement.

When a group R is depicted as existing on a ring system containing saturated carbons, for example as in the formula:

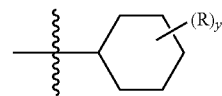

where, in this example, y can be more than one, and assuming each R replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can form a ring, thus creating a spirocyclic ring (a "spirocyclyl" group) structure. For example, shown below two Rs can form a piperidine ring in a spirocyclic arrangement with the cyclohexane, as

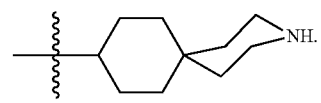

As used herein, the term "substituted" refers to all subsequent modifiers in a term, for example in the term "substituted arylC$_{1-8}$alkyl," substitution may occur on the "C$_{1-8}$alkyl" portion, the "aryl" portion or both portions of the arylC$_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" or a "pyrazolyl" moiety may be unsubstituted or substituted, but an "unsubstituted alkyl" or an "unsubstituted pyrazolyl" is not substituted.

"Substituents" or "substituent groups" for substituting for one or more hydrogen atoms on saturated carbon atoms in the specified group or moiety are, unless otherwise specified, —R$^{60}$, halo, =O, —OR$^{70}$, —SR$^{70}$, —N(R$^{80}$)$_2$, haloalkyl, perhaloalkyl, —CN, —NO$_2$, =N$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —P(O)(O$^-$)$_2$(M$^+$)$_2$, —P(O)(O$^-$)$_2$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)N(R$^{80}$)$_2$, —C(NR$^{70}$)(R$^{80}$)$_2$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ or —NR$^{70}$C(NR$^{70}$)N(R$^{80}$)$_2$, where R$^{60}$ is C$_{1-10}$aliphatic, heteroaliphatic, or cycloaliphatic, typically, C$_{1-6}$aliphatic, more typically C$_{1-6}$alkyl, where R$^{60}$ optionally may be substituted; each R$^{70}$ is independently for each occurrence hydrogen or R$^{60}$; each R$^{80}$ is independently for each occurrence R$^{70}$ or alternatively, two R$^{80}$ groups, taken together with the nitrogen atom to which they are attached, form a 3- to 7-membered heterocycloaliphatic, which optionally includes from 1 to 4 of the same or different additional heteroatoms selected from O, N and S, of which N optionally has $R^{70}$ substitution, such as H or $C_1$-$C_3$alkyl substitution; and each $M^+$ is a counter ion with a net single positive charge. Each $M^+$ is independently for each occurrence, for example, an alkali metal ion, such as $K^+$, $Na^+$, $Li^+$; an ammonium ion, such as $^+N(R^{70})_4$; a protonated amino acid ion, such as a lysine ion, or an arginine ion; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the invention and the other is a typical counter ion such as chloride, or two ionized compounds can serve as counter ions for such divalent alkali earth ions, or alternatively, a doubly ionized compound can serve as the counter ion for such divalent alkali earth ions). As specific examples, —$N(R^{80})_2$ includes —$NH_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, =O, =$NR^{70}$, =N—$OR^{70}$, =$N_2$ or =S.

Substituent groups for replacing hydrogen atoms on unsaturated carbon atoms in groups containing unsaturated carbons are, unless otherwise specified, —$R^{60}$, halo, —$O^-M^+$, —$OR^{70}$, —$SR^{70}$, —$S^-M^+$, —$N(R^{80})_2$, perhaloalkyl, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$PO_3^{-2}M^{2+}$, —P(O)$(OR^{70})O^-M^+$, —P(O)$(OR^{70})_2$, —C(O)$R^{70}$, —C(S)$R^{70}$, —C($NR^{70}$)$R^{70}$, —$CO_2^-M^+$, —$CO_2R^{70}$, —C(S)$OR^{70}$, —C(O)$NR^{80}R^{80}$, —C($NR^{70}$)$N(R^{80})_2$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$N(R^{80})_2$, —$NR^{70}$C($NR^{70}$)$R^{70}$ or —$NR^{70}$C($NR^{70}$)$N(R^{80})_2$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

Substituent groups for replacing hydrogen atoms on nitrogen atoms in groups containing such nitrogen atoms are, unless otherwise specified, —$R^{60}$, —$O^-M^+$, —$OR^{70}$, —$SR^{70}$, —$S^-M^+$, —$N(R^{80})_2$, perhaloalkyl, —CN, —NO, —$NO_2$, —S(O)$_2R^{70}$, —$SO_3^-M^+$, —$SO_3R^{70}$, —OS(O)$_2R^{70}$, —$OSO_3^-M^+$, —$OSO_3R^{70}$, —$PO_3^{2-}(M^+)_2$, —$PO_3^{2-}M^{2+}$, —P(O)$(OR^{70})O^-M^+$, —P(O)$(OR^{70})(OR^{70})$, —C(O)$R^{70}$, —C(S)$R^{70}$, —C($NR^{70}$)$R^{70}$, —$CO_2R^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2R^{70}$, —OC(S)$OR^{70}$, —$NR^{70}$C(O)$R^{70}$, —$NR^{70}$C(S)$R^{70}$, —$NR^{70}CO_2R^{70}$, —$NR^{70}$C(S)$OR^{70}$, —$NR^{70}$C(O)$N(R^{80})_2$, —$NR^{70}$C($NR^{70}$)$R^{70}$ or —$NR^{70}$C($NR^{70}$)$N(R^{80})_2$, where $R^{60}$, $R^{70}$, $R^{80}$ and $M^+$ are as previously defined.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, heterocyclic or aromatic. Exemplary acyl moieties include, but are not limited to, —C(O)H, —C(O)alkyl, —C(O)$C_1$-$C_6$alkyl, —C(O)$C_1$-$C_6$haloalkyl, —C(O)cycloalkyl, —C(O)alkenyl, —C(O)cycloalkenyl, —C(O)aryl, —C(O)heteroaryl, or —C(O)heterocyclyl. Specific examples include —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$) from one to six ($C_{1-6}$), or from one to four carbon atoms ($C_{1-4}$) for an acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group).

"Lower aliphatic" refers to an aliphatic group containing from one to ten carbon atoms ($C_{1-10}$), such as from one to six ($C_{1-6}$), or from one to four ($C_{1-4}$) carbon atoms; or from three to ten ($C_{3-10}$), such as from three to six ($C_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a $C_{1-6}$ alkyl group or a $C_{3-6}$cycloalkyl group. Methoxy (—$OCH_3$) and ethoxy (—$OCH_2CH_3$) are exemplary alkoxy groups. In a substituted alkoxy, R is substituted alkyl or substituted cycloalkyl, examples of which include haloalkoxy groups, such as —$OCF_2H$, or —$OCF_3$.

"Alkoxyalkyl" refers to the group -alkyl-OR, where R is a substituted or unsubstituted alkyl or a substituted or unsubstituted cycloalkyl group; —$CH_2CH_2$—O—$CH_2CH_3$ is an exemplary alkoxyalkyl group.

"Alkyl" refers to a saturated aliphatic hydrocarbyl group having from 1 to 25 ($C_{1-25}$) or more carbon atoms, more typically 1 to 10 ($C_{1-10}$) carbon atoms such as 1 to 6 ($C_{1-6}$) carbon atoms or 1 to 4 ($C_{1-4}$) carbon atoms. An alkyl moiety may be substituted or unsubstituted. This term includes, by way of example, linear and branched hydrocarbyl groups such as methyl ($CH_3$), ethyl (—$CH_2CH_3$), n-propyl (—$CH_2CH_2CH_3$), isopropyl (—$CH(CH_3)_2$), n-butyl (—$CH_2CH_2CH_2CH_3$), isobutyl (—$CH_2CH_2(CH_3)_2$), sec-butyl (—$CH(CH_3)(CH_2CH_3)$, t-butyl (—$C(CH_3)_3$), n-pentyl (—$CH_2CH_2CH_2CH_2CH_3$), and neopentyl (—$CH_2C(CH_3)_3$).

"Amino" refers to the group —NH₂, —NHR, or —NRR, where each R independently is selected from aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —(CH₂)₂₋₅— ring optionally interrupted by one or two additional heteroatom groups, such as —O— or —N(R$^g$) such as in the groups

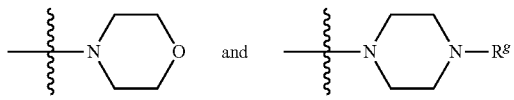

wherein R$^g$ is R$^{70}$, —C(O)R$^{70}$, —C(O)OR$^{60}$ or —C(O)N(R$^{80}$)₂.

"Amide" or "carboxamide" refers to the group —N(R)acyl, or —C(O)amino, where R is hydrogen, heteroaliphatic or aliphatic, such as alkyl, particularly $C_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

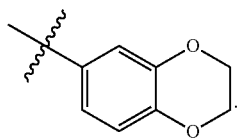 [SMILES: *c1ccc2c(c1)OCCO2]

However, in certain examples, context or express disclosure may indicate that the point of attachment is through a non-aromatic portion of the condensed ring system. For example,

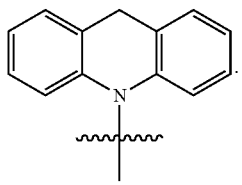 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl" or "carboxylate" refers to —CO₂H, —C(O)O⁻ or salts thereof.

"Carboxyl ester" or "carboxy ester" refers to the group —C(O)OR, where R is aliphatic, heteroaliphatic, cyclicaliphatic, heterocyclic, and aromatic, including both aryl and heteroaryl.

"Cyano" refers to the group —CN.

"Cycloaliphatic" refers to a cyclic aliphatic group having a single ring (e.g., cyclohexyl), or multiple rings, such as in a fused, bridged or spirocyclic system, at least one of which is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —CH₂F, —CHF₂ and —CF₃.

"Heteroaliphatic" refers to an aliphatic compound or group having at least one heteroatom and at least one carbon atom, i.e., one or more carbon atoms from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety of, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings that are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —NO$_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —O$^-$M$^+$, where M$^+$ is a counter ion with a single positive charge. Each M$^+$ may be an alkali ion, such as K$^+$, Na$^+$, Li$^+$; an ammonium ion, such as $^+$N(R")$_4$ where each R" independently is H, aliphatic, heterocyclyl or aryl; or an alkaline earth ion, such as [Ca$^{2+}$]$_{0.5}$, [Mg$^{2+}$]$_{0.5}$, or [Ba$^{2+}$]$_{0.5}$. Phosphonooxyalkyl refers to the group -alkyl-phosphate, such as, for example, —CH$_2$OP(O)(OH)$_2$, or a salt thereof, such as —CH$_2$OP(O)(O$^-$Na)$_2$, and (((dialkoxyphosphoryl)oxy)alkyl) refers to the dialkyl ester of a phosphonooxyalkyl group, such as, for example, —CH$_2$OP(O)(O-tert-butyl)$_2$.

"Phosphonate" refers to the group —P(O)(OR')$_2$, where each —OR' independently is —OH; —O-aliphatic such as —O-alkyl or —O-cycloalkyl; —O-aromatic, including both —O-aryl and —O-heteroaryl; or —O-aralkyl; or —OR' is —O$^-$M$^+$, and M$^+$ is a counter ion with a single positive charge. Each M$^+$ is a positively charged counterion and may be, by way of example, an alkali metal ion, such as K$^+$, Na$^+$, Li$^+$; an ammonium ion, such as $^+$N(R")$_4$ where each R" independently is H, aliphatic, heterocyclyl or aryl; or an alkaline earth metal ion, such as [Ca$^{2+}$]$_{0.5}$, [Mg$^{2+}$]$_{0.5}$, or [Ba$^{2+}$]$_{0.5}$. Phosphonoalkyl refers to the group -alkyl-phosphonate, such as, for example, —CH$_2$P(O)(OH)$_2$, or —CH$_2$P(O)(O$^-$Na$^+$)$_2$, and ((dialkoxyphosphoryl)alkyl) refers to the dialkyl ester of a phosphonoalkyl group, such as, for example, —CH$_2$P(O)(O-tert-butyl)$_2$.

"Patient" or "Subject" refers to mammals and other animals, particularly humans. Thus disclosed methods are applicable to both human therapy and veterinary applications.

"Pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, Pa., 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the compounds may be a formate, trifluoroactate, hydrochloride or sodium salt.

"Effective amount" with respect to a compound or composition refer to an amount of the compound or composition sufficient to achieve a particular desired result, such as to inhibit a protein or enzyme, particularly an interleukin-1 receptor-associated kinase; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the age of the patient to be treated, and the like.

"Prodrug" refers to compounds that are transformed in vivo to yield a biologically active compound, particularly the parent compound, for example, by hydrolysis in the gut or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —N(R)sulfonyl, where R is H, aliphatic, heteroaliphatic, cyclic, heterocyclic, including aromatic, both aryl and heteroaryl.

"Sulfanyl" refers to the group or —SH, —S-aliphatic, —S-heteroaliphatic, —S-cyclic, —S-heterocyclyl, including —S-aromatic, both-S-aryl and —S-heteroaryl.

"Sulfinyl" refers to the group or moiety —S(O)H, —S(O) aliphatic, —S(O)heteroaliphatic, —S(O)cyclic, —S(O)heterocyclyl, including aromatic, both-S(O)aryl and —S(O)heteroaryl.

"Sulfonyl" refers to the group: —$SO_2$H, —$SO_2$aliphatic, —$SO_2$heteroaliphatic, —$SO_2$cyclic, —$SO_2$heterocyclyl, including aromatic sulfonyls, including both —$SO_2$aryl and —$SO_2$heteroaryl.

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substituents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the pyrazolyl and pyridinyl rings, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$.

II. IRAK-Active Compounds and Compositions Comprising IRAK-Active Compounds

A. Compounds

Disclosed herein are compounds, methods of making the compounds, and methods of using the compounds. In one embodiment the disclosed compounds are kinase inhibitors, particularly tyrosine kinase inhibitors. In a particular embodiment the compounds are useful in blocking one or more cytokine signaling pathways, such as the IL-17 signaling pathway. For certain embodiments, the disclosed compounds are useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3 and/or IRAK4.

Exemplary compounds within the scope of the present invention have a general formula 1

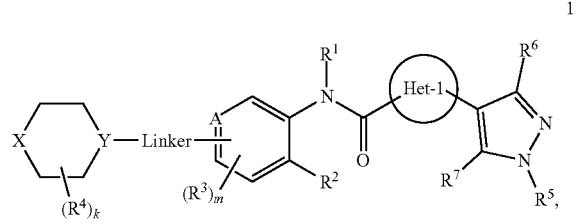

or salts thereof. A person of ordinary skill in the art will appreciate that N-oxides, hydrates, prodrugs, and/or solvates of such compounds also can be formed, and accordingly N-oxides, hydrates, prodrugs, and/or solvates are understood to be included within the scope of the disclosed general formulas.

With reference to formula 1, Het-1 is heteroaryl, and may be a 5- or 6-membered heteroaryl. In some embodiments, Het-1 is furanyl, thiazolyl, or pyridinyl, such as,

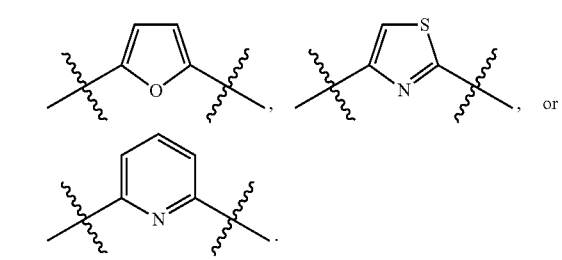

$R^1$ is H, or alkyl, such as $C_{1-6}$ alkyl. In particular embodiments, $R^1$ is H.

In particular embodiments, Het-1 is pyridinyl, furanyl or thiazolyl; and $R^1$ is H.

$R^2$ is alkoxy, such as $C_{1-6}$alkoxy and preferably $C_{1-3}$alkoxy, or $-N(R^c)_2$. In some embodiments, $R^2$ has a formula

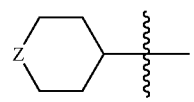

where Z is a bond, O, $-NR^a$, $-NC(O)R^a$, such as $-NC(O)C_{1-6}$alkyl, or $C(R^8)_2$ where each $R^8$ independently is $R^a$ or $R^b$. For examples, each $R^8$ independently may be H, $-OH$, $C_{1-3}$alkyl such as methyl, or halo, such as F. In some embodiments, Z is a bond, O, or $C(R^8)_2$. In certain embodiments, $R^2$ is $-OCH_3$,

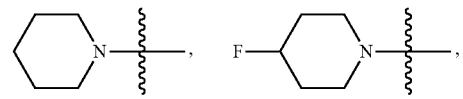

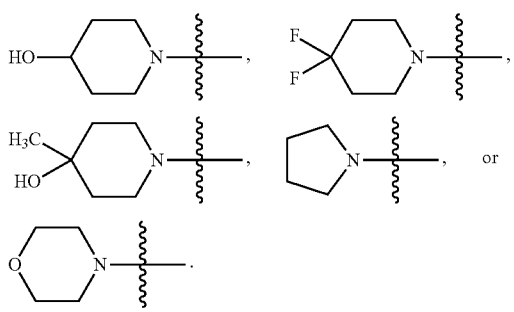

In any of these embodiments, Het-1 is pyridinyl, furanyl or thiazolyl; and R¹ is H.

With respect to formula 1, Het-1 may be: 1A) heteroaryl; 1B) 5-membered heteroaryl; 1C) 6-membered heteroaryl; 1D) furanyl; 1E) thiazolyl; 1F) pyridinyl; 1G)

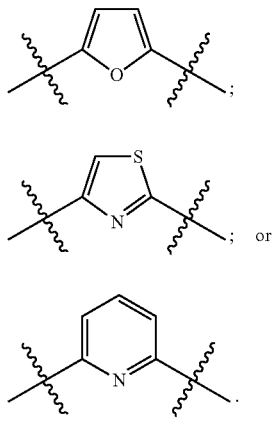

1H)

; or

1I)

.

With respect to the Het-1 embodiments 1A to 1I, R² may be, in any combination with 1A to 1I: 2A) alkoxy; 2B) —N(R^c)₂; 2C) $C_{1-6}$alkoxy; 2D) methoxy; 2E)

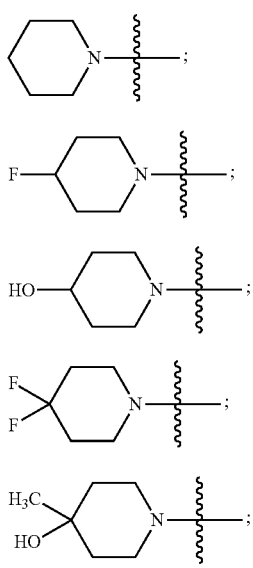

2F)
;

2G)
;

2H)
;

2I)
;

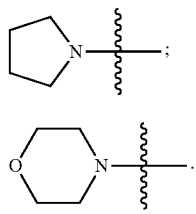

2J)

; or

2K)

.

A person of ordinary skill in the art will understand that any of 2A to 2K may be combined with any of 1A to 1I to form any and all combinations between such substituents.

Each R³ independently is $C_{1-6}$alkyl, $C_{1-3}$haloalkyl, or halo, such as F, Cl, Br, or I, preferably F, Cl, Br, and most preferably F.

m is 0, 1 or 2. In certain embodiments, m is 0, and in other particular embodiments, m is 1.

In particular embodiments, Het-1 is pyridinyl, furanyl or thiazolyl; R¹ is H; R² is —OCH₃,

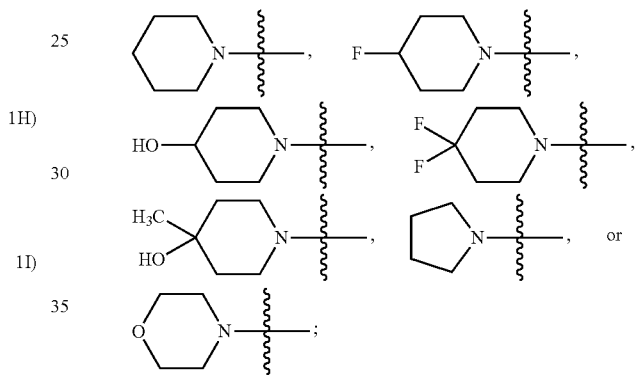

and m is 0, or m is 1 and R³ is F.

With respect to the Het-1 embodiments 1A to 1I and the R² embodiments 2A to 2K, R³ and m may be, in any combination with 1A to 1I and 2A to 2K: 3A) m=0; 3B) m=1 or 2 and each R³ independently is $C_{1-6}$alkyl or halo; 3C) m=1 or 2 and each R³ independently is halo; 3D) m=1 and R³ is halo; or 3E) m=1 and R³ is F.

A person of ordinary skill in the art will understand that any of 3A to 3E may be combined with any of 1A to 1I and 2A to 2K to form any and all combinations between such substituents.

Each R⁴ independently is selected from halo and $C_{1-6}$alkyl, more typically $C_{1-3}$alkyl with particular embodiments having R⁴ is methyl;

k is 0, 1, 2, 3, 4, 5, 6, 7, 8, or 9, such as 0, 1, 2, 3, or 4, preferably 0, 1 or 2, and in certain embodiments, k is 0.

A is N or CR^h, where R^h is H, R³ or the

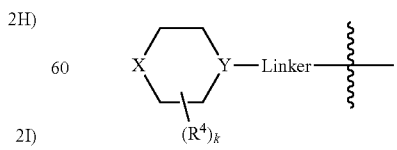

moiety.

R⁵ is H, aliphatic, such as alkyl, including $C_{1-6}$ alkyl or $C_{3-6}$cycloalkyl; phosphonooxyalkyl; phosphonoalkyl; or acyl. In some embodiments, $R^5$ is H; $C_{1-6}$alkyl; —CH$_2$OP(O)(R$^d$)$_2$; —CH$_2$P(O)(R$^d$)$_2$; or acyl, such as C(O)C$_{1-6}$alkyl, where each R$^d$ is independently for each occurrence —OR$^a$, —O$^-$M$^+$ where each M$^+$ independently is an alkali metal ion, such as K$^+$, Na$^+$, Li$^+$ or an ammonium ion, such as $^+$NH$_4$ or $^+$N(R$^a$)$_4$, or —O$^-$[M$^{2+}$]$_{0.5}$ where M$^{2+}$ is an alkaline metal earth ion, such as Mg$^{2+}$, Ca$^{2+}$ or Ba$^{2+}$. In certain embodiments, $R^5$ is H, C$_{1-6}$ alkyl, or —CH$_2$OP(O)(R$^d$)$_2$, such as —CH$_2$OP(O)(OH)$_2$ or a salt thereof. And in some embodiments, $R^5$ is H.

Each of $R^6$ and $R^7$ independently is H, aliphatic, such as alkyl, including C$_{1-6}$ alkyl or C$_{3-6}$cycloalkyl; or halo, such as F, Cl, Br, or I. In some embodiments, each of $R^6$ and $R^7$ independently is H, halo, or C$_{1-6}$ alkyl. In some embodiments, $R^6$ is H. In some embodiments, $R^7$ is H. In certain embodiments, $R^6$ and $R^7$ is H.

In particular embodiments, each of $R^5$, $R^6$ and $R^7$ is H.

In particular embodiments, Het-1 is pyridinyl, furanyl or thiazolyl; $R^1$ is H; $R^2$ is —OCH$_3$,

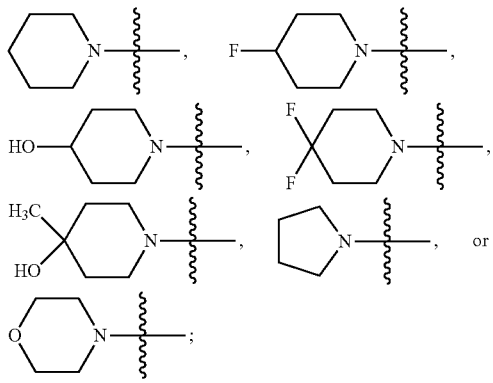

m is 0, or m is 1 and $R^3$ is F; each of $R^5$, $R^6$ and $R^7$ is H; k is 0; and A is N or CR$^h$.

X is O or NR$^9$, where $R^9$ is R$^a$, C(O)C$_{1-6}$aliphatic, C(O)N(R$^c$)$_2$, or CO$_2$R$^a$, and in some embodiments $R^9$ is H or C$_{1-6}$alkyl.

Y is N or CH.

In certain embodiments, the

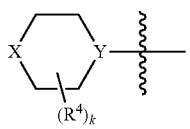

moiety is

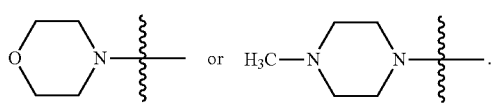

Linker is a bond, —(C(R$^{10}$)$_2$)$_n$—, —(C(R$^{10}$)$_2$)$_n$—O—, —C(O)—(C(R$^{10}$)$_2$)$_p$—, or —(C(R$^{10}$)$_2$)$_p$—N(R$^a$)—, where each R$^{10}$ independently is R$^a$ or R$^b$; n is 1, 2, 3, 4, 5, or 6, such as 1, 2, or 3; and p is 0, 1, or 2. In some embodiments, n is 1, and in other embodiments, n is 2. In some embodiments, p is 0, and in other embodiments, p is 1. In some embodiments, each R$^{10}$ independently is H, or halo, such as F. In certain embodiments, Linker is a bond, —CH$_2$—, —C(O)—, —C(O)—CH$_2$—, —CH$_2$CH$_2$—, —CH$_2$CH$_2$N(CH$_3$)—, —CH$_2$CH$_2$N(H)—, —CH$_2$CH$_2$O—, or —CH$_2$CF$_2$—. In particular embodiments, Linker is a bond. In other particular embodiments, Linker is —(C(R$^{10}$)$_2$)$_n$—, —(C(R$^{10}$)$_2$)$_n$—O—, —C(O)—(C(R$^{10}$)$_2$)$_p$—, or —(C(R$^{10}$)$_2$)$_p$—N(R$^a$)—, such as —CH$_2$—, —C(O)—, —C(O)—CH$_2$—, —CH$_2$CH$_2$—, —CH$_2$CH$_2$N(CH$_3$)—, —CH$_2$CH$_2$N(H)—, —CH$_2$CH$_2$O—, or —CH$_2$CF$_2$—.

In particular embodiments, Het-1 is pyridinyl, furanyl or thiazolyl; $R^1$ is H; $R^2$ is —OCH$_3$,

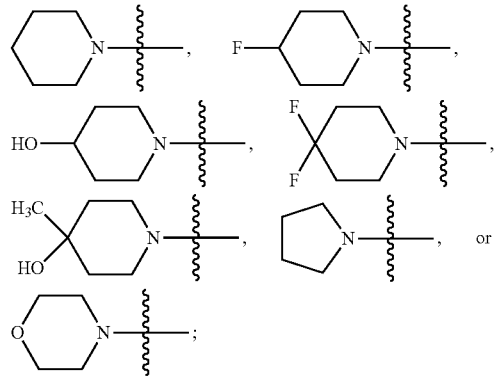

m is 0, or m is 1 and $R^3$ is F; each of $R^5$, $R^6$ and $R^7$ is H; k is 0; A is N or CR$^h$; X is O or NR$^{10}$, where R$^{10}$ is H or C$_{1-6}$alkyl; Y is N or CH; and Linker is a bond, —CH$_2$—, —C(O)—, —C(O)—CH$_2$—, —CH$_2$CH$_2$—, —CH$_2$CH$_2$N(CH$_3$)—, —CH$_2$CH$_2$N(H)—, —CH$_2$CH$_2$O—, or —CH$_2$CF$_2$—.

In certain embodiments, the

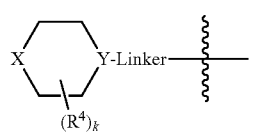

moiety is

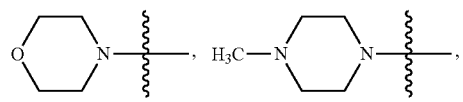

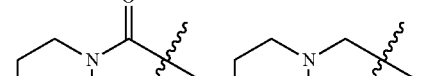

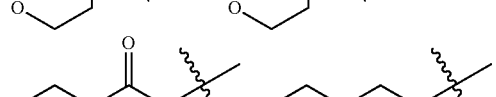

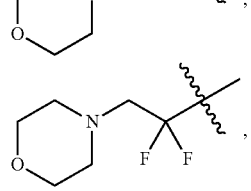

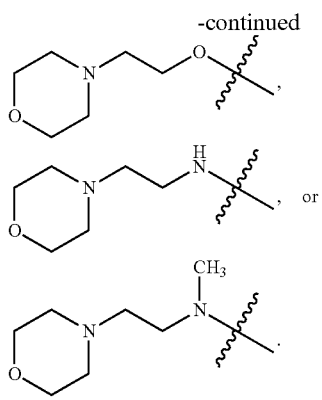

In any of these embodiments, Het-1 is pyridinyl, furanyl or thiazolyl; $R^1$ is H; $R^2$ is —$OCH_3$,

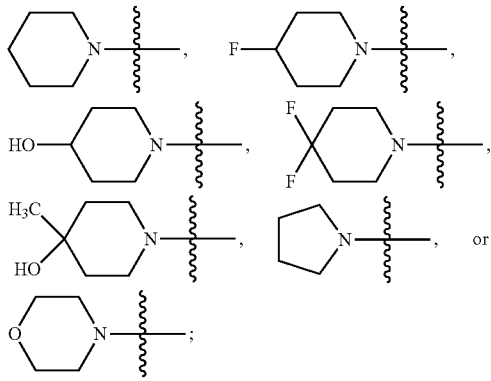

m is 0, or m is 1 and $R^3$ is F; each of $R^5$, $R^6$ and $R^7$ is H; k is 0; and A is N or $CR^h$.

With respect to the Het-1 embodiments 1A to 1I, the $R^2$ embodiments 2A to 2K, and the $R^3$ and m embodiments 3A to 3E, Linker may be, in any combination with 1A to 1I, 2A to 2K and 3A to 3E: 4A) a bond; 4B) —$(C(R^{10})_2)_n$—; 4C) —$(C(R^{10})_2)_n$—O—; 4D) —C(O)—$(C(R^{10})_2)_p$—; 4E) —$(C(R^{10})_2)_p$—$N(R^a)$—; 4F) —$CH_2$—; 4G) —C(O)—; 4H) —C(O)—$CH_2$—; 4I) —$CH_2CH_2$—; 4J) —$CH_2CH_2N(CH_3)$—; 4K) —$CH_2CH_2N(H)$—; 4L) —$CH_2CH_2O$—; or 4M) —$CH_2CF_2$—.

A person of ordinary skill in the art will understand that any of 4A to 4M may be combined with any of 1A to 1I, 2A to 2K, and 3A to 3E to form any and all combinations between such substituents.

With respect to the Het-1 embodiments 1A to 1I, the $R^2$ embodiments 2A to 2K, the $R^3$ and m embodiments 3A to 3E, and the Linker embodiments 4A to 4M, X and Y may be, in any combination with 1A to 1I, 2A to 2K, 3A to 3E and 4A to 4M: 5A) X=O and Y=N; 5B) X=O and Y=CH; 5C) X=$NR^9$ and Y=N; 5D) X=$NR^9$ and Y=CH; 5E) X=$NR^9$ and Y=N, where $R^9$ is H; 5F) X=$NR^9$ and Y=N, where $R^9$ is $C_{1-6}$alkyl; 5G) X=$NR^9$ and Y=CH, where $R^9$ is H; 5H) X=$NR^9$ and Y=CH, where $R^9$ is $C_{1-6}$alkyl; 5I) X=$NR^9$ and Y=CH, where $R^9$ is $CH_3$; or 5J) X=$NR^9$ and Y=N, where $R^9$ is $CH_3$.

A person of ordinary skill in the art will understand that any of 5A to 5J may be combined with any of 1A to 1I, 2A to 2K, 3A to 3E, and 4A to 4M to form any and all combinations between such substituents.

With respect to the Het-1 embodiments 1A to 1I, the $R^2$ embodiments 2A to 2K, the $R^3$ and m embodiments 3A to 3E, the Linker embodiments 4A to 4M, and the X and Y embodiments 5A to 5J, $R^4$ and k may be, in any combination with 1A to 1I, 2A to 2K, 3A to 3E, 4A to 4M and 5A to 5J: 6A) k=0; 6B) each $R^4$ independently is $C_{1-6}$alkyl, and k is 1, 2, 3, 4, 5, 6, 7, 8, or 9; 6C) each $R^4$ independently is $C_{1-6}$alkyl, and k is 1, 2, 3, or 4; or 6D) each $R^4$ independently is $C_{1-6}$alkyl, and k is 1 or 2.

A person of ordinary skill in the art will understand that any of 6A to 6D may be combined with any of 1A to 1I, 2A to 2K, 3A to 3E, 4A to 4M and 5A to 5J to form any and all combinations between such substituents.

With respect to the Het-1 embodiments 1A to 1I, the $R^2$ embodiments 2A to 2K, the $R^3$ and m embodiments 3A to 3E, the Linker embodiments 4A to 4M, the X and Y embodiments 5A to 5J, and the $R^4$ and k embodiments 6A to 6D, A may be, in any combination with 1A to 1I, 2A to 2K, 3A to 3E, 4A to 4M, 5A to 5J and 6A to 6D: 7A) N; 7B CH; 7C) $CR^3$; or 7D)

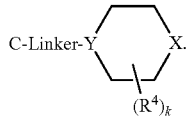

A person of ordinary skill in the art will understand that any of 7A to 7D may be combined with any of 1A to 1I, 2A to 2K, 3A to 3E, 4A to 4M, 5A to 5J and 6A to 6D to form any and all combinations between such substituents.

With respect to the Het-1 embodiments 1A to 1I, the $R^2$ embodiments 2A to 2K, the $R^3$ and m embodiments 3A to 3E, the Linker embodiments 4A to 4M, the X and Y embodiments 5A to 5J, the $R^4$ and k embodiments 6A to 6D, and the A embodiments 7A to 7D, $R^5$ may be, in any combination with 1A to 1I, 2A to 2K, 3A to 3E, 4A to 4M, 5A to 5J, 6A to 6D, and 7A to 7D: 8A) H; 8B $C_{1-6}$ alkyl; 8C) phosphonooxyalkyl; 8D) phosphonoalkyl; 8E) acyl; 8F) —$CH_2OP(O)(R^d)_2$; 8G) —$CH_2P(O)(R^d)_2$; 8H) C(O)$C_{1-6}$ alkyl; or 8I) —$CH_2OP(O)(OH)_2$ or a salt thereof.

A person of ordinary skill in the art will understand that any of 8A to 8I may be combined with any of 1A to 1I, 2A to 2K, 3A to 3E, 4A to 4M, 5A to 5J, 6A to 6D, and 7A to 7D to form any and all combinations between such substituents.

With respect to the Het-1 embodiments 1A to 1I, the $R^2$ embodiments 2A to 2K, the $R^3$ and m embodiments 3A to 3E, the Linker embodiments 4A to 4M, the X and Y embodiments 5A to 5J, the $R^4$ and k embodiments 6A to 6D, the A embodiments 7A to 7D, and the $R^5$ embodiments, 8A to 8I, $R^6$ may be, in any combination with 1A to 1I, 2A to 2K, 3A to 3E, 4A to 4M, 5A to 5J, 6A to 6D, 7A to 7D, and 8A to 8I: 9A) H; 9B) $C_{1-6}$ alkyl; 9C) halo; 9D) F; 9E) Cl; 9F) Br; or 9G) I.

A person of ordinary skill in the art will understand that any of 9A to 9G may be combined with any of 1A to 1I, 2A to 2K, 3A to 3E, 4A to 4M, 5A to 5J, 6A to 6D, 7A to 7D, and 8A to 8I to form any and all combinations between such substituents.

With respect to the Het-1 embodiments 1A to 1I, the $R^2$ embodiments 2A to 2K, the $R^3$ and m embodiments 3A to 3E, the Linker embodiments 4A to 4M, the X and Y embodiments 5A to 5J, the $R^4$ and k embodiments 6A to 6D, the A embodiments 7A to 7D, the $R^5$ embodiments, 8A to 8I, and the $R^6$ embodiments, 9A to 9G, $R^7$ may be, in any combination with 1A to 1I, 2A to 2K, 3A to 3E, 4A to 4M, 5A to 5J, 6A to 6D, 7A to 7D, 8A to 8I, and 9A to 9G: 10A) H; 10B) $C_{1-6}$ alkyl; 10C) halo; 10D) F; 10E) Cl; 10F) Br; or 10G) I.

A person of ordinary skill in the art will understand that any of 10A to 10G may be combined with any of 1A to 1I, 2A to 2K, 3A to 3E, 4A to 4M, 5A to 5J, 6A to 6D, 7A to 7D, 8A to 8I, and 9A to 9G to form any and all combinations between such substituents.

In any combination of embodiments 1A to 1I, 2A to 2K, 3A to 3E, 4A to 4M, 5A to 5J, 6A to 6D, 7A to 7D, 8A to 8I, 9A to 9G, and 10A to 10G, $R^1$ may be H, or $R^1$ may be $C_{1-6}$alkyl.

$R^a$ is independently for each occurrence H, D, $C_{1-6}$alkyl, or $C_{3-6}$cycloalkyl;

$R^b$ is independently for each occurrence —OH, —$OR^a$, or halo;

$R^c$ is independently for each occurrence $R^a$, or two $R^c$ groups together with the nitrogen bound thereto form a $C_{3-7}$heterocyclyl, preferably $C_{3-7}$heteroalicyclyl, optionally substituted with 1, 2, 3 or 4 substituents selected from $C_{1-6}$alkyl, $C_{1-3}$haloalkyl, —OH, or halo, and optionally interrupted with one or two additional heteroatoms selected from O, N, or S, preferably —O— or —N($R^g$) wherein $R^g$ is $R^{70}$, —C(O)$R^{70}$, —C(O)O$R^{60}$ or —C(O)N($R^{80}$)$_2$, and preferably $R^g$ is $R^a$, —C(O)$R^a$, —C(O)O$R^a$ or —C(O)N($R^a$)$_2$.

In some embodiments of formula 1, k=0. In other embodiments, $R^1$ is H. In some embodiments, k is 0 and $R^1$ is H, and the compound has a general formula 2

2

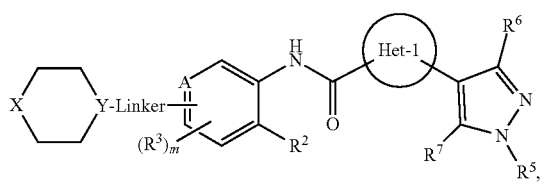

where Het-1, X, Y, Linker, A, $R^2$, $R^3$, $R^5$, $R^6$, $R^7$ and m are as previously defined for formula 1.

In some embodiments of formulas 1 or 2, A is $CR^h$. In certain embodiments, $R^h$ is H. In other embodiments, $R^h$ is the

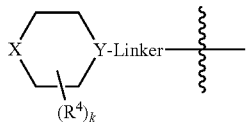

moiety. And in further embodiments, $R^h$ is $R^3$.

In some examples, the compounds have a general formula 3

3

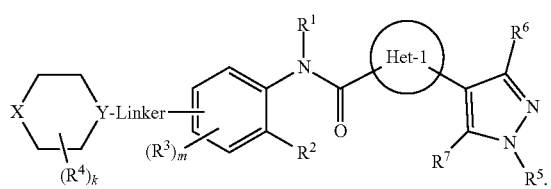

With respect to formula 3, Het-1, X, Y, Linker, $R^1$, $R^2$, $R^3$, $R^4$, $R^5$, $R^6$, $R^7$, k and m are as previously defined for formula 1.

In some embodiments of formulas 1, 2 or 3, the

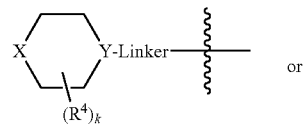 or

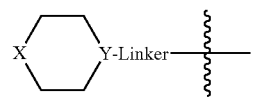

moiety is para to $R^2$. And in certain embodiments, m is 1 and $R^3$ is para to the amide.

In other embodiments of formulas 1, 2 or 3, the

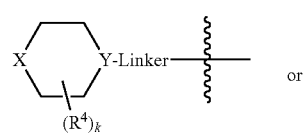 or

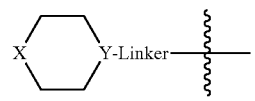

moiety is para to the amide. And in certain embodiments, m is 1 and $R^3$ is para to $R^2$.

In some embodiments of formula 3, k=0. In other embodiments, $R^1$ is H. In some embodiments, k is 0 and $R^1$ is H. In certain embodiments, the compounds have a general formula 4 or general formula 5

4

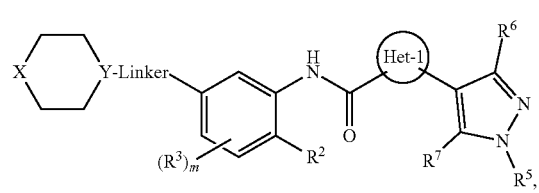

5

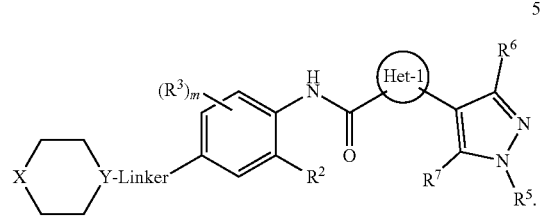

With respect to formulas 4 and 5, Het-1, X, Y, Linker, $R^2$, $R^3$, $R^5$, $R^6$, $R^7$ and m are as previously defined for formula 3.

In some embodiments of formula 4, m is 1 and $R^3$ is para to the amide, providing compounds having a general formula 6

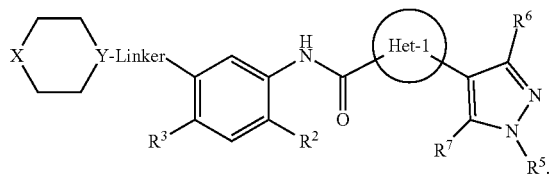

In some embodiments of formula 5, m is 1 and $R^3$ is para to $R^2$, providing compounds having a general formula 7

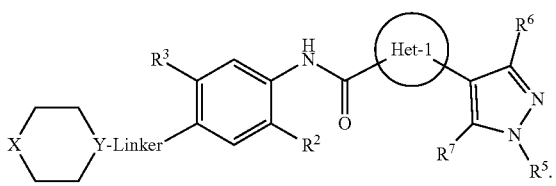

In some embodiments of formulas 1 or 2, A is N. In certain embodiments, the compounds have a general formula 8

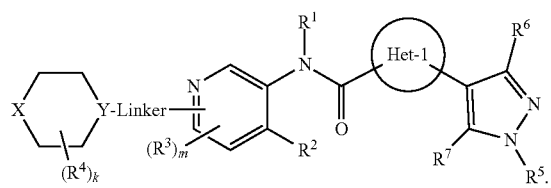

With respect to formula 8, Het-1, X, Y, Linker, $R^1$, $R^2$, $R^3$, $R^4$, $R^5$, $R^6$, $R^7$, k and m are as previously defined for formula 1. In some embodiments of formula 8, k=0. In other embodiments, $R^1$ is H. In some embodiments, k is 0 and $R^1$ is H.

In some embodiments of formula 8, the

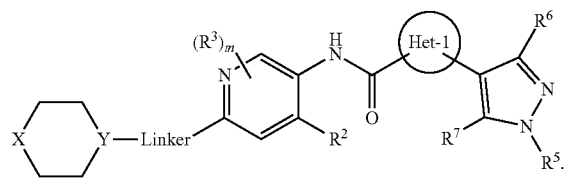

moiety is para to the amide. In certain embodiments, the compounds have a general formula 9

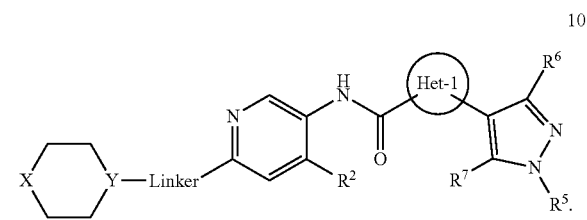

With respect to formula 9, Het-1, X, Y, Linker, $R^2$, $R^3$, $R^5$, $R^6$, $R^7$, and m are as previously defined for formula 8. In certain embodiments of formula 9, m is 0, providing compounds having a general formula 10

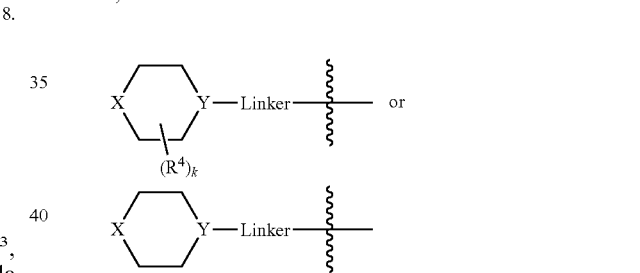

In certain embodiments of formulas 1, 2, 3, 4, 5, 8 or 9, m is 0.

In some embodiments of formulas 1, 2, 3, 4, 5, 8 or 9, m is 1. And in certain embodiments, $R^3$ is halo, preferably F.

In some embodiments of formulas 1, 2, 3, 4, 5, 6, 7, 8, 9 or 10, each of $R^5$, $R^6$ and $R^7$ independently is H or $C_{1-6}$ alkyl. In some embodiments, $R^5$ is H. In some embodiments, $R^6$ and/or $R^7$ is H. And in particular embodiments, each of $R^5$, $R^6$ and $R^7$ is H.

In some embodiments of formulas 1, 2, 3, 4, 5, 8 or 9, m is 0 and each of $R^5$, $R^6$ and $R^7$ is H. In other embodiments of formulas 1, 2, 3, 4, 5, 8 or 9, m is 1, $R^3$ is halo, preferably F, and each of $R^5$, $R^6$ and $R^7$ is H.

In any embodiments of formulas 1, 2, 3, 4, 5, 6, 7, 8, 9, or 10, the

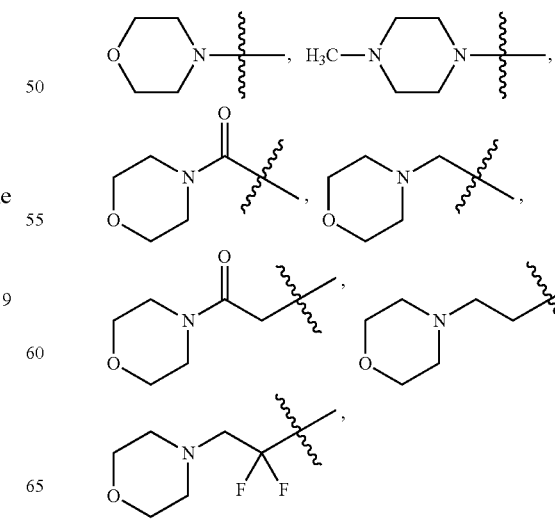

moiety may be

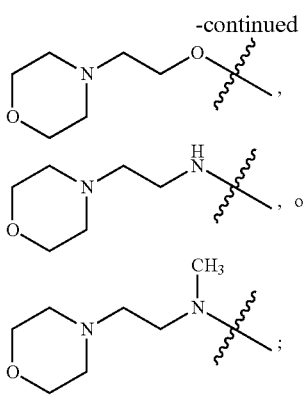
Het-1 is pyridinyl, furanyl or thiazolyl; R² is —OCH₃,
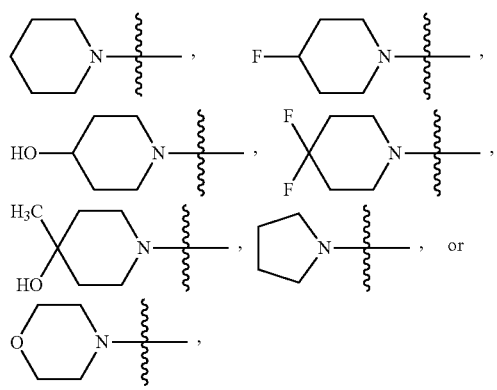
m is 0, or m is 1 and R³ is F; and each of R⁵, R⁶ and R⁷ is H.
In any embodiments of formulas 1, 2, 3, 4, 5, 6, 7, 8, 9, or 10, the
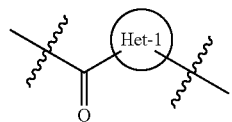
moiety may be
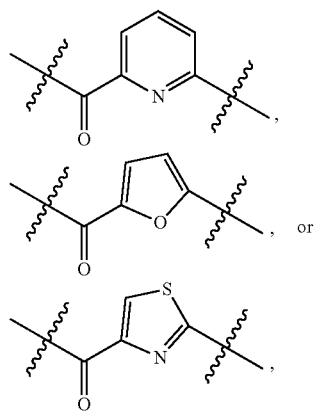
Certain disclosed exemplary compounds within the scope of one or more of the general formulas include:
I-1
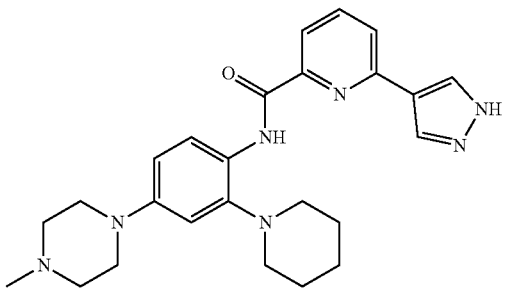
I-2
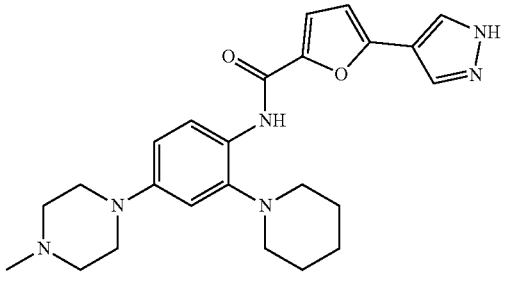
I-3
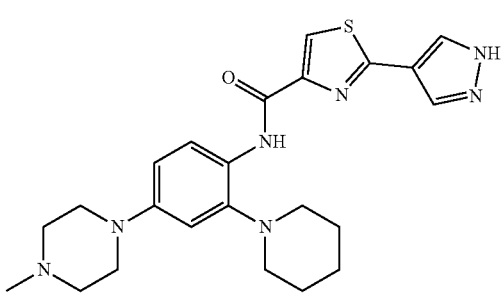
I-4
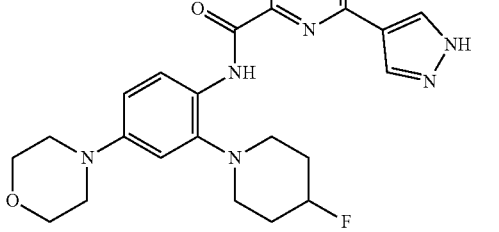
I-5
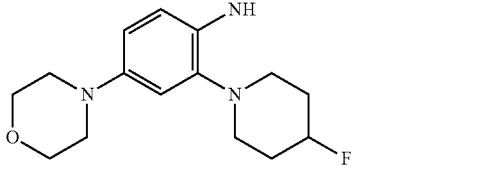

-continued
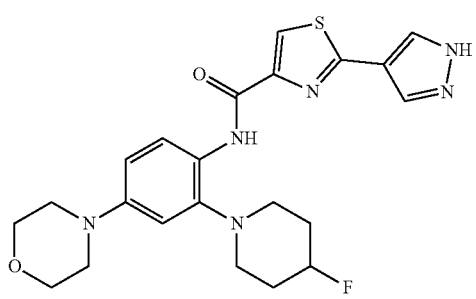
I-6
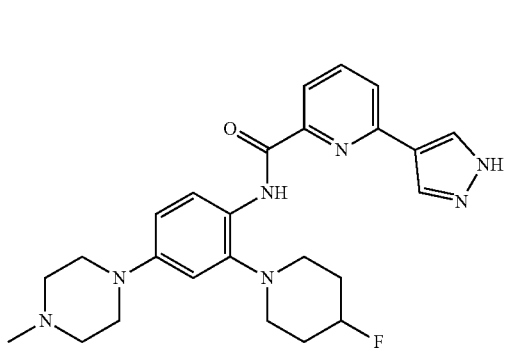
I-7
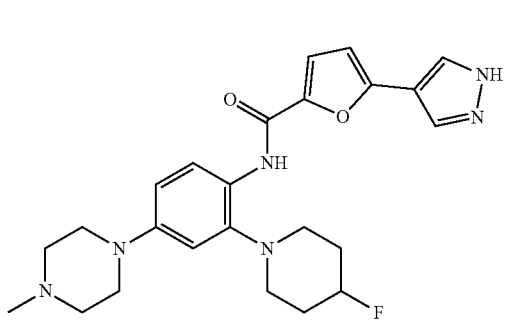
I-8
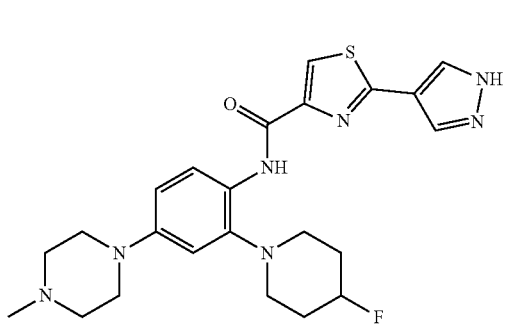
I-9
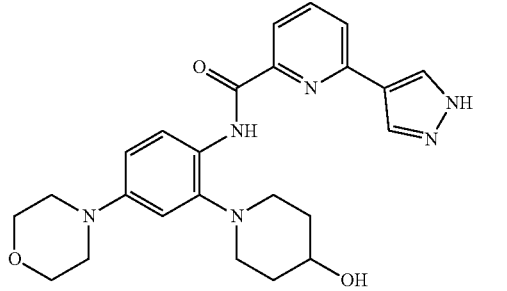
I-10
-continued
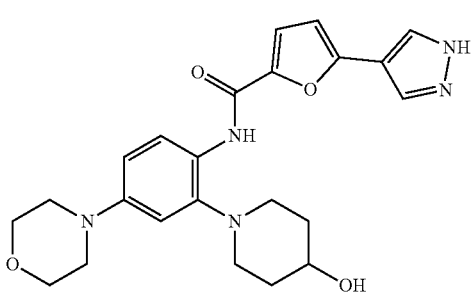
I-11
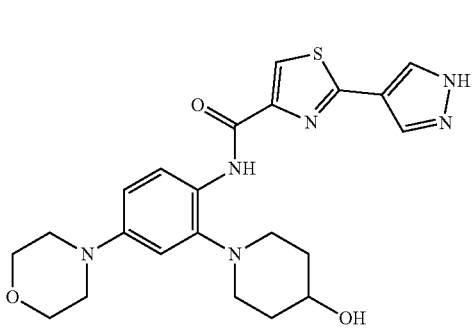
I-12
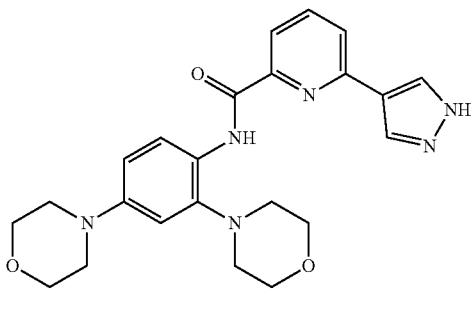
I-13
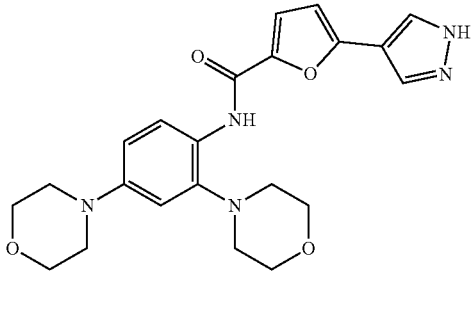
I-14
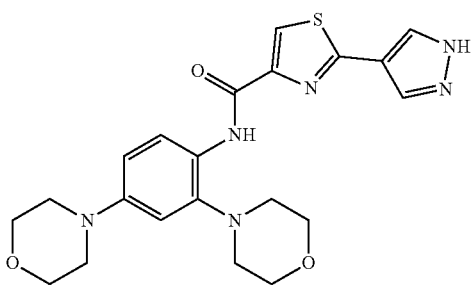
I-15

-continued
I-16
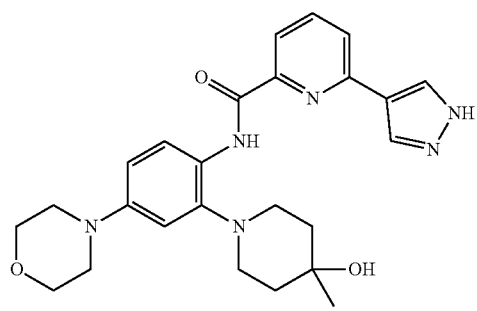
I-17
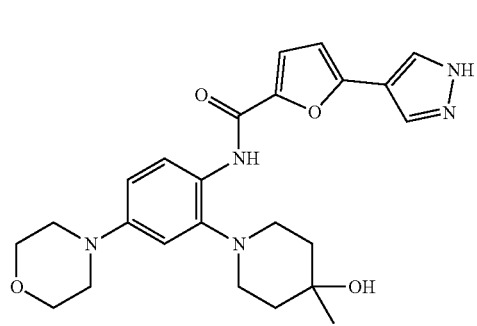
I-18
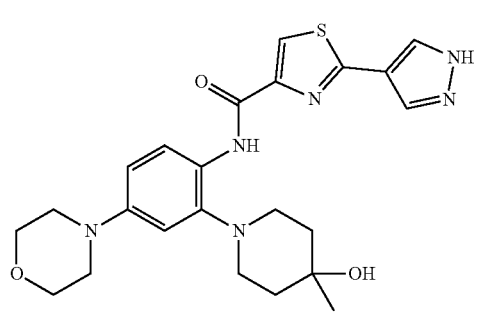
I-19
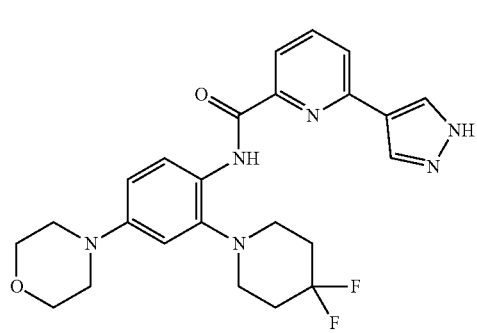
I-20
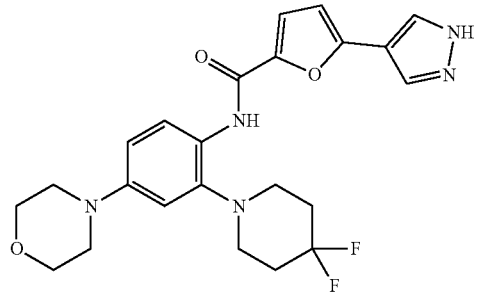
-continued
I-21
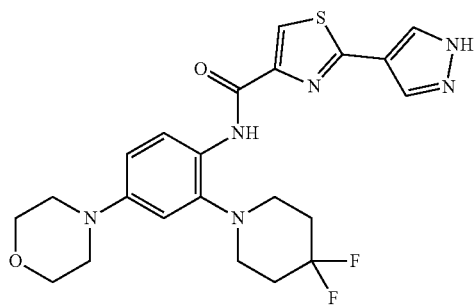
I-22
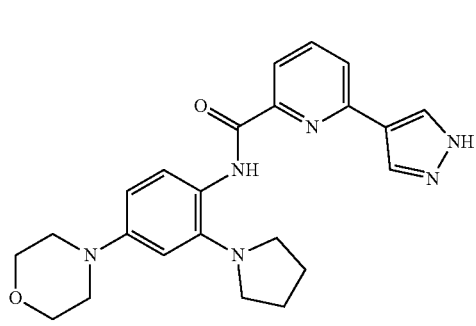
I-23
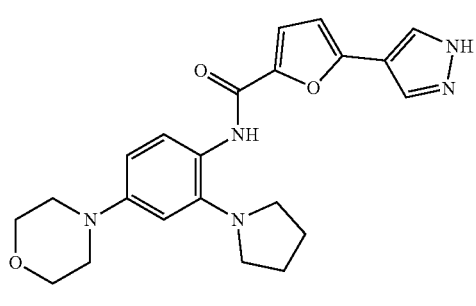
I-24
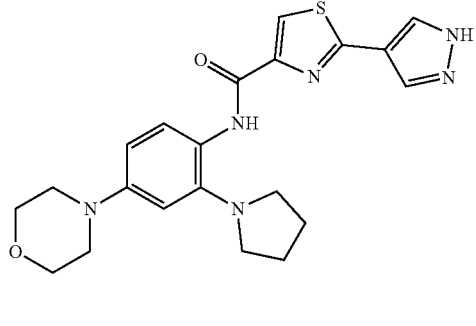
I-25
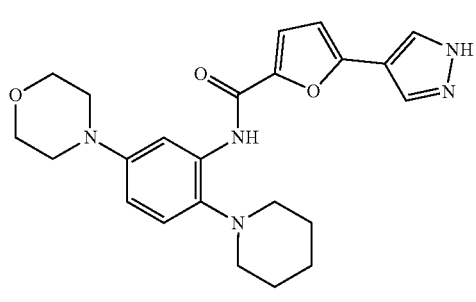

-continued
I-26
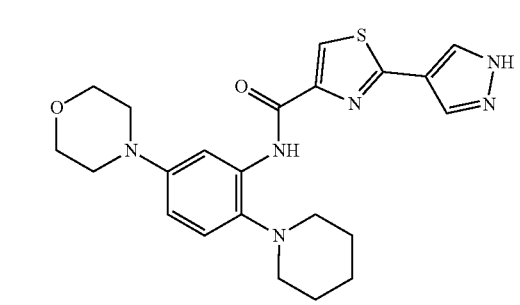
I-27
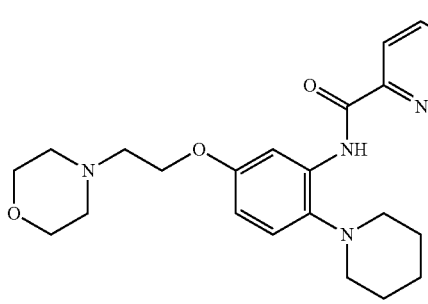
I-28
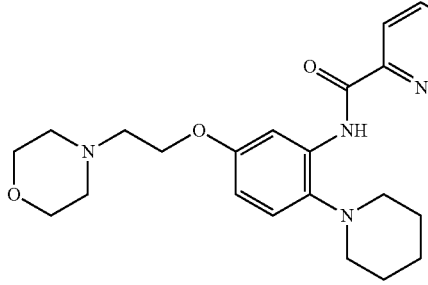
I-29
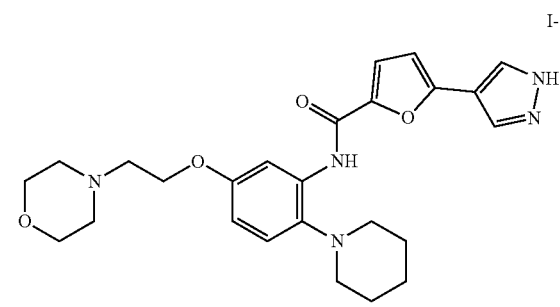
I-30
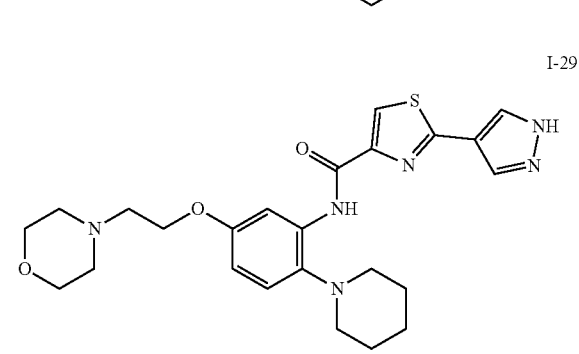
-continued
I-31
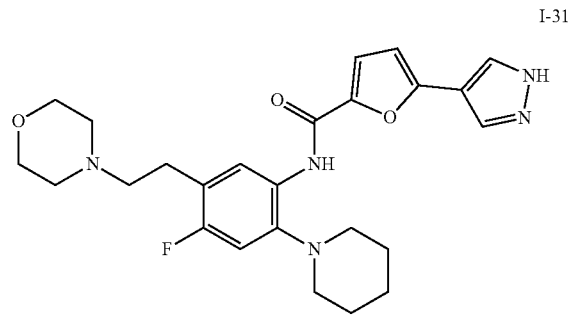
I-32
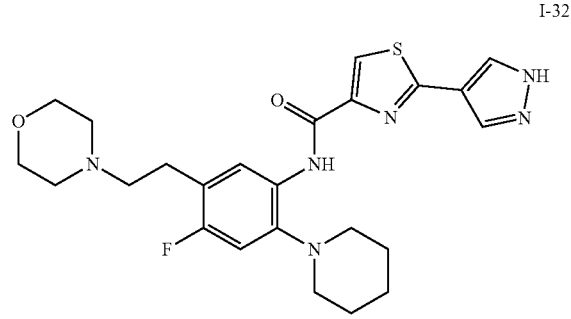
I-33
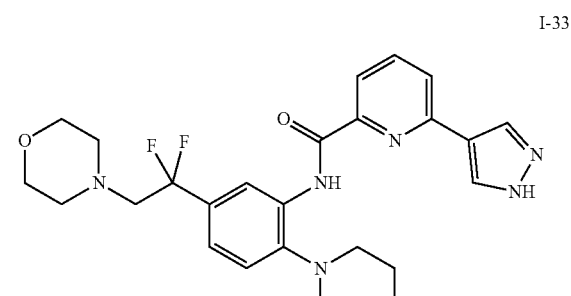
I-34
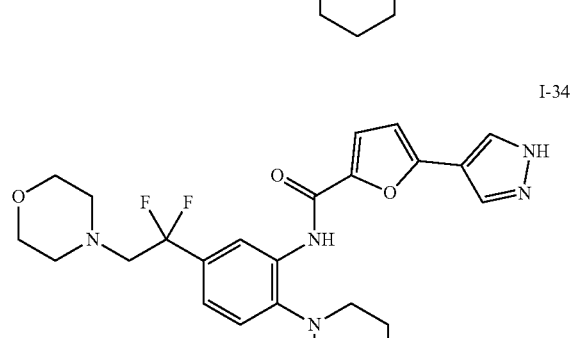
I-35
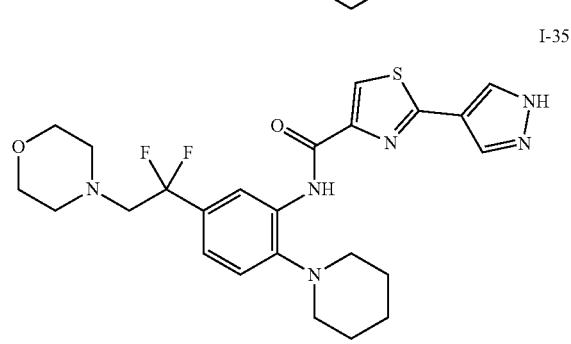

I-36
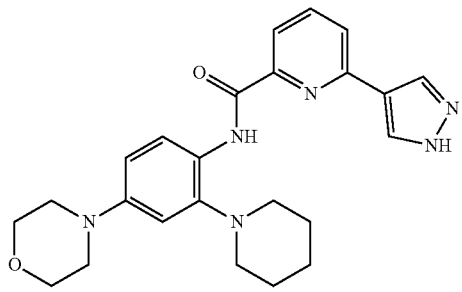
I-37
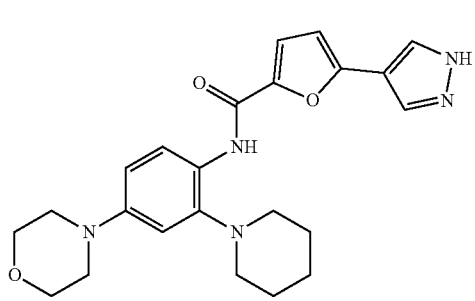
I-38
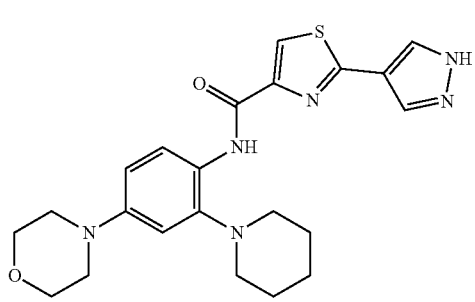
I-39
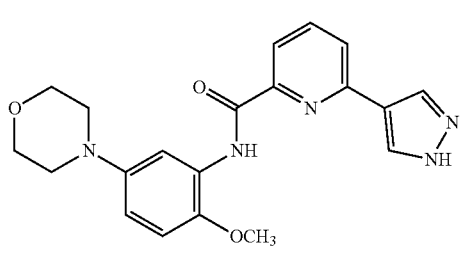
I-40
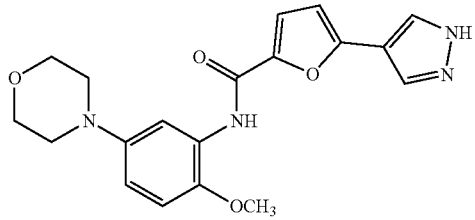
I-41
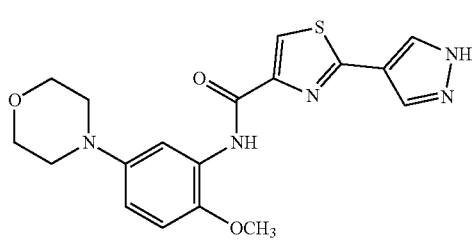
I-42
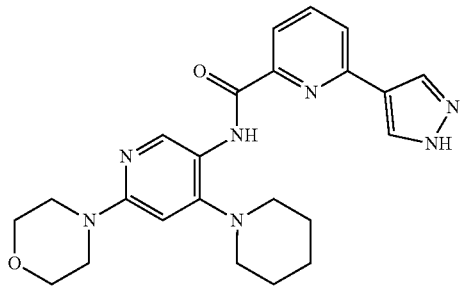
I-43
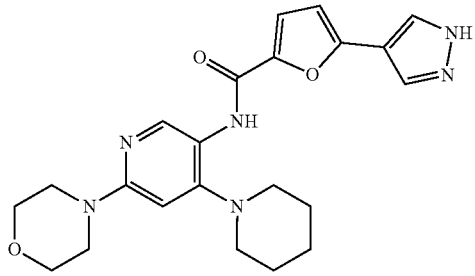
I-44
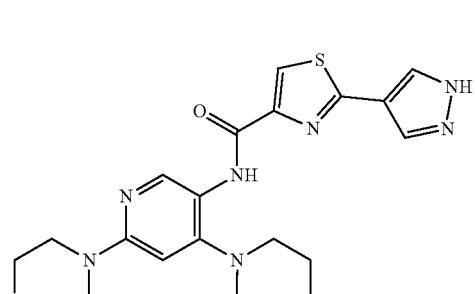
I-45
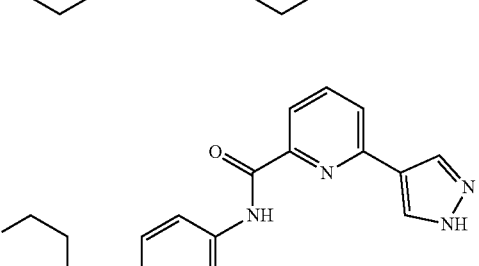
I-46
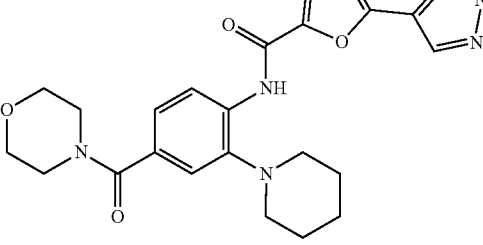

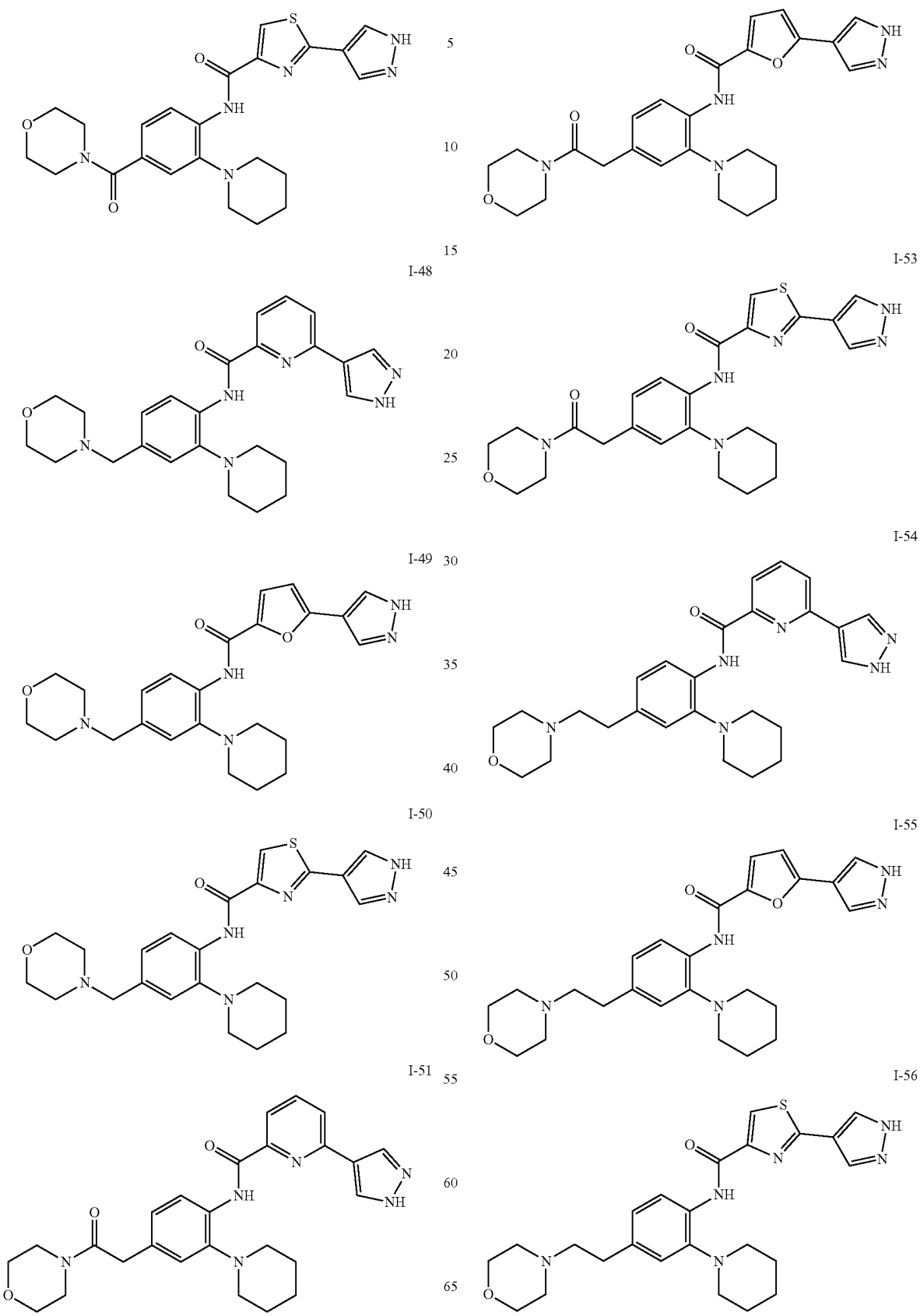

-continued
I-57
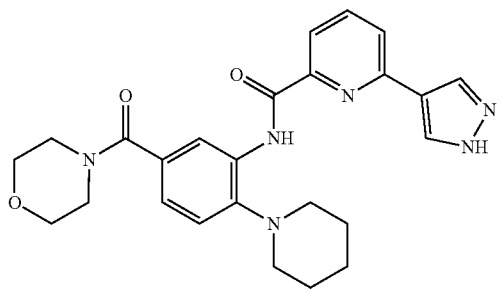
I-58
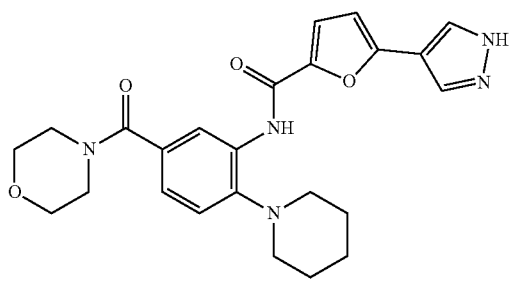
I-59
I-60
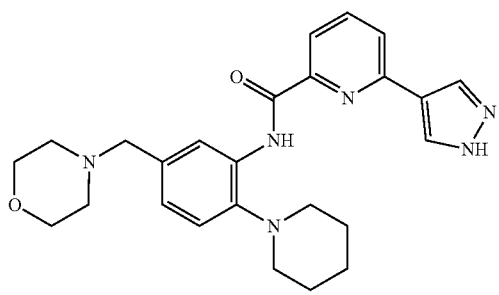
I-61
-continued
I-62
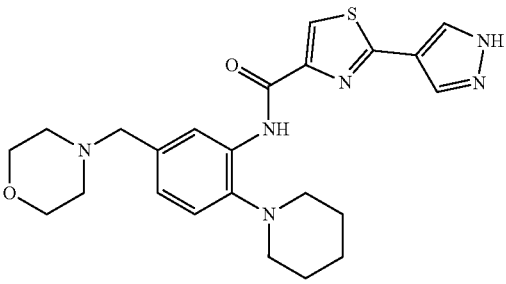
I-63
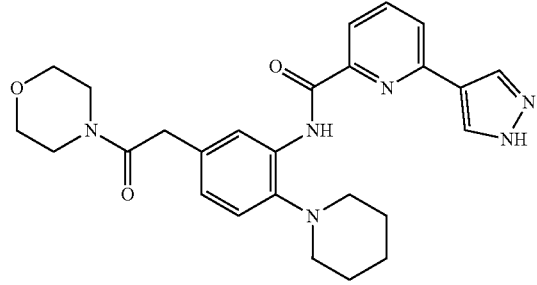
I-64
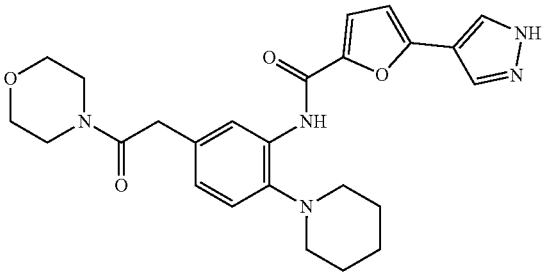
I-65
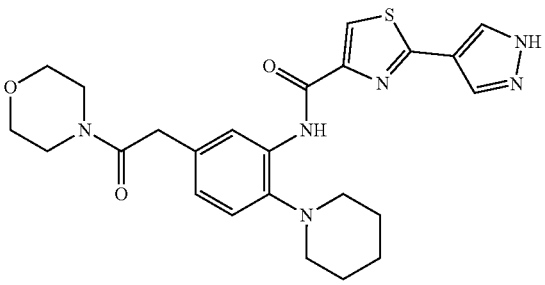
I-66
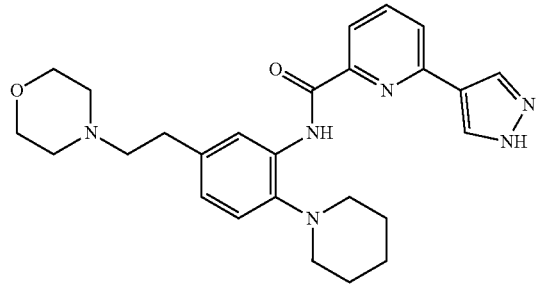

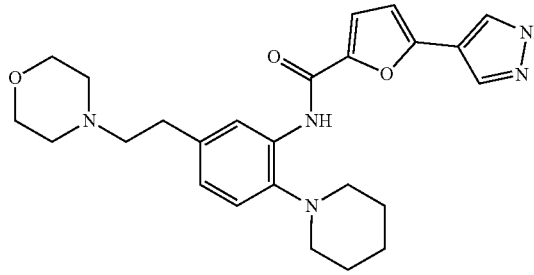

I-67

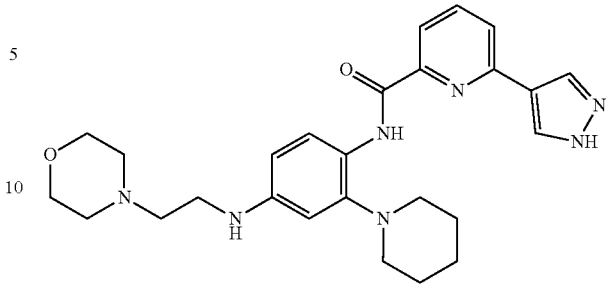

I-72

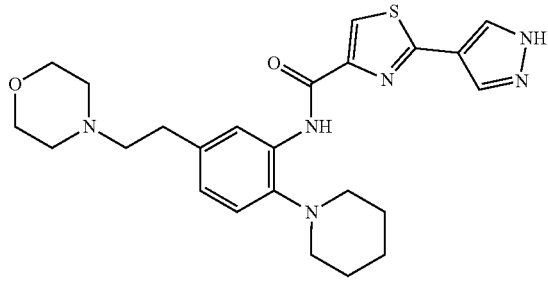

I-68

I-73

I-69

I-74

I-70

I-75

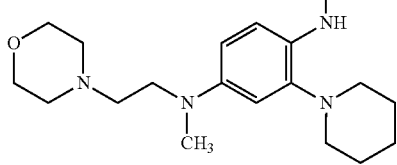

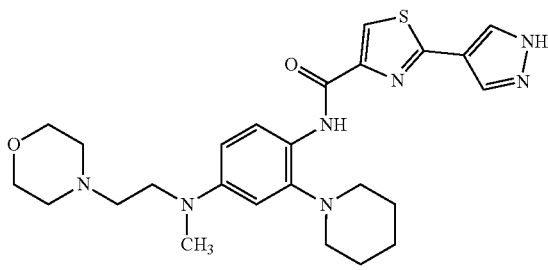

I-71

Exemplary disclosed compounds within the scope of one or more of the general formulas include:

I-1: N-(4-(4-methylpiperazin-1-yl)-2-(piperidin-1-yl)phenyl)-6-(1H-pyrazol-4-yl)picolinamide;

I-2: N-(4-(4-methylpiperazin-1-yl)-2-(piperidin-1-yl)phenyl)-5-(1H-pyrazol-4-yl)furan-2-carboxamide;

I-3: N-(4-(4-methylpiperazin-1-yl)-2-(piperidin-1-yl)phenyl)-2-(1H-pyrazol-4-yl)thiazole-4-carboxamide;

I-4: N-(2-(4-fluoropiperidin-1-yl)-4-morpholinophenyl)-6-(1H-pyrazol-4-yl)picolinamide;

I-5: N-(2-(4-fluoropiperidin-1-yl)-4-morpholinophenyl)-5-(1H-pyrazol-4-yl)furan-2-carboxamide;

I-6: N-(2-(4-fluoropiperidin-1-yl)-4-morpholinophenyl)-2-(1H-pyrazol-4-yl)thiazole-4-carboxamide;

I-7: N-(2-(4-fluoropiperidin-1-yl)-4-(4-methylpiperazin-1-yl)phenyl)-6-(1H-pyrazol-4-yl)picolinamide;

I-8: N-(2-(4-fluoropiperidin-1-yl)-4-(4-methylpiperazin-1-yl)phenyl)-5-(1H-pyrazol-4-yl)furan-2-carboxamide;

I-9: N-(2-(4-fluoropiperidin-1-yl)-4-(4-methylpiperazin-1-yl)phenyl)-2-(1H-pyrazol-4-yl)thiazole-4-carboxamide;

I-10: N-(2-(4-hydroxypiperidin-1-yl)-4-morpholinophenyl)-6-(1H-pyrazol-4-yl)picolinamide;

I-11: N-(2-(4-hydroxypiperidin-1-yl)-4-morpholinophenyl)-5-(1H-pyrazol-4-yl)furan-2-carboxamide;

I-12: N-(2-(4-hydroxypiperidin-1-yl)-4-morpholinophenyl)-2-(1H-pyrazol-4-yl)thiazole-4-carboxamide;

I-13: N-(2,4-dimorpholinophenyl)-6-(1H-pyrazol-4-yl)picolinamide;

I-14: N-(2,4-dimorpholinophenyl)-5-(1H-pyrazol-4-yl)furan-2-carboxamide;

I-15: N-(2,4-dimorpholinophenyl)-2-(1H-pyrazol-4-yl)thiazole-4-carboxamide;

I-16: N-(2-(4-hydroxy-4-methylpiperidin-1-yl)-4-morpholinophenyl)-6-(1H-pyrazol-4-yl)picolinamide;

I-17: N-(2-(4-hydroxy-4-methylpiperidin-1-yl)-4-morpholinophenyl)-5-(1H-pyrazol-4-yl)furan-2-carboxamide;

I-18: N-(2-(4-hydroxy-4-methylpiperidin-1-yl)-4-morpholinophenyl)-2-(1H-pyrazol-4-yl)thiazole-4-carboxamide;

I-19: N-(2-(4,4-difluoropiperidin-1-yl)-4-morpholinophenyl)-6-(1H-pyrazol-4-yl)picolinamide;

I-20: N-(2-(4,4-difluoropiperidin-1-yl)-4-morpholinophenyl)-5-(1H-pyrazol-4-yl)furan-2-carboxamide;

I-21: N-(2-(4,4-difluoropiperidin-1-yl)-4-morpholinophenyl)-2-(1H-pyrazol-4-yl)thiazole-4-carboxamide;

I-22: N-(4-morpholino-2-(pyrrolidin-1-yl)phenyl)-6-(1H-pyrazol-4-yl)picolinamide;

I-23: N-(4-morpholino-2-(pyrrolidin-1-yl)phenyl)-5-(1H-pyrazol-4-yl)furan-2-carboxamide;

I-24: N-(4-morpholino-2-(pyrrolidin-1-yl)phenyl)-2-(1H-pyrazol-4-yl)thiazole-4-carboxamide;

I-25: N-(5-morpholino-2-(piperidin-1-yl)phenyl)-5-(1H-pyrazol-4-yl)furan-2-carboxamide;

I-26: N-(5-morpholino-2-(piperidin-1-yl)phenyl)-2-(1H-pyrazol-4-yl)thiazole-4-carboxamide;

I-27: N-(5-(2-morpholinoethoxy)-2-(piperidin-1-yl)phenyl)-6-(1H-pyrazol-4-yl)picolinamide;

I-28: N-(5-(2-morpholinoethoxy)-2-(piperidin-1-yl)phenyl)-5-(1H-pyrazol-4-yl)furan-2-carboxamide;

I-29: N-(5-(2-morpholinoethoxy)-2-(piperidin-1-yl)phenyl)-2-(1H-pyrazol-4-yl)thiazole-4-carboxamide;

I-30: N-(4-fluoro-5-(2-morpholinoethyl)-2-(piperidin-1-yl)phenyl)-6-(1H-pyrazol-4-yl)picolinamide;

I-31: N-(4-fluoro-5-(2-morpholinoethyl)-2-(piperidin-1-yl)phenyl)-5-(1H-pyrazol-4-yl)furan-2-carboxamide;

I-32: N-(4-fluoro-5-(2-morpholinoethyl)-2-(piperidin-1-yl)phenyl)-2-(1H-pyrazol-4-yl)thiazole-4-carboxamide;

I-33: N-(5-(1,1-difluoro-2-morpholinoethyl)-2-(piperidin-1-yl)phenyl)-6-(1H-pyrazol-4-yl)picolinamide;

I-34: N-(5-(1,1-difluoro-2-morpholinoethyl)-2-(piperidin-1-yl)phenyl)-5-(1H-pyrazol-4-yl)furan-2-carboxamide;

I-35: N-(5-(1,1-difluoro-2-morpholinoethyl)-2-(piperidin-1-yl)phenyl)-2-(1H-pyrazol-4-yl)thiazole-4-carboxamide;

I-36: N-(4-morpholino-2-(piperidin-1-yl)phenyl)-6-(1H-pyrazol-4-yl)picolinamide;

I-37: N-(4-morpholino-2-(piperidin-1-yl)phenyl)-5-(1H-pyrazol-4-yl)furan-2-carboxamide;

I-38: N-(4-morpholino-2-(piperidin-1-yl)phenyl)-2-(1H-pyrazol-4-yl)thiazole-4-carboxamide;

I-39: N-(2-methoxy-5-morpholinophenyl)-6-(1H-pyrazol-4-yl)picolinamide;

I-40: N-(2-methoxy-5-morpholinophenyl)-5-(1H-pyrazol-4-yl)furan-2-carboxamide;

I-41: N-(2-methoxy-5-morpholinophenyl)-2-(1H-pyrazol-4-yl)thiazole-4-carboxamide;

I-42: N-(6-morpholino-4-(piperidin-1-yl)pyridin-3-yl)-6-(1H-pyrazol-4-yl)picolinamide;

I-43: N-(6-morpholino-4-(piperidin-1-yl)pyridin-3-yl)-5-(1H-pyrazol-4-yl)furan-2-carboxamide;

I-44: N-(6-morpholino-4-(piperidin-1-yl)pyridin-3-yl)-2-(1H-pyrazol-4-yl)thiazole-4-carboxamide;

I-45: N-(4-(morpholine-4-carbonyl)-2-(piperidin-1-yl)phenyl)-6-(1H-pyrazol-4-yl)picolinamide;

I-46: N-(4-(morpholine-4-carbonyl)-2-(piperidin-1-yl)phenyl)-5-(1H-pyrazol-4-yl)furan-2-carboxamide;

I-47: N-(4-(morpholine-4-carbonyl)-2-(piperidin-1-yl)phenyl)-2-(1H-pyrazol-4-yl)thiazole-4-carboxamide;

I-48: N-(4-(morpholinomethyl)-2-(piperidin-1-yl)phenyl)-6-(1H-pyrazol-4-yl)picolinamide;

I-49: N-(4-(morpholinomethyl)-2-(piperidin-1-yl)phenyl)-5-(1H-pyrazol-4-yl)furan-2-carboxamide;

I-50: N-(4-(morpholinomethyl)-2-(piperidin-1-yl)phenyl)-2-(1H-pyrazol-4-yl)thiazole-4-carboxamide;

I-51: N-(4-(2-morpholino-2-oxoethyl)-2-(piperidin-1-yl)phenyl)-6-(1H-pyrazol-4-yl)picolinamide;

I-52: N-(4-(2-morpholino-2-oxoethyl)-2-(piperidin-1-yl)phenyl)-5-(1H-pyrazol-4-yl)furan-2-carboxamide;

I-53: N-(4-(2-morpholino-2-oxoethyl)-2-(piperidin-1-yl)phenyl)-2-(1H-pyrazol-4-yl)thiazole-4-carboxamide;

I-54: N-(4-(2-morpholinoethyl)-2-(piperidin-1-yl)phenyl)-6-(1H-pyrazol-4-yl)picolinamide;

I-55: N-(4-(2-morpholinoethyl)-2-(piperidin-1-yl)phenyl)-5-(1H-pyrazol-4-yl)furan-2-carboxamide;

I-56: N-(4-(2-morpholinoethyl)-2-(piperidin-1-yl)phenyl)-2-(1H-pyrazol-4-yl)thiazole-4-carboxamide;

I-57: N-(5-(morpholine-4-carbonyl)-2-(piperidin-1-yl)phenyl)-6-(1H-pyrazol-4-yl)picolinamide;

I-58: N-(5-(morpholine-4-carbonyl)-2-(piperidin-1-yl)phenyl)-5-(1H-pyrazol-4-yl)furan-2-carboxamide;

I-59: N-(5-(morpholine-4-carbonyl)-2-(piperidin-1-yl)phenyl)-2-(1H-pyrazol-4-yl)thiazole-4-carboxamide;

I-60: N-(5-(morpholinomethyl)-2-(piperidin-1-yl)phenyl)-6-(1H-pyrazol-4-yl)picolinamide;

I-61: N-(5-(morpholinomethyl)-2-(piperidin-1-yl)phenyl)-5-(1H-pyrazol-4-yl)furan-2-carboxamide;

I-62: N-(5-(morpholinomethyl)-2-(piperidin-1-yl)phenyl)-2-(1H-pyrazol-4-yl)thiazole-4-carboxamide;

I-63: N-(5-(2-morpholino-2-oxoethyl)-2-(piperidin-1-yl)phenyl)-6-(1H-pyrazol-4-yl)picolinamide;

I-64: N-(5-(2-morpholino-2-oxoethyl)-2-(piperidin-1-yl)phenyl)-5-(1H-pyrazol-4-yl)furan-2-carboxamide;

I-65: N-(5-(2-morpholino-2-oxoethyl)-2-(piperidin-1-yl)phenyl)-2-(1H-pyrazol-4-yl)thiazole-4-carboxamide;

I-66: N-(5-(2-morpholinoethyl)-2-(piperidin-1-yl)phenyl)-6-(1H-pyrazol-4-yl)picolinamide;

I-67: N-(5-(2-morpholinoethyl)-2-(piperidin-1-yl)phenyl)-5-(1H-pyrazol-4-yl)furan-2-carboxamide;

I-68: N-(5-(2-morpholinoethyl)-2-(piperidin-1-yl)phenyl)-2-(1H-pyrazol-4-yl)thiazole-4-carboxamide;

I-69: N-(4-(methyl(2-morpholinoethyl)amino)-2-(piperidin-1-yl)phenyl)-6-(1H-pyrazol-4-yl)picolinamide;

I-70: N-(4-(methyl(2-morpholinoethyl)amino)-2-(piperidin-1-yl)phenyl)-5-(1H-pyrazol-4-yl)furan-2-carboxamide;

I-71: N-(4-(methyl(2-morpholinoethyl)amino)-2-(piperidin-1-yl)phenyl)-2-(1H-pyrazol-4-yl)thiazole-4-carboxamide;

I-72: N-(4-((2-morpholinoethyl)amino)-2-(piperidin-1-yl)phenyl)-6-(1H-pyrazol-4-yl)picolinamide;

I-73: N-(4-((2-morpholinoethyl)amino)-2-(piperidin-1-yl)phenyl)-5-(1H-pyrazol-4-yl)furan-2-carboxamide;

I-74: N-(4-((2-morpholinoethyl)amino)-2-(piperidin-1-yl)phenyl)-2-(1H-pyrazol-4-yl)thiazole-4-carboxamide; or
I-75: N-(5-morpholino-2-(piperidin-1-yl)phenyl)-6-(1H-pyrazol-4-yl)picolinamide.

B. Synthesis

Disclosed compounds can be prepared as exemplified below, as illustrated for specific compounds in the examples, and as will be understood by a person of ordinary skill in the art of organic synthesis. An exemplary synthesis may include the following first reaction step according to Scheme 1.

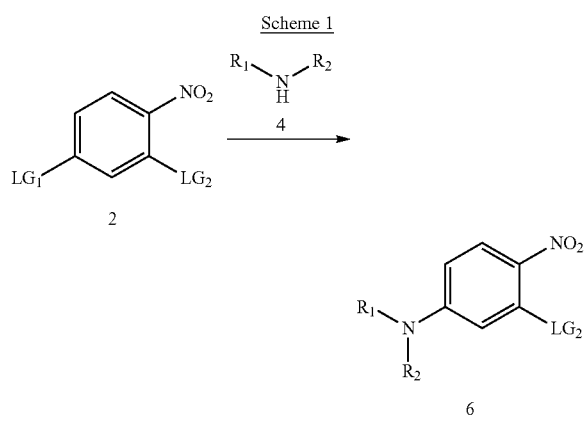

Nitro compound 2 is reacted with amine 4 at a suitable reaction temperature, such as from about 0° C. or less to about 30° C., and in the presence of a suitable base, to form compound 6. $LG_1$ and $LG_2$ are leaving groups selected such that amine 4 displaces with $LG_1$ preferentially in the presence of $LG_2$. In some examples, $LG_1$ is F, and $LG_2$ is Cl. The reaction is performed in a solvent suitable to facilitate the reaction. Suitable solvents include aprotic solvents, including, but not limited to, dioxane or acetonitrile. The reaction may be performed in the presence of a base, such as sodium hydrogen carbonate, potassium carbonate, sodium carbonate, cesium carbonate, triethylamine or diisopropylethylamine (DIEA).

A second reaction step in the exemplary synthesis is provided below according to Scheme 2.

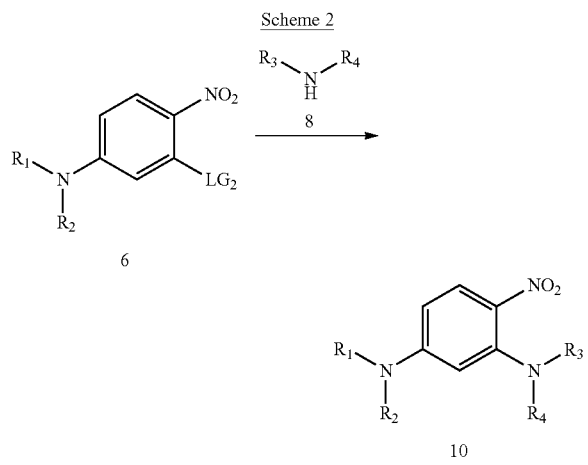

Compound 6 is reacted with amine 8 to form compound 10. The reaction may proceed at a suitable reaction temperature, such as from about 50° C. or less to about 120° C. or more, and in the presence of a suitable base, such as sodium hydrogen carbonate, potassium carbonate, sodium carbonate, cesium carbonate, triethylamine or diisopropylethylamine (DIEA). Alternatively, excess amine may be used as the base, such as by using two or more molar equivalents of amine 8 in the reaction. The reaction is typically performed in a solvent suitable to facilitate the reaction, such as aprotic solvents, including, but not limited to, dioxane or acetonitrile.

Alternatively, compound 6 and amine 8 may be reacted together in the presence of a palladium catalyst, an organophosphate compound, such as S-phos (2-dicyclohexylphosphino-2',6'-dimethoxybiphenyl) or XPhos (2-dicyclohexylphosphino-2',4',6'-triisopropylbiphenyl), and a base, to form compound 10. The palladium catalyst may be any suitable catalyst that facilitates the reaction, such as $Pd(OAc)_2$ or $Pd_2(dba)_3$. And the base may be any base suitable to facilitate the reaction, such as sodium hydrogen carbonate, potassium carbonate, sodium carbonate, sodium tert-butoxide, or potassium tert-butoxide. The reaction is performed in a solvent suitable to facilitate the reaction. Suitable solvents include aprotic solvents, such as dioxane or acetonitrile. The reaction is performed at a temperature suitable to facilitate the reaction proceeding to completion, such as from about 50° C. to about 120° C. or more.

A third reaction step in the exemplary synthesis is provided below according to Scheme 3.

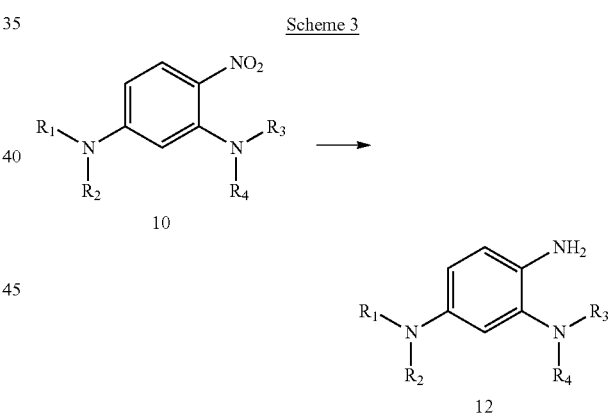

The nitro-functional group on compound 10 is reduced to form compound 12. Any suitable reducing agent can be used, such as $H_2$/palladium on carbon, $H_2$/platinum (IV) oxide, $H_2$/Raney nickel, Fe/HCl, Fe/acetic acid, zinc/acid, zinc/ammonium chloride, or tin chloride. The reaction is performed in a suitable solvent. Suitable solvents include, without limitation, an alcohol, including methanol, ethanol, propanol, or isopropanol; an organic acid, such as acetic acid or an ester thereof, such as ethyl acetate; water; or a combination thereof. A person of ordinary skill in the art will appreciate that compound 12 may form as a free base or a salt, such as an HCl salt or acetic acid salt, depending on the method used to reduce the nitro group.

A fourth step in the exemplary synthesis is provided below according to Scheme 4.

Scheme 4

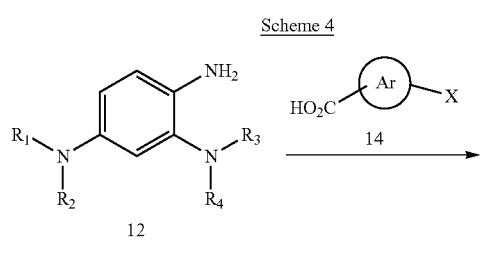

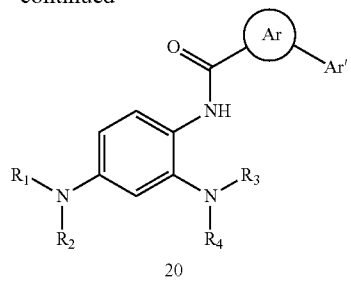

Compound 12 is reacted with carboxylic acid 14 to form compound 16. The carboxylic acid 14 is activated by any suitable method and then reacted with the amine on compound 12. Suitable activation methods include, but are not limited to: forming the acid chloride by treatment with thionyl chloride; by treatment with 1-[Bis(dimethylamino)methylene]-1H-1,2,3-triazolo[4,5-b]pyridinium 3-oxid hexafluorophosphate (HATU) and a base such as diisopropylethylamine (DIEA) or N-ethyl-N-isopropylpropan-2-amine; by treatment with carbonyldiimidazole (CDI); or by treatment with a carbodiimide, such as dicyclohexylcarbodiimide (DCC) or 1-Ethyl-3-(3-dimethylaminopropyl)carbodiimide (EDC). The reaction is performed in a solvent suitable to facilitate the reaction. Suitable solvents include, but are not limited to, halogenated alkyl solvents, such as chloroform and dichloromethane; ethers, such as dioxane; toluene; acetonitrile; DMF; tetrahydrofuran; or a combination thereof.

A fifth step in the exemplary synthesis is provided below according to Scheme 5.

Scheme 5

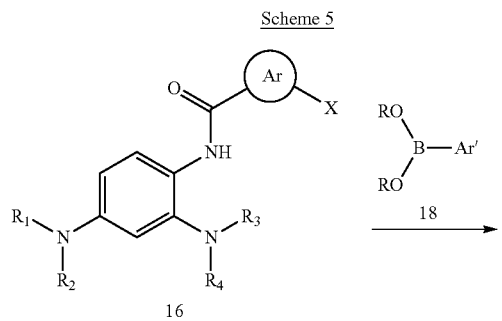

Compound 16 is coupled with compound 18 to form compound 20 using any coupling reaction suitable to form a bond between two rings. In the example above, a boronic acid coupling is shown, where the leaving group X on compound 16 is halo, such as bromo or iodo. Other suitable coupling functional groups include trialkyl tin or boronic esters, such as a boronic acid pinacol ester. The coupling reaction typically proceeds in the presence of a suitable catalyst. For a boronic acid coupling, the catalyst typically is a palladium catalyst, such as $PdCl_2(dppf)_2$, palladium acetate and triphenyl phosphine, or tetrakis(triphenylphosphine)palladium(0). The reaction is performed in the presence of a base, such as metal carbonates, including sodium, potassium or cesium carbonate, and is performed in a suitable solvent or solvent mixture. Suitable solvents include, without limitation, ethers, such as dioxane or dimethoxyethane (DME); ether/water combinations, such as dioxane/water; or ether/alcohol/water combinations, such as DME/ethanol/water. The reaction may be heated at a suitable temperature, such as from 50° C. to 180° C., typically about 150° C., and/or agitated for a suitable period of time, such as from 1 hour to 3 days, from 6 hours to 24 hours, or from 12 hours to 18 hours, to facilitate the reaction proceeding to completion. The reaction may be performed in a microwave, which typically reduces the reaction time. Compound 20 is then isolated from the reaction mixture and purified by a suitable technique.

A second exemplary synthesis proceeds with a first reaction step according to Scheme 6.

Scheme 6

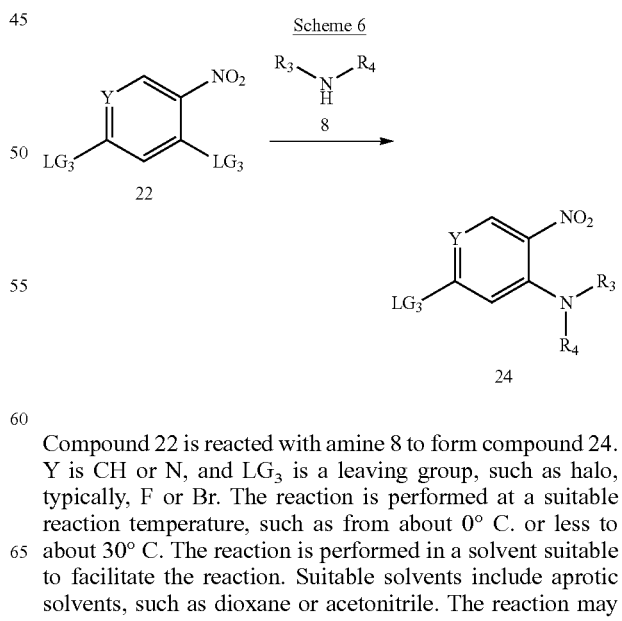

Compound 22 is reacted with amine 8 to form compound 24. Y is CH or N, and $LG_3$ is a leaving group, such as halo, typically, F or Br. The reaction is performed at a suitable reaction temperature, such as from about 0° C. or less to about 30° C. The reaction is performed in a solvent suitable to facilitate the reaction. Suitable solvents include aprotic solvents, such as dioxane or acetonitrile. The reaction may be performed in the presence of a suitable base, such as sodium hydrogen carbonate, potassium carbonate, sodium carbonate, triethylamine or diisopropylethylamine (DIEA).

A second reaction step in the alternative exemplary synthesis is provided below according to Scheme 7.

Scheme 7

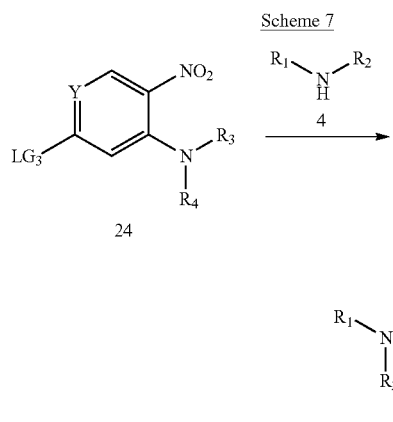

24

26

Compound 24 is reacted with amine 4 to form compound 26. The reaction may proceed at a suitable reaction temperature, such as from about 50° C. or less to about 120° C. or more, and in the presence of a suitable base, such as sodium hydrogen carbonate, potassium carbonate, sodium carbonate, cesium carbonate, triethylamine or diisopropylethylamine (DIEA). Alternatively, excess amine may be used as the base, such as by using two or more molar equivalents of amine 4 in the reaction. The reaction is typically performed in a solvent suitable to facilitate the reaction, such as aprotic solvents, including, but not limited to, ethers, such as dioxane; or aprotic solvents, such as acetonitrile. Compound 26 can then be used in place of compound 10 in Schemes 3-5.

A third exemplary synthesis proceeds with a first reaction step according to Scheme 8.

Scheme 8

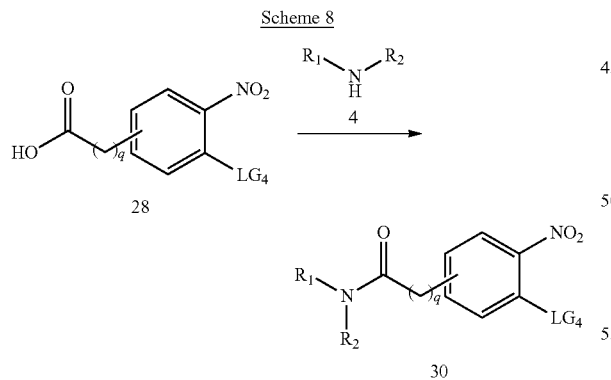

28

30

Compound 28 is reacted with amine 4 to form compound 30. q is 0 or an integer greater than zero, such as 1, 2, 3, 4 or more, typically 0 or 1. The carboxylic acid moiety on compound 28 may be activated by any suitable method. Suitable activation methods include, but are not limited to: forming the acid chloride, such as by treatment with thionyl chloride; treatment with 1-[Bis(dimethylamino)methylene]-1H-1,2,3-triazolo[4,5-b]pyridinium 3-oxid hexafluorophosphate (HATU) and a base such as diisopropylethylamine (DIPEA) or sodium hydrogen carbonate; treatment with carbonyldiimidazole (CDI); or treatment with a carbodiimide, such as dicyclohexylcarbodiimide (DCC) or 1-ethyl-3-(3-dimethylaminopropyl)carbodiimide (EDC). The reaction with amine 4 may be performed in the presence of an additional base, such as sodium, potassium or cesium carbonate, sodium hydrogen carbonate, triethylamine, diisopropylethylamine (DIEA), or excess amine 4.

A second reaction step in the third exemplary synthesis is provided below according to Scheme 9.

Scheme 9

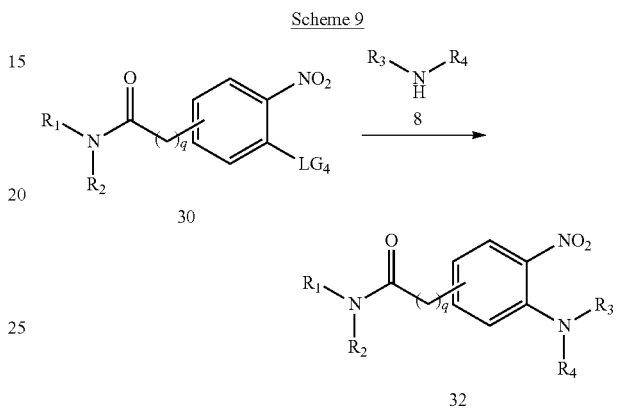

30

32

Compound 30 is reacted with amine 8 to form compound 32. The reaction may proceed at a suitable reaction temperature, such as from about 50° C. or less to about 120° C. or more, and in the presence of a suitable base, such as sodium hydrogen carbonate, potassium carbonate, sodium carbonate, cesium carbonate, triethylamine or diisopropylethylamine (DIEA). Alternatively, excess amine may be used as the base, such as by using two or more molar equivalents of amine 8 in the reaction. The reaction is typically performed in a solvent suitable to facilitate the reaction, such as aprotic solvents, including, but not limited to, ethers, such as dioxane, or nitriles, such as acetonitrile.

Subsequent steps in the third exemplary synthesis are provided below according to Scheme 10.

Scheme 10

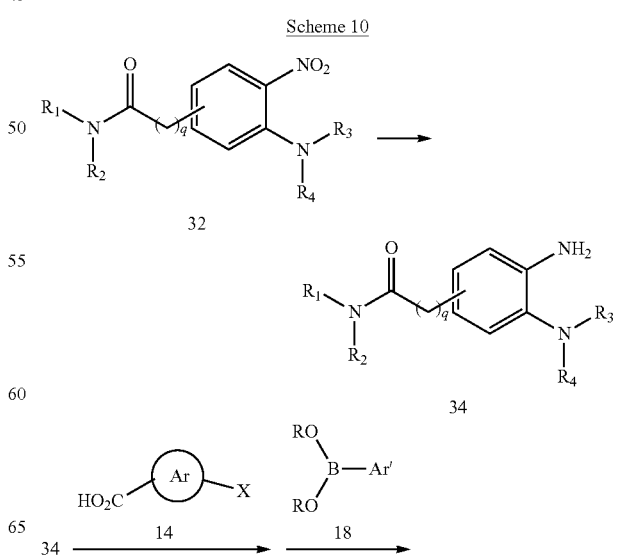

32

34

34   14   18

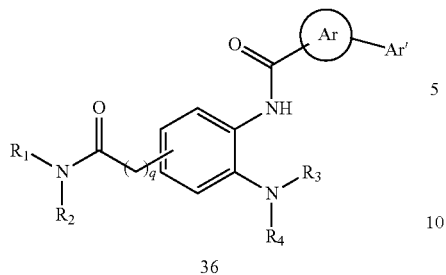

36

The nitro moiety on compound 32 is reduced to form compound 34 according to the method previously described with respect to Scheme 3. And compound 34 is reacted with compound 14 and then compound 18 to form compound 36 according to the methods previously described with respect to Schemes 4 and 5.

Alternatively, the amide moiety in compound 32 is reacted with a suitable reducing agent to form compound 38 according to Scheme 11.

Scheme 11

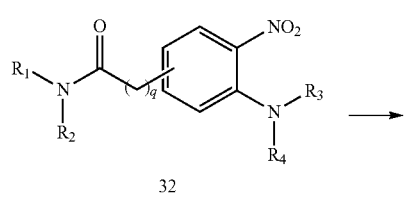

Suitable reducing agents include, but are not limited to borane, or borane-reagents, such as $B_2H_6$-THF solution. The reaction is performed at a temperature suitable to facilitate the reaction, such as from 0° C. to 100° C., from 20° C. to 80° C. or from 30° C. to 60° C., and for a time period suitable to facilitate the reaction substantially proceeding to completion. The time period may be from 8 hours or less to 24 hours or more, such as from 12 hours to 20 hours. After the reaction is quenched, such as by quenching with water, aqueous acid or aqueous base, compound 38 is isolated.

Subsequent reaction steps in the alternative synthesis are provided according to Scheme 12.

Scheme 12

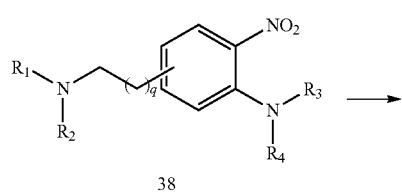

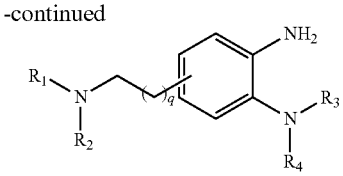

40

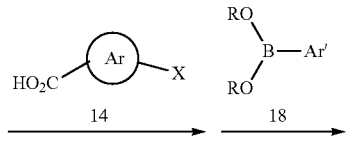

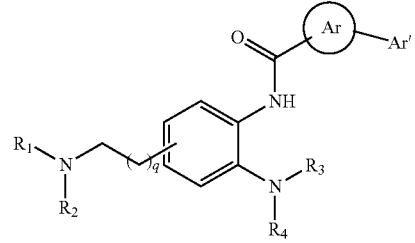

42

The nitro moiety on compound 38 is reduced to form compound 40 according to the method previously described with respect to Scheme 3. And compound 40 is reacted with compound 14 and then compound 18 to form compound 42 according to the methods previously described with respect to Schemes 4 and 5.

In alternative embodiments, when q is 1, compound 32 may be further reacted according to Scheme 13.

Scheme 13

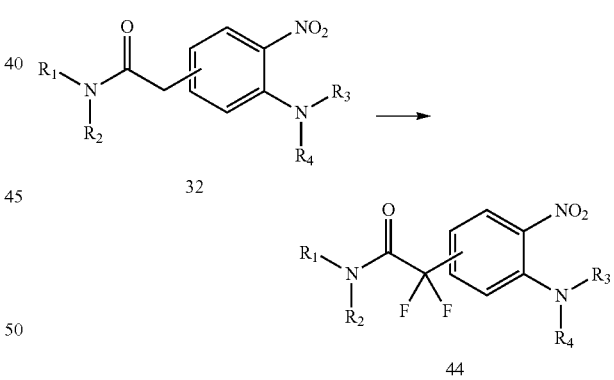

Compound 32 is reacted with a suitable fluorinating agent to form compound 44. Suitable fluorinating agents include, but are not limited to, N-fluorobenzenesulfonimide (NFSI), 1-chloromethyl-4-fluoro-1,4-diazoniabicyclo[2.2.2]octanebis(tetrafluoroborate) (F-TEDA-$BF_4$), 1-fluoro-4-hydroxy-1,4-diazoniabicyclo [2.2.2] octanebis(tetrafluoroborate), N-fluoropyridinium pyridine heptafluoro-diborate, or N-Fluoropyridinium trifluoromethane sulfonate. The reaction may proceed in the presence of a base, such as LiHMDS, and may be performed in a suitable solvent, including, but not limited to, ethers, such as THF or diethyl ether. The reaction is performed at a suitable temperature, such as from −100° C. to −50° C., or from −78° C. to −60° C.

The amide moiety in compound 44 is reacted with a suitable reducing agent, according to the method previously described for Scheme 10, to form compound 46 as shown in Scheme 14 below.

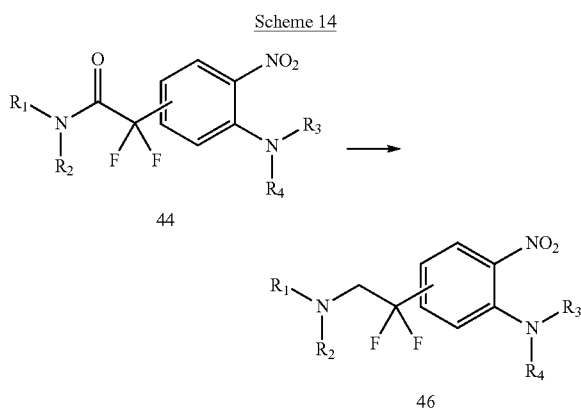

Compound 46 is then further reacted to form desired compounds, according to the previously described methods of Schemes 3, 4 and 5.

A fourth exemplary synthesis proceeds with initial reaction steps according to Scheme 15.

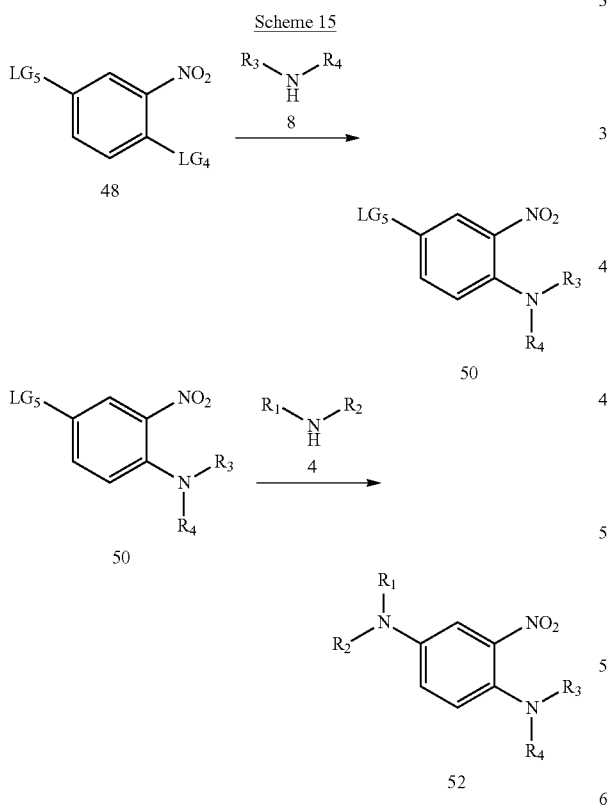

Compound 48 is reacted with amine 8 according to the method previously described for Scheme 6 to form compound 50, where $LG_4$ is a leaving group, such as halo, typically, F or Br, and $LG_5$ is leaving group that is suitable for use in a palladium-catalyzed coupling reaction, such as Cl, Br, or I, typically, Br. Compound 50 is then reacted with amine 4 in the presence of a palladium catalyst, an organophosphate compound, such as S-phos (2-dicyclohexylphosphino-2',6'-dimethoxybiphenyl) or XPhos (2-dicyclohexylphosphino-2',4',6'-triisopropylbiphenyl), and a base, to form compound 52. The palladium catalyst may be any suitable catalyst that facilitates the reaction, such as $Pd(OAc)_2$ or $Pd_2(dba)_3$. And the base may be any base suitable to facilitate the reaction, such as sodium hydrogen carbonate, potassium carbonate, sodium carbonate, sodium tert-butoxide, or potassium tert-butoxide. The reaction is performed in a solvent suitable to facilitate the reaction. Suitable solvents include aprotic solvents, including, but not limited to, ethers, such as dioxane, or nitriles, such as acetonitrile. The reaction is performed at a temperature suitable to facilitate the reaction proceeding to completion, such as from about 50° C. to about 120° C. or more. Compound 52 is then further reacted to form desired compounds, according to the previously described methods of Schemes 3, 4 and 5.

A fifth exemplary synthesis proceeds with initial reaction steps according to Scheme 16.

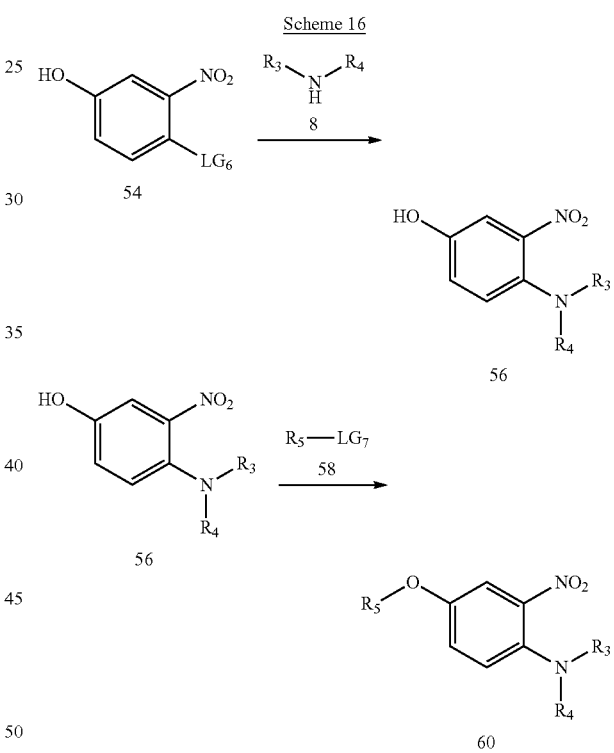

Compound 54 is reacted with amine 8 according to the method previously described for Scheme 6 to form compound 56, where $LG_6$ is a leaving group, such as halo, typically, F or Br. Compound 56 is then reacted with compound 58 to form compound 60. $LG_7$ is a leaving group such as halo, typically Cl or Br; mesylate; or tosylate. $R_5$ typically is an alkyl or substituted alkyl moiety, such as an alkyl substituted with an amine or substituted amine moiety. The reaction proceeds in a suitable solvent, such as acetonitrile, dioxane, DMF, THF or a combination thereof. The reaction typically is performed in the presence of a base, such as potassium carbonate, sodium carbonate, triethylamine or diisopropylethylamine (DIEA). The reaction is performed at a temperature suitable to facilitate the reaction, such as from 20° C. to 100° C. or more, from 30° C. to 80°

C., or from 40° C. to 60° C. Compound 60 is then further reacted to form desired compounds, according to the previously described methods of Schemes 3, 4 and 5.

C. Combinations of Therapeutic Agents

The compounds of the present invention may be used alone, in combination with one another, in separate pharmaceutical compositions, together in a single composition, or as an adjunct to, or in combination with, other established therapies. The compound or compounds may be administered once, or more likely plural administrations. In another aspect, the compounds of the present invention may be used in combination with other therapeutic agents useful for the disorder or condition being treated. These compounds and/or agents may be administered simultaneously, sequentially in any order, by the same route of administration, or by a different route. For sequential administration, the compound(s) and/or agent(s) may be administered such that an effective time period of at least one compound and/or agent overlaps with an effective time period of at least one other compound and/or agent. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. In some embodiments, the effective time periods of all compounds and/or agents overlap with each other.

In some embodiments, disclosed compounds are administered with another therapeutic agent, such as an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhbitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present compounds include proteasome inhibitors, such as bortezomib, carfilzomib, marizomib and the like.

Examples of kinase inhibitors that are useful in combination with the presently disclosed compounds, particularly in treating malignancies include: Btk inhibitors, such as ibrutinib; CDK inhibitors, such as palbociclib; EGFR inhibitors, such as afatinib, erlotinib, gefitinib, lapatinib, osimertinib and vandetinib; Mek inhibitors, such as trametinib; Raf inhibitors, such as dabrafenib, sorafenib and vemurafenib; VEGFR inhibitors, such as axitinib, lenvatinib, nintedanib, pazopanib; BCR-Abl inhibitors, such as bosutinib, dasatinib, imatinib and nilotinib; Syk inhibitors, such as fostamatinib; and JAK inhibitors, such as ruxolitinib.

In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, non-steroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues, for example linaclotide, sold under the name Linzess.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

D. Compositions Comprising the Disclosed Compounds

The disclosed compounds may be used alone, in any combination, and in combination with, or adjunctive to, at least one second therapeutic agent. Furthermore, the disclosed compound or compounds, and/or the at least one second therapeutic, may be used in combination with any suitable excipient useful for forming compositions for administration to a subject. Excipients can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. The pharmaceutically acceptable excipient(s) may include a pharmaceutically acceptable carrier(s) and/or a pharmaceutically acceptable adjuvant(s). Exemplary excipients include, but are not limited to: mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose), gelatin, synthetic polymers (such as polyvinylpyrrolidone, polyalkylene glycols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

III. Methods of Use

A. Diseases/Disorders

The disclosed compounds, as well as combinations and/or compositions thereof, may be used to ameliorate, treat or prevent a variety of diseases and/or disorders. In particular embodiments, the disclosed compound, combinations of disclosed compounds, or compositions thereof, may be useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3 and/or IRAK4. In certain embodiments, disclosed compounds are useful for treating, preventing or ameliorating auto-immune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, and bacterial and viral infections.

In some embodiments, the disclosed compound, combinations of disclosed compounds, or compositions thereof, may be used to treat or prevent allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy, or asthma.

The disclosed compound, combinations of disclosed compounds, or compositions thereof, may also be useful for ameliorating, treating or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the disclosed compound, combinations of disclosed compounds, or compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, or Parkinson's disease.

Proliferative diseases that may be treated by the disclosed compound, combinations of disclosed compounds, or compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the disclosed compound, combinations of disclosed compounds, or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed compound, combinations of disclosed compounds, or compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising one or more active compounds of the invention may be manufactured by any suitable method, such as mixing, dissolving, granulating, dragee-making, levigating, emulsifying, encapsulating, entrapping or lyophilization processes. The compositions may be formulated using one or more physiologically acceptable excipients, diluents, carriers, adjuvants or auxiliaries to provide preparations which can be used pharmaceutically.

The active compound(s) may be formulated in the pharmaceutical compositions per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), hydrate, solvate, N-oxide or pharmaceutically acceptable salt may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable excipients such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, or pharmaceutically acceptable salt can be conveniently delivered in the form of an aerosol spray from pressurized packs or a nebulizer with the use of a suitable propellant, e.g.) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (1 4 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL of the disclosed compound(s), 1% (v/v) polysorbate 80 (TWEEN® 80), 50 mM citrate and/or 0.9% sodium chloride.

For ocular administration, the active compound(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active compound(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The disclosed compound or combinations of disclosed compounds will generally be used in an amount effective to achieve the intended result, for example, in an amount effective to treat, prevent or ameliorate a particular condition. The disclosed compound(s), or compositions thereof, can be administered therapeutically to achieve therapeutic benefit or prophylactically to achieve a prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of disclosed compounds may depend on various factors, including the age, weight, general health, and severity of the condition of the patient or subject being treated. Dosage also may need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the disclosed compound(s) or compositions thereof, will also depend on whether the disclosed compound(s) are formulated for treatment of acute episodes of a condition or for the prophylactic treatment of a disorder. A person or ordinary skill in the art will be able to determine the optimal dose for a particular individual.

For prophylactic administration, the disclosed compound, combinations of disclosed compounds, or compositions thereof, can be administered to a patient or subject at risk of developing one of the previously described conditions. For example, if it is unknown whether a patient or subject is allergic to a particular drug, the disclosed compound, combinations of disclosed compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a disclosed compound(s), or composition thereof, can be administered to an allergy sufferer prior to expected exposure to the allergen. A disclosed compound, combinations of disclosed compounds, or compositions thereof, can also be administered prophylactically to healthy individuals who are repeatedly exposed to agents known to one of the above-described maladies to prevent the onset of the disorder. For example, a disclosed compound, combinations of disclosed compounds, or compositions thereof, can be administered to a healthy individual who is repeatedly exposed to an allergen known to induce allergies, such as latex, in an effort to prevent the individual from developing an allergy. Alternatively, a disclosed compound, combinations of disclosed compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ with respect to a kinase protein, such as an IRAK protein, of from greater than 0 to 20 µM, such as from greater than 0 to 10 µM, from greater than 0 to 5 µM, from greater than 0 to 1 µM, from greater than 0 to 0.5 µM, from greater than 0 to 0.1 µM, or from greater than 0 to 0.05 µM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed compounds will typically be in the range of from about greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the disclosed compound, its bioavailability, the mode of administration, and various factors discussed above.

Dosage amount and dosage interval can be adjusted for individuals to provide plasma levels of the disclosed compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed compounds typically comprise from greater than 0 up to 99% of the disclosed compound, or compounds, and/or other therapeutic agent by total weight percent. More typically, compositions comprising one or more of the disclosed compounds comprise from about 1 to about 20 total weight percent of the disclosed compound and other therapeutic agent, and from about 80 to about 99 weight percent of a pharmaceutically acceptable excipient.

Preferably, the disclosed compound, combinations of disclosed compounds, or compositions thereof, will provide therapeutic or prophylactic benefit without causing substantial toxicity. Toxicity of the disclosed compound can be determined using standard pharmaceutical procedures. The dose ratio between toxic and therapeutic (or prophylactic) effect is the therapeutic index. Disclosed compounds that exhibit high therapeutic indices are preferred.

IV. Examples

Example 1

General Procedures (A) for Amide Coupling Reactions

1-[Bis(dimethylamino)methylene]-1H-1,2,3-triazolo[4,5-b]pyridinium 3-oxid hexafluorophosphate (HATU) (1.2 equivalents) and N-ethyl-N-isopropylpropan-2-amine (2-4 equivalents) were added to a $CH_2Cl_2$ solution of aryl-carboxylic acid and amine/aniline (as parent or as an HCl salt, 1-1.2 equivalents), and the resulting solution/suspension was stirred at room temperature until the reaction went to completion as monitored by LC-MS. Volatiles were removed by rotary evaporation under reduced pressure, and the product was purified by silica gel column chromatography. If necessary, the product was further purified by trituration from Hexanes-ethyl acetate (EtOAc), or by aqueous work-up (partitioning between EtOAc and saturated aqueous $NaHCO_3$ solution).

Example 2

General Procedures (B) for Suzuki Reactions

In a microwave tube, a 1,4-dioxane solution/suspension of aryl-halide, aryl-boronic acid/ester (1.5-3 equivalents), tetrakis(triphenylphosphine)palladium(0) ($Pd(PPh_3)_4$) (10 mol %) and 2M aqueous solution of $Na_2CO_3$ (3 equivalents) was de-gassed with a stream of nitrogen for more than 1 minute. The solution/suspension was then microwaved at 150° C. for 30 minutes or longer until reaction went to completion as monitored by LC-MS. Solid was removed by filtration through a celite pad, with methanol washing. The filtrate was collected and the solvent was removed by rotary evaporation under reduced pressure. The product was purified by silica gel column chromatography or reverse-phase high performance liquid chromatography (HPLC). After HPLC purification, compounds were obtained as trifluoroacetic acid (TFA) or formic acid ($HCO_2H$) salts. Free base samples were prepared by passing a MeOH solution of corresponding sample through $PL-HCO_3$ column. If necessary, product was further purified by trituration from Hexanes-EtOAc.

Example 3

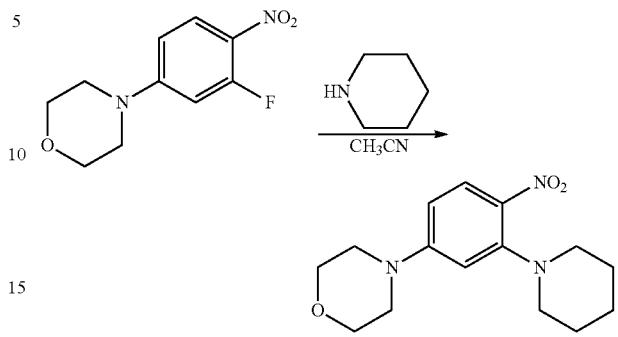

4-(4-nitro-3-(piperidin-1-yl)phenyl)morpholine

To a $CH_3CN$ (5 mL) solution of 4-(3-fluoro-4-nitrophenyl)morpholine (678.6 mg, 3 mmol), piperidine (415 μL, 4.2 mmol) was added, and the mixture stirred at 70° C. for 15 hours. The reaction went to completion as monitored by LC-MS, and was quenched by the addition of saturated aq. $NaHCO_3$ solution. EtOAc was added to extract aqueous layer (×2) and combined organic layers were further washed with $H_2O$, dried ($Na_2SO_4$), filtered, and the solvent was removed in vacuo. Compound 4-(4-nitro-3-(piperidin-1-yl)phenyl)morpholine was obtained as a bright yellow solid: 868 mg (99% yield); $^1$H NMR (300 MHz, Chloroform-d) δ 7.99 (d, J=9.3 Hz, 1H), 6.39 (dd, J=9.3, 2.6 Hz, 1H), 6.33 (d, J=2.6 Hz, 1H), 3.86-3.83 (m, 4H), 3.33-3.29 (m, 4H), 3.04-3.00 (m, 4H), 1.79-1.72 (m, 4H), 1.64-1.56 (m, 2H); LRMS (M+H) m/z 292.52.

Example 4

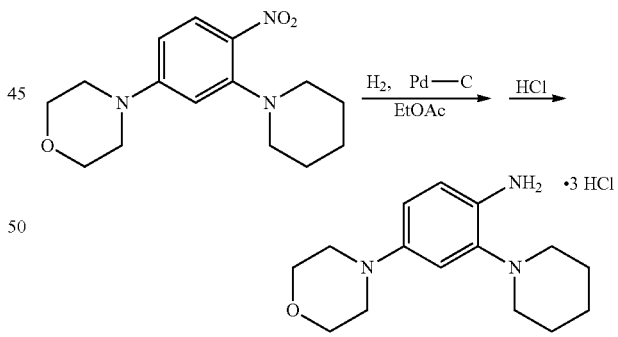

4-morpholino-2-(piperidin-1-yl)aniline
Tri-Hydrogen Chloride

In a Parr flask, under 30 psi of $H_2$, an EtOAc (50 mL) solution of 4-(4-nitro-3-(piperidin-1-yl)phenyl)morpholine (868 mg, 2.98 mmol) and Pd—C (10% Pd on C, 50% wet, 0.2 g) was shaken at room temperature for 3 hours. The reaction went to completion as monitored by LC-MS. Solid was removed by filtration through a celite pad, which was washed with EtOAc and MeOH. Filtrate was collected in a receiving flask containing 5 mL of 4M HCl-dioxane solution, and the solvent was removed in vacuo. Compound 4-morpholino-2-(piperidin-1-yl)aniline tri-hydrogen chloride was obtained as an off-white sticky solid: 970.8 mg (87% yield); $^1$H NMR (300 MHz, DMSO-$d_6$) δ 7.22 (d, J=8.4 Hz, 2H), 7.12 (s, 1H), 7.04-6.90 (m, 2H), 3.85-3.81 (m, 4H), 3.27-3.21 (m, 4H), 3.05-2.96 (m, 4H), 1.87-1.78 (m, 4H), 1.62-1.58 (m, 2H); LRMS (M+H) m/z 262.58.

Example 5

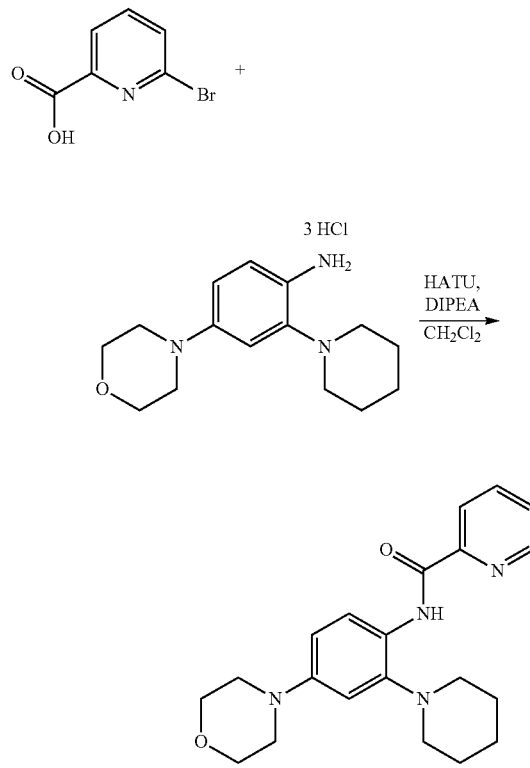

6-bromo-N-(4-morpholino-2-(piperidin-1-yl)phenyl)picolinamide

To a CH$_2$Cl$_2$ (5 mL) solution of 6-bromopicolinic acid (161.6 mg, 0.8 mmol) and 4-morpholino-2-(piperidin-1-yl)aniline tri-hydrogen chloride (311.4 mg, 0.84 mmol), HATU (365 mg, 0.96 mmol) and N-ethyl-N-isopropylpropan-2-amine (DIPEA; Hünig's base) (556 μL, 3.2 mmol) were added, and the solution was stirred at room temperature over a weekend. The reaction went to completion as monitored by LC-MS. Solvent was removed by rotary evaporation under reduced pressure, and the product was purified by silica gel column chromatography. Compound 6-bromo-N-(4-morpholino-2-(piperidin-1-yl)phenyl)picolinamide was obtained as a yellow solid: 286.6 mg (80% yield); $^1$H NMR (300 MHz, Chloroform-d) δ 10.89 (s, 1H), 8.47 (d, J=8.9 Hz, 1H), 8.24 (dd, J=7.5, 1.0 Hz, 1H), 7.78-7.73 (m, 1H), 7.63 (dd, J=7.9, 1.0 Hz, 1H), 6.78 (d, J=2.7 Hz, 1H), 6.72 (dd, J=8.9, 2.7 Hz, 1H), 3.89-3.86 (m, 4H), 3.16-3.13 (m, 4H), 2.89-2.85 (m, 4H), 1.96-1.88 (m, 4H), 1.68-1.58 (m, 2H); LRMS (M+H) m/z 445.62, 447.72.

Example 6

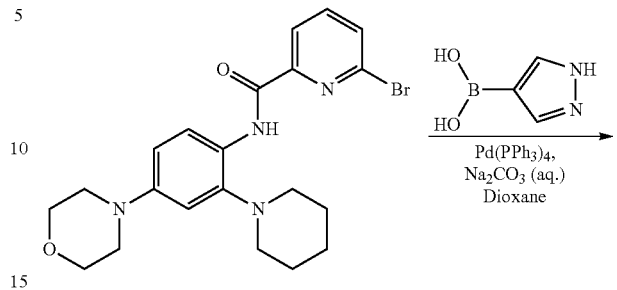

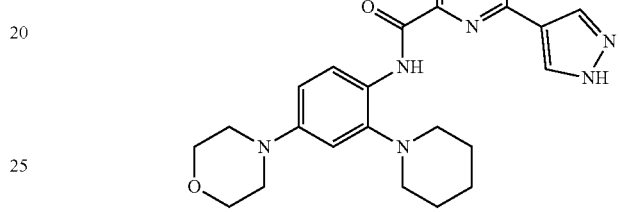

I-36: N-(4-morpholino-2-(piperidin-1-yl)phenyl)-6-(1H-pyrazol-4-yl)picolinamide

A 1,4-dioxane (2 mL) solution of 6-bromo-N-(4-morpholino-2-(piperidin-1-yl)phenyl)picolinamide (44.5 mg, 0.1 mmol), (1H-pyrazol-4-yl)boronic acid (16.8 mg, 0.15 mmol), Pd(PPh$_3$)$_4$ (11.6 mg, 0.01 mmol) and 2M aq. Na$_2$CO$_3$ (150 μL, 0.3 mmol) was de-gassed with a stream of nitrogen for more than one minute and was microwaved at 150° C. for 30 minutes. Reaction went to completion as monitored by LC-MS. Solid was removed by filtration through a celite pad, and washed with MeOH. Filtrate was collected and solvent was removed by rotary evaporation under reduced pressure. Product was purified by reverse-phase HPLC and was obtained as a TFA salt. A free-base sample was obtained by passing a MeOH—CH$_2$Cl$_2$ suspension of the salt through a PL-HCO$_3$ column, washing with CH$_2$Cl$_2$. Filtrate was collected, and solvent was removed in vacuo. Compound N-(4-morpholino-2-(piperidin-1-yl)phenyl)-6-(1H-pyrazol-4-yl)picolinamide was obtained as a yellow solid: 19.1 mg (44% yield); $^1$H NMR (300 MHz, Chloroform-d) δ 10.81 (s, 1H), 10.37 (br s, 1H), 8.48 (d, J=8.8 Hz, 1H), 8.26 (s, 2H), 8.17 (dd, J=7.7, 1.0 Hz, 1H), 7.89 (dd, J=7.8, 7.8 Hz, 1H), 7.65 (dd, J=7.9, 1.0 Hz, 1H), 6.77 (d, J=2.7 Hz, 1H), 6.73 (dd, J=8.8, 2.7 Hz, 1H), 3.90-3.87 (m, 4H), 3.17-3.14 (m, 4H), 2.90-2.87 (m, 4H), 1.83-1.76 (m, 4H), 1.62-1.55 (m, 2H); LRMS (M+H) m/z 433.70.

Example 7

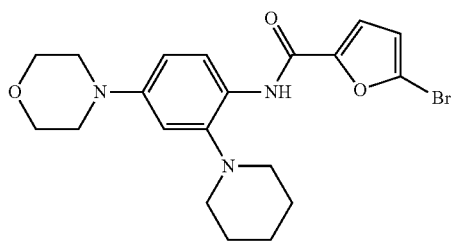 [SMILES: O=C(Nc1ccc(N2CCOCC2)cc1N1CCCCC1)c1ccc(Br)o1]

5-bromo-N-(4-morpholino-2-(piperidin-1-yl)phenyl)
furan-2-carboxamide

The compound was prepared according to general procedure (A): 0.8 mmol scale, 92% yield.

$^1$H NMR (300 MHz, Chloroform-d) δ 9.41 (s, 1H), 8.34 (d, J=8.9 Hz, 1H), 7.13 (d, J=3.5 Hz, 1H), 6.76 (d, J=2.7 Hz, 1H), 6.70 (dd, J=8.9, 2.7 Hz, 1H), 6.49 (d, J=3.5 Hz, 1H), 3.88-3.85 (m, 4H), 3.14-3.11 (m, 4H), 2.87-2.83 (m, 4H), 1.86-1.79 (m, 4H), 1.67-1.60 (m, 2H); LRMS (M+H) m/z 434.62, 436.59.

Example 8

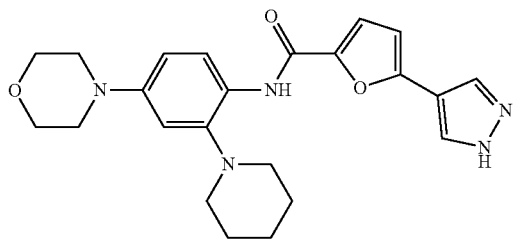 [SMILES: O=C(Nc1ccc(N2CCOCC2)cc1N1CCCCC1)c1ccc(-c2cn[nH]c2)o1]

I-37: N-(4-morpholino-2-(piperidin-1-yl)phenyl)-5-
(1H-pyrazol-4-yl)furan-2-carboxamide The compound was prepared according to general procedure (B): 0.1 mmol scale, 57% yield.

$^1$H NMR (300 MHz, Chloroform-d) δ 10.28 (br s, 1H), 9.45 (s, 1H), 8.41 (d, J=8.8 Hz, 1H), 7.92 (s, 2H), 7.24 (d, J=3.5 Hz, 1H), 6.78 (d, J=2.7 Hz, 1H), 6.72 (dd, J=8.8, 2.7 Hz, 1H), 6.53 (d, J=3.5 Hz, 1H), 3.89-3.86 (m, 4H), 3.15-3.12 (m, 4H), 2.89-2.86 (m, 4H), 1.86-1.79 (m, 4H), 1.69-1.64 (m, 2H); LRMS (M+H) m/z 422.69.

Example 9

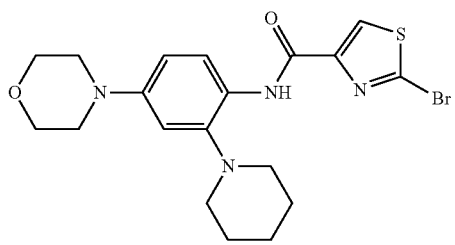 [SMILES: O=C(Nc1ccc(N2CCOCC2)cc1N1CCCCC1)c1csc(Br)n1]

2-bromo-N-(4-morpholino-2-(piperidin-1-yl)phenyl)
thiazole-4-carboxamide

The compound was prepared according to general procedure (A): 0.8 mmol scale, 72% yield.

$^1$H NMR (300 MHz, Chloroform-d) δ 10.19 (s, 1H), 8.39 (d, J=8.9 Hz, 1H), 8.09 (s, 1H), 6.75 (d, J=2.7 Hz, 1H), 6.70 (dd, J=8.9, 2.7 Hz, 1H), 3.88-3.85 (m, 4H), 3.15-3.12 (m, 4H), 2.87-2.84 (m, 4H), 1.89-1.81 (m, 4H), 1.67-1.60 (m, 2H); LRMS (M+H) m/z 451.58, 453.62.

Example 10

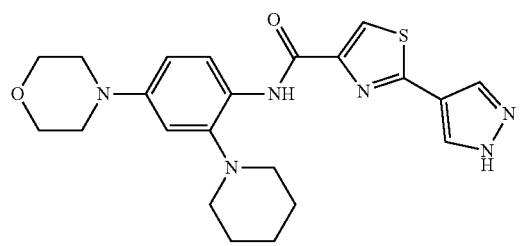 [SMILES: O=C(Nc1ccc(N2CCOCC2)cc1N1CCCCC1)c1csc(-c2cn[nH]c2)n1]

I-38: N-(4-morpholino-2-(piperidin-1-yl)phenyl)-2-
(1H-pyrazol-4-yl)thiazole-4-carboxamide The compound was prepared according to general procedure (B): 0.1 mmol scale, 54% yield.

$^1$H NMR (300 MHz, Chloroform-d) δ 10.44 (v br s, 1H), 10.35 (s, 1H), 8.46 (d, J=8.8 Hz, 1H), 8.10 (s, 2H), 8.07 (s, 1H), 6.77 (d, J=2.7 Hz, 1H), 6.72 (dd, J=8.8, 2.7 Hz, 1H), 3.89-3.86 (m, 4H), 3.16-3.13 (m, 4H), 2.90-2.87 (m, 4H), 1.91-1.83 (m, 4H), 1.70-1.63 (m, 2H); LRMS (M+H) m/z 439.74.

Example 11

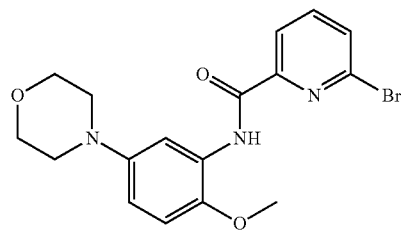 [SMILES: COc1ccc(N2CCOCC2)cc1NC(=O)c1cccc(Br)n1]

6-bromo-N-(2-methoxy-5-morpholinophenyl)pico-
linamide

The compound was prepared according to general procedure (A): 1.0 mmol scale, 70% yield.

$^1$H NMR (300 MHz, Chloroform-d) δ 10.31 (s, 1H), 8.35 (d, J=2.9 Hz, 1H), 8.22 (dd, J=7.5, 1.0 Hz, 1H), 7.76 (dd, J=8.9, 8.9 Hz, 1H), 7.65 (dd, J=7.9, 1.0 Hz, 1H), 6.87 (d, J=8.9 Hz, 1H), 6.65 (dd, J=8.9, 2.9 Hz, 1H), 3.93 (s, 3H), 3.88-3.85 (m, 4H), 3.16-3.13 (m, 4H); LRMS (M+H) m/z 392.49, 394.45.

Example 12

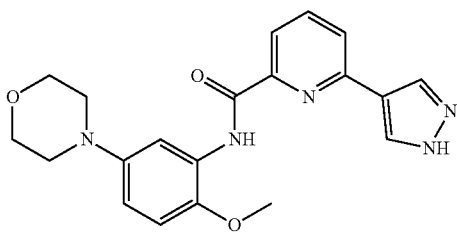 [SMILES: COc1ccc(N2CCOCC2)cc1NC(=O)c1cccc(-c2cn[nH]c2)n1]

I-39: N-(2-methoxy-5-morpholinophenyl)-6-(1H-pyrazol-4-yl)picolinamide

The compound was prepared according to general procedure (B): 0.1 mmol scale, 42% yield.
$^1$H NMR (300 MHz, Chloroform-d) δ 10.84 (s, 1H), 9.89 (v br s, 1H), 8.43 (d, J=2.9 Hz, 1H), 8.21 (s, 2H), 8.10 (br d, J=7.7 Hz, 1H), 7.89 (dd, J=7.8, 7.8 Hz, 1H), 7.66 (br d, J=7.9 Hz, 1H), 6.89 (d, J=8.9 Hz, 1H), 6.64 (dd, J=8.9, 2.9 Hz, 1H), 3.98 (s, 3H), 3.89-3.86 (m, 4H), 3.18-3.15 (m, 4H); LRMS (M+H) m/z 380.55.

Example 13

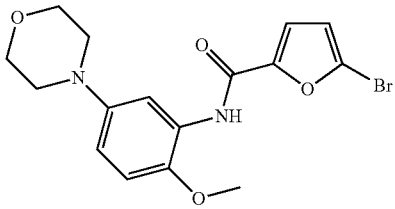 [SMILES: COc1ccc(N2CCOCC2)cc1NC(=O)c1ccc(Br)o1]

5-bromo-N-(2-methoxy-5-morpholinophenyl)furan-2-carboxamide

The compound was prepared according to general procedure (A): 1.0 mmol scale, 88% yield.
$^1$H NMR (300 MHz, Chloroform-d) δ 8.64 (s, 1H), 8.24 (d, J=2.9 Hz, 1H), 7.15 (d, J=3.5 Hz, 1H), 6.85 (d, J=8.9 Hz, 1H), 6.62 (dd, J=8.9, 2.9 Hz, 1H), 6.50 (d, J=3.5 Hz, 1H), 3.91 (s, 3H), 3.87-3.84 (m, 4H), 3.13-3.10 (m, 4H); LRMS (M+H) m/z 381.48, 383.43.

Example 14

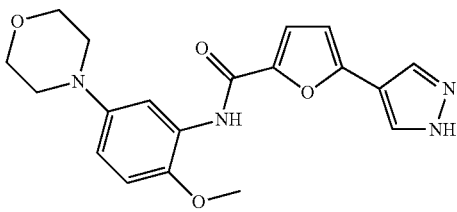 [SMILES: COc1ccc(N2CCOCC2)cc1NC(=O)c1ccc(-c2cn[nH]c2)o1]

I-40: N-(2-methoxy-5-morpholinophenyl)-5-(1H-pyrazol-4-yl)furan-2-carboxamide

The compound was prepared according to general procedure (B): 0.1 mmol scale, 40% yield.
$^1$H NMR (300 MHz, Chloroform-d) δ 10.16 (v br s, 1H), 8.75 (s, 1H), 8.30 (d, J=2.9 Hz, 1H), 7.93 (s, 2H), 7.24 (d, J=3.6 Hz, 1H), 6.86 (d, J=8.9 Hz, 1H), 6.62 (dd, J=8.9, 2.9 Hz, 1H), 6.53 (d, J=3.6 Hz, 1H), 3.92 (s, 3H), 3.88-3.85 (m, 4H), 3.15-3.12 (m, 4H); LRMS (M+H) m/z 365.52.

Example 15

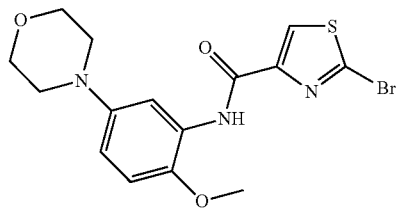 [SMILES: COc1ccc(N2CCOCC2)cc1NC(=O)c1csc(Br)n1]

2-bromo-N-(2-methoxy-5-morpholinophenyl)thiazole-4-carboxamide

The compound was prepared according to general procedure (A): 1.0 mmol scale, 89% yield.
$^1$H NMR (300 MHz, Chloroform-d) δ 9.60 (s, 1H), 8.30 (d, J=2.9 Hz, 1H), 8.12 (s, 1H), 6.85 (d, J=8.9 Hz, 1H), 6.64 (dd, J=8.9, 2.9 Hz, 1H), 3.92 (s, 3H), 3.88-3.85 (m, 4H), 3.15-3.11 (m, 4H); LRMS (M+H) m/z 398.46, 400.41.

Example 16

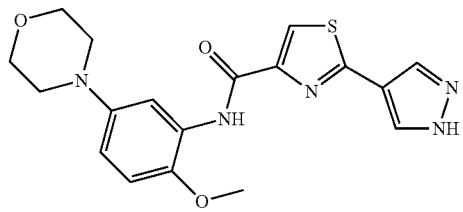 [SMILES: COc1ccc(N2CCOCC2)cc1NC(=O)c1csc(-c2cn[nH]c2)n1]

I-41: N-(2-methoxy-5-morpholinophenyl)-2-(1H-pyrazol-4-yl)thiazole-4-carboxamide The compound was prepared according to general procedure (B): 0.1 mmol scale, 42% yield.
$^1$H NMR (300 MHz, Chloroform-d) δ 10.35 (v br s, 1H), 9.88 (s, 1H), 8.36 (d, J=2.9 Hz, 1H), 8.12-8.07 (m, 3H), 6.87 (d, J=8.9 Hz, 1H), 6.63 (dd, J=8.9, 2.9 Hz, 1H), 3.93 (s, 3H), 3.88-3.85 (m, 4H), 3.16-3.13 (m, 4H); LRMS (M+H) m/z 386.53.

Example 17

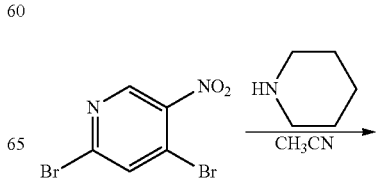

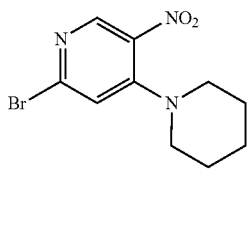

2-bromo-5-nitro-4-(piperidin-1-yl)pyridine
Di-Hydrogen Bromide

A CH₃CN (5 mL) solution of 2,4-dibromo-5-nitropyridine (845.7 mg, 3 mmol) and piperidine (311 μL, 3.15 mmol) was stirred at room temperature and the progress of the reaction was monitored by LC-MS. After 4 hours, additional piperidine (0.1 mL) was added, and the reaction stopped at 5 hours. Precipitate was collected by filtration, washed with CH₃CN-EtOAc, and was further dried in vacuo. Compound 2-bromo-5-nitro-4-(piperidin-1-yl)pyridine di-hydrogen bromide was obtained as a bright yellow solid: 799.3 mg (59% yield); $^1$H NMR (300 MHz, Chloroform-d) δ 8.97 (s, 2H), 8.55 (s, 1H), 7.03 (s, 1H), 3.19-3.16 (m, 4H), 2.01-1.88 (m, 4H), 1.76-1.65 (m, 2H); LRMS (M+H) m/z 286.37.

Example 18

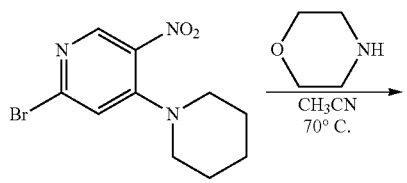

4-(5-nitro-4-(piperidin-1-yl)pyridin-2-yl)morpholine

A CH₃CN (5 mL) solution of 2-bromo-5-nitro-4-(piperidin-1-yl)pyridine di-hydrogen bromide (799 mg, 1.78 mmol) and morpholine (185 μL, 2.1 mmol) was stirred at 70° C. After 2 hours, NaHCO₃ (0.32 g, 3.56 mmol) and additional morpholine (185 μL) were added, and after 24 hours, the reaction went to completion as monitored by LC-MS. Solid was removed by filtration, and solvent of the filtrate was removed by rotary evaporation under reduced pressure to provide crude product which was purified by silica gel column chromatography. Compound 4-(5-nitro-4-(piperidin-1-yl)pyridin-2-yl)morpholine was obtained as a yellow solid: 320.9 mg (62% yield); $^1$H NMR (300 MHz, Chloroform-d) δ 8.77 (s, 1H), 5.83 (s, 1H), 3.81-3.78 (m, 4H), 3.64-3.61 (m, 4H), 3.11-3.07 (m, 4H), 1.77-1.70 (m, 4H), 1.68-1.62 (m, 2H); LRMS (M+H) m/z 293.58.

Example 19

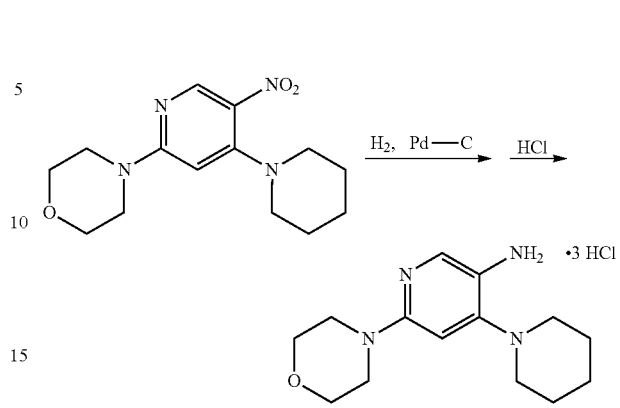

6-morpholino-4-(piperidin-1-yl)pyridin-3-amine
Tri-Hydrogen Chloride

In a Parr flask, under 30 psi of H₂, an EtOAc (20 mL) solution of 4-(5-nitro-4-(piperidin-1-yl)pyridin-2-yl)morpholine (320 mg, 1.09 mmol) and Pd—C (10% Pd on C, 50% wet, 0.1 g) was shaken at room temperature for 21 hours. The reaction went to completion as monitored by LC-MS. Solid was removed by filtration through a celite pad, washing with MeOH. Filtrate was collected in a receiving flask containing 2 mL of 4M HCl-dioxane solution, and solvent was removed in vacuo. Compound 6-morpholino-4-(piperidin-1-yl)pyridin-3-amine tri-hydrogen chloride was obtained as a purple thick oil: 405 mg (>99% yield); $^1$H NMR (300 MHz, DMSO-d₆) δ 7.44 (br s, 1H), 6.44 (s, 1H), 4.81 (br s, 3H), 4.03 (br zs, 3H), 3.78-3.75 (m, 4H), 3.47-3.44 (m, 4H), 3.25-3.22 (m, 4H), 1.73-1.61 (m, 6H); LRMS (M+H) m/z 263.55.

Example 20

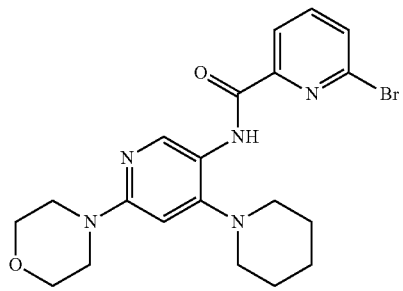 [SMILES: O=C(Nc1cnc(N2CCOCC2)cc1N1CCCCC1)c1cccc(Br)n1]

6-bromo-N-(6-morpholino-4-(piperidin-1-yl)pyridin-3-yl)picolinamide

The compound was prepared according to general procedure (A): 0.4 mmol scale, 68% yield.

$^1$H NMR (300 MHz, Chloroform-d) δ 10.14 (s, 1H), 9.26 (s, 1H), 8.25 (dd, J=7.5, 1.0 Hz, 1H), 7.79-7.74 (m, 1H), 7.64 (dd, J=7.9, 1.0 Hz, 1H), 6.34 (s, 1H), 3.86-3.83 (m, 4H), 3.50-3.47 (m, 4H), 2.95-2.91 (m, 4H), 1.94-1.87 (m, 4H), 1.70-1.62 (m, 2H); LRMS (M+H) m/z 446.53, 448.51.

Example 21

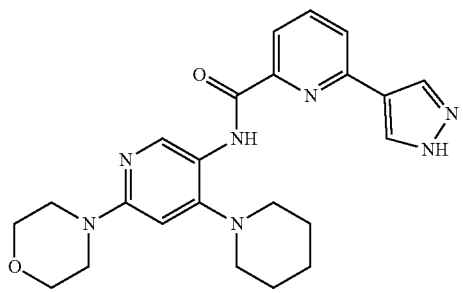 [SMILES: O=C(Nc1cnc(N2CCOCC2)cc1N1CCCCC1)c1cccc(-c2cn[nH]c2)n1]

I-42: N-(6-morpholino-4-(piperidin-1-yl)pyridin-3-yl)-6-(1H-pyrazol-4-yl)picolinamide The compound was prepared according to general procedure (B): 0.1 mmol scale, 33% yield.

$^1$H NMR (300 MHz, Chloroform-d) δ 10.56 (br s, 1H), 10.28 (s, 1H), 9.21 (s, 1H), 8.23 (s, 2H), 8.17 (br d, J=7.7 Hz, 1H), 7.89 (dd, J=7.8, 7.8 Hz, 1H), 7.66 (dd, J=7.9, 1.0 Hz, 1H), 6.35 (s, 1H), 3.86-3.83 (m, 4H), 3.50-3.47 (m, 4H), 2.95-2.91 (m, 4H), 1.81-1.73 (m, 4H), 1.65-1.56 (m, 2H); LRMS (M+H) m/z 434.82.

Example 22

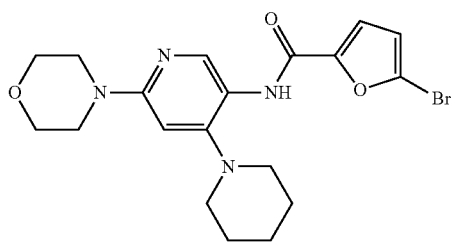

5-bromo-N-(6-morpholino-4-(piperidin-1-yl)pyridin-3-yl)furan-2-carboxamide

The compound was prepared according to general procedure (A): 0.4 mmol scale, 64% yield.

$^1$H NMR (300 MHz, Chloroform-d) δ 9.11 (s, 1H), 8.49 (s, 1H), 7.16 (d, J=3.5 Hz, 1H), 6.50 (d, J=3.5 Hz, 1H), 6.33 (s, 1H), 3.85-3.82 (m, 4H), 3.48-3.45 (m, 4H), 2.93-2.89 (m, 4H), 1.86-1.78 (m, 4H), 1.69-1.64 (m, 2H); LRMS (M+H) m/z 435.53, 437.42.

Example 23

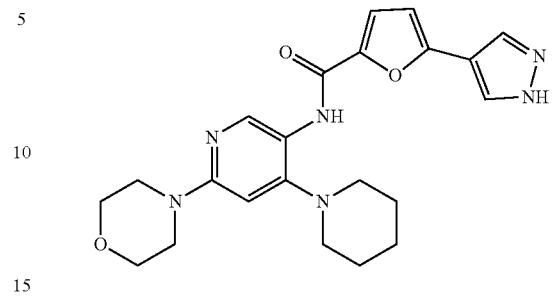

I-43: N-(6-morpholino-4-(piperidin-1-yl)pyridin-3-yl)-5-(1H-pyrazol-4-yl)furan-2-carboxamide The compound was prepared according to general procedure (B): 0.1 mmol scale, 9% yield.

$^1$H NMR (300 MHz, Chloroform-d) δ 10.42 (br s, 1H), 9.17 (s, 1H), 8.55 (s, 1H), 7.91 (s, 2H), 7.27 (d, J=3.6 Hz, 1H), 6.54 (d, J=3.6 Hz, 1H), 6.35 (s, 1H), 3.86-3.82 (m, 4H), 3.49-3.46 (m, 4H), 2.94-2.91 (m, 4H), 1.85-1.78 (m, 4H), 1.70-1.62 (m, 2H); LRMS (M+H) m/z 423.80.

Example 24

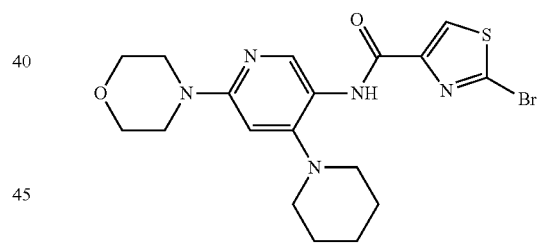

2-bromo-N-(6-morpholino-4-(piperidin-1-yl)pyridin-3-yl)thiazole-4-carboxamide

The compound was prepared according to general procedure (A): 0.4 mmol scale, 72% yield.

$^1$H NMR (300 MHz, Chloroform-d) δ 9.40 (s, 1H), 9.15 (s, 1H), 8.12 (s, 1H), 6.32 (s, 1H), 3.85-3.82 (m, 4H), 3.49-3.46 (m, 4H), 2.93-2.90 (m, 4H), 1.88-1.80 (m, 4H), 1.69-1.61 (m, 2H); LRMS (M+H) m/z 452.53, 454.54.

Regiochemistry of the amine was confirmed by 1D-NOESY experiment: NOE was observed between N<u>H</u> and α-<u>H</u> of piperidine.

Example 25

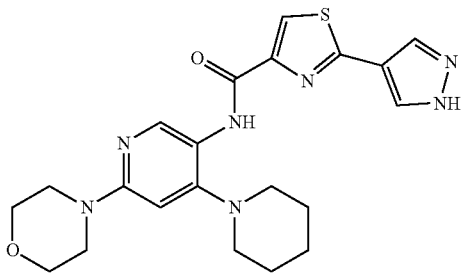 [SMILES: O=C(Nc1cnc(N2CCOCC2)cc1N1CCCCC1)c1csc(-c2cn[nH]c2)n1]

I-44: N-(6-morpholino-4-(piperidin-1-yl)pyridin-3-yl)-2-(1H-pyrazol-4-yl)thiazole-4-carboxamide The compound was prepared according to general procedure (B): 0.1 mmol scale, 39% yield.

$^1$H NMR (300 MHz, Chloroform-d) δ 10.57 (br s, 1H), 9.62 (s, 1H), 9.23 (s, 1H), 8.10 (s, 1H), 8.09 (s, 2H), 6.34 (s, 1H), 3.86-3.83 (m, 4H), 3.50-3.46 (m, 4H), 2.96-2.93 (m, 4H), 1.89-1.82 (m, 4H), 1.70-1.63 (m, 2H); LRMS (M+H) m/z 440.80.

General procedures A and B are representative exemplary embodiments of a method to synthesize the compounds of Examples 26-49. A person of ordinary skill in the art will understand that certain variations in these exemplary embodiments may be useful for synthesizing such compounds, such as variations in temperature, time, and/or reagent amounts.

Example 26

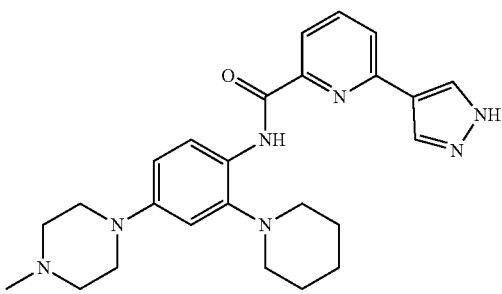 [SMILES: CN1CCN(c2ccc(NC(=O)c3cccc(-c4cn[nH]c4)n3)c(N3CCCCC3)c2)CC1]

I-1: N-(4-(4-methylpiperazin-1-yl)-2-(piperidin-1-yl)phenyl)-6-(1H-pyrazol-4-yl)picolinamide $^1$H NMR (300 MHz, DMSO-d$_6$) δ 13.29 (s, 1H), 10.78 (s, 1H), 8.52 (s, 1H), 8.34 (d, J=8.9 Hz, 1H), 8.31 (s, 1H), 8.11-7.96 (m, 3H), 6.87 (d, J=2.7 Hz, 1H), 6.77 (dd, J=9.0, 2.6 Hz, 1H), 3.17 (t, J=4.9 Hz, 4H), 2.87 (t, J=5.2 Hz, 4H), 2.51 (t, J=5.2 Hz, 4H), 2.28 (s, 3H), 1.83-1.75 (br m, 4H), 1.58 (br s, 2H). LCMS (m/z): 446.3 (MH+).

Example 27

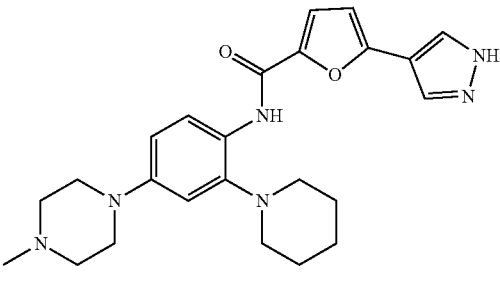 [SMILES: CN1CCN(c2ccc(NC(=O)c3ccc(-c4cn[nH]c4)o3)c(N3CCCCC3)c2)CC1]

I-2: N-(4-(4-methylpiperazin-1-yl)-2-(piperidin-1-yl)phenyl)-5-(1H-pyrazol-4-yl)furan-2-carboxamide $^1$H NMR (300 MHz, DMSO-d$_6$) δ 13.29 (s, 1H), 9.40 (s, 1H), 8.22 (s, 1H), 8.11 (d, J=8.8 Hz, 1H), 7.95 (s, 1H), 7.28 (d, J=3.5 Hz, 1H), 6.86 (s, 1H), 6.80 (d, J=3.5 Hz, 1H), 6.73 (d, J=8.9 Hz, 1H), 3.17-3.10 (m, 4H), 2.89-2.82 (m, 4H), 2.51-2.45 (m, 4H), 2.26 (s, 3H), 1.84-1.73 (br m, 4H), 1.63 (br s, 2H). LCMS (m/z): 435.8 (MH+).

Example 28

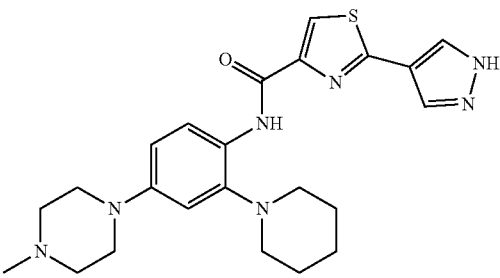 [SMILES: CN1CCN(c2ccc(NC(=O)c3csc(-c4cn[nH]c4)n3)c(N3CCCCC3)c2)CC1]

I-3: N-(4-(4-methylpiperazin-1-yl)-2-(piperidin-1-yl)phenyl)-2-(1H-pyrazol-4-yl)thiazole-4-carboxamide $^1$H NMR (300 MHz, DMSO-d$_6$) δ 13.46 (s, 1H), 10.31 (s, 1H), 8.45 (s, 1H), 8.34-8.24 (m, 2H), 8.07 (s, 1H), 6.87 (d, J=2.7 Hz, 1H), 6.75 (dd, J=8.9, 2.7 Hz, 1H), 3.15 (t, J=4.9 Hz, 4H), 2.87 (t, J=5.1 Hz, 4H), 2.50 (t, J=5.0 Hz, 4H), 2.27 (s, 3H), 1.92-1.79 (br m, 4H), 1.65 (br s, 2H). LCMS (m/z): 452.8 (MH+).

Example 29

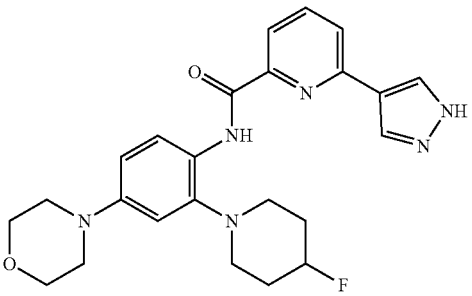 [SMILES: O=C(Nc1ccc(N2CCOCC2)cc1N1CCC(F)CC1)c1cccc(-c2cn[nH]c2)n1]

I-4: N-(2-(4-fluoropiperidin-1-yl)-4-morpholinophenyl)-6-(1H-pyrazol-4-yl)picolinamide ¹H NMR (300 MHz, DMSO-d$_6$) δ 10.72 (s, 1H), 8.47-8.29 (m, 3H), 8.16-7.96 (m, 3H), 6.91 (d, J=2.9 Hz, 1H), 6.80 (dd, J=9.0, 2.7 Hz, 1H), 4.83 (wide d, J=48.4 Hz, 1H), 3.78 (t, J=4.8 Hz, 4H), 3.15 (t, J=4.8 Hz, 4H), 3.11-3.00 (m, 2H), 2.93-2.83 (m, 2H), 2.24-1.94 (br m, 4H). LCMS (m/z): 451.8 (MH+).

Example 30

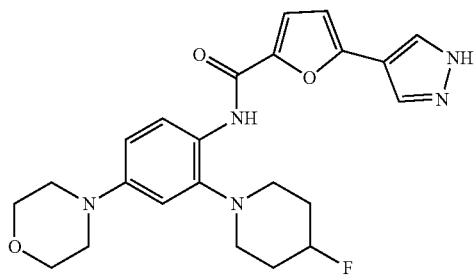 [SMILES: O=C(Nc1ccc(N2CCOCC2)cc1N1CCC(F)CC1)c1ccc(-c2cn[nH]c2)o1]

I-5: N-(2-(4-fluoropiperidin-1-yl)-4-morpholinophenyl)-5-(1H-pyrazol-4-yl)furan-2-carboxamide ¹H NMR (300 MHz, DMSO-d6) δ 9.31 (s, 1H), 8.12-8.05 (m, 3H), 7.31 (d, J=3.6 Hz, 1H), 6.90 (d, J=2.6 Hz, 1H), 6.82-6.74 (m, 2H), 4.89 (wide d, J=48.5 Hz, 1H), 3.81-3.72 (m, 4H), 3.16-3.10 (m, 4H), 3.10-2.99 (m, 2H), 2.92-2.81 (m, 2H), 2.25-1.93 (br m, 4H). LCMS (m/z): 440.7 (MH+).

Example 31

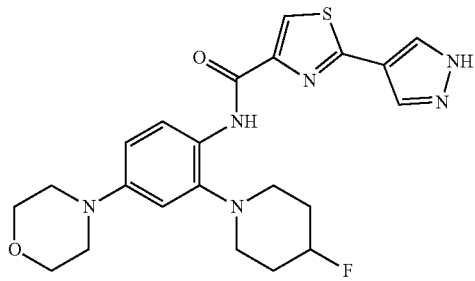 [SMILES: O=C(Nc1ccc(N2CCOCC2)cc1N1CCC(F)CC1)c1csc(-c2cn[nH]c2)n1]

I-6: N-(2-(4-fluoropiperidin-1-yl)-4-morpholinophenyl)-2-(1H-pyrazol-4-yl)thiazole-4-carboxamide ¹H NMR (300 MHz, DMSO-d6) δ 10.21 (s, 1H), 8.38-8.17 (m, 4H), 6.91 (d, J=2.7 Hz, 1H), 6.78 (dd, J=9.0, 2.7 Hz, 1H), 4.92 (wide d, J=48.5 Hz, 1H), 3.81-3.72 (m, 4H), 3.16-3.10 (m, 4H), 3.10-2.98 (m, 2H), 2.94-2.83 (m, 2H), 2.31-1.98 (br m, 4H). LCMS (m/z): 457.8 (MH+).

Example 32

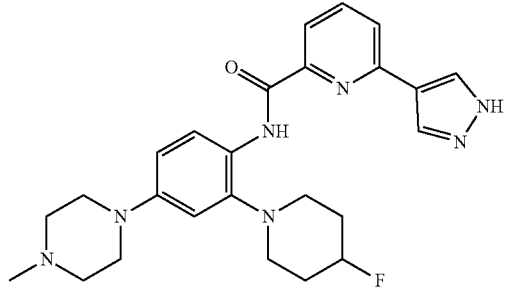 [SMILES: CN1CCN(c2ccc(NC(=O)c3cccc(-c4cn[nH]c4)n3)c(N3CCC(F)CC3)c2)CC1]

I-7: N-(2-(4-fluoropiperidin-1-yl)-4-(4-methylpiperazin-1-yl)phenyl)-6-(1H-pyrazol-4-yl)picolinamide ¹H NMR (300 MHz, DMSO-d6) δ 13.27 (s, 1H), 10.71 (s, 1H), 8.49 (s, 1H), 8.30 (d, J=8.9 Hz, 1H), 8.25 (s, 1H), 8.12-7.95 (m, 3H), 6.89 (d, J=2.7 Hz, 1H), 6.78 (dd, J=9.0, 2.6 Hz, 1H), 4.82 (wide d, J=48.8 Hz, 1H), 3.17 (t, J=5.0 Hz, 4H), 3.11-2.99 (m, 2H), 2.92-2.81 (m, 2H), 2.49 (t, J=5.0 Hz, 4H), 2.22-1.91 (br m, 4H). LCMS (m/z): 464.4 (MH+).

Example 33

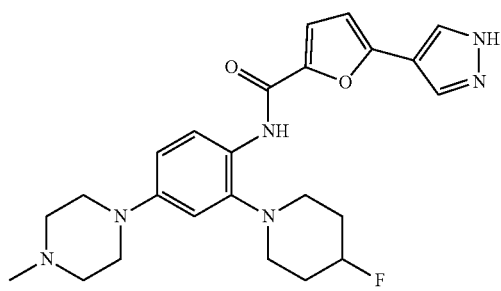 [SMILES: CN1CCN(c2ccc(NC(=O)c3ccc(-c4cn[nH]c4)o3)c(N3CCC(F)CC3)c2)CC1]

I-8: N-(2-(4-fluoropiperidin-1-yl)-4-(4-methylpiperazin-1-yl)phenyl)-5-(1H-pyrazol-4-yl)furan-2-carboxamide ¹H NMR (300 MHz, DMSO-d6) δ 13.28 (s, 1H), 9.30 (s, 1H), 8.23 (s, 1H), 8.06 (d, J=8.9 Hz, 1H), 7.95 (s, 1H), 7.30 (d, J=3.6 Hz, 1H), 6.87 (d, J=2.6 Hz, 1H), 6.80 (d, J=3.5 Hz, 1H), 6.75 (dd, J=9.0, 2.6 Hz, 1H), 4.89 (wide d, J=48.3 Hz, 1H), 3.15 (t, J=5.0 Hz, 4H), 3.09-2.99 (m, 2H), 2.92-2.82 (m, 2H), 2.49 (t, J=5.0 Hz, 4H), 2.26 (s, 3H), 2.22-1.93 (br m, 4H). LCMS (m/z): 453.7 (MH+).

Example 34

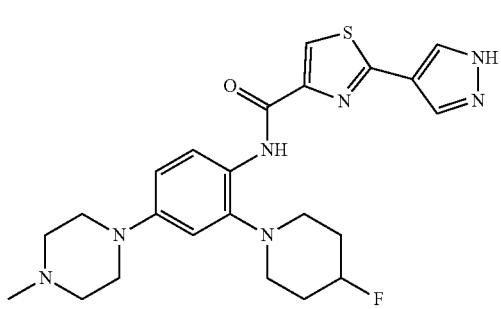 [SMILES: CN1CCN(c2ccc(NC(=O)c3csc(-c4cn[nH]c4)n3)c(N3CCC(F)CC3)c2)CC1]

I-9: N-(2-(4-fluoropiperidin-1-yl)-4-(4-methylpiper-azin-1-yl)phenyl)-2-(1H-pyrazol-4-yl)thiazole-4-carboxamide $^1$H NMR (300 MHz, DMSO-d6) δ 13.48 (s, 1H), 10.21 (s, 1H), 8.52-8.02 (m, 4H), 6.89 (d, J=2.6 Hz, 1H), 6.77 (dd, J=9.0, 2.6 Hz, 1H), 4.91 (wide d, J=48.2 Hz, 1H), 3.15 (t, J=5.0 Hz, 4H), 3.10-3.00 (m, 2H), 2.93-2.83 (m, 2H), 2.49 (t, J=5.0 Hz, 4H), 2.26 (s, 3H), 2.24-1.98 (br m, 4H). LCMS (m/z): 470.8 (MH+).

Example 35

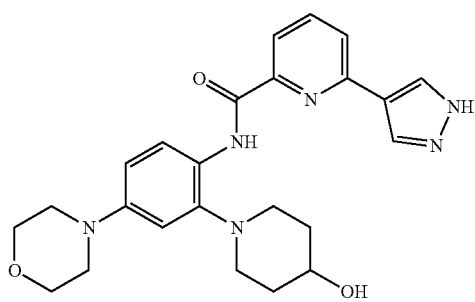 [SMILES: O=C(Nc1ccc(N2CCOCC2)cc1N1CCC(O)CC1)c1cccc(-c2cn[nH]c2)n1]

I-10: N-(2-(4-hydroxypiperidin-1-yl)-4-morpholino-phenyl)-6-(1H-pyrazol-4-yl)picolinamide $^1$H NMR (300 MHz, DMSO-d6) δ 10.69 (s, 1H), 8.39 (s, 2H), 8.32 (d, J=8.9 Hz, 1H), 8.14-7.95 (m, 3H), 6.90 (d, J=2.7 Hz, 1H), 6.77 (dd, J=9.0, 2.6 Hz, 1H), 3.81-3.70 (m, 5H), 3.17-3.02 (m, 6H), 2.82-2.71 (m, 2H), 2.02-1.90 (m, 2H), 1.79-1.65 (m, 2H). LCMS (m/z): 449.8 (MH+).

Example 36

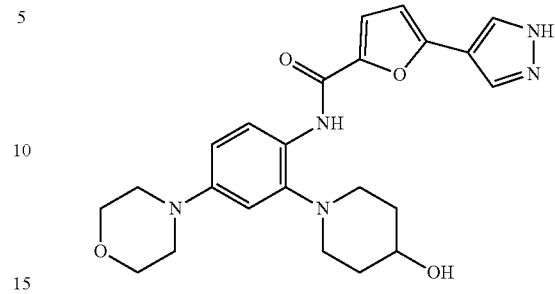

I-11: N-(2-(4-hydroxypiperidin-1-yl)-4-morpholino-phenyl)-5-(1H-pyrazol-4-yl)furan-2-carboxamide $^1$H NMR (300 MHz, DMSO-d6) δ 13.31 (s, 1H), 9.35 (s, 1H), 8.28-7.89 (m, 3H), 7.29 (d, J=3.5 Hz, 1H), 6.93-6.70 (m, 3H), 4.86 (d, J=3.3 Hz, 1H), 3.82-3.68 (m, 5H), 3.12 (t, J=4.8 Hz, 4H), 3.06-2.97 (m, 2H), 2.85-2.72 (m, 2H), 2.09-1.88 (m, 2H), 1.83-1.60 (m, 2H). LCMS (m/z): 438.7 (MH+).

Example 37

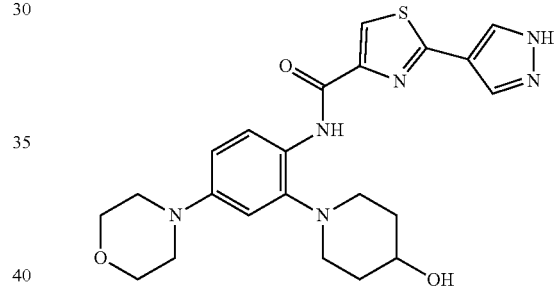

I-12: N-(2-(4-hydroxypiperidin-1-yl)-4-morpholino-phenyl)-2-(1H-pyrazol-4-yl)thiazole-4-carboxamide $^1$H NMR (300 MHz, DMSO-d6) δ 10.26 (s, 1H), 8.44-8.14 (m, 4H), 6.89 (d, J=2.7 Hz, 1H), 6.76 (dd, J=8.9, 2.7 Hz, 1H), 3.86-3.67 (m, 5H), 3.12 (t, J=4.8 Hz, 4H), 3.06-2.96 (m, 2H), 2.87-2.74 (m, 2H), 2.06-1.96 (m, 2H), 1.88-1.76 (m, 2H). LCMS (m/z): 455.9 (MH+).

Example 38

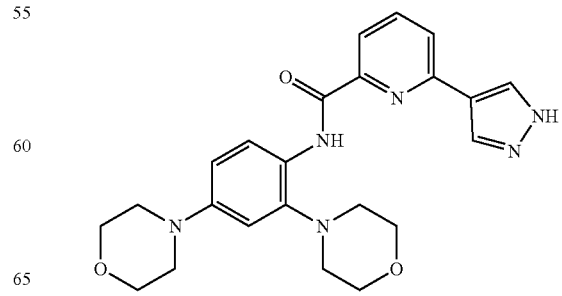

I-13: N-(2,4-dimorpholinophenyl)-6-(1H-pyrazol-4-yl)picolinamide

¹H NMR (300 MHz, DMSO-d6) δ 13.31 (s, 1H), 10.73 (s, 1H), 8.55 (s, 1H), 8.39-8.29 (m, 2H), 8.13-7.94 (m, 3H), 6.92 (d, J=2.6 Hz, 1H), 6.81 (dd, J=9.0, 2.6 Hz, 1H), 3.81 (dt, J=14.6, 4.5 Hz, 8H), 3.15 (t, J=4.8 Hz, 4H), 2.92 (t, J=4.5 Hz, 4H). LCMS (m/z): 435.1 (MH+).

Example 39

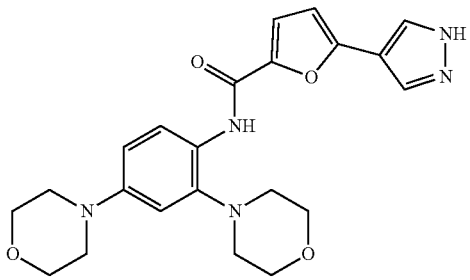 [SMILES: O=C(Nc1ccc(N2CCOCC2)cc1N1CCOCC1)c1ccc(-c2cn[nH]c2)o1]

I-14: N-(2,4-dimorpholinophenyl)-5-(1H-pyrazol-4-yl)furan-2-carboxamide

¹H NMR (300 MHz, DMSO-d6) δ 13.30 (s, 1H), 9.37 (s, 1H), 8.27 (s, 1H), 8.10 (d, J=8.8 Hz, 1H), 7.98 (s, 1H), 7.30 (d, J=3.6 Hz, 1H), 6.91 (d, J=2.6 Hz, 1H), 6.82-6.74 (m, 2H), 3.82 (dt, J=23.8, 4.6 Hz, 8H), 3.14 (t, J=4.8 Hz, 4H), 2.92 (t, J=4.6 Hz, 4H). LCMS (m/z): 424.8 (MH+).

Example 40

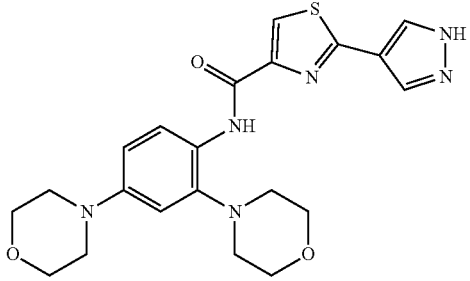 [SMILES: O=C(Nc1ccc(N2CCOCC2)cc1N1CCOCC1)c1csc(-c2cn[nH]c2)n1]

I-15: N-(2,4-dimorpholinophenyl)-2-(1H-pyrazol-4-yl)thiazole-4-carboxamide

¹H NMR (300 MHz, DMSO-d6) δ 13.49 (s, 1H), 10.26 (s, 1H), 8.50 (s, 1H), 8.36-8.29 (m, 2H), 8.10 (s, 1H), 6.93 (d, J=2.6 Hz, 1H), 6.80 (dd, J=8.9, 2.7 Hz, 1H), 3.92 (t, J=4.4 Hz, 4H), 3.78 (t, J=4.8 Hz, 4H), 3.14 (t, J=4.8 Hz, 4H), 2.92 (t, J=4.6 Hz, 4H). LCMS (m/z): 442.0 (MH+).

Example 41

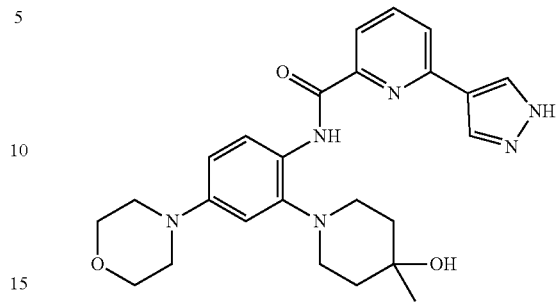

I-16: N-(2-(4-hydroxy-4-methylpiperidin-1-yl)-4-morpholinophenyl)-6-(1H-pyrazol-4-yl)picolinamide ¹H NMR (300 MHz, DMSO-d6) δ 13.28 (s, 1H), 10.75 (s, 1H), 8.50 (s, 1H), 8.34 (d, J=8.9 Hz, 1H), 8.27 (s, 1H), 8.12-7.92 (m, 3H), 6.91 (d, J=2.7 Hz, 1H), 6.77 (dd, J=9.0, 2.6 Hz, 1H), 4.26 (s, 1H), 3.78 (t, J=4.7 Hz, 4H), 3.17-3.00 (m, 6H), 2.78 (d, J=11.2 Hz, 2H), 1.81 (t, J=10.9 Hz, 2H), 1.62 (d, J=12.7 Hz, 2H), 1.15 (s, 3H). LCMS (m/z): 463.9 (MH+).

Example 42

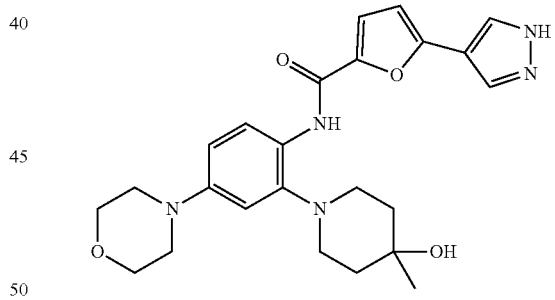

I-17: N-(2-(4-hydroxy-4-methylpiperidin-1-yl)-4-morpholinophenyl)-5-(1H-pyrazol-4-yl)furan-2-carboxamide ¹H NMR (300 MHz, DMSO-d6) δ 13.31 (s, 1H), 9.36 (s, 1H), 8.24 (s, 1H), 8.15 (d, J=8.9 Hz, 1H), 7.96 (s, 1H), 7.28 (d, J=3.6 Hz, 1H), 6.91 (d, J=2.7 Hz, 1H), 6.79 (d, J=3.6 Hz, 1H), 6.74 (dd, J=9.0, 2.6 Hz, 1H), 4.40 (s, 1H), 3.81-3.74 (m, 4H), 3.16-3.00 (m, 6H), 2.81-2.71 (m, 2H), 1.84-1.67 (m, 4H), 1.25 (s, 3H). LCMS (m/z): 453.0 (MH+).

Example 43

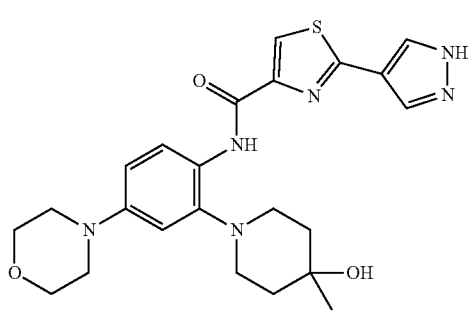 [SMILES: CC1(O)CCN(c2cc(N3CCOCC3)ccc2NC(=O)c2csc(-c3cn[nH]c3)n2)CC1]

I-18: N-(2-(4-hydroxy-4-methylpiperidin-1-yl)-4-morpholinophenyl)-2-(1H-pyrazol-4-yl)thiazole-4-carboxamide $^1$H NMR (300 MHz, DMSO-d6) δ 13.48 (s, 1H), 10.25 (s, 1H), 8.48 (s, 1H), 8.35-8.28 (m, 2H), 8.10 (s, 1H), 6.91 (d, J=2.7 Hz, 1H), 6.75 (dd, J=8.9, 2.6 Hz, 1H), 4.41 (s, 1H), 3.89-3.67 (m, 4H), 3.15-3.00 (m, 6H), 2.84-2.70 (m, 2H), 1.98-1.63 (m, 4H), 1.28 (s, 3H). LCMS (m/z): 469.6 (MH+).

Example 44

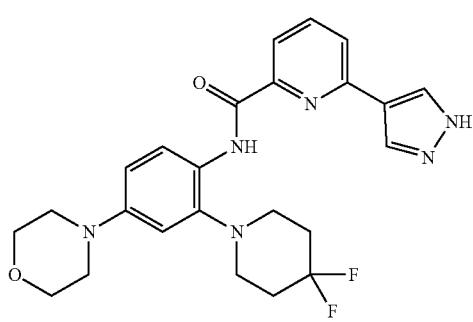 [SMILES: O=C(Nc1ccc(N2CCOCC2)cc1N1CCC(F)(F)CC1)c1cccc(-c2cn[nH]c2)n1]

I-19: N-(2-(4,4-difluoropiperidin-1-yl)-4-morpholinophenyl)-6-(1H-pyrazol-4-yl)picolinamide $^1$H NMR (300 MHz, DMSO-d6) δ 13.26 (s, 1H), 10.66 (s, 1H), 8.49 (s, 1H), 8.29 (d, J=8.9 Hz, 1H), 8.22 (s, 1H), 8.11-7.95 (m, 3H), 6.94 (d, J=2.0 Hz, 1H), 6.81 (dd, J=9.0, 2.5 Hz, 1H), 3.89-3.71 (m, 4H), 3.15 (t, J=4.4 Hz, 4H), 3.04 (t, J=5.7 Hz, 4H), 2.32-2.08 (m, 4H). LCMS (m/z): 470.0 (MH+).

Example 45

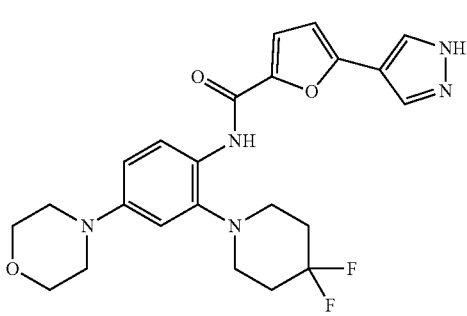 [SMILES: O=C(Nc1ccc(N2CCOCC2)cc1N1CCC(F)(F)CC1)c1ccc(-c2cn[nH]c2)o1]

I-20: N-(2-(4,4-difluoropiperidin-1-yl)-4-morpholinophenyl)-5-(1H-pyrazol-4-yl)furan-2-carboxamide $^1$H NMR (300 MHz, DMSO-d6) δ 13.29 (s, 1H), 9.29 (s, 1H), 8.24 (s, 1H), 8.05 (d, J=8.9 Hz, 1H), 7.95 (s, 1H), 7.32 (d, J=3.6 Hz, 1H), 6.92 (d, J=2.6 Hz, 1H), 6.82-6.74 (m, 2H), 3.86-3.69 (m, 4H), 3.18-3.11 (m, 4H), 3.04 (t, J=5.5 Hz, 4H), 2.33-2.16 (m, 4H). LCMS (m/z): 459.0 (MH+).

Example 46

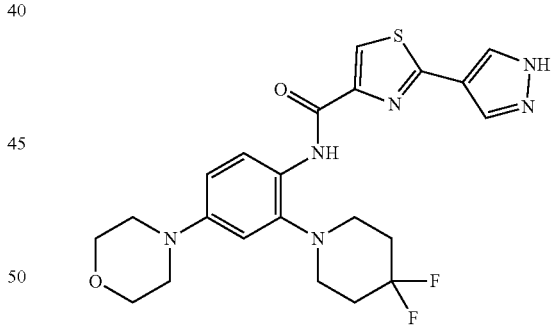

I-21: N-(2-(4,4-difluoropiperidin-1-yl)-4-morpholinophenyl)-2-(1H-pyrazol-4-yl)thiazole-4-carboxamide $^1$H NMR (300 MHz, DMSO-d6) δ 13.50 (s, 1H), 10.18 (s, 1H), 8.44 (s, 1H), 8.34-8.27 (m, 2H), 8.04 (s, 1H), 6.96 (d, J=2.7 Hz, 1H), 6.80 (dd, J=9.0, 2.6 Hz, 1H), 3.77 (t, J=4.8 Hz, 4H), 3.14 (t, J=4.8 Hz, 4H), 3.05 (t, J=5.4 Hz, 4H), 2.40-2.25 (m, 4H). LCMS (m/z): 476.0 (MH+).

Example 47

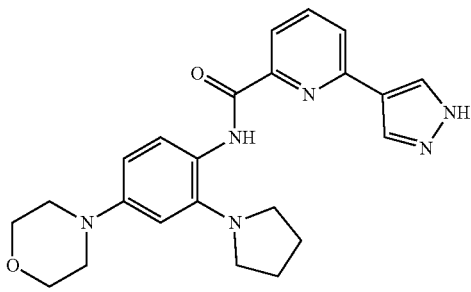 [SMILES: O=C(Nc1ccc(N2CCOCC2)cc1N1CCCC1)c1cccc(-c2cn[nH]c2)n1]

I-22: N-(4-morpholino-2-(pyrrolidin-1-yl)phenyl)-6-(1H-pyrazol-4-yl)picolinamide $^1$H NMR (300 MHz, DMSO-d6) δ 13.25 (s, 1H), 10.58 (s, 1H), 8.52 (s, 1H), 8.24 (s, 1H), 8.11-7.91 (m, 4H), 6.76 (d, J=2.6 Hz, 1H), 6.66 (dd, J=8.8, 2.6 Hz, 1H), 3.88-3.70 (m, 4H), 3.24-3.11 (m, 8H), 1.97 (q, J=3.3 Hz, 4H). LCMS (m/z): 419.9 (MH+).

Example 48

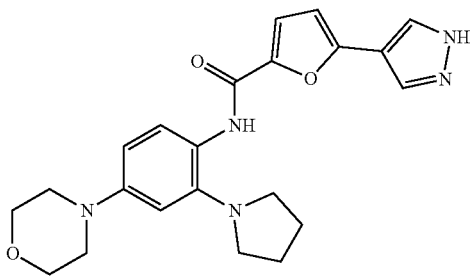 [SMILES: O=C(Nc1ccc(N2CCOCC2)cc1N1CCCC1)c1ccc(-c2cn[nH]c2)o1]

I-23: N-(4-morpholino-2-(pyrrolidin-1-yl)phenyl)-5-(1H-pyrazol-4-yl)furan-2-carboxamide $^1$H NMR (300 MHz, DMSO-d6) δ 13.19 (s, 1H), 9.47 (s, 1H), 8.26 (s, 1H), 7.97 (s, 1H), 7.27 (d, J=3.6 Hz, 1H), 7.16 (d, J=8.3 Hz, 1H), 6.72 (d, J=3.5 Hz, 1H), 6.50-6.36 (m, 2H), 3.77 (t, J=4.7 Hz, 4H), 3.30-3.23 (m, 4H), 3.13 (t, J=4.7 Hz, 4H), 1.90-1.84 (m, 4H). LCMS (m/z): 408.6 (MH+).

Example 49

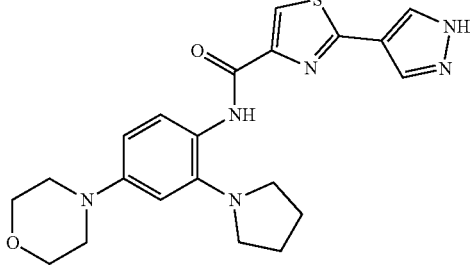

I-24: N-(4-morpholino-2-(pyrrolidin-1-yl)phenyl)-2-(1H-pyrazol-4-yl)thiazole-4-carboxamide $^1$H NMR (300 MHz, DMSO-d6) δ 13.43 (s, 1H), 9.85 (s, 1H), 8.46 (s, 1H), 8.28 (s, 1H), 8.06 (s, 1H), 7.92 (d, J=8.8 Hz, 1H), 6.72 (d, J=2.6 Hz, 1H), 6.63 (dd, J=8.8, 2.6 Hz, 1H), 3.88-3.67 (m, 4H), 3.18-3.09 (m, 8H), 2.01-1.93 (m, 4H). LCMS (m/z): 425.5 (MH+).

Example 50

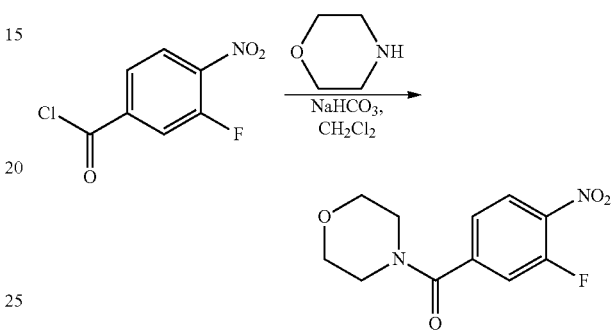

(3-fluoro-4-nitrophenyl)(morpholino)methanone

To a CH$_2$Cl$_2$ (20 mL) solution of 3-fluoro-4-nitrobenzoyl chloride (2.04 g, 10 mmol) and NaHCO$_3$ (924 mg, 11 mmol), morpholine (908 μL, 10.5 mmol) was added dropwise with cooling in an ice bath. After 1.5 hours, the ice bath was removed and the reaction was allowed to warm up to room temperature. After 22 hours, the reaction was quenched by H$_2$O and saturated aqueous NH$_4$Cl solution (about 20 mL). Two layers were separated and the aqueous layer was extracted with CH$_2$Cl$_2$ (10 mL×2). The organic layers were combined, dried (Na$_2$SO$_4$), and filtered, and the solvent was removed in vacuo. Compound (3-fluoro-4-nitrophenyl)(morpholino)methanone was obtained as a bright orange color thick oil and was used without further purification: 2.76 g; $^1$H NMR (300 MHz, Chloroform-d) δ 8.13 (dd, J=8.6, 7.2 Hz, 1H), 7.38-7.31 (m, 2H), 3.84-3.40 (m, 8H).

Example 51

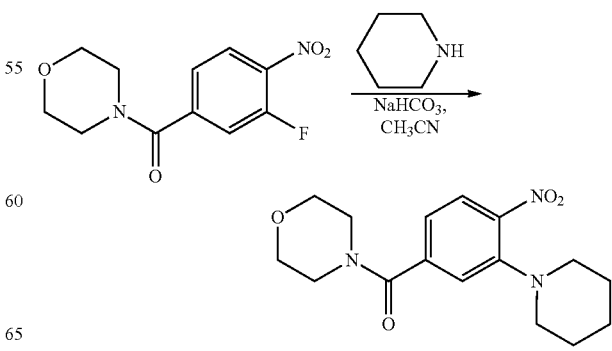

morpholino(4-nitro-3-(piperidin-1-yl)phenyl)methanone

A CH₃CN (10 mL) solution of (3-fluoro-4-nitrophenyl)(morpholino)methanone (about 10 mmol), piperidine (1.09 mL, 11 mmol) and NaHCO₃ (1.0 g, 12 mmol) was stirred at 70° C. for 2 hours. Volatiles were removed in vacuo and product was purified by silica gel column chromatography. Compound morpholino(4-nitro-3-(piperidin-1-yl)phenyl)methanone was obtained as a reddish-orange color solid: 2.75 g (86% yield over 2 steps); ¹H NMR (300 MHz, Chloroform-d) δ 7.77 (d, J=8.2 Hz, 1H), 7.13 (d, J=1.6 Hz, 1H), 6.88 (dd, J=8.2, 1.6 Hz, 1H), 3.84-3.60 (m, 6H), 3.40 (br s, 2H), 3.07-3.03 (m, 4H), 1.75-1.68 (m, 4H), 1.64-1.58 (m, 2H); LRMS (M+H) m/z 320.60.

Example 52

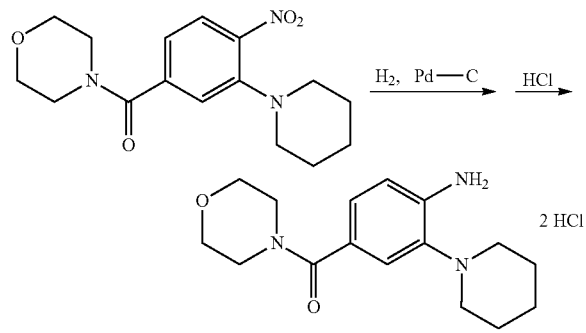

(4-amino-3-(piperidin-1-yl)phenyl)(morpholino)methanone Di-Hydrogen Chloride In a Parr flask under 30 psi of H₂, an EtOAc (30 mL) solution of morpholino(4-nitro-3-(piperidin-1-yl)phenyl)methanone (1.12 g, 3.5 mmol) and Pd—C (10% Pd on C, 50% wet, 0.2 g) was shaken at room temperature for 16 hours. The reaction went to completion as monitored by LC-MS. Solid was removed by filtration through a celite pad washed with EtOAc and MeOH. Filtrate was collected in a receiving flask containing 3.5 mL of 4M HCl-dioxane solution, and solvent was removed in vacuo. Compound (4-amino-3-(piperidin-1-yl)phenyl)(morpholino)methanone di-hydrogen chloride was obtained as a pale yellow sticky solid: 1.48 g (>99% yield); ¹H NMR (300 MHz, Methanol-d₄) δ 7.20 (d, J=2.0 Hz, 1H), 7.11 (dd, J=8.2, 2.0 Hz, 1H), 6.87 (d, J=8.2 Hz, 1H), 3.81-3.75 (m, 8H), 2.96-2.93 (m, 4H), 1.89-1.82 (m, 4H), 1.75-1.70 (m, 2H); LRMS (M+H) m/z 290.53.

Example 53

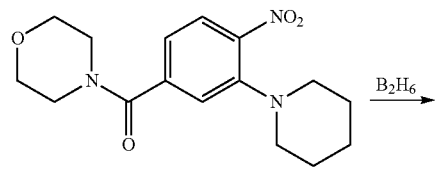

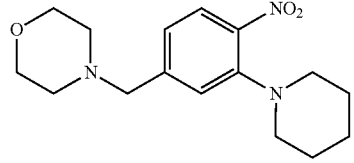

4-(4-nitro-3-(piperidin-1-yl)benzyl)morpholine

To a THF (20 mL) solution of morpholino(4-nitro-3-(piperidin-1-yl)phenyl)methanone (1.277 g, 4 mmol), B₂H₆-THF solution (1M in THF, 12 mL, 12 mmol) was added at room temperature, and the solution was stirred at 50° C. for 16 hours. The reaction went to completion as monitored by LC-MS, and was quenched by H₂O and 1N HCl aqueous solution (about 5 mL). The mixture was stirred at 30° C. for 2 hours. Most of the THF was removed by rotary evaporation under reduced pressure, and the resulting aqueous layer was basified with 1N NaOH solution, then extracted twice with EtOAc. The combined organic layers were dried (Na₂SO₄), filtered, and the solvent was removed in vacuo. Product was purified by silica gel column chromatography, and compound 4-(4-nitro-3-(piperidin-1-yl)benzyl)morpholine was obtained as an orange color thick oil: 702.9 mg; ¹H NMR (300 MHz, Chloroform-d) δ 7.73 (d, J=8.3 Hz, 1H), 7.08 (d, J=1.6 Hz, 1H), 6.93 (dd, J=8.3, 1.6 Hz, 1H), 3.74-3.71 (m, 4H), 3.48 (s, 2H), 3.04-3.00 (m, 4H), 2.46-2.43 (m, 4H), 1.76-1.69 (m, 4H), 1.63-1.60 (m, 2H); LRMS (M+H) m/z 306.54. An impure fraction (about 80% pure) was also obtained: 562 mg.

Example 54

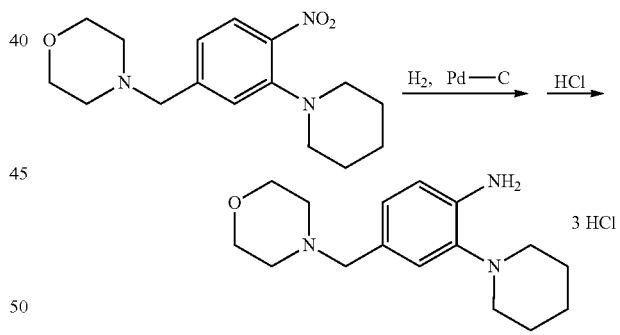

4-(morpholinomethyl)-2-(piperidin-1-yl)aniline Tri-Hydrogen Chloride

In a Parr flask under 30 psi of H₂, an EtOAc (25 mL) solution of 4-(4-nitro-3-(piperidin-1-yl)benzyl)morpholine (702 mg, 2.3 mmol) and Pd—C (10% Pd on C, 50% wet, 0.2 g) was shaken at room temperature for 18 hours. The reaction went to completion as monitored by LC-MS. Solid was removed by filtration through a celite pad, washing with EtOAc and MeOH. Filtrate was collected in a receiving flask containing 2 mL of 4M HCl-dioxane solution, and solvent was removed in vacuo. Compound 4-(morpholinomethyl)-2-(piperidin-1-yl)aniline tri-hydrogen chloride was obtained as an off-white solid: 820.1 mg (93% yield); ¹H NMR (300

MHz, Methanol-d₄) δ 7.92 (d, J=2.0 Hz, 1H), 7.52 (dd, J=8.3, 2.0 Hz, 1H), 7.25 (d, J=8.3 Hz, 1H), 4.44 (s, 2H), 4.4.19-4.13 (m, 4H), 3.99-3.90 (m, 4H), 3.66-3.63 (m, 4H), 2.22-2.15 (m, 4H), 1.95-1.88 (m, 2H); LRMS (M+H) m/z 276.61.

Example 55

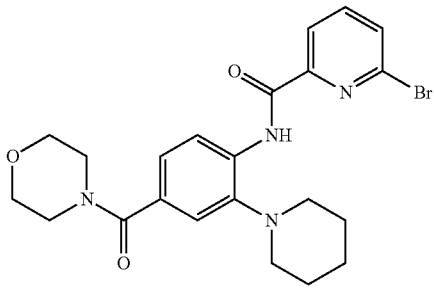 [SMILES: O=C(Nc1ccc(C(=O)N2CCOCC2)cc1N1CCCCC1)c1cccc(Br)n1]

6-bromo-N-(4-(morpholine-4-carbonyl)-2-(piperidin-1-yl)phenyl)picolinamide

The compound was prepared according to general procedure (A): 1 mmol scale, 89% yield.

¹H NMR (300 MHz, Chloroform-d) δ 11.13 (s, 1H), 8.59 (d, J=8.2 Hz, 1H), 8.26 (dd, J=7.5, 0.7 Hz, 1H), 7.79 (dd, J=7.8, 7.8 Hz, 1H), 7.68 (dd, J=7.9, 0.8 Hz, 1H), 7.30 (ddd, J=2.0, 0.5, 0.5 Hz, 1H), 7.20 (dd, J=8.5, 2.0 Hz, 1H), 3.71 (br s, 8H), 2.90-2.87 (m, 4H), 1.95-1.92 (m, 4H), 1.66 (br s, 2H); LRMS (M+H) m/z 473.70, 475.86.

Example 56

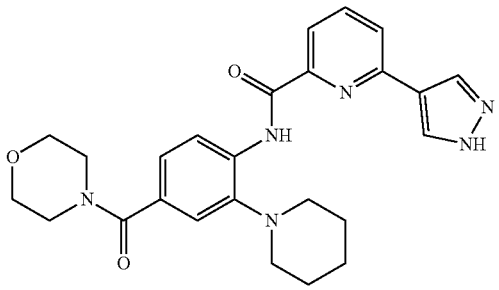 [SMILES: O=C(Nc1ccc(C(=O)N2CCOCC2)cc1N1CCCCC1)c1cccc(-c2cn[nH]c2)n1]

I-45: N-(4-(morpholine-4-carbonyl)-2-(piperidin-1-yl)phenyl)-6-(1H-pyrazol-4-yl)picolinamide The compound was prepared according to general procedure (B): 0.1 mmol scale, 65% yield.

¹H NMR (300 MHz, Chloroform-d) δ 12.6 (v br s, 1H), 11.04 (s, 1H), 8.61 (d, J=8.3 Hz, 1H), 8.26 (s, 2H), 8.17 (dd, J=7.7, 1.0 Hz, 1H), 7.91 (dd, J=7.8, 7.8 Hz, 1H), 7.68 (dd, J=7.9, 1.1 Hz, 1H), 7.31 (d, J=1.9 Hz, 1H), 7.21 (dd, J=8.3, 1.9 Hz, 1H), 3.71-3.67 (m, 8H), 2.91-2.87 (m, 4H), 1.84-1.77 (m, 4H), 1.63-1.54 (m, 2H); LRMS (M+H) m/z 461.77.

Example 57

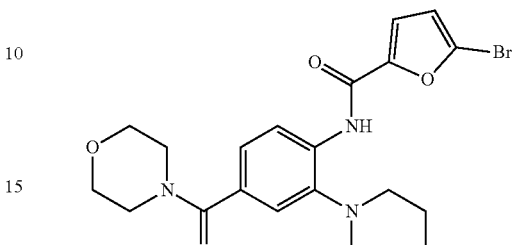

5-bromo-N-(4-(morpholine-4-carbonyl)-2-(piperidin-1-yl)phenyl)furan-2-carboxamide The compound was prepared according to general procedure (A): 1 mmol scale, 91% yield.

¹H NMR (300 MHz, Chloroform-d) δ 9.67 (s, 1H), 8.47 (d, J=8.4 Hz, 1H), 7.30 (br d, J=2.0 Hz, 1H), 7.19 (d, J=3.5 Hz, 1H), 7.19-7.16 (m, partially overlapped, 1H), 6.52 (d, J=3.5 Hz, 1H), 3.73-3.63 (m, 8H), 2.89-2.85 (m, 4H), 1.88-1.81 (m, 4H), 1.66 (br s, 2H); LRMS (M+H) m/z 462.67, 464.80.

Example 58

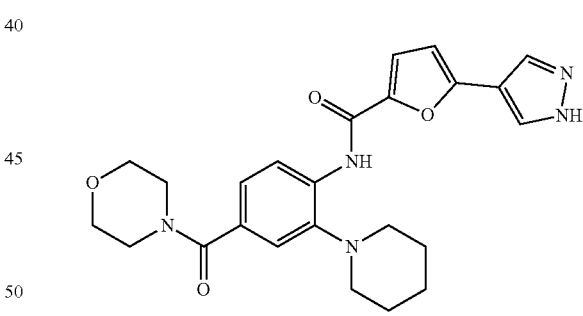

I-46: N-(4-(morpholine-4-carbonyl)-2-(piperidin-1-yl)phenyl)-5-(1H-pyrazol-4-yl)furan-2-carboxamide The compound was prepared according to general procedure (B): 0.1 mmol scale, 69% yield.

¹H NMR (300 MHz, Chloroform-d) δ 12.4 (v br s, 1H), 9.67 (s, 1H), 8.53 (d, J=8.4 Hz, 1H), 7.93 (s, 2H), 7.32 (d, J=1.9 Hz, 1H), 7.30 (d, J=3.6 Hz, 1H), 7.20 (dd, J=8.4, 1.9 Hz, 1H), 6.56 (d, J=3.6 Hz, 1H), 3.73-3.57 (m, 8H), 2.91-2.87 (m, 4H), 1.88-1.80 (m, 4H), 1.70-1.64 (m, 2H); LRMS (M+H) m/z 450.81.

Example 59

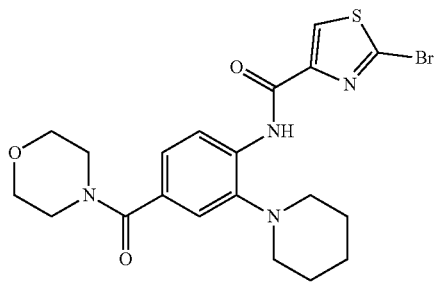 [SMILES: O=C(Nc1ccc(C(=O)N2CCOCC2)cc1N1CCCCC1)c1csc(Br)n1]

2-bromo-N-(4-(morpholine-4-carbonyl)-2-(piperidin-1-yl)phenyl)thiazole-4-carboxamide The compound was prepared according to general procedure (A): 1 mmol scale, 78% yield.

$^1$H NMR (300 MHz, Chloroform-d) δ 10.44 (s, 1H), 8.51 (d, J=8.5 Hz, 1H), 8.14 (s, 1H), 7.29 (d, J=1.7 Hz, 1H), 7.18 (dd, J=8.5, 1.7 Hz, 1H), 3.73-3.63 (m, 8H), 289-2.85 (m, 4H), 1.91-1.83 (m, 4H), 1.68-1.61 (m, 2H); LRMS (M+H) m/z 479.65, 481.65.

Example 60

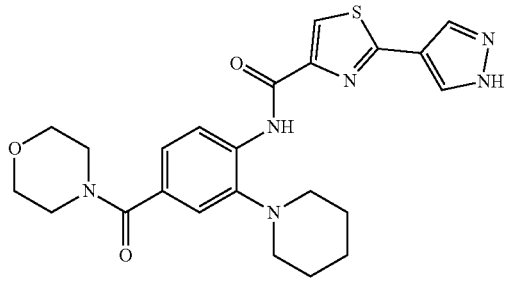 [SMILES: O=C(Nc1ccc(C(=O)N2CCOCC2)cc1N1CCCCC1)c1csc(-c2cn[nH]c2)n1]

I-47: N-(4-(morpholine-4-carbonyl)-2-(piperidin-1-yl)phenyl)-2-(1H-pyrazol-4-yl)thiazole-4-carboxamide The compound was prepared according to general procedure (B): 0.1 mmol scale, 70% yield.

$^1$H NMR (300 MHz, Chloroform-d) δ 12.6 (v br s, 1H), 10.58 (s, 1H), 8.58 (d, J=8.3 Hz, 1H), 8.12 (s, 1H), 8.08 (s, 2H), 7.30 (d, J=1.9 Hz, 1H), 7.19 (dd, J=8.3, 1.9 Hz, 1H), 3.74-3.60 (m, 8H), 2.91-2.87 (m, 4H), 1.91-1.84 (m, 4H), 1.70-1.63 (m, 2H); LRMS (M+H) m/z 467.65.

Example 61

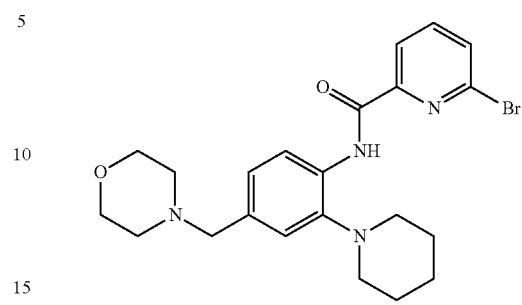

6-bromo-N-(4-(morpholinomethyl)-2-(piperidin-1-yl)phenyl)picolinamide

The compound was prepared according to general procedure (A): 0.8 mmol scale, 56% yield.

$^1$H NMR (300 MHz, Chloroform-d) δ 11.06 (s, 1H), 8.49 (d, J=8.2 Hz, 1H), 8.25 (dd, J=7.5, 1.0 Hz, 1H), 7.79-7.74 (m, 1H), 7.65 (dd, J=7.9, 1.0 Hz, 1H), 7.16 (d, J=1.9 Hz, 1H), 7.11 (dd, J=8.1, 1.9 Hz, 1H), 3.74-3.71 (m, 4H), 3.48 (s, 2H), 2.90-2.86 (m, 4H), 2.47-2.44 (m, 4H), 1.96-1.89 (m, 4H), 1.72-1.61 (m, 2H); LRMS (M+H) m/z 459.68.

Example 62

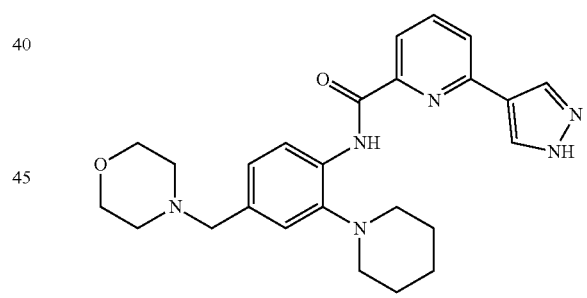

I-48: N-(4-(morpholinomethyl)-2-(piperidin-1-yl)phenyl)-6-(1H-pyrazol-4-yl)picolinamide The compound was prepared according to general procedure (B): 0.1 mmol scale, 40% yield.

$^1$H NMR (300 MHz, Chloroform-d) δ 10.96 (s, 1H), 8.51 (d, J=8.2 Hz, 1H), 8.27 (s, 2H), 8.18 (dd, J=7.7, 1.1 Hz, 1H), 7.90 (dd, J=7.8, 7.8 Hz, 1H), 7.67 (dd, J=7.9, 1.1 Hz, 1H), 7.15-7.10 (m, 2H), 3.74-3.71 (m, 4H), 3.48 (s, 2H), 2.91-2.87 (m, 4H), 2.47-2.44 (m, 4H), 1.84-1.76 (m, 4H), 1.93-1.55 (m, 2H); LRMS (M+H) m/z 447.74.

Example 63

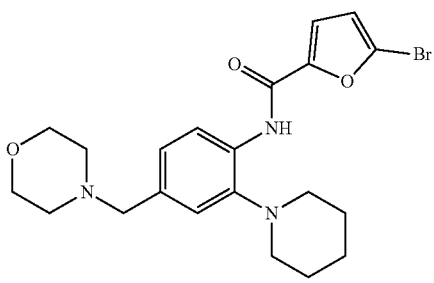 [SMILES: O=C(Nc1ccc(CN2CCOCC2)cc1N1CCCCC1)c1ccc(Br)o1]

5-bromo-N-(4-(morpholinomethyl)-2-(piperidin-1-yl)phenyl)furan-2-carboxamide

The compound was prepared according to general procedure (A): 0.8 mmol scale, 45% yield.

$^1$H NMR (300 MHz, Chloroform-d) δ 9.62 (s, 1H), 8.37 (d, J=8.2 Hz, 1H), 7.16 (d, J=3.5 Hz, 1H), 7.16-7.14 (m, partially overlapped, 1H), 7.09 (dd, J=8.3, 1.8 Hz, 1H), 6.50 (d, J=3.5 Hz, 1H), 3.74-3.71 (m, 4H), 3.48 (s, 2H), 2.87-2.84 (m, 4H), 2.48-2.45 (m, 4H), 1.87-1.80 (m, 4H), 1.69-1.62 (m, 2H); LRMS (M+H) m/z 448.66.

Example 64

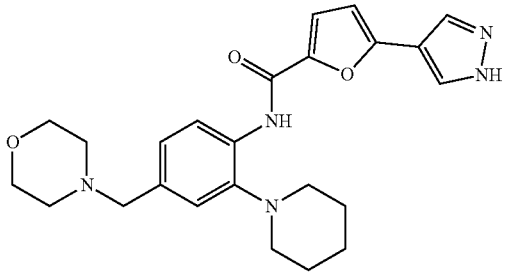 [SMILES: O=C(Nc1ccc(CN2CCOCC2)cc1N1CCCCC1)c1ccc(-c2cn[nH]c2)o1]

I-49: N-(4-(morpholinomethyl)-2-(piperidin-1-yl)phenyl)-5-(1H-pyrazol-4-yl)furan-2-carboxamide The compound was prepared according to general procedure (B): 0.1 mmol scale, 22% yield.

$^1$H NMR (300 MHz, Chloroform-d) δ 9.62 (s, 1H), 8.43 (d, J=8.2 Hz, 1H), 7.93 (s, 2H), 7.27 (d, J=3.6 Hz, 1H), 7.16 (d, J=1.9 Hz, 1H), 7.11 (dd, J=8.3, 1.9 Hz, 1H), 6.54 (d, J=3.6 Hz, 1H), 3.74-3.70 (m, 4H), 3.47 (s, 2H), 2.89-2.86 (m, 4H), 2.46-2.43 (m, 4H), 1.87-1.79 (m, 4H), 1.70-1.64 (m, 2H); LRMS (M+H) m/z 436.79.

Example 65

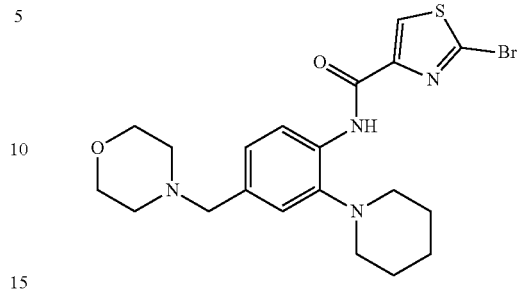

2-bromo-N-(4-(morpholinomethyl)-2-(piperidin-1-yl)phenyl)thiazole-4-carboxamide

The compound was prepared according to general procedure (A): 0.8 mmol scale, 76% yield.

$^1$H NMR (300 MHz, Chloroform-d) δ 10.38 (s, 1H), 8.42 (d, J=8.2 Hz, 1H), 8.11 (s, 1H), 7.14 (d, J=1.8 Hz, 1H), 7.09 (dd, J=8.2, 1.8 Hz, 1H), 3.74-3.71 (m, 4H), 3.48 (s, 2H), 2.88-2.84 (m, 4H), 2.48-2.45 (m, 4H), 1.90-1.82 (m, 4H), 1.68-1.61 (m, 2H); LRMS (M+H) m/z 465.66

Example 66

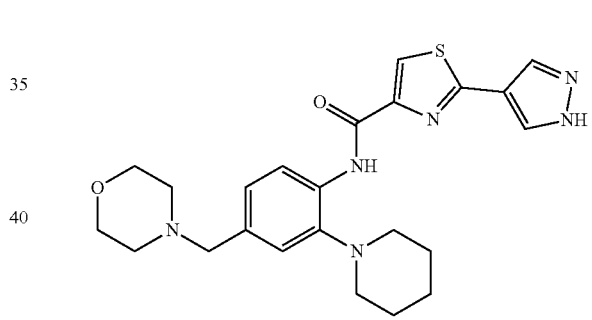

I-50: N-(4-(morpholinomethyl)-2-(piperidin-1-yl)phenyl)-2-(1H-pyrazol-4-yl)thiazole-4-carboxamide The compound was prepared according to general procedure (B): 0.1 mmol scale, 18% yield.

$^1$H NMR (300 MHz, Chloroform-d) δ 10.52 (s, 1H), 8.48 (d, J=8.2 Hz, 1H), 8.10 (s, 2H), 8.10 (s, 1H), 7.14 (d, J=1.8 Hz, 1H), 7.11 (dd, J=8.1, 1.8 Hz, 1H), 3.74-3.71 (m, 4H), 3.47 (s, 2H), 2.91-2.87 (m, 4H), 2.47-2.44 (m, 4H), 1.89-1.84 (m, 4H), 1.71-1.63 (m, 2H); LRMS (M+H) m/z 453.72.

Example 67

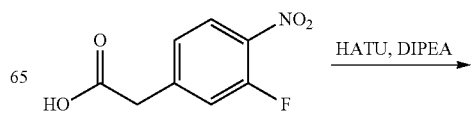

-continued

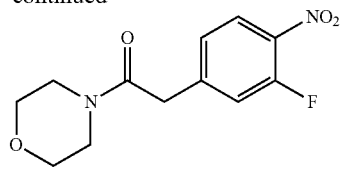

2-(3-fluoro-4-nitrophenyl)-1-morpholinoethan-1-one

To a CH$_2$Cl$_2$ (10 mL) solution of 2-(3-fluoro-4-nitrophenyl)acetic acid (995.7 mg, 5 mmol) and morpholine (454 μL, 5.25 mmol), HATU (2.09 g, 5.5 mmol) and NaHCO$_3$ (504 mg, 6 mmol) were added, and the solution was stirred at room temperature. Additional morpholine (0.2 mL) was added at 16 hours, 19 hours and 20 hours. At 23 hours, the reaction went to completion as monitored by LC-MS. Solvent was removed by rotary evaporation under reduced pressure, and the product was purified by silica gel column chromatography. Compound 2-(3-fluoro-4-nitrophenyl)-1-morpholinoethan-1-one was obtained as a light yellow oil and was used without further purification: $^1$H NMR (300 MHz, Chloroform-d) δ 8.05 (dd, J=8.1, 8.1 Hz, 1H), 7.24-7.15 (m, 2H), 3.77 (s, 2H), 3.71-3.63 (m, 6H), 3.50-3.47 (m, 2H); LRMS (M+H) m/z 269.50.

Example 68

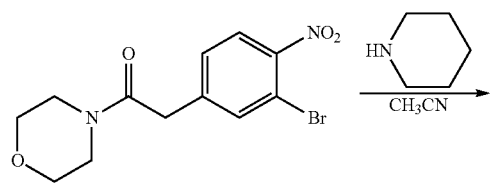

1-morpholino-2-(4-nitro-3-(piperidin-1-yl)phenyl)
ethan-1-one

A CH$_3$CN (10 mL) solution of 2-(3-fluoro-4-nitrophenyl)-1-morpholinoethan-1-one (about 5 mmol) and piperidine (543 μL, 5.5 mmol) was stirred at 70° C. After 4 hours, additional piperidine (0.2 mL) was added and the reaction went to completion at 6 hours as monitored by LC-MS. Volatiles were removed by rotary evaporation and product was purified by silica gel column chromatography. Compound 1-morpholino-2-(4-nitro-3-(piperidin-1-yl)phenyl) ethan-1-one was obtained as a brownish-orange color thick oil: 1.41 g (85% yield over 2 steps); $^1$H NMR (300 MHz, Chloroform-d) δ 7.75 (d, J=8.3 Hz, 1H), 6.98 (d, J=1.6 Hz, 1H), 6.79 (dd, J=8.3, 1.8 Hz, 1H), 3.71 (s, 2H), 3.67-3.65 (m, 4H), 3.60-3.57 (m, 2H), 3.46-3.43 (m, 2H), 3.03-3.00 (m, 4H), 1.74-1.67 (m, 4H), 1.62-1.57 (m, 2H); LRMS (M+H) m/z 334.60.

Example 69

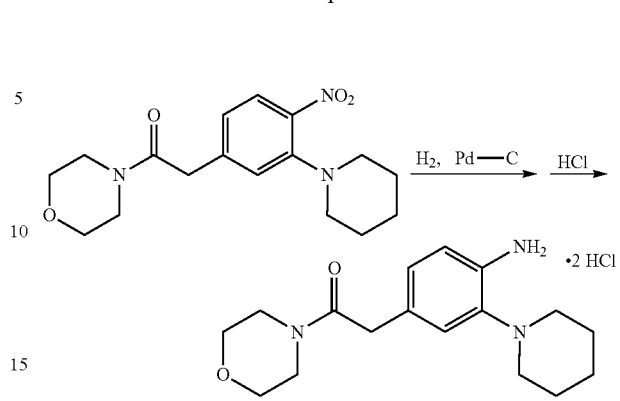

2-(4-amino-3-(piperidin-1-yl)phenyl)-1-morpholinoethan-1-one Di-Hydrogen Chloride In a Parr flask under 30 psi of H$_2$, an EtOAc (20 mL) solution of 1-morpholino-2-(4-nitro-3-(piperidin-1-yl)phenyl)ethan-1-one (500 mg, 1.5 mmol) and Pd—C (10% Pd on C, 50% wet, 0.15 g) was shaken at room temperature for 16 hours. The reaction went to completion as monitored by LC-MS. Solid was removed by filtration through a celite pad, washing with EtOAc. Filtrate was collected in a receiving flask containing 1 mL of 4M HCl-dioxane solution, and solvent was removed in vacuo. Compound 2-(4-amino-3-(piperidin-1-yl)phenyl)-1-morpholinoethan-1-one di-hydrogen chloride was obtained as a pale yellow sticky solid: 455 mg (>99% yield); $^1$H NMR (300 MHz, Methanol-d$_4$) δ 7.69 (d, J=1.3 Hz, 1H), 7.373-3.370 (m, 2H), 3.91 (s, 2H), 3.70-3.61 (m, 8H), 3.57-3.53 (m, 4H), 2.18-2.10 (m, 4H), 1.84-1.76 (m, 2H); LRMS (M+H) m/z 304.56.

Example 70

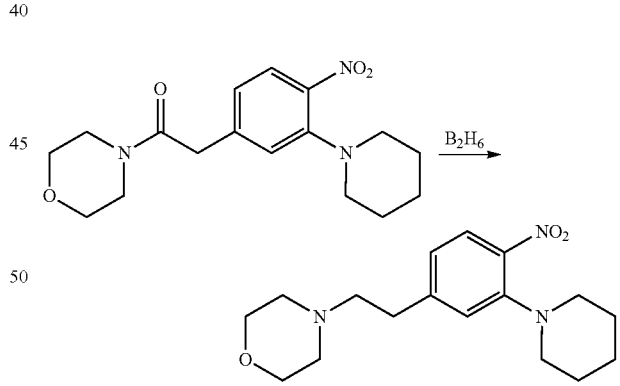

4-(4-nitro-3-(piperidin-1-yl)phenethyl)morpholine

To a THF (20 mL) solution of 1-morpholino-2-(4-nitro-3-(piperidin-1-yl)phenyl)ethan-1-one (0.9 g, 2.7 mmol), B$_2$H$_6$-THF solution (1M in THF, 8.1 mL, 8.1 mmol) was added at room temperature. After 2 hours, the reaction went to completion as monitored by LC-MS, and was quenched by H$_2$O and 1N HCl aqueous solution (about 5 mL). The mixture was stirred at room temperature for 18 hours. Most of the THF was removed by rotary evaporation under reduced pressure. The aqueous layer was basified with saturated aqueous NaHCO₃ solution, and then extracted with EtOAc (20 mL×2). Combined organic layers were dried (Na₂SO₄), filtered, and the solvent was removed in vacuo. Product was purified by silica gel column chromatography, and compound 4-(4-nitro-3-(piperidin-1-yl)phenethyl)morpholine was obtained as a brownish-orange thick oil: 0.68 g (79% yield); ¹H NMR (300 MHz, Chloroform-d) δ 7.72 (d, J=8.3 Hz, 1H), 6.94 (d, J=1.8 Hz, 1H), 6.78 (dd, J=8.3, 1.8 Hz, 1H), 3.75-3.72 (m, 4H), 3.03-2.99 (m, 4H), 2.82-2.77 (m, 2H), 2.62-2.57 (m, 2H), 2.53-2.50 (m, 4H), 1.76-1.68 (m, 4H), 1.64-1.55 (m, 2H); LRMS (M+H) m/z 320.53.

Example 71

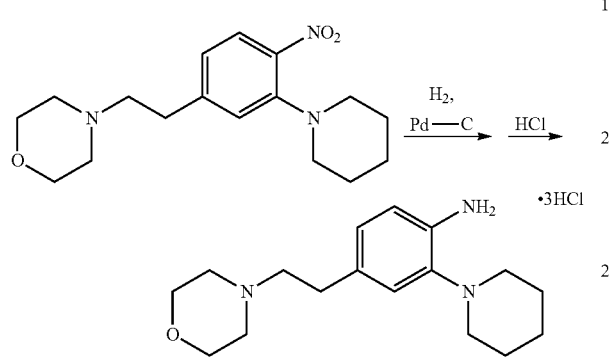

4-(2-morpholinoethyl)-2-(piperidin-1-yl)aniline Tri-Hydrogen Chloride

In a Parr flask, under 30 psi of H₂, an EtOAc (20 mL) solution of 4-(4-nitro-3-(piperidin-1-yl)phenethyl)morpholine (0.68 g, 2.1 mmol) and Pd—C (10% Pd on C, 50% wet, 0.1 g) was shaken at room temperature for 5 hours. The reaction went to completion as monitored by LC-MS. Solid was removed by filtration through a celite pad, washing with EtOAc. Filtrate was collected in a receiving flask containing 1.5 mL of 4M HCl-dioxane solution, and solvent was removed in vacuo. Compound 4-(2-morpholinoethyl)-2-(piperidin-1-yl)aniline tri-hydrogen chloride was obtained as an off-white foamy solid: 931 mg (86% yield); ¹H NMR (300 MHz, Methanol-d₄) δ 7.61-7.58 (m, 1H), 7.33-7.26 (m, 1H), 7.25 (dd, J=8.2, 2.3 Hz, 1H), 4.11 (dd, J=13.0, 3.7 Hz, 2H), 3.90 (t, J=12.5 Hz, 2H), 3.64-3.59 (m, 2H), 3.48-3.42 (m, 2H), 3.39-3.29 (m, partially overlapped with CH₃OH, 6H), 3.20-3.14 (m, 2H), 2.05-1.98 (m, 4H), 1.81-1.73 (m, 2H); LRMS (M+H) m/z 290.55.

Example 72

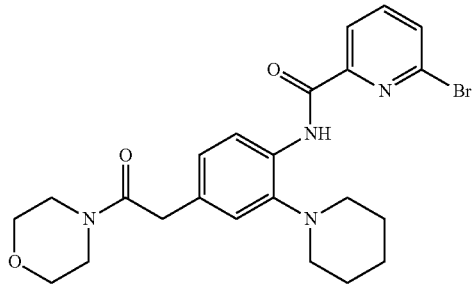 [SMILES: O=C(Nc1ccc(CC(=O)N2CCOCC2)cc1N1CCCCC1)c1cccc(Br)n1]

6-bromo-N-(4-(2-morpholino-2-oxoethyl)-2-(piperidin-1-yl)phenyl)picolinamide

The compound was prepared according to general procedure (A): 0.4 mmol scale, 91% yield.
¹H NMR (300 MHz, Chloroform-d) δ 11.04 (s, 1H), 8.50 (d, J=8.2 Hz, 1H), 8.25 (dd, J=7.5, 1.0 Hz, 1H), 7.77 (dd, J=7.7, 7.7 Hz, 1H), 7.65 (d, J=7.9 Hz, 1H), 7.09 (br s, 1H), 7.00 (d, J=8.2 Hz, 1H), 3.72 (s, 2H), 3.65 (br s, 4H), 3.45 (br s, 4H), 2.88-2.84 (m, 4H), 1.96-1.88 (m, 4H), 1.68-1.60 (m, 2H); LRMS (M+H) m/z 487.61.

Example 73

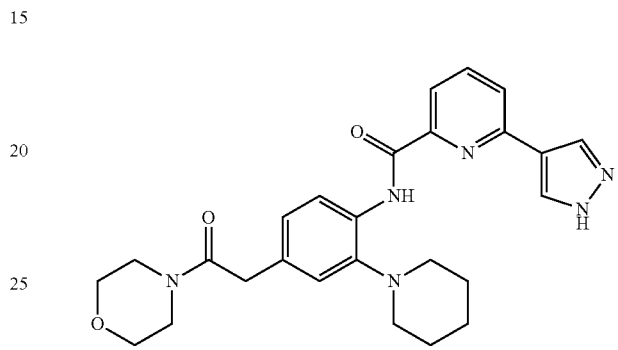

I-51: N-(4-(2-morpholino-2-oxoethyl)-2-(piperidin-1-yl)phenyl)-6-(1H-pyrazol-4-yl)picolinamide The compound was prepared according to general procedure (B): 0.1 mmol scale, 58% yield.
¹H NMR (300 MHz, Chloroform-d) δ 10.91 (s, 1H), 8.53 (d, J=8.2 Hz, 1H), 8.21 (s, 2H), 8.10 (dd, J=7.7, 1.0 Hz, 1H), 7.86 (dd, J=7.8, 7.8 Hz, 1H), 7.63 (dd, J=7.9, 1.0 Hz, 1H), 7.07 (d, J=1.9 Hz, 1H), 7.01 (dd, J=8.4, 2.0 Hz, 1H), 3.73 (s, 2H), 3.68-3.65 (m, 4H), 3.52-3.46 (m, 4H), 2.87-2.84 (m, 4H), 1.82-1.75 (m, 4H), 1.61-1.55 (m, 2H); LRMS (M+H) m/z 475.76.

Example 74

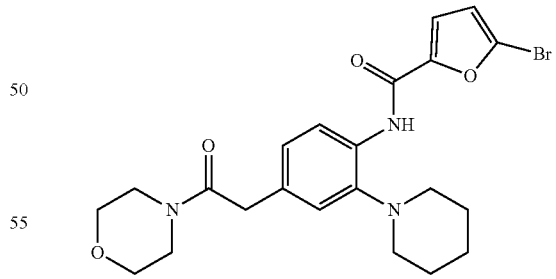

5-bromo-N-(4-(2-morpholino-2-oxoethyl)-2-(piperidin-1-yl)phenyl)furan-2-carboxamide The compound was prepared according to general procedure (A): 0.4 mmol scale, 88% yield.
¹H NMR (300 MHz, Chloroform-d) δ 9.59 (s, 1H), 8.39 (d, J=8.3 Hz, 1H), 7.16 (d, J=3.5 Hz, 1H), 7.09 (d, J=1.5 Hz, 1H), 6.99 (dd, J=8.3, 1.5 Hz, 2H), 6.50 (d, J=3.5 Hz, 1H), 3.70 (s, 2H), 3.65 (br s, 4H), 3.49-3.42 (m, 4H), 2.86-2.83 (m, 4H), 1.86-1.79 (m, 4H), 1.67-1.63 (m, 2H); LRMS (M+H) m/z 476.52.

Example 75

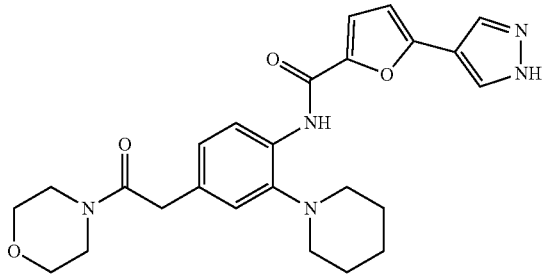 [SMILES: O=C(Nc1ccc(CC(=O)N2CCOCC2)cc1N1CCCCC1)c1ccc(-c2cn[nH]c2)o1]

I-52: N-(4-(2-morpholino-2-oxoethyl)-2-(piperidin-1-yl)phenyl)-5-(1H-pyrazol-4-yl)furan-2-carboxamide The compound was prepared according to general procedure (B): 0.1 mmol scale, 56% yield.

$^1$H NMR (300 MHz, Chloroform-d) δ 11.06 (v br s, 1H), 9.56 (s, 1H), 8.45 (d, J=8.3 Hz, 1H), 7.87 (s, 2H), 7.24 (d, J=3.6 Hz, 1H), 7.08 (d, J=2.0 Hz, 1H), 7.00 (dd, J=8.3, 2.0 Hz, 1H), 6.52 (d, J=3.6 Hz, 1H), 3.71 (s, 2H), 3.68-3.64 (m, 4H), 3.52-3.46 (m, 4H), 2.86-2.83 (m, 4H), 1.85-1.78 (m, 4H), 1.69-1.61 (m, 2H); LRMS (M+H) m/z 464.73.

Example 76

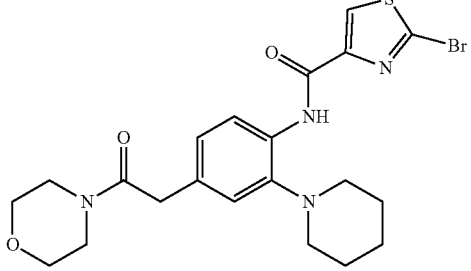

2-bromo-N-(4-(2-morpholino-2-oxoethyl)-2-(piperidin-1-yl)phenyl)thiazole-4-carboxamide The compound was prepared according to general procedure (A): 0.4 mmol scale, 81% yield.

$^1$H NMR (300 MHz, Chloroform-d) δ 10.36 (s, 1H), 8.41 (d, J=8.3 Hz, 1H), 8.13 (s, 1H), 7.08 (br s, 1H), 6.99 (d, J=8.3 Hz, 1H), 3.71 (s, 2H), 3.65 (br s, 4H), 3.49-3.43 (m, 4H), 2.88-2.82 (m, 4H), 1.89-1.82 (m, 4H), 1.67-1.61 (m, 2H); LRMS (M+H) m/z 493.59, 495.13.

Example 77

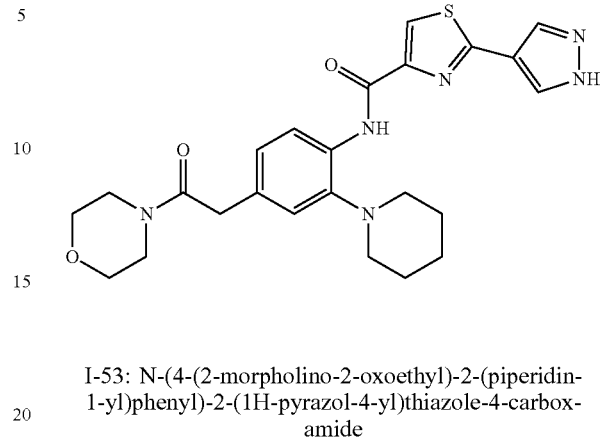

I-53: N-(4-(2-morpholino-2-oxoethyl)-2-(piperidin-1-yl)phenyl)-2-(1H-pyrazol-4-yl)thiazole-4-carboxamide The compound was prepared according to general procedure (B): 0.1 mmol scale, 37% yield.

$^1$H NMR (300 MHz, Chloroform-d) δ 10.77 (v br s, 1H), 10.42 (s, 1H), 8.50 (d, J=8.2 Hz, 1H), 8.02 (s, 1H), 7.98 (s, 2H), 7.03 (d, J=2.0 Hz, 1H), 6.99 (dd, J=8.2, 2.0 Hz, 1H), 3.71 (s, 2H), 3.68-3.65 (m, 4H), 3.54-3.47 (m, 4H), 2.85-2.82 (m, 4H), 1.89-1.82 (m, 4H), 1.68-1.60 (m, 2H); LRMS (M+H) m/z 481.71.

Example 78

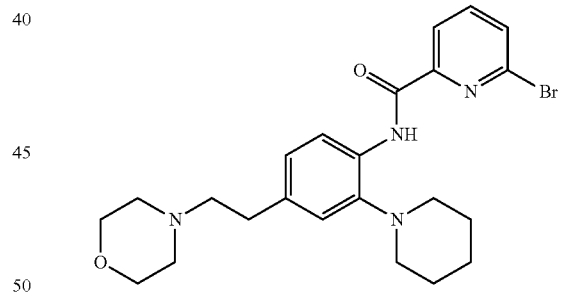

6-bromo-N-(4-(2-morpholinoethyl)-2-(piperidin-1-yl)phenyl)picolinamide

The compound was prepared according to general procedure (A): 0.65 mmol scale, >99% yield.

$^1$H NMR (300 MHz, Chloroform-d) δ 11.03 (s, 1H), 8.47 (d, J=8.1 Hz, 1H), 8.24 (dd, J=7.5, 1.0 Hz, 1H), 7.79-7.74 (m, 1H), 7.64 (dd, J=7.9, 1.0 Hz, 1H), 7.03-6.99 (m, 2H), 3.78-3.75 (m, 4H), 2.88-2.85 (m, 4H), 2.80-2.77 (m, 2H), 2.66-2.61 (m, 2H), 2.59-2.56 (m, 4H), 1.9-1.89 (m, 4H), 1.68-1.63 (m, 2H); LRMS (M+H) m/z 475.52.

Example 79

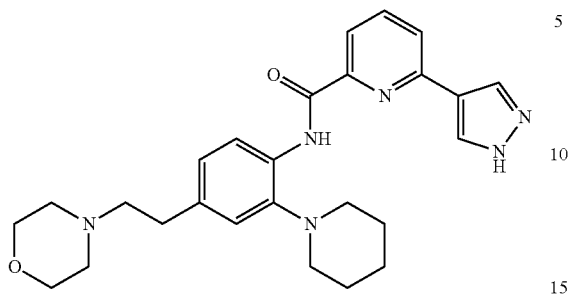

I-54: N-(4-(2-morpholinoethyl)-2-(piperidin-1-yl) phenyl)-6-(1H-pyrazol-4-yl)picolinamide The compound was prepared according to general procedure (B): 0.1 mmol scale, 53% yield.

$^1$H NMR (300 MHz, Chloroform-d) δ 10.93 (s, 1H), 10.62 (v br s, 1H), 8.48 (d, J=8.8 Hz, 1H), 8.26 (s, 2H), 8.17 (dd, J=7.7, 1.0 Hz, 1H), 7.89 (dd, J=7.8, 7.8 Hz, 1H), 7.66 (dd, J=7.9, 1.1 Hz, 1H), 7.03-7.00 (m, 2H), 3.78-3.75 (m, 4H), 2.89-2.86 (m, 4H), 2.79 (dd, J=10.3, 5.9 Hz, 2H), 2.61 (dd, J=10.3, 5.9 Hz, 2H), 2.56-2.53 (m, 4H), 1.83-1.76 (m, 4H), 1.62-1.55 (m, 2H); LRMS (M+H) m/z 461.75.

Example 80

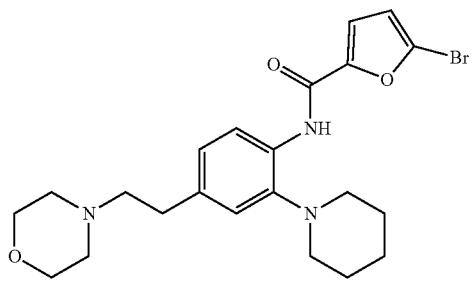 [SMILES: O=C(Nc1ccc(CCN2CCOCC2)cc1N1CCCCC1)c1ccc(Br)o1]

5-bromo-N-(4-(2-morpholinoethyl)-2-(piperidin-1-yl)phenyl)furan-2-carboxamide

The compound was prepared according to general procedure (A): 0.65 mmol scale, 89% yield.

$^1$H NMR (300 MHz, Chloroform-d) δ 9.58 (s, 1H), 8.35 (d, J=8.2 Hz, 1H), 7.15 (d, J=3.5 Hz, 1H), 7.02 (d, J=1.9 Hz, 1H), 6.99 (dd, J=8.2, 2.0 Hz, 1H), 6.50 (d, J=3.5 Hz, 1H), 3.78-3.75z (m, 4H), 2.86-2.83 (m, 4H), 2.80-2.76 (m, 2H), 2.64-2.54 (m, 6H), 1.87-1.79 (m, 4H), 1.68-1.62 (m, 2H); LRMS (M+H) m/z 462.57.

Example 81

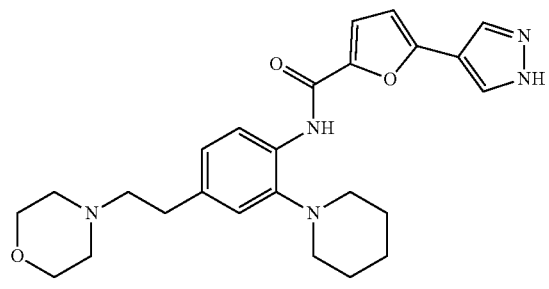 [SMILES: O=C(Nc1ccc(CCN2CCOCC2)cc1N1CCCCC1)c1ccc(-c2cn[nH]c2)o1]

I-55: N-(4-(2-morpholinoethyl)-2-(piperidin-1-yl) phenyl)-5-(1H-pyrazol-4-yl)furan-2-carboxamide The compound was prepared according to general procedure (B): 0.1 mmol scale, 34% yield.

$^1$H NMR (300 MHz, Chloroform-d) δ 10.47 (v br s, 1H), 9.58 (s, 1H), 8.41 (d, J=8.0 Hz, 1H), 7.92 (s, 2H), 7.26 (d, J=3.6 Hz, partially overlapped with CHCl$_3$, 1H), 7.03-6.99 (m, 2H), 6.54 (d, J=3.6 Hz, 1H), 3.77-3.74 (m, 4H), 2.88-2.85 (m, 4H), 2.77 (dd, J=10.0, 5.7 Hz, 2H), 2.60 (dd, J=10.0, 5.7 Hz, 2H), 2.55-2.52 (m, 4H), 1.86-1.79 (m, 4H), 1.70-1.63 (m, 2H); LRMS (M+H) m/z 450.77.

Example 82

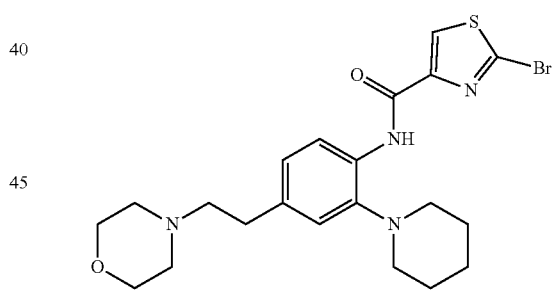

2-bromo-N-(4-(2-morpholinoethyl)-2-(piperidin-1-yl)phenyl)thiazole-4-carboxamide The compound was prepared according to general procedure (A): 0.65 mmol scale, 81% yield.

$^1$H NMR (300 MHz, Chloroform-d) δ 10.34 (s, 1H), 8.43 (d, J=8.3 Hz, 1H), 8.12 (s, 1H), 7.10 (d, J=2.0 Hz, 1H), 6.97 (dd, J=8.3, 2.0 Hz, 1H), 4.35 (br dd, J=12.2, 12.2 Hz, 2H), 3.99 (dd, J=13.0, 3.6 Hz, 2H), 3.48 (d, J=12.1 Hz, 2H), 3.29-3.16 (m, 4H), 2.95-2.86 (m, 2H), 2.86-2.82 (m, 4H), 1.89-1.82 (m, 4H), 1.68-1.62 (m, 2H); LRMS (M+H) m/z 479.56.

Example 83

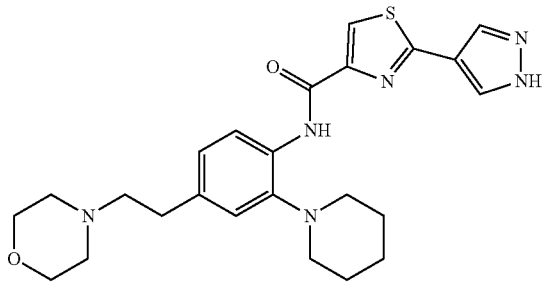 [SMILES: O=C(Nc1ccc(CCN2CCOCC2)cc1N1CCCCC1)c1csc(-c2cn[nH]c2)n1]

I-60: N-(4-(2-morpholinoethyl)-2-(piperidin-1-yl)phenyl)-2-(1H-pyrazol-4-yl)thiazole-4-carboxamide The compound was prepared according to general procedure (B): 0.1 mmol scale, 73% yield.
$^1$H NMR (300 MHz, Chloroform-d) δ 11.12 (v br s, 1H), 10.46 (s, 1H), 8.46 (d, J=8.7 Hz, 1H), 8.06 (d, J=3.6 Hz, 1H), 8.05 (s, 1H), 7.02-6.99 (m, 3H), 3.78-3.74 (m, 4H), 2.88-2.85 (m, 4H), 2.79 (dd, J=9.9, 6.0 Hz, 2H), 2.63 (dd, J=9.9, 6.0 Hz, 2H), 2.57-2.54 (m, 4H), 1.91-1.83 (m, 4H), 1.71-1.63 (m, 2H); LRMS (M+H) m/z 467.60.

Example 84

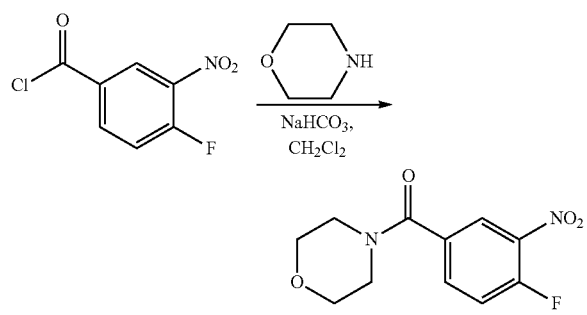

(4-fluoro-3-nitrophenyl)(morpholino)methanone

To a CH$_2$Cl$_2$ (50 mL) solution of 4-fluoro-3-nitrobenzoyl chloride (5 g, 24.56 mmol) and NaHCO$_3$ (2.27 g, 27 mmol), morpholine (2.23 mL, 25.8 mmol) was added with cooling in an ice bath. After 30 minutes, the ice bath was removed and the mixture was stirred at room temperature for 16 hours. The reaction went to completion as monitored by LC-MS, and was quenched by saturated aqueous NH$_4$Cl solution (about 40 mL). The aqueous layer was extracted with EtOAc (about 20 mL) which was again washed with saturates aqueous NH$_4$Cl solution. Combined organic layers were dried (Na$_2$SO$_4$), filtered, and the solvent was removed in vacuo. Compound (4-fluoro-3-nitrophenyl)(morpholino)methanone was obtained as a bright yellow solid and was used without further purification: 5.93 g (95% yield); $^1$H NMR (300 MHz, Chloroform-d) δ 8.15 (dd, J=7.0, 2.2 Hz, 1H), 7.73 (ddd, J=8.5, 4.2, 2.2 Hz, 1H), 7.38 (dd, J=10.3, 8.5 Hz, 1H), 3.79-3.41 (m, 8H); LRMS (M+H) m/z 255.25.

Example 85

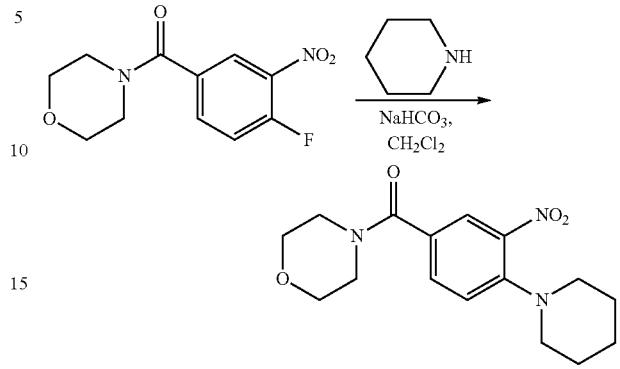

morpholino(3-nitro-4-(piperidin-1-yl)phenyl)methanone

A CH$_3$CN (45 mL) solution of (4-fluoro-3-nitrophenyl)(morpholino)methanone (5.93 g, 23.3 mmol), NaHCO$_3$ (2.16 g, 25.6 mmol) and piperidine (2.42 mL, 24.5 mmol) was stirred at 70° C. After 2 hours, the reaction went to completion as monitored by LC-MS. Volatiles were removed by rotary evaporation and product was purified by silica gel column chromatography. Compound morpholino(3-nitro-4-(piperidin-1-yl)phenyl)methanone was obtained as a bright orangish-yellow color solid: 6.46 g (82% yield); $^1$H NMR (300 MHz, Chloroform-d) δ 7.86 (d, J=2.1 Hz, 1H), 7.52 (dd, J=8.6, 2.1 Hz, 1H), 7.10 (d, J=8.6 Hz, 1H), 3.730-3.63 (m, 8H), 3.11-3.07 (m, 4H), 1.75-1.60 (m, 6H); LRMS (M+H) m/z 320.48.

Example 86

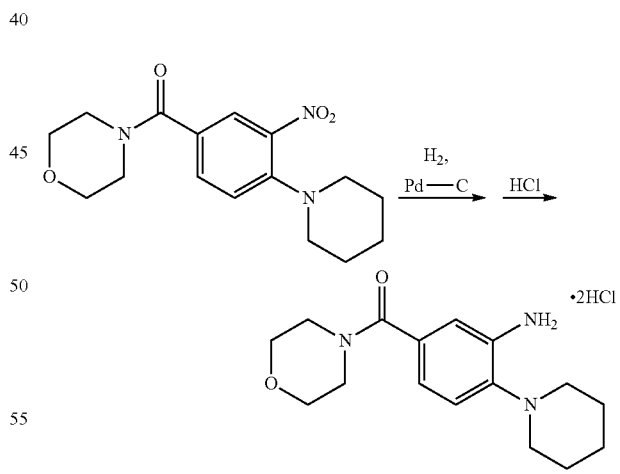

(3-amino-4-(piperidin-1-yl)phenyl)(morpholino)methanone Di-Hydrogen Chloride

In a Parr flask under 30 psi of H$_2$, an EtOAc (50 mL) solution of morpholino(3-nitro-4-(piperidin-1-yl)phenyl)methanone (2.55 g, 8 mmol) and Pd—C (10% Pd on C, 50% wet, 0.5 g) was shaken at room temperature for 4 hours. The reaction went to completion as monitored by LC-MS. Solid was removed by filtration through a celite pad, washing with EtOAc. Filtrate was collected in a receiving flask containing 5 mL of 4M HCl-dioxane solution, and the solvent was removed in vacuo. Compound (3-amino-4-(piperidin-1-yl)phenyl)(morpholino)methanone di-hydrogen chloride was obtained as an off-white foamy solid: 2.9 g (>99% yield); $^1$H NMR (300 MHz, Methanol-$d_4$) δ 7.60 (d, J=8.4 Hz, 1H), 7.24 (d, J=1.8 Hz, 1H), 7.19 (dd, J=8.3, 1.8 Hz, 1H), 3.79-3.62 (m, 8H), 3.44-3.39 (m, 4H), 2.09-2.00 (m, 4H), 1.82-1.74 (m, 2H); LRMS (M+H) m/z 290.54.

Example 87

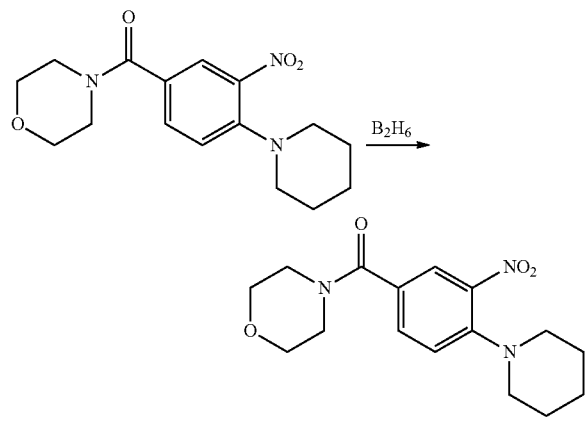

4-(3-nitro-4-(piperidin-1-yl)benzyl)morpholine

To a THF (25 mL) solution of morpholino(3-nitro-4-(piperidin-1-yl)phenyl)methanone (3.91 g, 12.2 mmol), $B_2H_6$-THF solution (1M in THF, 36.7 mL, 36.7 mmol) was added dropwise over 30 minutes with cooling in an ice bath. The reaction was continued at room temperature for 2 hours, and went to completion as monitored by LC-MS. It was quenched with 1N HCl aqueous solution (15 mL) and the mixture was stirred at room temperature for 20 hours. Most of the THF was removed by rotary evaporation under reduced pressure. The aqueous layer was basified with saturated aqueous $NaHCO_3$ solution, and then extracted with EtOAc (80 mL×2). The combined organic layers were dried ($Na_2SO_4$), filtered, and the solvent was removed in vacuo. Product was purified by silica gel column chromatography, and compound 4-(3-nitro-4-(piperidin-1-yl)benzyl)morpholine was obtained as a bright orange color oil which was used without further purification; $^1$H NMR (300 MHz, Chloroform-d) δ 7.71 (d, J=2.1 Hz, 1H), 7.40 (dd, J=8.4, 2.1 Hz, 1H), 7.06 (d, J=8.4 Hz, 1H), 3.73-3.69 (m, 4H), 3.44 (s, 2H), 3.01-2.98 (m, 4H), 2.44-2.41 (m, 4H), 1.75-1.67 (m, 4H), 1.62-1.56 (m, 2H); LRMS (M+H) m/z 306.54.

Example 88

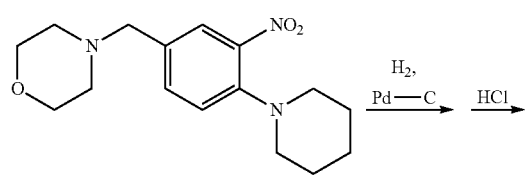

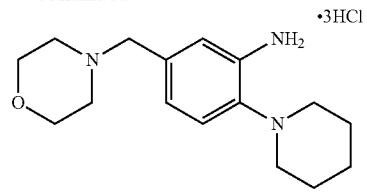

4-(morpholinomethyl)-2-(piperidin-1-yl)aniline Tri-Hydrogen Chloride

In a Parr flask under 30 psi of $H_2$, an EtOAc (50 mL) solution of 4-(3-nitro-4-(piperidin-1-yl)benzyl)morpholine (about 12.2 mmol) and Pd—C (10% Pd on C, 50% wet, 0.5 g) was shaken at room temperature for 17 hours. The reaction went to completion as monitored by LC-MS. Solid was removed by filtration through a celite pad, washing with EtOAc. Filtrate was collected in a receiving flask containing 10 mL of 4M HCl-dioxane solution, and free-flowing solid was formed after the addition of MeOH (about 10 mL). Precipitate was collected by filtration, washed with EtOAc-MeOH (<5%), and was further dried in vacuo. Compound 4-(morpholinomethyl)-2-(piperidin-1-yl)aniline tri-hydrogen chloride was obtained as a white solid: 4.03 g (86% yield over 2 steps); $^1$H NMR (300 MHz, Methanol-$d_4$) δ 7.63 (d, J=8.4 Hz, 1H), 7.41 (d, J=2.1 Hz, 1H), 7.30 (dd, J=8.4, 2.1 Hz, 1H), 4.37 (s, 2H), 4.07 (dd, J=13.2, 3.7 Hz, 2H), 3.86 (ddd, J=13.2, 11.8, 2.3 Hz, 3H), 3.45-3.41 (m, 4H), 3.34-3.19 (m, partially overlapped with $CH_3OH$, 4H), 2.10-2.02 (m, 4H), 1.82-1.75 (m, 2H); LRMS (M+H) m/z 276.47.

Example 89

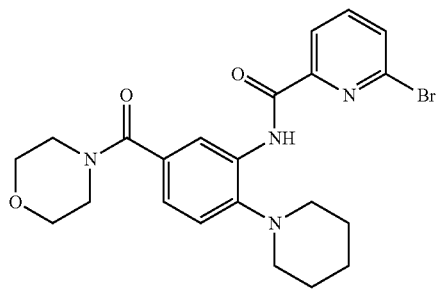 [SMILES: O=C(Nc1cc(C(=O)N2CCOCC2)ccc1N1CCCCC1)c1cccc(Br)n1]

6-bromo-N-(5-(morpholine-4-carbonyl)-2-(piperidin-1-yl)phenyl)picolinamide

The compound was prepared according to general procedure (A): 1.0 mmol scale, 90% yield.

$^1$H NMR (300 MHz, Chloroform-d) δ 11.02 (s, 1H), 8.64 (d, J=1.6 Hz, 1H), 8.24 (dd, J=7.5, 1.0 Hz, 1H), 7.78 (dd, J=7.9, 7.5 Hz, 1H), 7.67 (dd, J=7.9, 1.0 Hz, 1H), 7.23 (d, J=1.8 Hz, 1H), 7.22 (d, J=0.6 Hz, 1H), 3.78-3.62 (m, 8H), 2.90-2.87 (m, 4H), 1.98-1.90 (m, 4H), 1.74-1.62 (m, 2H); LRMS (M+H) m/z 473.59, 475.81.

Example 90

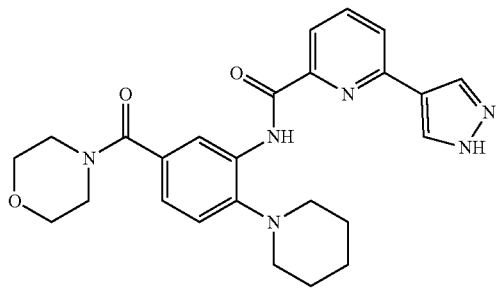 [SMILES: O=C(Nc1cc(C(=O)N2CCOCC2)ccc1N1CCCCC1)c1cccc(-c2cn[nH]c2)n1]

I-57: N-(5-(morpholine-4-carbonyl)-2-(piperidin-1-yl)phenyl)-6-(1H-pyrazol-4-yl)picolinamide The compound was prepared according to general procedure (B): 0.1 mmol scale, 59% yield $^1$H NMR (300 MHz, Chloroform-d) δ 10.96 (s, 1H), 9.86 (v br s, 1H), 8.65 (d, J=1.9 Hz, 1H), 8.25 (s, 2H), 8.16 (dd, J=7.7, 1.0 Hz, 1H), 7.91 (dd, J=7.8, 7.8 Hz, 1H), 7.68 (dd, J=7.9, 1.1 Hz, 1H), 7.26-7.24 (m, partially overlapped with CHCl$_3$, 1H), 7.20 (d, J=8.1 Hz, 1H), 3.80-3.61 (m, 8H), 2.90-2.87 (m, 4H), 1.83-1.75 (m, 4H), 1.62-1.55 (m, 2H); LRMS (M+H) m/z 461.75.

Example 91

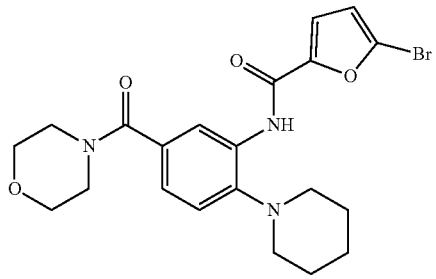 [SMILES: O=C(Nc1cc(C(=O)N2CCOCC2)ccc1N1CCCCC1)c1ccc(Br)o1]

5-bromo-N-(5-(morpholine-4-carbonyl)-2-(piperidin-1-yl)phenyl)furan-2-carboxamide The compound was prepared according to general procedure (A): 1.0 mmol scale, 93% yield.

$^1$H NMR (300 MHz, Chloroform-d) δ 9.55 (s, 1H), 8.51 (dd, J=1.6, 0.5 Hz, 1H), 7.22 (d, J=1.7 Hz, 1H), 7.21 (d, J=0.7 Hz, 1H), 7.18 (d, J=3.5 Hz, 1H), 6.52 (d, J=3.5 Hz, 1H), 3.77-3.58 (m, 8H), 2.88-2.85 (m, 4H), 1.88-1.81 (m, 4H), 1.70-1.63 (m, 2H); LRMS (M+H) m/z 462.59, 464.70.

Example 92

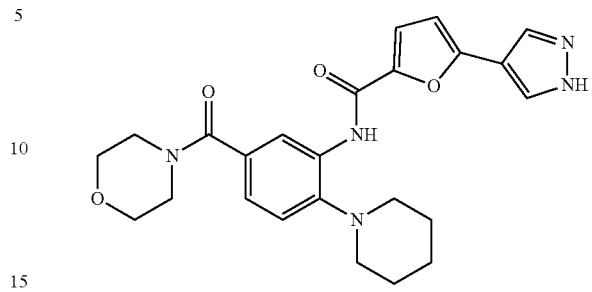

I-58: N-(5-(morpholine-4-carbonyl)-2-(piperidin-1-yl)phenyl)-5-(1H-pyrazol-4-yl)furan-2-carboxamide The compound was prepared according to general procedure (B): 0.1 mmol scale, 51% yield.

$^1$H NMR (300 MHz, Chloroform-d) δ 10.38 (v br s, 1H), 9.55 (s, 1H), 8.57 (dd, J=1.1, 1.1 Hz, 1H), 7.92 (s, 2H), 7.29 (d, J=3.6 Hz, 1H), 7.23-7.22 (m, 2H), 6.55 (d, J=3.6 Hz, 1H), 3.79-3.60 (m, 8H), 2.90-2.86 (m, 4H), 1.87-1.80 (m, 4H), 1.71-1.64 (m, 2H); LRMS (M+H) m/z 450.72.

Example 93

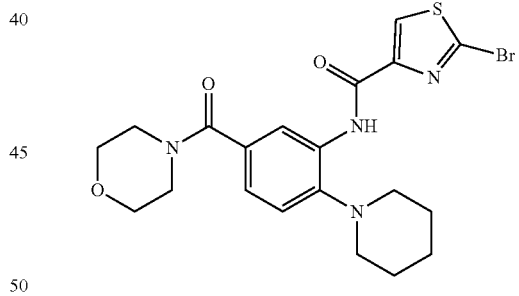

2-bromo-N-(5-(morpholine-4-carbonyl)-2-(piperidin-1-yl)phenyl)thiazole-4-carboxamide The compound was prepared according to general procedure (A): 1.0 mmol scale, 59% yield.

$^1$H NMR (300 MHz, Chloroform-d) δ 10.33 (s, 1H), 8.56 (d, J=1.8 Hz, 1H), 8.13 (s, 1H), 7.22 (d, J=1.9 Hz, 1H), 7.20 (d, J=0.5 Hz, 1H), 3.81-3.56 (m, 8H), 2.89-2.85 (m, 4H), 1.91-1.84 (m, 4H), 1.69-1.61 (m, 2H); LRMS (M+H) m/z 479.58, 481.66.

Example 94

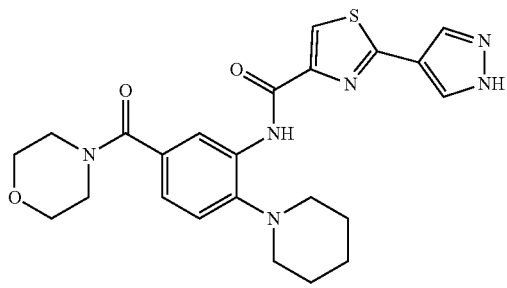 [SMILES: O=C(Nc1cc(C(=O)N2CCOCC2)ccc1N1CCCCC1)c1csc(-c2cn[nH]c2)n1]

I-59: N-(5-(morpholine-4-carbonyl)-2-(piperidin-1-yl)phenyl)-2-(1H-pyrazol-4-yl)thiazole-4-carboxamide The compound was prepared according to general procedure (B): 0.1 mmol scale, 68% yield.

$^1$H NMR (300 MHz, Chloroform-d) δ 11.09 (v br s, 1H), 10.46 (s, 1H), 8.62 (d, J=1.8 Hz, 1H), 8.09 (s, 1H), 8.05 (s, 2H), 7.22 (dd, J=8.1, 1.8 Hz, 1H), 7.18 (d, J=8.1 Hz, 1H), 3.81-3.60 (m, 8H), 2.90-2.86 (m, 4H), 1.90-1.82 (m, 4H), 1.73-1.61 (m, 2H); LRMS (M+H) m/z 467.70.

Example 95

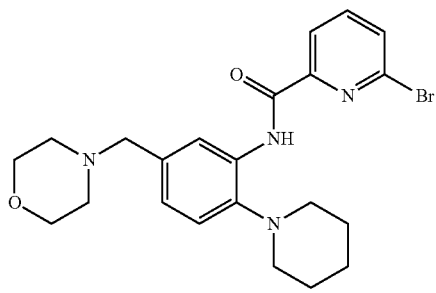 [SMILES: O=C(Nc1cc(CN2CCOCC2)ccc1N1CCCCC1)c1cccc(Br)n1]

6-bromo-N-(5-(morpholinomethyl)-2-(piperidin-1-yl)phenyl)picolinamide

The compound was prepared according to general procedure (A): 1.0 mmol scale, 68% yield.

$^1$H NMR (300 MHz, Chloroform-d) δ 10.98 (s, 1H), 8.59 (br s, 1H), 8.23 (dd, J=7.5, 1.0 Hz, 1H), 7.79 (dd, J=7.7, 7.7 Hz, 1H), 7.70 (dd, J=7.9, 1.1 Hz, 1H), 7.44 (dd, J=8.3, 2.1 Hz, 1H), 7.33 (d, J=8.3 Hz, 1H), 4.30 (s, 2H), 4.05-4.00 (m, 4H), 3.47 (d, J=9.0 Hz, 2H), 3.06-3.01 (m, 2H), 2.94-2.90 (m, 4H), 2.00-1.92 (m, 4H), 1.73-1.65 (m, 2H); LRMS (M+H) m/z 459.60.

Example 96

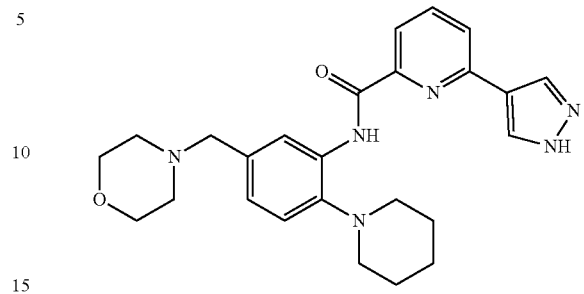

I-60: N-(5-(morpholinomethyl)-2-(piperidin-1-yl)phenyl)-6-(1H-pyrazol-4-yl)picolinamide The compound was prepared according to general procedure (B): 0.1 mmol scale, 35% yield.

$^1$H NMR (300 MHz, Chloroform-d) δ 11.00 (s, 1H), 8.54 (d, J=1.8 Hz, 1H), 8.26 (s, 2H), 8.17 (dd, J=7.7, 1.0 Hz, 1H), 7.90 (dd, J=7.8, 1.8 Hz, 1H), 7.67 (dd, J=7.9, 1.1 Hz, 1H), 7.64-7.58 (m, 1H), 7.13 (d, J=8.0 Hz, 1H), 7.08 (dd, J=8.1, 1.9 Hz, 1H), 3.74-3.71 (m, 4H), 3.52 (s, 2H), 2.88-2.85 (m, 4H), 2.51-2.48 (m, 4H), 1.81-1.73 (m, 4H), 1.60-1.53 (m, 2H); LRMS (M+H) m/z 447.76.

Example 97

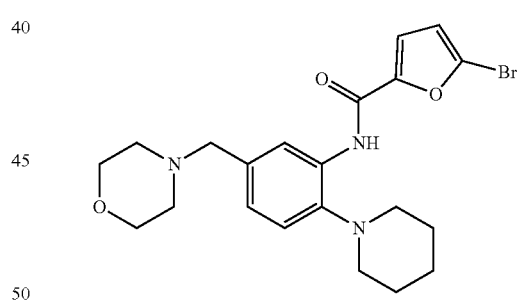

5-bromo-N-(5-(morpholinomethyl)-2-(piperidin-1-yl)phenyl)furan-2-carboxamide

The compound was prepared according to general procedure (A): 1.0 mmol scale, 99% yield.

$^1$H NMR (300 MHz, Chloroform-d) δ 9.67 (s, 1H), 8.40 (d, J=1.9 Hz, 1H), 7.16 (d, J=3.5 Hz, 1H), 7.13 (d, J=8.1 Hz, 1H), 7.07 (dd, J=8.1, 1.9 Hz, 1H), 6.50 (d, J=3.5 Hz, 1H), 3.74-3.70 (m, 4H), 3.52 (s, 2H), 2.86-2.82 (m, 4H), 2.51-2.48 (m, 4H), 1.87-1.79 (m, 4H), 1.67-1.59 (m, 2H); LRMS (M+H) m/z 448.58.

Example 98

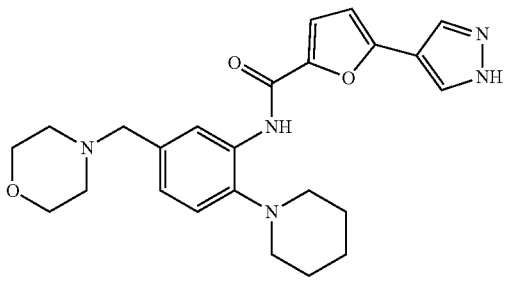 [SMILES: O=C(Nc1cc(CN2CCOCC2)ccc1N1CCCCC1)c1ccc(-c2cn[nH]c2)o1]

I-61: N-(5-(morpholinomethyl)-2-(piperidin-1-yl)
phenyl)-5-(1H-pyrazol-4-yl)furan-2-carboxamide The compound was prepared according to general procedure (B): 0.1 mmol scale, 71% yield.

$^1$H NMR (300 MHz, Chloroform-d) δ 10.46 (v br s, 1H), 9.67 (s, 1H), 8.46 (d, J=1.9 Hz, 1H), 7.92 (s, 2H), 7.27 (d, J=3.6 Hz, 1H), 7.13 (d, J=8.0 Hz, 1H), 7.06 (dd, J=8.1, 2.0 Hz, 1H), 6.54 (d, J=3.6 Hz, 1H), 3.74-3.70 (m, 4H), 3.50 (s, 2H), 2.86-2.84 (m, 4H), 2.50-2.47 (m, 4H), 1.86-1.78 (m, 4H), 1.69-1.62 (m, 2H); LRMS (M+H) m/z 436.75.

Example 99

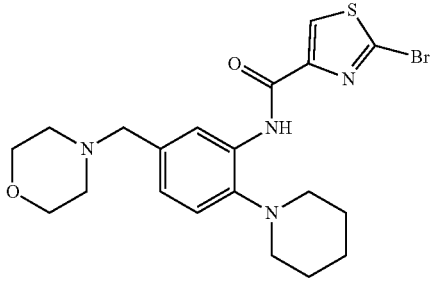 [SMILES: O=C(Nc1cc(CN2CCOCC2)ccc1N1CCCCC1)c1csc(Br)n1]

2-bromo-N-(5-(morpholinomethyl)-2-(piperidin-1-yl)phenyl)thiazole-4-carboxamide

The compound was prepared according to general procedure (A): 1.0 mmol scale, 84% yield.

$^1$H NMR (300 MHz, Chloroform-d) δ 10.35 (s, 1H), 8.48 (d, J=2.1 Hz, 1H), 7.71 (dd, J=8.2, 2.2 Hz, 1H), 7.26 (d, J=8.2 Hz, 1H), 4.37-4.29 (m, 2H), 4.14 (s, 2H), 3.94 (br d, J=13.1 Hz, 2H), 3.33 (br d, J=12.0 Hz, 2H), 2.94-2.85 (m, 6H), 1.91-1.84 (m, 4H), 1.70-1.62 (m, 2H); LRMS (M+H) m/z 465.57.

Example 100

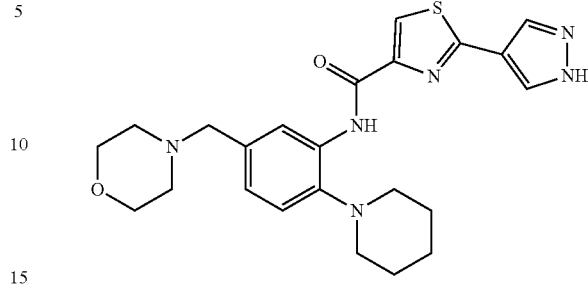

I-62: N-(5-(morpholinomethyl)-2-(piperidin-1-yl)
phenyl)-2-(1H-pyrazol-4-yl)thiazole-4-carboxamide The compound was prepared according to general procedure (B): 0.1 mmol scale, 68% yield.

$^1$H NMR (300 MHz, Chloroform-d) δ 10.90 (v br s, 1H), 10.57 (s, 1H), 8.51 (d, J=1.9 Hz, 1H), 8.09 (s, 1H), 8.088 (s, 2H), 7.12 (d, J=8.1 Hz, 1H), 7.06 (dd, J=8.1, 1.9 Hz, 1H), 3.74-3.71 (m, 4H), 3.51 (s, 2H), 2.89-2.85 (m, 4H), 2.51-2.48 (m, 4H), 1.90-1.82 (m, 4H), 1.69-1.61 (m, 2H); LRMS (M+H) m/z 453.65.

Example 101

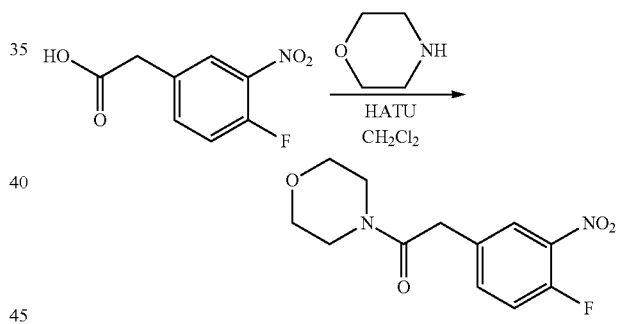

2-(4-fluoro-3-nitrophenyl)-1-morpholinoethan-1-one

HATU (10.4 g, 27.5 mmol) and NaHCO$_3$ (2.52 g, 30 mmol) were added to a CH$_2$Cl$_2$ (50 mL) solution of 2-(4-fluoro-3-nitrophenyl)acetic acid (4.97 g, 24.96 mmol) and morpholine (2.27 mL, 26.2 mmol) and the resulting solution was stirred at room temperature. Additional morpholine (about 0.5 mL) was added at 48 hours. At 66 hours, the reaction went to completion as monitored by LC-MS. Solvent was removed by rotary evaporation under reduced pressure, and product was purified by silica gel column chromatography. Fractions with product were combined, concentrated and re-dissolved in EtOAc which was washed with saturated aqueous NaHCO$_3$ solution, and then dried (Na$_2$SO$_4$), filtered, solvent was removed in vacuo. Compound 2-(4-fluoro-3-nitrophenyl)-1-morpholinoethan-1-one was obtained as a brown color oil and was used directly in next reaction: $^1$H NMR (300 MHz, Chloroform-d) δ $^1$H NMR (300 MHz, Chloroform-d) δ 7.94 (dd, J=7.0, 2.4 Hz, 1H), 7.54 (ddd, J=8.6, 4.2, 2.4 Hz, 1H), 7.30-7.23 (m, partially overlapped with CHCl₃, 1H), 3.74 (s, 2H), 3.71-3.66 (m, 6H), 3.53-3.50 (m, 2H); LRMS (M+H) m/z 269.40.

Example 102

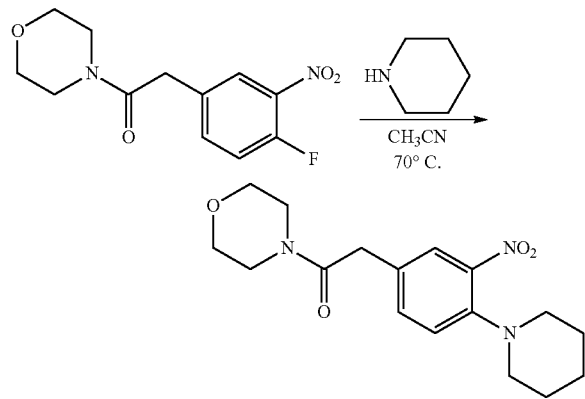

1-morpholino-2-(3-nitro-4-(piperidin-1-yl)phenyl)ethan-1-one

A CH₃CN (50 mL) solution of 2-(4-fluoro-3-nitrophenyl)-1-morpholinoethan-1-one (about 25 mmol), piperidine (2.6 mL, 26.2 mmol), and NaHCO₃ (2.31 g, 27.5 mmol) was stirred at 70° C. After 3 hours, additional piperidine (about 0.5 mL) was added, and the reaction went to completion at 22 hours, as monitored by LC-MS. Volatiles were removed in vacuo and product was purified by silica gel column chromatography. Compound morpholino(4-nitro-3-(piperidin-1-yl)phenyl)methanone was obtained as a reddish-orange color oil: 9 g (>99% yield); ¹H NMR (300 MHz, Chloroform-d) δ 7.63 (d, J=2.3 Hz, 1H), 7.35 (dd, J=8.5, 2.3 Hz, 1H), 7.09 (d, J=8.5 Hz, 1H), 3.66-3.60 (m, 8H), 3.50-3.47 (m, 2H), 3.02-2.99 (m, 4H), 1.75-1.67 (m, 4H), 1.62-1.55 (m, 2H); LRMS (M+H) m/z 334.57.

Example 103

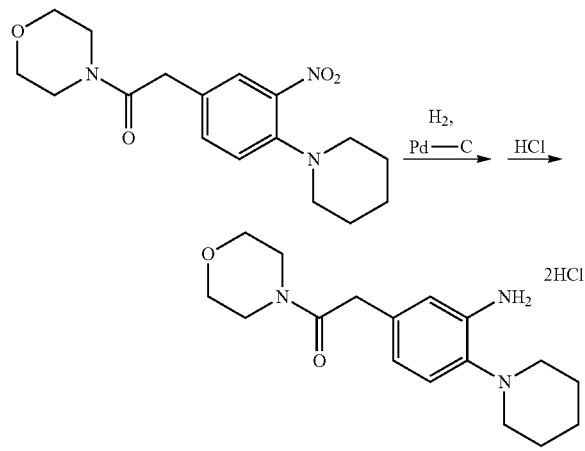

2-(3-amino-4-(piperidin-1-yl)phenyl)-1-morpholinoethan-1-one Di-Hydrogen Chloride In a Parr flask under 30 psi of H₂, an EtOAc (100 mL) solution of 1-morpholino-2-(3-nitro-4-(piperidin-1-yl)phenyl)ethan-1-one (4 g, 12 mmol) and Pd—C (10% Pd on C, 50% wet, 0.5 g) was shaken at room temperature for 3 hours. The reaction went to completion as monitored by LC-MS. Solid was removed by filtration through a celite pad, washing with EtOAc. Filtrate was collected in a receiving flask containing 5 mL of 4M HCl-dioxane solution, and a free-flowing solid was formed after the addition of MeOH and EtOH. Precipitate was collected by filtration, washed with EtOAc-EtOH (<5%), and was dried in vacuo. Compound 2-(3-amino-4-(piperidin-1-yl)phenyl)-1-morpholinoethan-1-one di-hydrogen chloride was obtained as a white solid: 1.9 g; ¹H NMR (300 MHz, Methanol-d₄) δ 7.47 (dd, J=8.0, 0.7 Hz, 1H), 7.10-7.06 (m, 2H), 3.80 (s, 2H), 3.69-3.58 (m, 8H), 3.35-3.30 (m, partially overlapped with CH₃OH, 4H), 2.02-1.94 (m, 4H), 1.79-1.75 (m, 2H); LRMS (M+H) m/z 304.57. Additional product was obtained as an off-white solid from filtrate after removal of solvent: 2.18 g, with a total yield of 90%.

Example 104

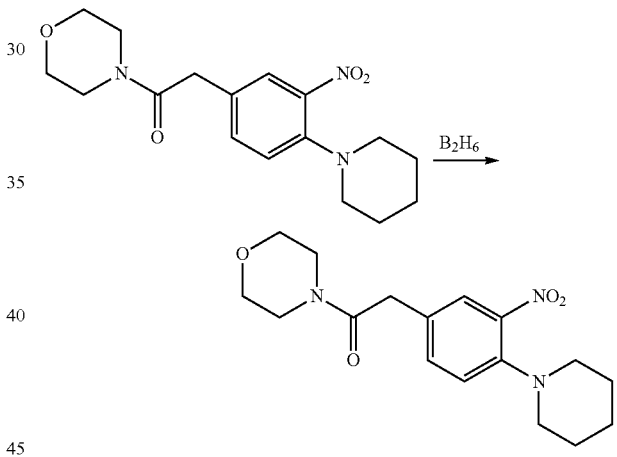

4-(3-nitro-4-(piperidin-1-yl)phenethyl)morpholine

To a THF (60 mL) solution of 1-morpholino-2-(3-nitro-4-(piperidin-1-yl)phenyl)ethan-1-one (5 g, 15 mmol), B₂H₆-THF solution (1M in THF, 45 mL, 45 mmol) was added dropwise over 10 minutes with cooling in an ice bath. The reaction was continued at room temperature for 2 hours, and went to completion as monitored by LC-MS. It was quenched with 1N HCl aqueous solution (20 mL) and was stirred at room temperature overnight. Another 5 mL of 1N HCl aqueous solution was added and the stirring was continued at room temperature, then at 30° C. overnight. Most of the THF was removed by rotary evaporation under reduced pressure. The aqueous layer was basified with saturated aqueous NaHCO₃ solution, and then extracted with EtOAc (80 mL×2). The combined organic layers were dried (Na₂SO₄), filtered, and the solvent was removed in vacuo. The product was purified by silica gel column chromatography, and compound 4-(3-nitro-4-(piperidin-1-yl)phenethyl)morpholine was obtained as an orange color oil: 3.52 g (73% yield); ¹H NMR (300 MHz, Chloroform-d) δ 7.60 (d, J=2.1 Hz, 1H), 7.29 (dd, J=8.4, 2.1 Hz, 1H), 7.05 (d, J=8.4 Hz, 1H), 3.75-3.72 (m, 4H), 2.99-2.96 (m, 4H), 2.80-2.74 (m, 2H), 2.60-2.55 (m, 2H), 2.53-2.50 (m, 4H), 1.74-1.67 (m, 4H), 1.61-1.54 (m, 2H); LRMS (M+H) m/z 320.59.

Example 105

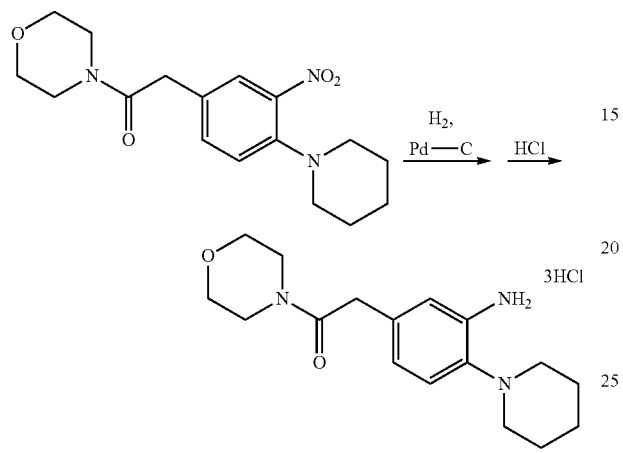

5-(2-morpholinoethyl)-2-(piperidin-1-yl)aniline Tri-Hydrogen Chloride

In a Parr flask under 30 psi of H₂, an EtOAc (50 mL) solution of morpholino(3-nitro-4-(piperidin-1-yl)phenyl) methanone (3.52 g, 11 mmol) and Pd—C (10% Pd on C, 50% wet, 0.2 g) was shaken at room temperature for 18 hours. The reaction went to completion as monitored by LC-MS. Solid was removed by filtration through a celite pad, washing with EtOAc. Filtrate was collected in a receiving flask containing 10 mL of 4M HCl-dioxane solution, and a free-flowing solid was formed. Precipitate was collected by filtration, washed with EtOAc, and was dried in vacuo. Compound 5-(2-morpholinoethyl)-2-(piperidin-1-yl)aniline tri-hydrogen chloride was obtained as a white solid: 4.4 g (>99% yield); ¹H NMR (300 MHz, Methanol-d₄) δ 7.56-7.52 (m, 1H), 7.17-7.15 (m, 1H), 7.13-7.09 (m, 1H), 4.11 (dd, J=13.1, 3.7 Hz, 2H), 3.94-3.85 (m, 2H), 3.61 (br d, J=12.3 Hz, 2H), 3.48-3.40 (m, 6H), 3.25 (ddd, J=12.2, 12.2, 3.8 Hz, 2H), 3.17-3.12 (m, 2H), 2.19-2.05 (m, 4H), 1.82-1.74 (m, 2H); LRMS (M+H) m/z 290.52.

Example 106

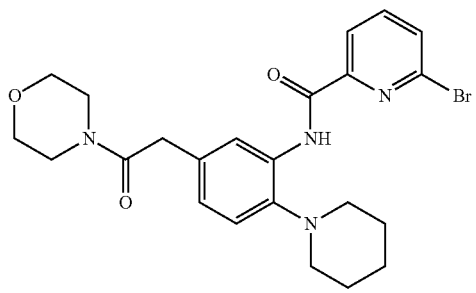 [SMILES: O=C(Nc1cc(CC(=O)N2CCOCC2)ccc1N1CCCCC1)c1cccc(Br)n1]

6-bromo-N-(5-(2-morpholino-2-oxoethyl)-2-(piperidin-1-yl)phenyl)picolinamide

The compound was prepared according to general procedure (A): 1 mmol scale, 75% yield.
¹H NMR (300 MHz, Chloroform-d) δ 11.11 (s, 1H), 8.46 (d, J=2.1 Hz, 1H), 8.23 (dd, J=7.5, 1.0 Hz, 1H), 7.76 (dd, J=7.6, 7.6 Hz, 1H), 7.65 (dd, J=7.9, 1.0 Hz, 1H), 7.15 (d, J=8.1 Hz, 1H), 7.03 (dd, J=8.0, 2.0 Hz, 1H), 3.73 (s, 2H), 3.67-3.65 (m, 4H), 3.56-3.48 (m, 4H), 2.87-2.84 (m, 4H), 1.96-1.88 (m, 4H), 1.69-1.61 (m, 2H); LRMS (M+H) m/z 487.69, 489.89.

Example 107

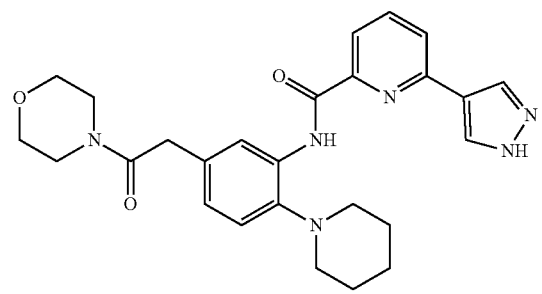 [SMILES: O=C(Nc1cc(CC(=O)N2CCOCC2)ccc1N1CCCCC1)c1cccc(-c2cn[nH]c2)n1]

I-63: N-(5-(2-morpholino-2-oxoethyl)-2-(piperidin-1-yl)phenyl)-6-(1H-pyrazol-4-yl)picolinamide The compound was prepared according to general procedure (B): 0.1 mmol scale, 42% yield.
¹H NMR (300 MHz, Chloroform-d) δ 11.00 (s, 1H), 10.23 (v br s, 1H), 8.50 (d, J=2.1 Hz, 1H), 8.23 (s, 2H), 8.13 (dd, J=7.7, 1.0 Hz, 1H), 7.87 (dd, J=7.8, 7.8 Hz, 1H), 7.66 (dd, J=7.9, 1.0 Hz, 1H), 7.12 (d, J=8.2 Hz, 1H), 7.02 (dd, J=8.2, 2.1 Hz, 1H), 3.75 (s, 2H), 3.68 (br s, 4H), 3.59-3.52 (m, 4H), 2.85-2.81 (m, 4H), 1.78-1.70 (m, 4H), 1.59-1.52 (m, 2H); LRMS (M+H) m/z 475.80.

Example 108

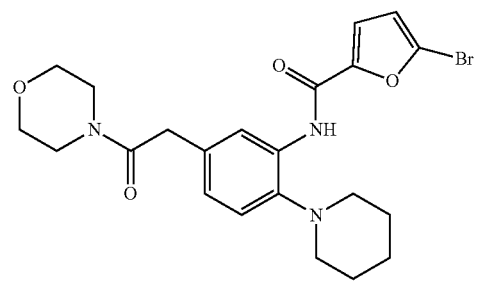 [SMILES: O=C(Nc1cc(CC(=O)N2CCOCC2)ccc1N1CCCCC1)c1ccc(Br)o1]

5-bromo-N-(5-(2-morpholino-2-oxoethyl)-2-(piperidin-1-yl)phenyl)furan-2-carboxamide The compound was prepared according to general procedure (A): 1 mmol scale, 72% yield.
¹H NMR (300 MHz, Chloroform-d) δ 9.67 (s, 1H), 8.32 (br s, 1H), 7.17-7.12 (m, 2H), 7.02 (br d, J=8.6 Hz, 1H), 6.51

(d, J=3.5 Hz, 1H), 3.71 (s, 2H), 3.67-3.64 (m, 4H), 3.57-3.48 (m, 4H), 2.85-2.82 (m, 4H), 1.87-1.79 (m, 4H), 1.68-1.59 (m, 2H); LRMS (M+H) m/z 476.67, 478.91.

Example 109

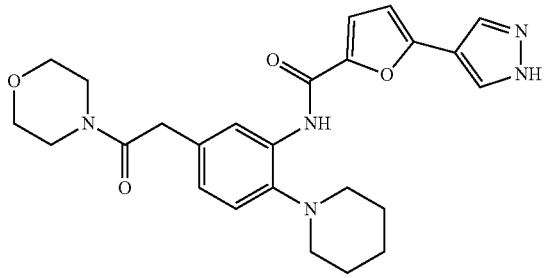 [SMILES: O=C(Nc1cc(CC(=O)N2CCOCC2)ccc1N1CCCCC1)c1ccc(-c2cn[nH]c2)o1]

I-64: N-(5-(2-morpholino-2-oxoethyl)-2-(piperidin-1-yl)phenyl)-5-(1H-pyrazol-4-yl)furan-2-carboxamide The compound was prepared according to general procedure (B): 0.1 mmol scale, 44% yield.

$^1$H NMR (300 MHz, Chloroform-d) δ 10.90 (v br s, 1H), 9.64 (s, 1H), 8.39 (d, J=2.0 Hz, 1H), 7.88-7.86 (m, 2H), 7.24 (d, J=3.6 Hz, 1H), 7.11 (d, J=8.1 Hz, 1H), 6.99 (dd, J=8.1, 2.3 Hz, 1H), 6.51 (d, J=3.6 Hz, 1H), 3.73 (s, 2H), 3.67 (br s, 4H), 3.60-3.49 (m, 4H), 2.84-2.80 (m, 4H), 1.83-1.75 (m, 4H), 1.68-1.60 (m, 2H); LRMS (M+H) m/z 464.78.

Example 110

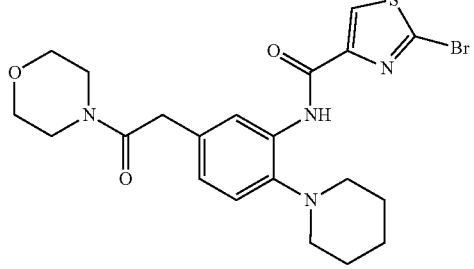

2-bromo-N-(5-(2-morpholino-2-oxoethyl)-2-(piperidin-1-yl)phenyl)thiazole-4-carboxamide The compound was prepared according to general procedure (A): 1 mmol scale, 80% yield.

$^1$H NMR (300 MHz, Chloroform-d) δ 10.43 (s, 1H), 8.38 (d, J=2.1 Hz, 1H), 8.10 (s, 1H), 7.13 (d, J=8.2 Hz, 1H), 7.02 (dd, J=8.1, 2.1 Hz, 1H), 3.72 (s, 2H), 3.68-3.64 (m, 4H), 3.57-3.51 (m, 4H), 2.86-2.82 (m, 4H), 1.89-1.82 (m, 4H), 1.68-1.60 (m, 2H); LRMS (M+H) m/z 493.65, 495.76.

Example 111

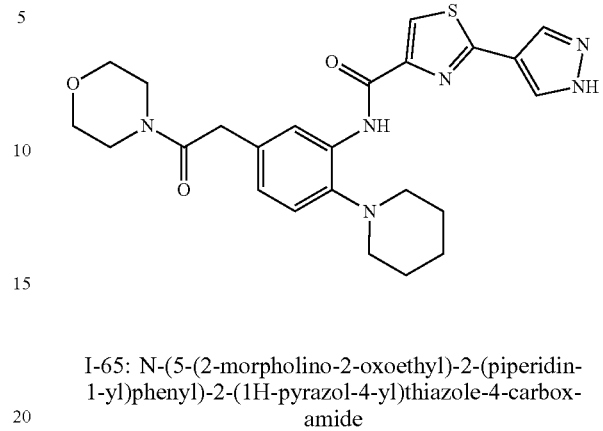

I-65: N-(5-(2-morpholino-2-oxoethyl)-2-(piperidin-1-yl)phenyl)-2-(1H-pyrazol-4-yl)thiazole-4-carboxamide The compound was prepared according to general procedure (B): 0.1 mmol scale, 47% yield.

$^1$H NMR (300 MHz, Chloroform-d) δ 11.06 (v br s, 1H), 10.52 (s, 1H), 8.43 (d, J=2.1 Hz, 1H), 8.03 (s, 1H), 8.00 (s, 2H), 7.09 (d, J=8.1 Hz, 1H), 6.98 (dd, J=8.1, 2.1 Hz, 1H), 3.74 (s, 2H), 3.69 (br s, 4H), 3.62-3.52 (m, 4H), 2.84-2.81 (m, 4H), 1.86-1.78 (m, 4H), 1.67-1.59 (m, 2H); LRMS (M+H) m/z 481.80.

Example 112

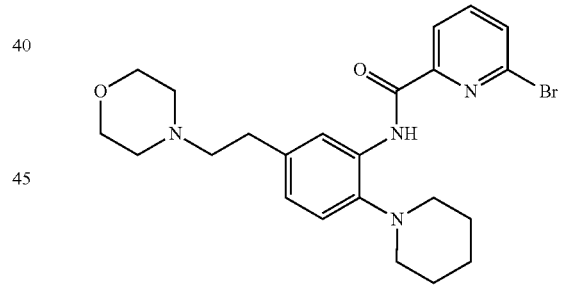

6-bromo-N-(5-(2-morpholinoethyl)-2-(piperidin-1-yl)phenyl)picolinamide

The compound was prepared according to general procedure (A): 1 mmol scale, 98% yield.

$^1$H NMR (300 MHz, Chloroform-d) δ 11.14 (s, 1H), 8.46 (d, J=2.0 Hz, 1H), 8.24 (dd, J=7.5, 1.0 Hz, 1H), 7.77 (dd, J=7.5, 7.5 Hz, 1H), 7.65 (dd, J=8.0, 1.0 Hz, 1H), 7.11 (d, J=8.0 Hz, 1H), 6.95 (dd, J=8.0, 2.1 Hz, 1H), 3.78-3.74 (m, 4H), 2.86-2.82 (m, 6H), 2.69-2.63 (m, 2H), 2.58-2.54 (m, 4H), 1.95-1.88 (m, 4H), 1.69-1.61 (m, 2H); LRMS (M+H) m/z 473.70.

Example 113

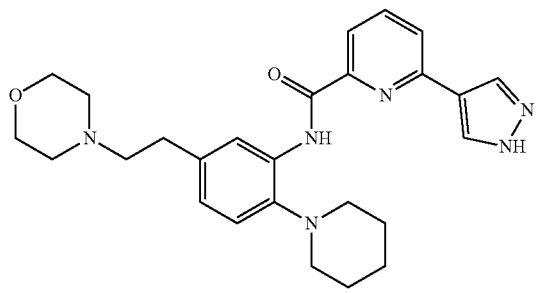 [SMILES: O=C(Nc1cc(CCN2CCOCC2)ccc1N1CCCCC1)c1cccc(-c2cn[nH]c2)n1]

I-66: N-(5-(2-morpholinoethyl)-2-(piperidin-1-yl)phenyl)-6-(1H-pyrazol-4-yl)picolinamide The compound was prepared according to general procedure (B): 0.1 mmol scale, 49% yield.

$^1$H NMR (300 MHz, Chloroform-d) δ 11.02 (s, 1H), 10.24 (v br s, 1H), 8.49 (d, J=1.9 Hz, 1H), 8.27 (s, 1H), 8.17 (d, J=7.5 Hz, 1H), 7.89 (dd, J=7.8, 7.8 Hz, 1H), 7.66 (d, J=8.0 Hz, 1H), 7.10 (d, J=8.1 Hz, 1H), 6.95 (dd, J=8.1, 2.0 Hz, 1H), 3.77-3.74 (m, 4H), 2.87-2.81 (m, 6H), 2.68-2.63 (m, 2H), 2.57-2.54 (m, 4H), 1.82-1.75 (m, 4H), 1.62-1.54 (m, 2H); LRMS (M+H) m/z 461.82.

Example 114

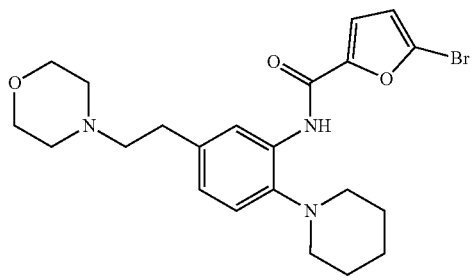 [SMILES: O=C(Nc1cc(CCN2CCOCC2)ccc1N1CCCCC1)c1ccc(Br)o1]

5-bromo-N-(5-(2-morpholinoethyl)-2-(piperidin-1-yl)phenyl) furan-2-carboxamide

The compound was prepared according to general procedure (A): 1 mmol scale, >99% yield.

$^1$H NMR (300 MHz, Chloroform-d) δ 9.71 (s, 1H), 8.34 (d, J=2.0 Hz, 1H), 7.15 (d, J=3.5 Hz, 1H), 7.09 (d, J=8.0 Hz, 1H), 6.93 (dd, J=8.1, 2.1 Hz, 1H), 6.50 (d, J=3.5 Hz, 1H), 3.77-3.73 (m, 4H), 2.84-2.78 (m, 6H), 2.66-2.60 (m, 2H), 2.56-2.53 (m, 4H), 1.86-1.78 (m, 4H), 1.68-1.60 (m, 2H); LRMS (M+H) m/z 462.67.

Example 115

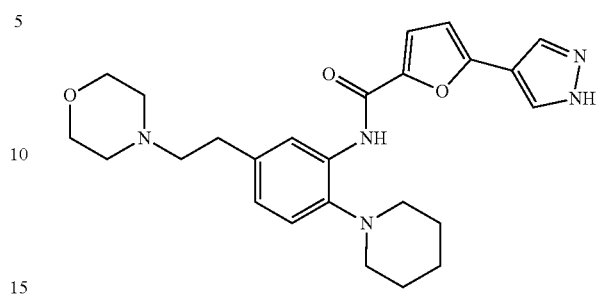

I-67: N-(5-(2-morpholinoethyl)-2-(piperidin-1-yl)phenyl)-5-(1H-pyrazol-4-yl)furan-2-carboxamide The compound was prepared according to general procedure (B): 0.1 mmol scale, 71% yield.

$^1$H NMR (300 MHz, Chloroform-d) δ 10.54 (v br s, 1H), 9.70 (s, 1H), 8.41 (d, J=1.8 Hz, 1H), 7.92 (s, 2H), 7.27-7.26 (m, partially overlapped with CHCl$_3$, 1H), 7.10 (d, J=8.0 Hz, 1H), 6.92 (dd, J=8.0, 1.7 Hz, 1H), 6.54 (d, J=3.5 Hz, 1H), 3.77-3.74 (m, 4H), 2.86-2.79 (m, 6H), 2.67-2.62 (m, 2H), 2.56-2.53 (m, 4H), 1.86-1.78 (m, 4H), 1.69-1.62 (m, 2H); LRMS (M+H) m/z 450.78.

Example 116

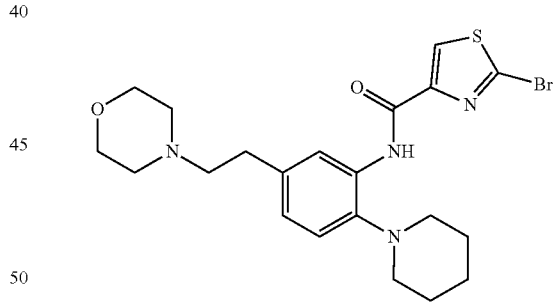

2-bromo-N-(5-(2-morpholinoethyl)-2-(piperidin-1-yl)phenyl)thiazole-4-carboxamide The compound was prepared according to general procedure (A): 1 mmol scale, >99% yield.

$^1$H NMR (300 MHz, Chloroform-d) δ 10.47 (s, 1H), 8.38 (d, J=2.0 Hz, 1H), 8.11 (s, 1H), 7.09 (d, J=8.0 Hz, 1H), 6.94 (dd, J=8.0, 2.0 Hz, 1H), 3.77-3.74 (m, 4H), 2.85-2.78 (m, 6H), 2.67-2.61 (m, 2H), 2.56-2.53 (m, 4H), 1.89-1.81 (m, 4H), 1.69-1.59 (m, 2H); LRMS (M+H) m/z 479.66.

Example 117

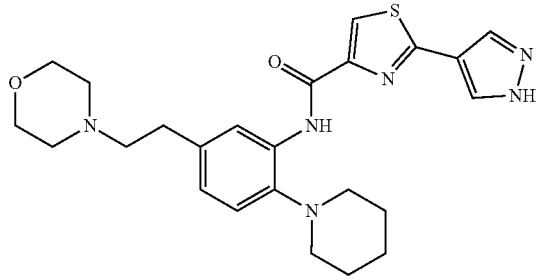 [SMILES: O=C(Nc1cc(CCN2CCOCC2)ccc1N1CCCCC1)c1csc(-c2cn[nH]c2)n1]

I-68: N-(5-(2-morpholinoethyl)-2-(piperidin-1-yl)phenyl)-2-(1H-pyrazol-4-yl)thiazole-4-carboxamide The compound was prepared according to general procedure (B): 0.1 mmol scale, 35% yield.

¹H NMR (300 MHz, Chloroform-d) δ 10.60 (s, 1H), 9.97 (v br s, 1H), 8.46 (d, J=1.8 Hz, 1H), 8.09 (s, 3H), 7.09 (d, J=8.0 Hz, 1H), 6.94 (dd, J=8.0, 2.0 Hz, 1H), 3.78-3.74 (m, 4H), 2.87-2.80 (m, 6H), 2.69-2.63 (m, 2H), 2.57-2.54 (m, 4H), 1.90-1.82 (m, 4H), 1.69-1.63 (m, 2H); LRMS (M+H) m/z 467.67.

Example 118

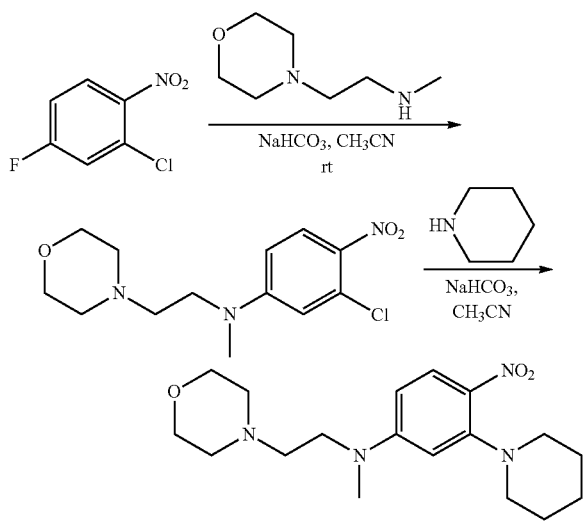

N-methyl-N-(2-morpholinoethyl)-4-nitro-3-(piperidin-1-yl)aniline

A CH₃CN (40 mL) solution of 2-chloro-4-fluoro-1-nitrobenzene (3.51 g, 20 mmol), NaHCO₃ (1.85 g, 22 mmol) and N-methyl-2-morpholinoethan-1-amine (2.94 g, 20.4 mmol) was stirred at room temperature. After 16 hours, the reaction went to completion as monitored by LC-MS. To the crude reaction mixture, NaHCO₃ (1.85 g, 22 mmol) and piperidine (2.17 mL, 22 mmol) were added and the reaction was stirred at 70° C., then at 75° C. for a total of 6 days until about 4% starting material was left. Volatiles were removed by rotary evaporation and product was purified by silica gel column chromatography. Compound N-methyl-N-(2-morpholinoethyl)-4-nitro-3-(piperidin-1-yl)aniline was obtained as an orange color thick oil: 5.55 g (80% yield over 2 steps); ¹H NMR (300 MHz, Chloroform-d) δ 8.05 (d, J=9.4 Hz, 1H), 6.23 (dd, J=9.4, 2.7 Hz, 1H), 6.10 (d, J=2.7 Hz, 1H), 3.73-3.70 (m, 4H), 3.54 (t, J=7.2 Hz, 2H), 3.06 (s, 3H), 3.03-3.00 (m, 4H), 2.56 (t, J=7.2 Hz, 2H), 2.53-2.49 (m, 4H), 1.81-1.73 (m, 4H), 1.64-1.57 (m, 2H); LRMS (M+H) m/z 349.61.

Example 119

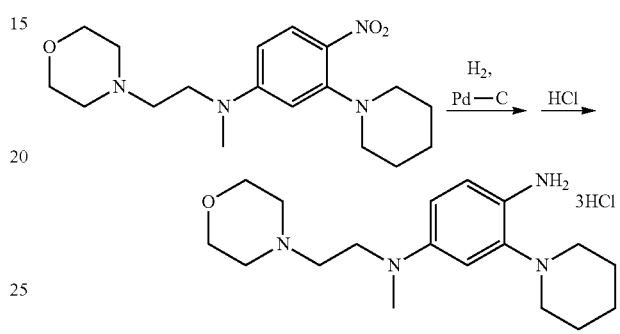

N1-methyl-N1-(2-morpholinoethyl)-3-(piperidin-1-yl)benzene-1,4-diamine Tri-Hydrogen Chloride In a Parr flask under 30 psi of H₂, an EtOAc (50 mL) solution of N-methyl-N-(2-morpholinoethyl)-4-nitro-3-(piperidin-1-yl)aniline (5.55 g, 16 mmol) and Pd—C (10% Pd on C, 50% wet, 0.5 g) was shaken at room temperature for 20 hours. The reaction went to completion as monitored by LC-MS. Solid was removed by filtration through a celite pad, washing with EtOAc. Filtrate was collected in a receiving flask containing 12 mL of 4M HCl-dioxane solution, and a free-flowing solid was formed after the addition of EtOH (<5 mL). Precipitate was collected by filtration, washed with EtOAc-EtOH (<5%), and was dried in vacuo. Compound N1-methyl-N1-(2-morpholinoethyl)-3-(piperidin-1-yl)benzene-1,4-diamine tri-hydrogen chloride was obtained as an off-white solid: 5.96 g (87% yield); ¹H NMR (300 MHz, Methanol-d₄) δ 7.35 (d, J=9.0 Hz, 1H), 7.24 (d, J=2.5 Hz, 1H), 7.02 (dd, J=9.1, 2.6 Hz, 1H), 4.03-3.98 (m, 6H), 3.60-3.44 (m, 6H), 3.42-3.28 (m, partially overlapped with CH₃OH, 4H), 3.12 (s, 3H), 2.11-2.03 (m, 4H), 1.86-1.78 (m, 2H); LRMS (M+H) m/z 318.44.

Example 120

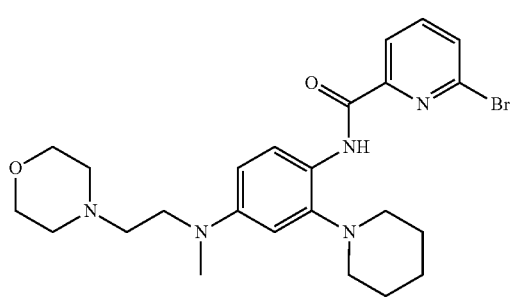 [SMILES: CN(CCN1CCOCC1)c1ccc(NC(=O)c2cccc(Br)n2)c(N2CCCCC2)c1]

6-bromo-N-(4-(methyl(2-morpholinoethyl)amino)-2-(piperidin-1-yl)phenyl)picolinamide The compound was prepared according to general procedure (A): 1 mmol scale, 98% yield.

$^1$H NMR (300 MHz, Chloroform-d) δ 10.83 (s, 1H), 8.41 (d, J=8.8 Hz, 1H), 8.23 (dd, J=7.5, 1.0 Hz, 1H), 7.74 (dd, J=7.7, 7.7 Hz, 1H), 7.61 (dd, J=7.9, 1.0 Hz, 1H), 6.56 (d, J=2.8 Hz, 1H), 6.52 (dd, J=8.8z, 2.8 Hz, 1H), 3.74-3.71 (m, 4H), 3.49-3.44 (m, 2H), 2.96 (s, 3H), 2.89-2.85 (m, 4H), 2.57-2.50 (m, 6H), 1.96-1.88 (m, 4H), 1.68-1.61 (m, 2H); LRMS (M+H) m/z 504.22.

Example 121

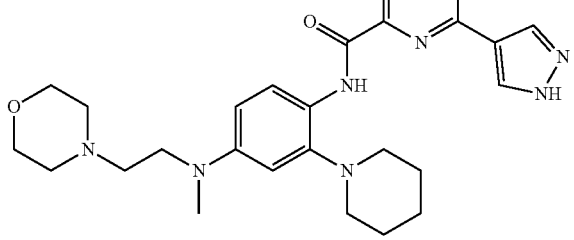

I-69: N-(4-(methyl(2-morpholinoethyl)amino)-2-(piperidin-1-yl)phenyl)-6-(1H-pyrazol-4-yl)picolinamide The compound was prepared according to general procedure (B): 0.1 mmol scale, 27% yield.

$^1$H NMR (300 MHz, Chloroform-d) δ 10.75 (s, 1H), 9.93 (v br s, 1H), 8.43-8.40 (m, 1H), 8.26 (s, 2H), 8.16 (dd, J=7.7, 1.0 Hz, 1H), 7.88 (dd, J=7.8, 7.8 Hz, 1H), 7.63 (dd, J=7.8, 1.1 Hz, 1H), 6.56-6.52 (m, 2H), 3.75-3.72 (m, 4H), 3.50-3.45 (m, 2H), 2.96 (s, 3H), 2.90-2.86 (m, 4H), 2.58-2.51 (m, 6H), 1.83-1.75 (m, 4H), 1.63-1.55 (m, 2H); LRMS (M+H) m/z 490.35.

Example 122

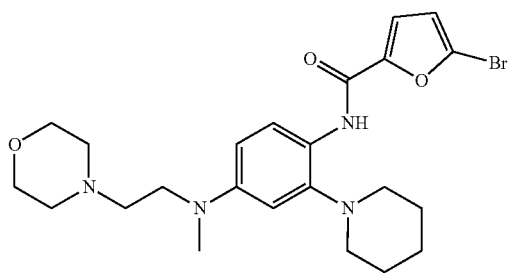 [SMILES: CN(CCN1CCOCC1)c1ccc(NC(=O)c2ccc(Br)o2)c(N2CCCCC2)c1]

5-bromo-N-(4-(methyl(2-morpholinoethyl)amino)-2-(piperidin-1-yl)phenyl)furan-2-carboxamide The compound was prepared according to general procedure (A): 1 mmol scale, 60% yield.

$^1$H NMR (300 MHz, Chloroform-d) δ 9.33 (s, 1H), 8.28 (d, J=8.8 Hz, 1H), 7.11 (d, J=3.5 Hz, 1H), 6.55 (d, J=2.8 Hz, 1H), 6.51 (dd, J=8.8, 2.8 Hz, 1H), 6.48 (d, J=3.5 Hz, 1H), 3.74-3.71 (m, 4H), 3.48-3.44 (m, 2H), 2.94 (s, 3H), 2.86-2.83 (m, 4H), 2.57-2.51 (m, 6H), 1.86-1.78 (m, 4H), 1.67-1.60 (m, 2H); LRMS (M+H) m/z 493.23.

Example 123

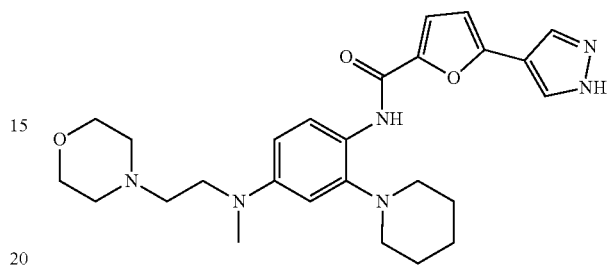

I-70: N-(4-(methyl(2-morpholinoethyl)amino)-2-(piperidin-1-yl)phenyl)-5-(1H-pyrazol-4-yl)furan-2-carboxamide The compound was prepared according to general procedure (B): 0.1 mmol scale, 38% yield.

$^1$H NMR (300 MHz, Chloroform-d) δ 10.10 (v br s, 1H), 9.35 (s, 1H), 8.34 (d, J=8.7 Hz, 1H), 7.92 (s, 2H), 7.23 (d, J=3.5 Hz, 1H), 6.56-6.51 (m, 3H), 3.75-3.72 (m, 4H), 3.49-3.44 (m, 2H), 2.95 (s, 3H), 2.89-2.85 (m, 4H), 2.57-2.50 (m, 6H), 1.86-1.78 (m, 4H), 1.69-1.61 (m, 2H); LRMS (M+H) m/z 479.32.

Example 124

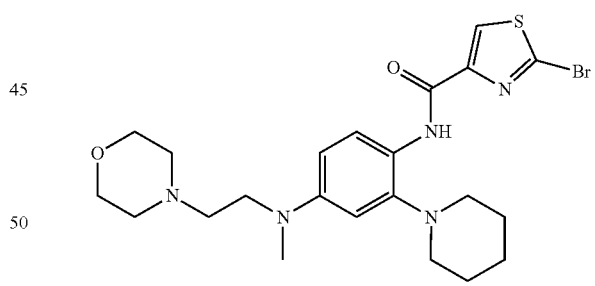

2-bromo-N-(4-(methyl(2-morpholinoethyl)amino)-2-(piperidin-1-yl)phenyl)thiazole-4-carboxamide The compound was prepared according to general procedure (A): 1 mmol scale, >99% yield.

$^1$H NMR (300 MHz, Chloroform-d) δ 10.12 (s, 1H), 8.32 (d, J=8.8 Hz, 1H), 8.07 (s, 1H), 6.54 (d, J=2.7 Hz, 1H), 6.50 (dd, J=8.8, 2.8 Hz, 1H), 3.74-3.71 (m, 4H), 3.49-3.44 (m, 2H), 2.95 (s, 3H), 2.87-2.83 (m, 4H), 2.57-2.50 (m, 6H), 1.89-1.81 (m, 4H), 1.66-1.60 (m, 2H); LRMS (M+H) m/z 510.20.

Example 125

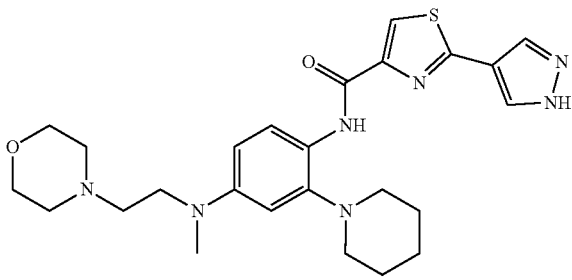 [SMILES: CN(CCN1CCOCC1)c1ccc(NC(=O)c2csc(-c3cn[nH]c3)n2)c(N2CCCCC2)c1]

I-71: N-(4-(methyl(2-morpholinoethyl)amino)-2-(piperidin-1-yl)phenyl)-2-(1H-pyrazol-4-yl)thiazole-4-carboxamide The compound was prepared according to general procedure (B): 0.1 mmol scale, 15% yield.

$^1$H NMR (300 MHz, Chloroform-d) δ 10.29 (s, 1H), 9.90 (v br s, 1H), 8.40 (d, J=8.6 Hz, 1H), 8.09 (s, 2H), 8.06 (dd, J=3.3, 0.5 Hz, 1H), 6.56-6.51 (m, 2H), 3.75-3.72 (m, 4H), 3.50-3.45 (m, 2H), 2.96 (s, 3H), 2.90-2.87 (m, 4H), 2.58-2.51 (m, 6H), 1.90-1.83 (m, 4H), 1.70-1.62 (m, 2H); LRMS (M+H) m/z 496.31.

Example 126

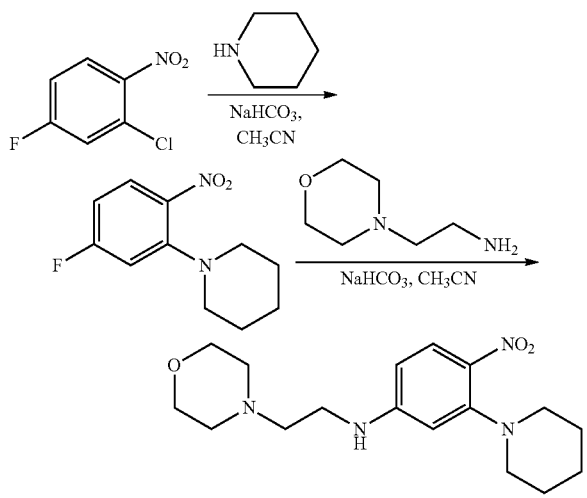

N-(2-morpholinoethyl)-4-nitro-3-(piperidin-1-yl)aniline

To a CH$_3$CN (30 mL) solution of 2,4-difluoro-1-nitrobenzene (2.39 g, 15 mmol) and NaHCO$_3$ (1.39 g, 16.5 mmol), piperidine (1.51 mL, 15.3 mmol) was added dropwise, and the resulting mixture was stirred at room temperature for 16 hours. To this solution, NaHCO$_3$ (1.32 g, 15.75 mmol) and 2-morpholinoethan-1-amine (2.0 mL, 15.3 mmol) were added and the reaction was stirred at 70° C., then at 75° C. for a total of 11 days until less than 15% starting material was left. Volatiles were removed by rotary evaporation and product was purified by silica gel column chromatography. Compound 1-(5-fluoro-2-nitrophenyl)piperidine was obtained as an orange color thick oil: 4.25 g (85% yield over two steps); $^1$H NMR (300 MHz, Chloroform-d) δ 8.00 (d, J=9.1 Hz, 1H), 6.13 (dd, J=9.1, 2.4 Hz, 1H), 6.06 (d, J=2.4 Hz, 1H), 4.99 (t, J=3.9 Hz, 1H), 3.75-3.72 (m, 4H), 3.26-3.20 (m, 2H), 3.03-2.99 (m, 4H), 2.67-2.63 (m, 2H), 2.50-2.47 (m, 4H), 1.80-1.72 (m, 4H), 1.64-1.56 (m, 2H); LRMS (M+H) m/z 335.57.

Regiochemistry was confirmed by 1D-NOESY experiment: NOE was observed between N$\underline{H}$ and two protons on Ph.

Example 127

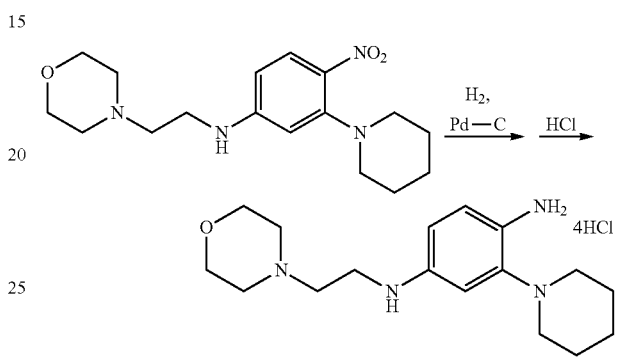

N1-(2-morpholinoethyl)-3-(piperidin-1-yl)benzene-1,4-diamine Tetra-Hydrogen Chloride In a Parr flask under 35 psi of H$_2$, an EtOAc (50 mL) solution of N-methyl-N-(2-morpholinoethyl)-4-nitro-3-(piperidin-1-yl)aniline (4.25 g, 12.7 mmol) and Pd—C (10% Pd on C, 50% wet, 0.5 g) was shaken at room temperature for 17 hours. The reaction went to completion as monitored by LC-MS. Solid was removed by filtration through a celite pad, washing with EtOAc. Filtrate was collected in a receiving flask containing 15 mL of 4M HCl-dioxane solution, and volatiles were removed in vacuo. Compound N1-(2-morpholinoethyl)-3-(piperidin-1-yl)benzene-1,4-diamine tetrahydrogen chloride was obtained as a brown solid: 6 g (>99% yield); $^1$H NMR (300 MHz, Methanol-d$_4$) δ 7.35-7.32 (m, 2H), 7.02 (dd, J=8.9, 2.3 Hz, 1H), 4.12-3.93 (m, 4H), 3.80 (t, J=6.5 Hz, 2H), 3.73-3.70 (m, 4H), 3.65-3.60 (m, 2H), 3.47 (t, J=6.5 Hz, 2H), 3.32-3.23 (m, partially overlapped with CH$_3$OH, 2H), 2.22-2.15 (m, 4H), 1.90-1.82 (m, 2H); LRMS (M+H) m/z 305.76.

Example 128

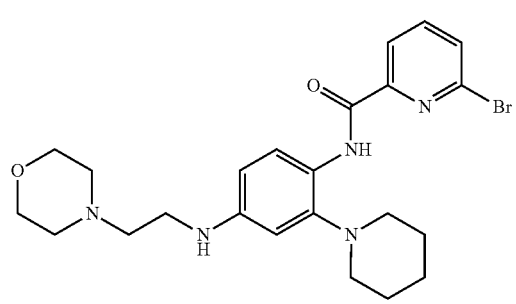 [SMILES: O=C(Nc1ccc(NCCN2CCOCC2)cc1N1CCCCC1)c1cccc(Br)n1]

6-bromo-N-(4-((2-morpholinoethyl)amino)-2-(piperidin-1-yl)phenyl)picolinamide The compound was prepared according to general procedure (A): 1 mmol scale, 68% yield.

$^1$H NMR (300 MHz, Chloroform-d) δ 10.82 (s, 1H), 8.39 (d, J=8.6 Hz, 1H), 8.23 (dd, J=7.6, 1.0 Hz, 1H), 7.74 (dd, J=7.7, 7.7 Hz, 1H), 7.61 (dd, J=7.9, 1.0 Hz, 1H), 6.49 (d, J=2.5 Hz, 1H), 6.44 (dd, J=8.7, 2.6 Hz, 1H), 3.75-3.72 (m, 4H), 3.70-3.66 (m, 1H), 3.20-3.16 (m, 2H), 2.88-2.84 (m, 4H), 2.66-2.62 (m, 2H), 2.50-2.47 (m, 4H), 1.95-1.87 (m, 4H), 1.67-1.62 (m, 2H); LRMS (M+H) m/z 488.66.

Example 129

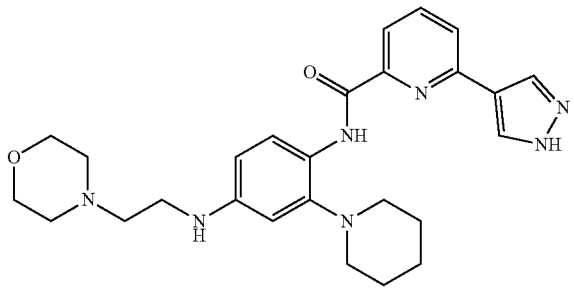 [SMILES: O=C(Nc1ccc(NCCN2CCOCC2)cc1N1CCCCC1)c1cccc(-c2cn[nH]c2)n1]

I-72: N-(4-((2-morpholinoethyl)amino)-2-(piperidin-1-yl)phenyl)-6-(1H-pyrazol-4-yl)picolinamide The compound was prepared according to general procedure (B): 0.1 mmol scale, 54% yield.

$^1$H NMR (300 MHz, Chloroform-d) δ 10.75 (s, 1H), 10.03 (v br s, 1H), 8.39 (d, J=8.7 Hz, 1H), 8.26 (s, 2H), 8.16 (dd, J=7.7, 1.0 Hz, 1H), 7.87 (dd, J=7.8, 7.8 Hz, 1H), 7.63 (dd, J=7.9, 1.0 Hz, 1H), 6.48-6.44 (m, 2H), 4.26 (br s, 1H), 3.76-3.73 (m, 4H), 3.19 (t, J=5.9 Hz, 2H), 2.88-2.84 (m, 4H), 2.65-2.62 (m, 2H), 2.51-2.48 (m, 4H), 1.81-1.74 (m, 4H), 1.60-1.52 (m, 2H); LRMS (M+H) m/z 476.90.

Example 130

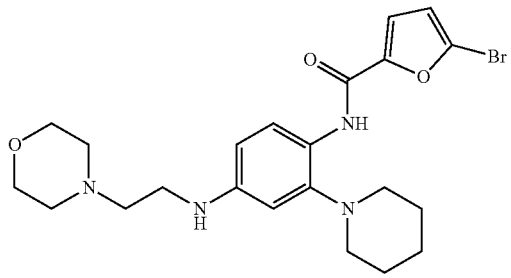 [SMILES: O=C(Nc1ccc(NCCN2CCOCC2)cc1N1CCCCC1)c1ccc(Br)o1]

5-bromo-N-(4-((2-morpholinoethyl)amino)-2-(piperidin-1-yl)phenyl)furan-2-carboxamide The compound was prepared according to general procedure (A): 1 mmol scale, 60% yield.

$^1$H NMR (300 MHz, Chloroform-d) δ 9.32 (s, 1H), 8.26 (d, J=8.6 Hz, 1H), 7.11 (d, J=3.5 Hz, 1H), 6.48-6.45 (m, 2H), 6.43 (dd, J=8.7, 2.6 Hz, 1H), 3.75-3.72 (m, 4H), 3.70-3.67 (m, 1H), 3.16 (dd, J=6.6, 5.1 Hz, 2H), 2.85-2.82 (m, 4H), 2.64 (dd, J=6.6, 5.1 Hz, 2H), 2.50-2.47 (m, 4H), 1.85-1.78 (m, 4H), 1.68-1.59 (m, 2H); LRMS (M+H) m/z 477.54.

Example 131

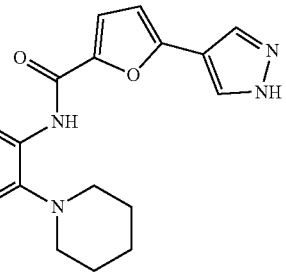

I-73: N-(4-((2-morpholinoethyl)amino)-2-(piperidin-1-yl)phenyl)-5-(1H-pyrazol-4-yl)furan-2-carboxamide The compound was prepared according to general procedure (B): 0.1 mmol scale, 63% yield.

$^1$H NMR (300 MHz, Chloroform-d) δ 10.57 (v br s, 1H), 9.35 (s, 1H), 8.32 (d, J=8.6 Hz, 1H), 7.92 (s, 2H), 7.22 (d, J=3.6 Hz, 1H), 6.52 (d, J=3.6 Hz, 1H), 6.49 (d, J=2.5 Hz, 1H), 6.45 (dd, J=8.6, 2.5 Hz, 1H), 4.20 (br s, 1H), 3.75-3.72 (m, 4H), 3.19-3.15 (m, 2H), 2.87-2.84 (m, 4H), 2.66-2.62 (m, 2H), 2.50-2.47 (m, 4H), 1.85-1.77 (m, 4H), 1.68-1.60 (m, 2H); LRMS (M+H) m/z 465.86.

Example 132

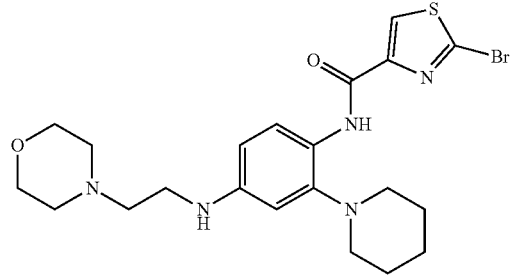 [SMILES: O=C(Nc1ccc(NCCN2CCOCC2)cc1N1CCCCC1)c1csc(Br)n1]

2-bromo-N-(4-((2-morpholinoethyl)amino)-2-(piperidin-1-yl)phenyl)thiazole-4-carboxamide The compound was prepared according to general procedure (A): 1 mmol scale, 68% yield.

$^1$H NMR (300 MHz, Chloroform-d) δ 10.11 (s, 1H), 8.30 (d, J=8.6 Hz, 1H), 8.06 (s, 1H), 6.47 (d, J=2.5 Hz, 1H), 6.43 (dd, J=8.6, 2.6 Hz, 1H), 3.75-3.72 (m, 4H), 3.69-3.67 (m, 1H), 3.17 (dd, J=6.6, 5.1 Hz, 2H), 2.86-2.82 (m, 4H), 2.64 (dd, J=6.6, 5.1 Hz, 2H), 2.50-2.47 (m, 4H), 1.88-1.80 (m, 4H), 1.68-1.58 (m, 2H); LRMS (M+H) m/z 494.59.

Example 133

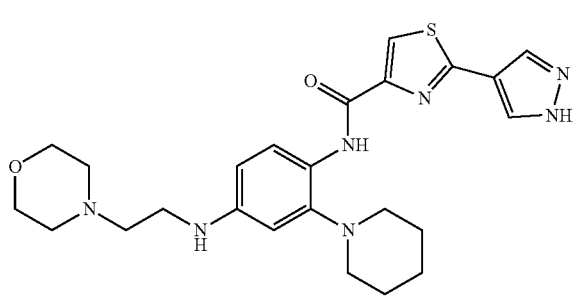 [SMILES: O=C(Nc1ccc(NCCN2CCOCC2)cc1N1CCCCC1)c1csc(-c2cn[nH]c2)n1]

I-74: N-(4-((2-morpholinoethyl)amino)-2-(piperidin-1-yl)phenyl)-2-(1H-pyrazol-4-yl)thiazole-4-carboxamide The compound was prepared according to general procedure (B): 0.1 mmol scale, 45% yield.

$^1$H NMR (300 MHz, Chloroform-d) δ 10.73 (br s, 1H), 10.29 (s, 1H), 8.37 (d, J=8.5 Hz, 1H), 8.09-8.06 (m, 3H), 6.48-6.43 (m, 2H), 4.24 (br s, 1H), 3.76-3.72 (m, 4H), 3.20-3.16 (m, 2H), 2.89-2.85 (m, 4H), 2.67-2.63 (m, 2H), 2.51-2.48 (m, 4H), 1.89-1.82 (m, 4H), 1.70-1.59 (m, 2H); LRMS (M+H) m/z 482.88.

Example 134

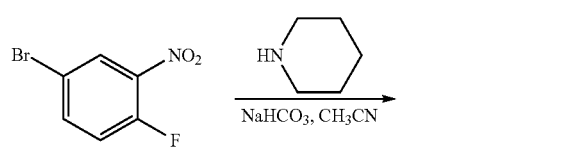

1-(4-bromo-2-nitrophenyl)piperidine

A CH$_3$CN (60 mL) solution of 4-bromo-1-fluoro-2-nitrobenzene (6.6 g, 30 mmol), NaHCO$_3$ (2.65 g, 31.5 mmol) and piperidine (3.02 mL, 30.6 mmol) was stirred at room temperature for 22 hours. Volatiles were removed by rotary evaporation and the residual was suspended in CH$_2$Cl$_2$ (100 mL). Solid was removed by filtration, washing with CH$_2$Cl$_2$. Filtrate was collected and the solvent was removed in vacuo. Compound 1-(4-bromo-2-nitrophenyl)piperidine was obtained as an orange color oil: 8.53 g (>99% yield); $^1$H NMR (300 MHz, Chloroform-d) δ 7.88 (d, J=2.4 Hz, 1H), 7.51 (dd, J=8.9, 2.4 Hz, 1H), 6.99 (d, J=8.9 Hz, 1H), 3.01-2.98 (m, 4H), 1.74-1.66 (m, 4H), 1.65-1.57 (m, 2H); LRMS (M+H) m/z 285.29, 287.23.

Example 135

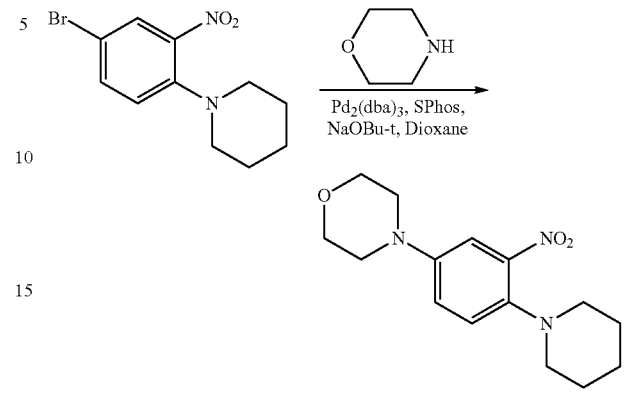

4-(3-nitro-4-(piperidin-1-yl)phenyl)morpholine

A 1,4-Dioxane (20 mL) solution of 1-(4-bromo-2-nitrophenyl)piperidine (2.85 g, 10 mmol), morpholine (1.73 mL, 20 mmol), Pd$_2$(dba)$_3$ (275 mg, 0.3 mmol), S-Phos (246 mg, 0.6 mmol) and NaOBu$^t$ (1.35 g, 14 mmol) was de-gassed and backed filled with nitrogen, three times. The solution was then stirred under nitrogen at 100° C. for 4 hours. The reaction went to completion as monitored by LC-MS. Solid was removed by filtration through a celite pad, washing with MeOH. The filtrate was collected and the solvent was removed in vacuo. The product was purified by silica gel column chromatography to provide 4-(3-nitro-4-(piperidin-1-yl)phenyl)morpholine as a reddish-brown color thick oil: 2.9 g (>99% yield); $^1$H NMR (300 MHz, Chloroform-d) δ 7.24 (d, J=3.0, 1H), 7.12 (d, J=8.9 Hz, 1H), 7.04 (dd, J=8.9, 3.0 Hz, 1H), 3.87-3.84 (m, 4H), 3.13-3.10 (m, 4H), 2.93-2.89 (m, 4H), 1.73-1.66 (m, 4H), 1.58-1.52 (m, 2H); LRMS (M+H) m/z 292.49.

Example 136

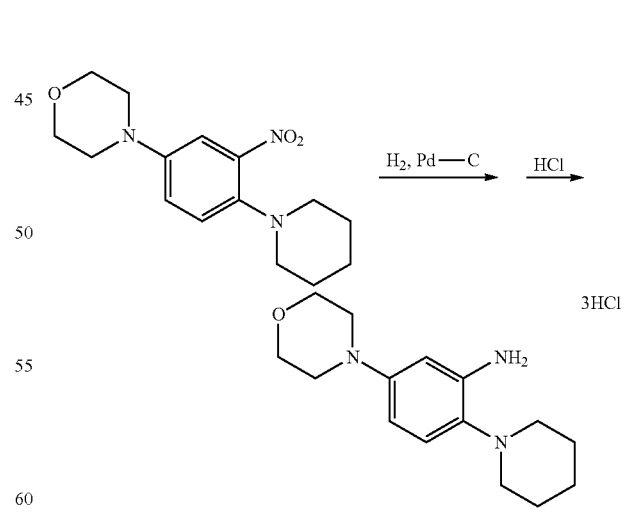

5-morpholino-2-(piperidin-1-yl)aniline Tri-Hydrogen Chloride

In a Parr flask under 35 psi of H$_2$, an EtOAc (50 mL) solution of 4-(3-nitro-4-(piperidin-1-yl)phenyl)morpholine (2.9 g, 10 mmol) and Pd—C (10% Pd on C, 50% wet, 0.5 g) was shaken at room temperature for 18 hours. The reaction went to completion as monitored by LC-MS. Solid was removed by filtration through a celite pad, washing with EtOAc and MeOH. Filtrate was collected in a receiving flask containing 10 mL of 4M HCl-dioxane solution, and the volatiles were removed in vacuo. The crude oily material was suspended in EtOAc-MeOH (<5%)-EtOH (<10%), and mixed well until free-flowing solid was formed. Precipitate was collected by filtration, washed with EtOAc and was dried in vacuo. Compound 5-morpholino-2-(piperidin-1-yl) aniline tri-hydrogen chloride was obtained as a greyish-green solid: 2.45 g (66% yield); $^1$H NMR (300 MHz, Methanol-$d_4$) δ 7.70-7.61 (m, 1H), 7.19-7.03 (m, 2H), 4.06-3.98 (m, 2H), 3.89-3.86 (m, 2H), 3.63-3.52 (m, 6H), 3.10-3.06 (m, 2H), 2.13-2.09 (m, 4H), 2.05-1.99 (m, 2H); LRMS (M+H) m/z 262.49.

Example 137

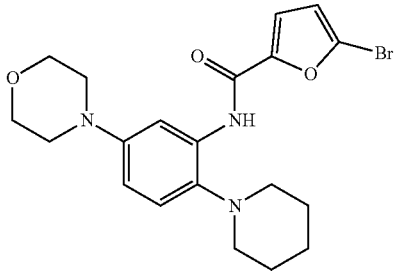 [SMILES: O=C(Nc1cc(N2CCOCC2)ccc1N1CCCCC1)c1ccc(Br)o1]

5-bromo-N-(5-morpholino-2-(piperidin-1-yl)phenyl) furan-2-carboxamide

The compound was prepared according to general procedure (A): 1.0 mmol scale, 62% yield.

$^1$H NMR (300 MHz, Chloroform-d) δ 9.83 (s, 1H), 8.20 (d, J=2.8 Hz, 1H), 7.14 (d, J=3.5 Hz, 1H), 7.10 (d, J=8.7 Hz, 1H), 6.61 (dd, J=8.7, 2.8 Hz, 1H), 6.50 (d, J=3.5 Hz, 1H), 3.86-3.83 (m, 4H), 3.19-3.16 (m, 4H), 2.82-2.78 (m, 4H), 1.85-1.77 (m, 4H), 1.70-1.62 (m, 2H); LRMS (M+H) m/z 434.55, 436.85.

Example 138

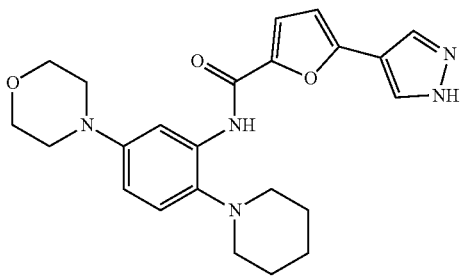 [SMILES: O=C(Nc1cc(N2CCOCC2)ccc1N1CCCCC1)c1ccc(-c2cn[nH]c2)o1]

I-25: N-(5-morpholino-2-(piperidin-1-yl)phenyl)-5-(1H-pyrazol-4-yl)furan-2-carboxamide The compound was prepared according to general procedure (B): 0.1 mmol scale, 50% yield.

$^1$H NMR (300 MHz, Chloroform-d) δ 10.43 (br s, 1H), 9.82 (s, 1H), 8.28 (d, J=2.8 Hz, 1H), 7.94 (s, 2H), 7.25 (d, J=3.5 Hz, 1H), 7.11 (d, J=8.7 Hz, 1H), 6.62 (dd, J=8.7, 2.9 Hz, 1H), 6.54 (d, J=3.5 Hz, 1H), 3.87-3.84 (m, 4H), 3.21-3.17 (m, 4H), 2.87-2.79 (m, 4H), 1.85-1.78 (m, 4H), 1.70-1.56 (m, 2H); LRMS (M+H) m/z 422.66.

Example 139

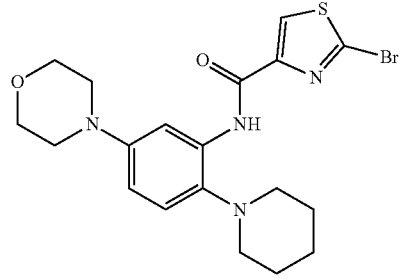 [SMILES: O=C(Nc1cc(N2CCOCC2)ccc1N1CCCCC1)c1csc(Br)n1]

2-bromo-N-(5-morpholino-2-(piperidin-1-yl)phenyl) thiazole-4-carboxamide

The compound was prepared according to general procedure (A): 1.0 mmol scale, 60% yield.

$^1$H NMR (300 MHz, Chloroform-d) δ 10.58 (s, 1H), 8.25 (d, J=2.9 Hz, 1H), 8.09 (s, 1H), 7.09 (d, J=8.7 Hz, 1H), 6.63 (dd, J=8.7, 2.9 Hz, 1H), 3.87-3.84 (m, 4H), 3.20-3.17 (m, 4H), 2.82-2.79 (m, 4H), 1.88-1.80 (m, 4H), 1.66-1.56 (m, 2H); LRMS (M+H) m/z 451.39, 453.65.

Example 140

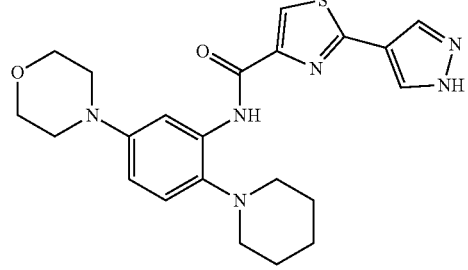

I-26: N-(5-morpholino-2-(piperidin-1-yl)phenyl)-2-(1H-pyrazol-4-yl)thiazole-4-carboxamide The compound was prepared according to general procedure (B): 0.1 mmol scale, 54% yield.

$^1$H NMR (300 MHz, Chloroform-d) δ 10.71 (s, 1H), 10.30 (v br s, 1H), 8.33 (d, J=2.9 Hz, 1H), 8.11 (s, 2H), 8.08 (s, 1H), 7.11 (d, J=8.7 Hz, 1H), 6.63 (dd, J=8.7, 2.9 Hz, 1H), 3.88-3.85 (m, 4H), 3.22-3.18 (m, 4H), 2.86-2.82 (m, 4H), 1.89-1.82 (m, 4H), 1.70-1.61 (m, 2H); LRMS (M+H) m/z 439.61.

Example 141

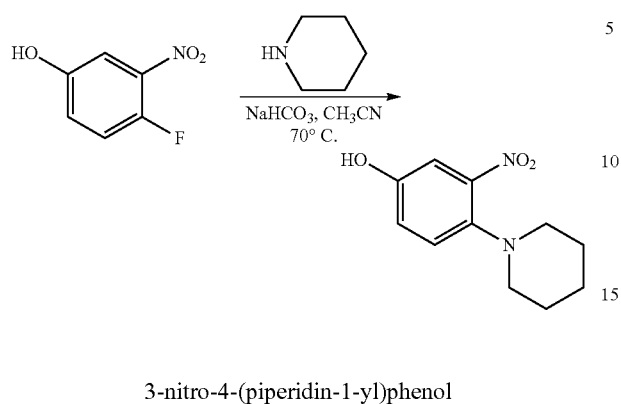

3-nitro-4-(piperidin-1-yl)phenol

A CH₃CN (50 mL) solution of 4-fluoro-3-nitrophenol (4.71 g, 30 mmol), NaHCO₃ (2.65 g, 31.5 mmol) and piperidine (3.02 mL, 30.6 mmol) was stirred at 70° C. for 13 days until less than 2% starting material was left unreacted. Volatiles were removed in vacuo and the product was purified by silica gel column chromatography. Compound 3-nitro-4-(piperidin-1-yl)phenol was obtained as a reddish-brown color oil: 6.6 g (>99% yield); $^1$H NMR (300 MHz, Chloroform-d) δ 7.23 (d, J=3.0 Hz, 1H), 7.10 (d, J=8.8 Hz, 1H), 6.98 (dd, J=8.8, 3.0 Hz, 1H), 5.14 (br s, 1H), 2.92-2.88 (m, 4H), 1.73-1.64 (m, 4H), 1.58-1.52 (m, 2H); LRMS (M+H) m/z 223.41.

Example 142

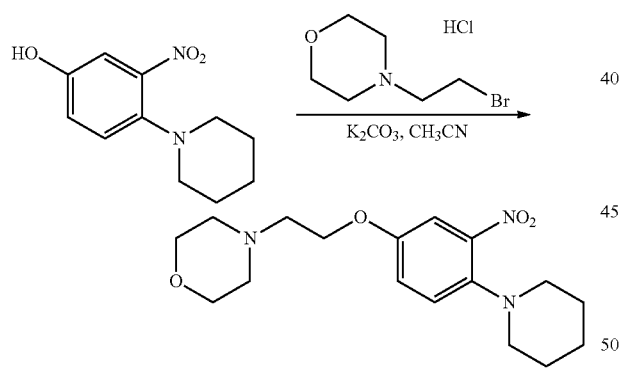

4-(2-(3-nitro-4-(piperidin-1-yl)phenoxy)ethyl)morpholine

A CH₃CN (20 mL) solution of 3-nitro-4-(piperidin-1-yl)phenol (2.22 g, 10 mmol), 4-(2-bromoethyl)morpholine hydrogen chloride (2.89 g, 10.5 mmol) and K₂CO₃ (3.04 g, 22 mmol) was stirred at room temperature for 30 minutes, then at 35° C. for 15 hours, then at 50° C. for a total of 5 days, until the reaction went to completion as monitored by LC-MS. Additional 4-(2-bromoethyl)morpholine hydrogen chloride (1 g at day 2 and 0.6 g at day 4) and K₂CO₃ (276 mg at day 4) were added during the course of the reaction. The solvent was then removed in vacuo and product was purified by silica gel column chromatography. Compound 4-(2-(3-nitro-4-(piperidin-1-yl)phenoxy)ethyl)morpholine was obtained as a reddish-brown color thick oil: 1.70 g (51% yield); $^1$H NMR (300 MHz, Chloroform-d) δ 7.28 (dd, J=2.9, 0.5 Hz, 1H), 7.12 (dd, J=9.0, 0.5 Hz, 1H), 7.05 (dd, J=9.0, 2.9 Hz, 1H), 4.09 (t, J=5.6 Hz, 2H), 3.75-3.72 (m, 4H), 2.93-2.89 (m, 4H), 2.79 (t, J=5.6 Hz, 2H), 2.58-2.55 (m, 4H), 1.734-1.66 (m, 4H), 1.59-1.51 (m, 2H); LRMS (M+H) m/z 336.51.

Example 143

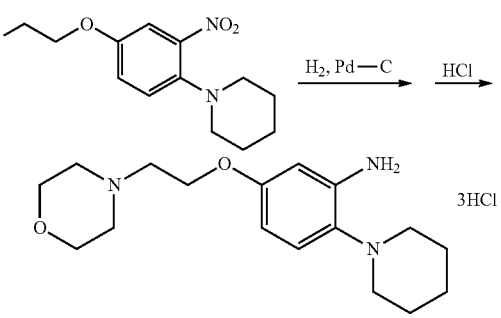

5-(2-morpholinoethoxy)-2-(piperidin-1-yl)aniline Tri-Hydrogen Chloride

In a Parr flask under 35 psi of H₂, an EtOAc (30 mL) solution of 4-(2-(3-nitro-4-(piperidin-1-yl)phenoxy)ethyl)morpholine (1.7 g, 5 mmol) and Pd—C (10% Pd on C, 50% wet, 0.5 g) was shaken at room temperature for 22 hours. The reaction went to completion as monitored by LC-MS. Solid was removed by filtration through a celite pad, washing with EtOAc. Filtrate was collected in a receiving flask containing 5 mL of 4M HCl-dioxane solution, and the volatiles were removed in vacuo. The crude solid was suspended in EtOAc-EtOH (<5%), and mixed well until free-flowing solid was formed. Precipitate was collected by filtration, washed with EtOAc and was dried in vacuo. Compound 5-(2-morpholinoethoxy)-2-(piperidin-1-yl)aniline tri-hydrogen chloride was obtained as an off-white solid: 2.01 g (96% yield); $^1$H NMR (300 MHz, Methanol-d₄) δ 7.49 (d, J=9.1 Hz, 1H), 6.72 (d, J=2.8 Hz, 1H), 6.66 (dd, J=9.1, 2.8 Hz, 1H), 4.45-4.42 (m, 2H), 4.10 (dd, J=13.2, 3.6 Hz, 2H), 3.88 (td, J=13.2, 12.6, 2.4 Hz, 2H), 3.70-3.64 (m, 2H), 3.64-3.54 (m, 6H), 3.38-3.28 (m, partially overlapped with CH₃OH, 2H), 2.14-2.06 (m, 4H), 1.86-1.77 (m, 2H); LRMS (M+H) m/z 306.45.

Example 144

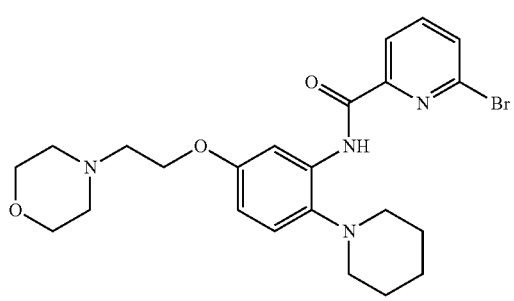 [SMILES: O=C(Nc1cc(OCCN2CCOCC2)ccc1N1CCCCC1)c1cccc(Br)n1]

6-bromo-N-(5-(2-morpholinoethoxy)-2-(piperidin-1-yl)phenyl)picolinamide

The compound was prepared according to general procedure (A): 1.0 mmol scale, >99% yield.

¹H NMR (300 MHz, Chloroform-d) δ 11.28 (s, 1H), 8.26 (d, J=2.9 Hz, 1H), 8.23 (dd, J=7.5, 1.0 Hz, 1H), 7.77 (dd, J=7.9, 7.5 Hz, 1H), 7.65 (dd, J=7.9, 1.0 Hz, 1H), 7.11 (d, J=8.7 Hz, 1H), 6.65 (dd, J=8.7, 2.9 Hz, 1H), 4.16 (t, J=5.7 Hz, 2H), 3.75-3.72 (m, 4H), 2.84-2.80 (m, 6H), 2.61-2.58 (m, 4H), 1.98-1.85 (m, 4H), 1.72-1.58 (m, 2H); LRMS (M+H) m/z 489.67.

Example 145

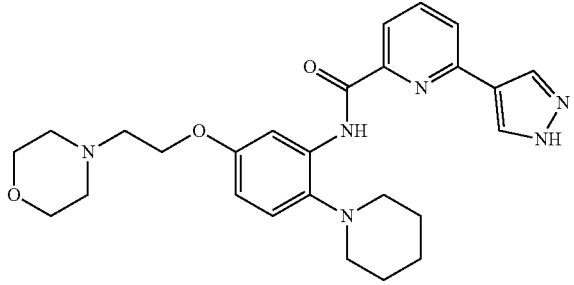 [SMILES: O=C(Nc1cc(OCCN2CCOCC2)ccc1N1CCCCC1)c1cccc(-c2cn[nH]c2)n1]

I-27: N-(5-(2-morpholinoethoxy)-2-(piperidin-1-yl)phenyl)-6-(1H-pyrazol-4-yl)picolinamide The compound was prepared according to general procedure (B): 0.1 mmol scale, 64% yield.

¹H NMR (300 MHz, Chloroform-d) δ 11.09 (s, 1H), 8.32 (d, J=2.9 Hz, 1H), 8.28 (s, 2H), 8.13 (dd, J=7.7, 1.1 Hz, 1H), 7.89 (dd, J=7.8, 7.8 Hz, 1H), 7.67 (dd, J=7.9, 1.0 Hz, 1H), 7.08 (d, J=8.7 Hz, 1H), 6.64 (dd, J=8.7, 2.9 Hz, 1H), 4.18 (t, J=5.6 Hz, 2H), 3.78-3.75 (m, 4H), 2.85-2.80 (m, 6H), 2.64-2.61 (m, 4H), 1.81-1.73 (m, 4H), 1.61-1.52 (m, 2H); LRMS (M+H) m/z 477.84.

Example 146

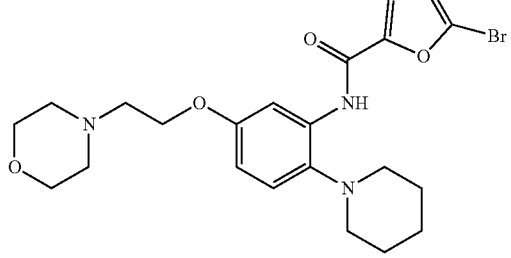

5-bromo-N-(5-(2-morpholinoethoxy)-2-(piperidin-1-yl)phenyl)furan-2-carboxamide

The compound was prepared according to general procedure (A): 1.0 mmol scale, 95% yield.

¹H NMR (300 MHz, Chloroform-d) δ 9.87 (s, 1H), 8.14 (d, J=2.9 Hz, 1H), 7.15 (d, J=3.5 Hz, 1H), 7.09 (d, J=8.7 Hz, 1H), 6.63 (dd, J=8.7, 2.9 Hz, 1H), 6.50 (d, J=3.5 Hz, 1H), 4.13 (t, J=5.7 Hz, 2H), 3.74-3.71 (m, 4H), 2.82-2.78 (m, 6H), 2.59-2.56 (m, 4H), 1.85-1.78 (m, 4H), 1.68-1.58 (m, 2H); LRMS (M+H) m/z 478.66.

Example 147

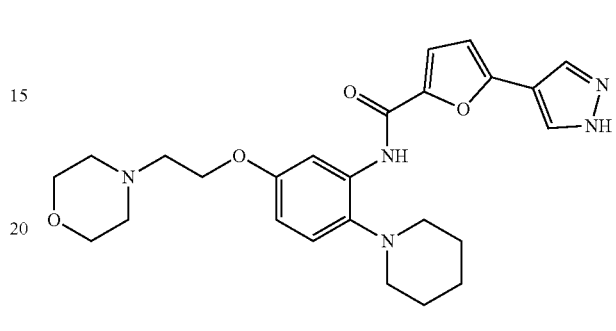

I-28: N-(5-(2-morpholinoethoxy)-2-(piperidin-1-yl)phenyl)-5-(1H-pyrazol-4-yl)furan-2-carboxamide The compound was prepared according to general procedure (B): 0.1 mmol scale, 63% yield.

¹H NMR (300 MHz, Chloroform-d) δ 9.85 (s, 1H), 8.22 (d, J=2.9 Hz, 1H), 7.93 (s, 2H), 7.26 (d, J=3.5 Hz, 1H), 7.10 (d, J=8.7 Hz, 1H), 6.62 (dd, J=8.7, 2.9 Hz, 1H), 6.54 (d, J=3.5 Hz, 1H), 4.15 (t, J=5.7 Hz, 2H), 3.76-3.73 (m, 4H), 2.83-2.79 (m, 6H), 2.61-2.58 (m, 4H), 1.84-1.77 (m, 4H), 1.69-1.58 (m, 2H); LRMS (M+H) m/z 466.79.

Example 148

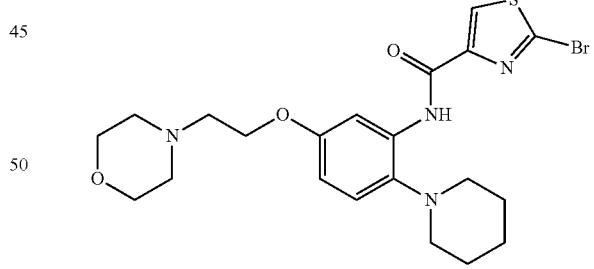

2-bromo-N-(5-(2-morpholinoethoxy)-2-(piperidin-1-yl)phenyl)thiazole-4-carboxamide The compound was prepared according to general procedure (A): 1.0 mmol scale, 90% yield.

¹H NMR (300 MHz, Chloroform-d) δ 10.61 (s, 1H), 8.19 (d, J=2.9 Hz, 1H), 8.10 (s, 1H), 7.09 (d, J=8.7 Hz, 1H), 6.64 (dd, J=8.7, 2.9 Hz, 1H), 4.14 (t, J=5.7 Hz, 2H), 3.75-3.71 (m, 4H), 2.82-2.78 (m, 6H), 2.60-2.57 (m, 4H), 1.88-1.80 (m, 4H), 1.68-1.57 (m, 2H); LRMS (M+H) m/z 495.62.

Example 149

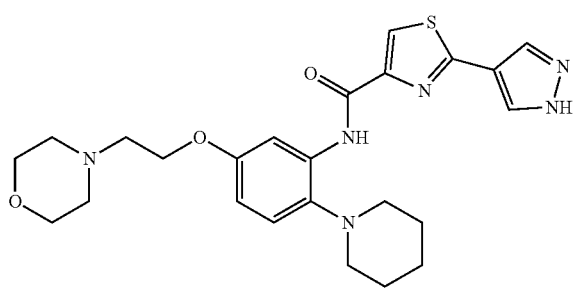 [SMILES: O=C(Nc1cc(OCCN2CCOCC2)ccc1N1CCCCC1)c1csc(-c2cn[nH]c2)n1]

I-29: N-(5-(2-morpholinoethoxy)-2-(piperidin-1-yl) phenyl)-2-(1H-pyrazol-4-yl)thiazole-4-carboxamide The compound was prepared according to general procedure (B): 0.1 mmol scale, 73% yield.

¹H NMR (300 MHz, Chloroform-d) δ 10.73 (s, 1H), 8.26 (d, J=2.9 Hz, 1H), 8.10 (s, 2H), 8.08 (s, 1H), 7.09 (d, J=8.7 Hz, 1H), 6.63 (dd, J=8.7, 2.9 Hz, 1H), 4.17 (t, J=5.6 Hz, 2H), 3.77-3.74 (m, 4H), 2.85-2.81 (m, 6H), 2.63-2.60 (m, 4H), 1.87-1.81 (m, 4H), 1.69-1.61 (m, 2H); LRMS (M+H) m/z 483.73.

Example 150

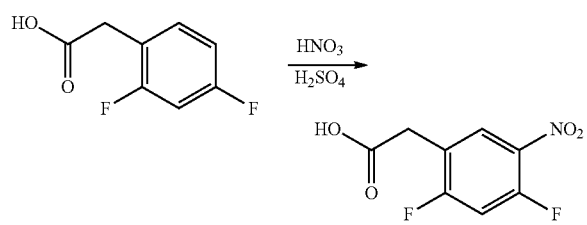

(Reference of 1st Step: U.S. Pat. No. 8,461,179)

2-(2,4-difluoro-5-nitrophenyl)acetic Acid

To a H₂SO₄ (50 mL) solution of 2-(2,4-difluorophenyl) acetic acid (8.61 g, 50 mmol) in an ice bath, HNO₃ (90% aq., 2.75 mL, 55 mmol) was added dropwise. After 30 minutes, the reaction mixture was poured over ice, and precipitate was collected by filtration, washed with H₂O, and was dried in vacuo. Compound 2-(2,4-difluoro-5-nitrophenyl)acetic acid was obtained as an off-white solid: 9.82 g (90% yield); ¹H NMR (300 MHz, Chloroform-d) δ 8.13 (ddd, J=8.0, 7.5, 0.5 Hz, 1H), 7.07 (dd, J=10.3, 8.9 Hz, 1H), 3.77-3.76 (m, 2H).

Example 151

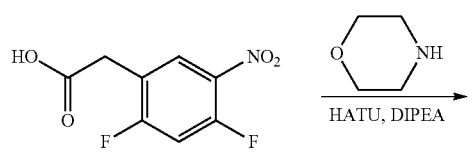

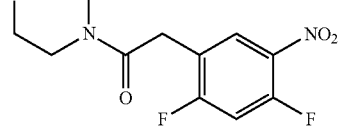

2-(2,4-difluoro-5-nitrophenyl)-1-morpholinoethan-1-one

A CH₂Cl₂ (100 mL) solution of 2-(2,4-difluoro-5-nitrophenyl)acetic acid (9.82 g, 45 mmol), morpholine (4.1 mL, 47 mmol), HATU (18.8 g, 49.5 mmol) and N-ethyl-N-isopropylpropan-2-amine (9.4 mL, 54 mmol) was stirred at room temperature for 16 hours, and the reaction went to completion as monitored by LC-MS. The reaction was quenched by the addition of saturated aqueous NaHCO₃ solution (100 mL), and CH₂Cl₂ was removed by rotary evaporation under reduced pressure. The aqueous solution was extracted with EtOAc (150 mL), and the organic layer was washed with saturated aqueous NH₄Cl solution (100 mL×2), dried (Na₂SO₄), filtered, and the solvent was removed in vacuo. Compound 2-(2,4-difluoro-5-nitrophenyl)-1-morpholinoethan-1-one was obtained as an orange color thick oil and was used without further purification; ¹H NMR (300 MHz, Chloroform-d) δ 8.10 (dd, J=7.8, 7.8 Hz, 1H), 7.04 (dd, J=10.4, 9.0 Hz, 1H), 3.75-3.55 (m, 10H); LRMS (M+H) m/z 287.43.

Example 152

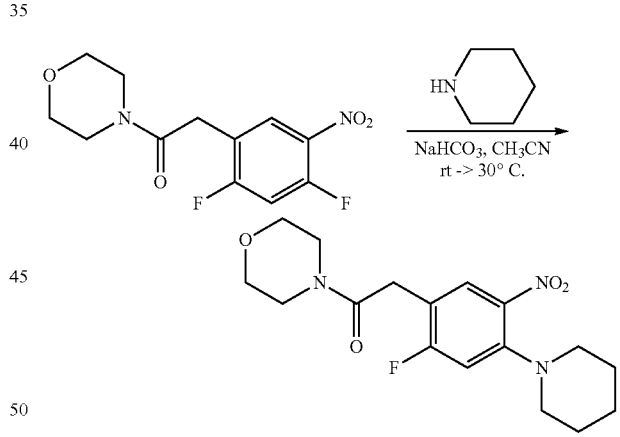

2-(2-fluoro-5-nitro-4-(piperidin-1-yl)phenyl)-1-morpholinoethan-1-one

A CH₃CN (45 mL) solution of 2-(2,4-difluoro-5-nitrophenyl)-1-morpholinoethan-1-one (6.4 g, 22.5 mmol), NaHCO₃ (2.08 g, 25 mmol) and piperidine (2.22 mL, 22.5 mmol) was stirred at room temperature for 24 hours, and then at 30° C. for a total of 42 hours, until less than 5% starting material was left by LC-MS. Additional piperidine (180 μL) was added at 24 hours. Volatiles were removed by rotary evaporation under reduced pressure and the product was purified by silica gel column chromatography. Compound 2-(2-fluoro-5-nitro-4-(piperidin-1-yl)phenyl)-1-morpholinoethan-1-one was obtained as an orange color solid:

7.47 g (94% yield); ¹H NMR (300 MHz, Chloroform-d) δ 7.81 (d, J=7.9 Hz, 1H), 6.76 (d, J=12.0 Hz, 1H), 3.71-3.63 (m, 6H), 3.62 (s, 2H), 3.55-3.52 (m, 2H), 3.03-2.99 (m, 4H), 1.76-1.68 (m, 4H), 1.64-1.57 (m, 2H); LRMS (M+H) m/z 352.63.

Example 153

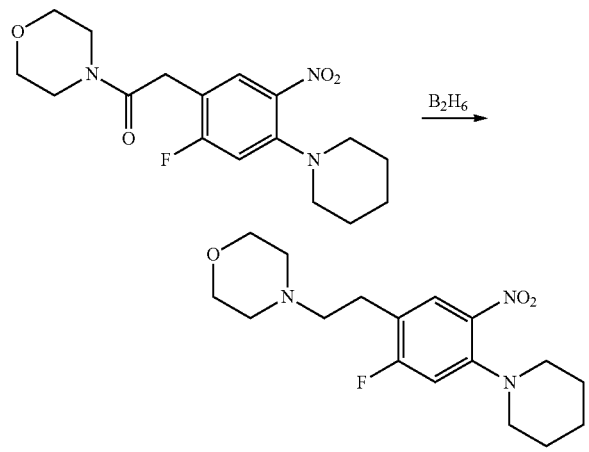

4-(2-fluoro-5-nitro-4-(piperidin-1-yl)phenethyl)morpholine

To a THF (30 mL) solution of 2-(2-fluoro-5-nitro-4-(piperidin-1-yl)phenyl)-1-morpholinoethan-1-one (5.27 g, 15 mmol) in an ice bath, B₂H₆-THF solution (1M in THF, 30 mL, 30 mmol) was added dropwise over 5 minutes. The reaction was continued at room temperature for 6 hours, and then was quenched with 1N HCl aqueous solution (30 mL). Stirring was continued at 30° C. overnight. Most of the THF was removed by rotary evaporation under reduced pressure, and after aqueous layer was basified with saturate NaHCO₃ aqueous solution, it was extracted with EtOAc (80 mL×2). Combined organic layers were dried (Na₂SO₄), filtered, and the solvent was removed in vacuo. Product was purified by silica gel column chromatography, and compound 4-(2-fluoro-5-nitro-4-(piperidin-1-yl)phenethyl)morpholine was obtained as an orangish-yellow color thick oil: 4.85 g (96% yield); ¹H NMR (300 MHz, Chloroform-d) δ 7.78 (d, J=8.0 Hz, 1H), 6.73 (d, J=11.9 Hz, 1H), 3.74-3.71 (m, 4H), 3.01-2.97 (m, 4H), 2.78-2.73 (m, 2H), 2.58-2.49 (m, 6H), 1.76-1.68 (m, 4H), 1.63-1.57 (m, 2H); LRMS (M+H) m/z 338.62.

Example 154

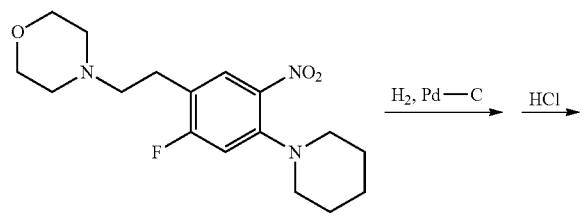

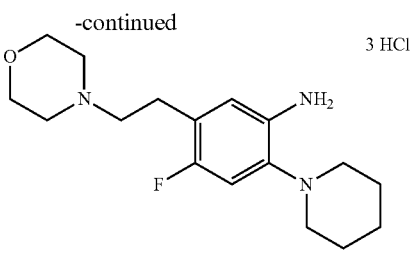

4-fluoro-5-(2-morpholinoethyl)-2-(piperidin-1-yl) aniline Tri-Hydrogen Chloride

In a Parr flask under 35 psi of H₂, an EtOAc (50 mL) solution of 4-(2-fluoro-5-nitro-4-(piperidin-1-yl)phenethyl) morpholine (4.85 g, 14 mmol) and Pd—C (10% Pd on C, 50% wet, 0.5 g) was shaken at room temperature for 19 hours. The reaction went to completion as monitored by LC-MS. Solid was removed by filtration through a celite pad, washing with EtOAc. Filtrate was collected in a receiving flask containing 15 mL of 4M HCl-dioxane solution, and the volatiles were removed in vacuo. The crude solid was suspended in EtOAc-MeO-EtOH, and mixed well until a free-flowing solid was formed. The precipitate was collected by filtration, washed with EtOAc and was dried in vacuo. Compound 4-fluoro-5-(2-morpholinoethyl)-2-(piperidin-1-yl)aniline tri-hydrogen chloride was obtained as a white solid: 4.65 g (78% yield); ¹H NMR (300 MHz, Methanol-d₄) δ 7.40 (d, J=7.4 Hz, 1H), 7.32 (d, J=11.2 Hz, 1H), 4.13 (br d, J=12.8 Hz, 2H), 3.86 (t, J=12.6 Hz, 2H), 3.63 (br d, J=12.4 Hz, 2H), 3.46-3.40 (m, 2H), 3.32-3.17 (m, 4H), 3.01-2.98 (m, 4H), 1.91-1.83 (m, 4H), 1.72-1.64 (m, 2H); LRMS (M+H) m/z 308.68.

Example 155

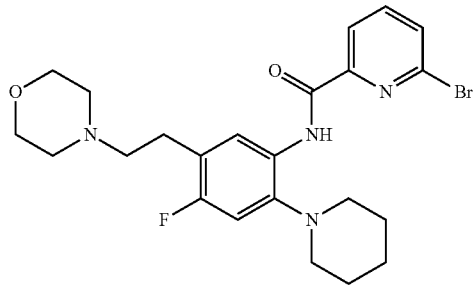 [SMILES: O=C(Nc1cc(CCN2CCOCC2)c(F)cc1N1CCCCC1)c1cccc(Br)n1]

6-bromo-N-(4-fluoro-5-(2-morpholinoethyl)-2-(piperidin-1-yl)phenyl)picolinamide

The compound was prepared according to general procedure (A): 1.0 mmol scale, 90% yield.

¹H NMR (300 MHz, Chloroform-d) δ 10.90 (s, 1H), 8.46 (d, J=8.1 Hz, 1H), 8.24 (dd, J=7.5, 0.9 Hz, 1H), 7.77 (dd, J=7.7, 7.7 Hz, 1H), 7.65 (dd, J=7.9, 0.9 Hz, 1H), 6.85 (d, J=10.9 Hz, 1H), 3.76-3.73 (m, 4H), 2.87-2.80 (m, 6H), 2.65-2.59 (m, 2H), 2.56-2.53 (m, 4H), 1.95-1.88 (m, 4H), 1.68-1.60 (m, 2H); LRMS (M+H) m/z 491.75.

Example 156

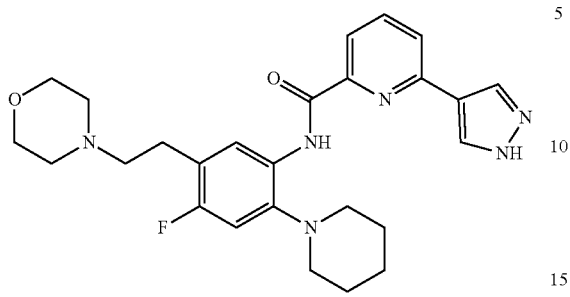

I-30: N-(4-fluoro-5-(2-morpholinoethyl)-2-(piperidin-1-yl)phenyl)-6-(1H-pyrazol-4-yl)picolinamide The compound was prepared according to general procedure (B): 0.1 mmol, 69% yield.

$^1$H NMR (300 MHz, Chloroform-d) δ 10.84 (s, 1H), 10.63 (v br s, 1H), 8.47 (d, J=8.2 Hz, 1H), 8.26 (s, 2H), 8.16 (dd, J=7.7, 1.0 Hz, 1H), 7.90 (dd, J=7.8, 7.8 Hz, 1H), 7.67 (dd, J=7.9, 1.0 Hz, 1H), 6.85 (d, J=11.0 Hz, 1H), 377-3.74 (m, 4H), 2.88-2.82 (m, 6H), 2.67-2.61 (m, 2H), 2.57-2.54 (m, 4H), 1.82-1.75 (m, 4H), 1.64-1.56 (m, 2H); LRMS (M+H) m/z 479.90.

Example 157

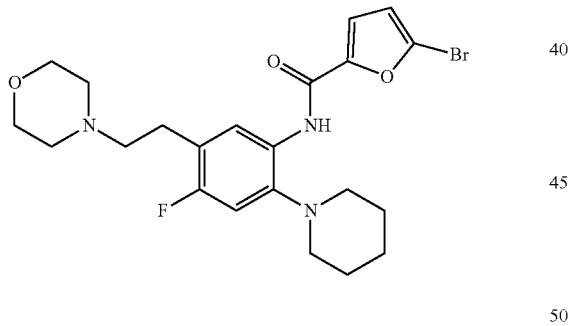

5-bromo-N-(4-fluoro-5-(2-morpholinoethyl)-2-(piperidin-1-yl)phenyl)furan-2-carboxamide The compound was prepared according to general procedure (A): 1.0 mmol scale, 72% yield.

$^1$H NMR (300 MHz, Chloroform-d) δ 9.40 (s, 1H), 8.33 (d, J=8.1 Hz, 1H), 7.15 (dd, J=3.5, 0.5 Hz, 1H), 6.84 (d, J=10.8 Hz, 1H), 6.50 (dd, J=3.5, 0.5 Hz, 2H), 3.76-3.72 (m, 4H), 2.85-2.79 (m, 6H), 2.63-2.58 (m, 2H), 2.55-2.52 (m, 4H), 1.86-1.78 (m, 4H), 1.72-1.63 (m, 2H); LRMS (M+H) m/z 480.73. Regiochemistry was confirmed by d-NOE experiment: NOE was observed between NH and protons on piperidine.

Example 158

I-31: N-(4-fluoro-5-(2-morpholinoethyl)-2-(piperidin-1-yl)phenyl)-5-(1H-pyrazol-4-yl)furan-2-carboxamide The compound was prepared according to general procedure (B): 0.1 mmol, 69% yield.

$^1$H NMR (300 MHz, Chloroform-d) δ 11.02 (v br s, 1H), 9.41 (s, 1H), 8.40 (d, J=8.1 Hz, 1H), 7.91 (s, 2H), 7.26 (d, J=3.5 Hz, 1H), 6.85 (d, J=10.7 Hz, 1H), 6.53 (d, J=3.6 Hz, 1H), 3.77-3.74 (m, 4H), 2.86-2.80 (m, 6H), 2.66-2.61 (m, 2H), 2.57-2.54 (m, 4H), 1.85-1.78 (m, 4H), 1.69-1.59 (m, 2H); LRMS (M+H) m/z 468.91.

Example 159

2-bromo-N-(4-fluoro-5-(2-morpholinoethyl)-2-(piperidin-1-yl)phenyl)thiazole-4-carboxamide The compound was prepared according to general procedure (A): 1.0 mmol scale, 61% yield.

$^1$H NMR (300 MHz, Chloroform-d) δ 10.20 (s, 1H), 8.38 (d, J=8.1 Hz, 1H), 8.11 (d, J=0.4 Hz, 1H), 6.83 (d, J=10.9 Hz, 1H), 3.76-3.73 (m, 4H), 2.86-2.79 (m, 7H), 2.65-2.59 (m, 2H), 2.56-2.53 (m, 4H), 1.89-1.81 (m, 4H), 1.67-1.59 (m, 2H); LRMS (M+H) m/z 497.75.

Example 160

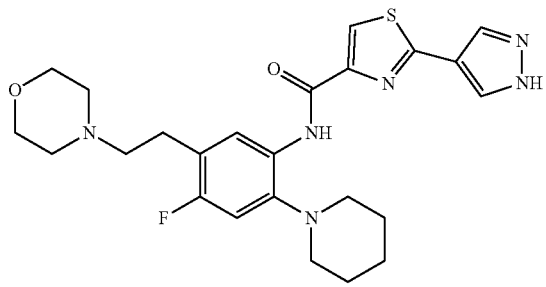 [SMILES: O=C(Nc1cc(CCN2CCOCC2)c(F)cc1N1CCCCC1)c1csc(-c2cn[nH]c2)n1]

I-32: N-(4-fluoro-5-(2-morpholinoethyl)-2-(piperidin-1-yl)phenyl)-2-(1H-pyrazol-4-yl)thiazole-4-carboxamide The compound was prepared according to general procedure (B): 0.1 mmol, 67% yield.

$^1$H NMR (300 MHz, Chloroform-d) δ 10.76 (v br s, 1H), 10.35 (s, 1H), 8.44 (d, J=8.1 Hz, 1H), 8.08 (s, 1H), 8.08 (s, 2H), 6.84 (d, J=10.9 Hz, 1H), 3.77-3.74 (m, 4H), 2.87-2.82 (m, 6H), 2.67-2.62 (m, 2H), 2.58-2.54 (m, 4H), 189-1.82 (m, 4H), 1.69-1.61 (m, 2H); LRMS (M+H) m/z 485.90.

Example 161

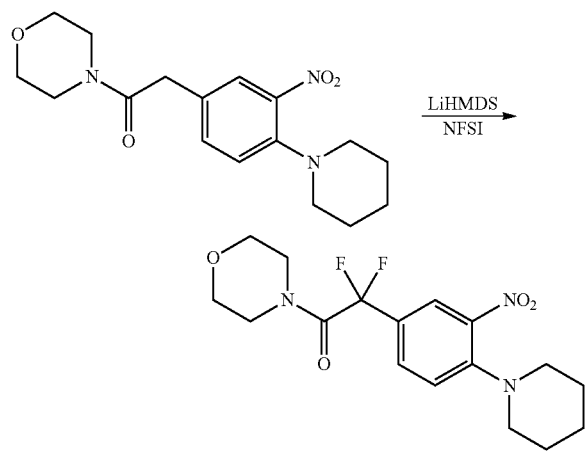

2,2-difluoro-1-morpholino-2-(3-nitro-4-(piperidin-1-yl)phenyl)ethan-1-one

To a THF (35 mL) solution of 1-morpholino-2-(3-nitro-4-(piperidin-1-yl)phenyl)ethan-1-one (6.47 g, 19.4 mmol) at −78° C., LiHMDS (1M in THF, 43 mL, 43 mmol) was added dropwise over 10 minutes. After 30 minutes, a THF (25 mL) solution of NFSI (14.1 g, 44.6 mmol) was added dropwise over 15 minutes. Stirring continued at −78° C. for another 30 minutes, and the reaction was quenched with saturated aqueous NH$_4$Cl solution. Most of the THF was removed by rotary evaporation under reduced pressure, and the mixture was extracted with EtOAc. Combined organic layers were dried (Na$_2$SO$_4$), filtered, and the solvent was removed in vacuo. The product was purified by silica gel column chromatography, and compound 2,2-difluoro-1-morpholino-2-(3-nitro-4-(piperidin-1-yl)phenyl)ethan-1-one was obtained as an orange color thick oil: 3.38 g (63% yield); $^1$H NMR (300 MHz, Chloroform-d) δ 7.96 (br d, J=2.3 Hz, 1H), 7.53 (dd, J=8.8, 2.3 Hz, 1H), 7.13 (d, J=8.8 Hz, 1H), 3.71-3.69 (m, 4H), 3.63 (br s, 4H), 3.13-3.09 (m, 4H), 1.76-1.68 (m, 4H), 1.68-1.61 (m, 2H); LRMS (M+H) m/z 370.75.

Example 162

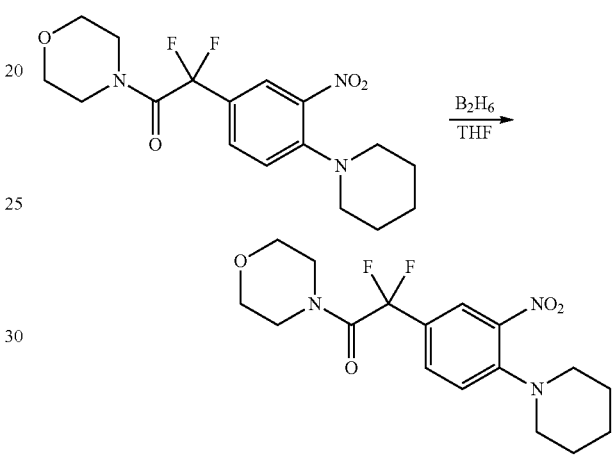

4-(2,2-difluoro-2-(3-nitro-4-(piperidin-1-yl)phenyl)ethyl)morpholine

To a THF (36 mL) solution of 2,2-difluoro-1-morpholino-2-(3-nitro-4-(piperidin-1-yl)phenyl)ethan-1-one (3.37 g, 9.1 mmol) in an ice bath, B$_2$H$_6$-THF solution (1M in THF, 22.8 mL, 22.8 mmol) was added dropwise over 10 minutes. The ice bath was removed and stirring was continued at room temperature. After 23 hours, the reaction went to completion as monitored by LC-MS, and was quenched with 1N HCl aqueous solution (20 mL). After stirring at room temperature for another 2 hours, most of the THF was removed by rotary evaporation under reduced pressure. The aqueous layer was basified with saturated NaHCO$_3$ aqueous solution, and was extracted with EtOAc (80 mL×2). The combined organic layers were dried (Na$_2$SO$_4$), filtered, and the solvent was removed in vacuo. After silica gel column chromatography, compound 4-(2,2-difluoro-2-(3-nitro-4-(piperidin-1-yl)phenyl)ethyl)morpholine was obtained as an orange color oil: 2.69 g (83% yield); $^1$H NMR (300 MHz, Chloroform-d) δ 7.96 (br d, J=2.3 Hz, 1H), 7.55 (ddt, J=8.7, 2.3, 0.6 Hz, 1H), 7.10 (dt, J=8.7, 0.7 Hz, 1H), 3.66-3.62 (m, 4H), 3.09-3.06 (m, 4H), 2.92 (t, J=13.6 Hz, 2H), 2.58-2.55 (m, 4H), 1.76-1.69 (m, 4H), 1.67-1.60 (m, 2H); LRMS (M+H) m/z 356.69.

Example 163

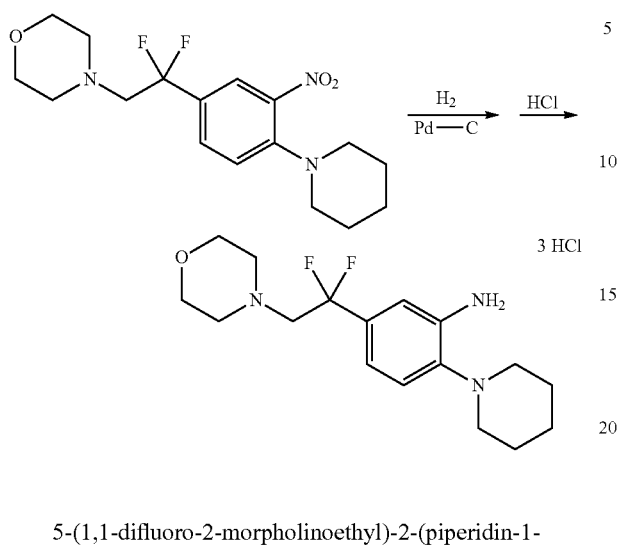

5-(1,1-difluoro-2-morpholinoethyl)-2-(piperidin-1-yl)aniline Tri-Hydrogen Chloride In a Parr flask under 30 psi of H₂, an EtOAc (30 mL) solution of 4-(2,2-difluoro-2-(3-nitro-4-(piperidin-1-yl)phenyl)ethyl)morpholine (2.69 g, 7.57 mmol) and Pd—C (10% Pd on C, 50% wet, 0.25 g) was shaken at room temperature for 4 hours. The reaction went to completion as monitored by LC-MS. Solid was removed by filtration through a celite pad, washing with EtOAc. The filtrate was collected in a receiving flask containing 6 mL of 4M HCl-dioxane solution, and a free-flowing solid was formed after the addition of EtOH. Precipitate was collected by filtration, washed with EtOAc and was dried in vacuo. Compound 5-(1,1-difluoro-2-morpholinoethyl)-2-(piperidin-1-yl)aniline tri-hydrogen chloride was obtained as a white solid: 2.83 g (86% yield); ¹H NMR (300 MHz, Methanol-d₄) δ 7.69 (d, J=8.6 Hz, 1H), 7.42 (d, J=2.1 Hz, 1H), 7.32 (dd, J=8.6, 2.1 Hz, 1H), 4.17 (t, J=16.1 Hz, 2H), 4.06-3.97 (m, 4H), 3.65-3.57 (m, 4H), 3.50-3.45 (m, 4H), 2.13-2.04 (m, 4H), 1.83-1.75 (m, 2H); LRMS (M+H) m/z 326.27.

Example 164

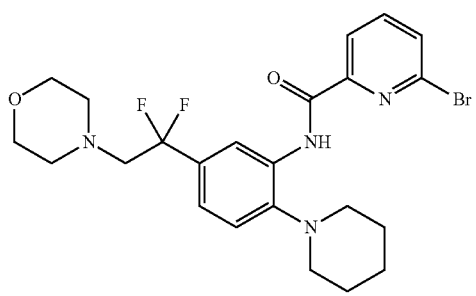 [SMILES: O=C(Nc1cc(C(F)(F)CN2CCOCC2)ccc1N1CCCCC1)c1cccc(Br)n1]

6-bromo-N-(5-(1,1-difluoro-2-morpholinoethyl)-2-(piperidin-1-yl)phenyl)picolinamide The compound was prepared according to general procedure (A): 1.0 mmol scale, 82% yield.

¹H NMR (300 MHz, Chloroform-d) δ 11.04 (s, 1H), 8.76 (d, J=2.0 Hz, 1H), 8.25 (dd, J=7.5, 1.0 Hz, 1H), 7.78 ddt, J=7.7, 7.7 Hz, 1H), 7.67 (dd, J=7.9, 1.0 Hz, 1H), 7.27 (dd, partially overlapped with CHCl₃, J=8.3, 2.0 Hz, 1H), 7.19 (d, J=8.3 Hz, 1H), 3.68-3.65 (m, 4H), 2.99 (t, J=14.4 Hz, 2H), 2.91-2.87 (m, 4H), 2.62-2.59 (m, 4H), 1.98-1.90 (m, 4H), 1.72-1.62 (m, 2H); LRMS (M+H) m/z 509.24.

Example 165

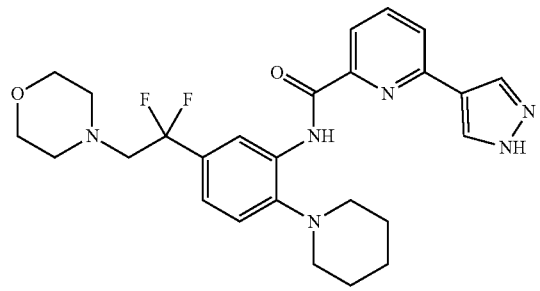 [SMILES: O=C(Nc1cc(C(F)(F)CN2CCOCC2)ccc1N1CCCCC1)c1cccc(-c2cn[nH]c2)n1]

I-33: N-(5-(1,1-difluoro-2-morpholinoethyl)-2-(piperidin-1-yl)phenyl)-6-(1H-pyrazol-4-yl)picolinamide The compound was prepared according to general procedure (B): 0.1 mmol scale, 42% yield.

¹H NMR (300 MHz, Chloroform-d) δ 10.98 (s, 1H), 10.44 (br s, 1H), 8.77 (d, J=2.1 Hz, 1H), 8.27 (s, 2H), 8.18 (dd, J=7.7, 1.1 Hz, 1H), 7.91 (dd, J=7.8, 7.8 Hz, 1H), 7.68 (dd, J=7.9, 1.1 Hz, 1H), 7.30-7.26 (m, partially overlapped with CHCl₃, 1H), 7.19 (d, J=8.3 Hz, 1H), 3.69-3.66 (m, 4H), 3.01 (t, J=14.5 Hz, 2H), 2.92-2.88 (m, 4H), 2.64-2.61 (m, 4H), 1.85-1.78 (m, 4H), 1.65-1.56 (m, 2H); LRMS (M+H) m/z 497.41.

Example 166

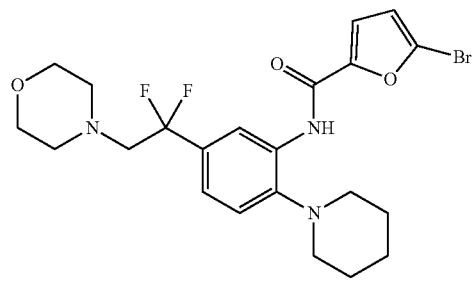 [SMILES: O=C(Nc1cc(C(F)(F)CN2CCOCC2)ccc1N1CCCCC1)c1ccc(Br)o1]

5-bromo-N-(5-(1,1-difluoro-2-morpholinoethyl)-2-(piperidin-1-yl)phenyl)furan-2-carboxamide The compound was prepared according to general procedure (A): 1.0 mmol scale, 77% yield.

¹H NMR (300 MHz, Chloroform-d) δ 9.58 (s, 1H), 8.64 (d, J=2.0 Hz, 1H), 7.24 (ddd, J=2.5, 0.6, 0.6 Hz, 1H), 7.20 (br s, 1H), 7.18 (d, J=3.5 Hz, 1H), 6.52 (d, J=3.5 Hz, 1H), 3.68-3.65 (m, 4H), 2.98 (t, J=14.4 Hz, 2H), 2.89-2.85 (m, 4H), 2.62-2.58 (m, 4H), 1.88-1.81 (m, 4H), 1.74-1.64 (m, 2H); LRMS (M+H) m/z 500.25.

Example 167

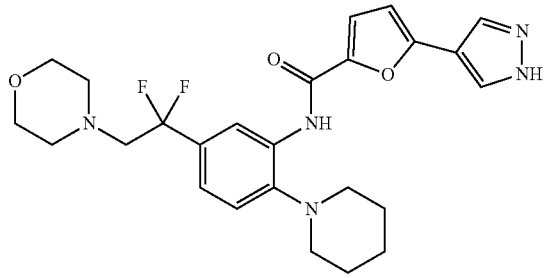 [SMILES: O=C(Nc1cc(C(F)(F)CN2CCOCC2)ccc1N1CCCCC1)c1ccc(-c2cn[nH]c2)o1]

I-34: N-(5-(1,1-difluoro-2-morpholinoethyl)-2-(piperidin-1-yl)phenyl)-5-(1H-pyrazol-4-yl)furan-2-carboxamide The compound was prepared according to general procedure (B): 0.1 mmol scale, 59% yield.

$^1$H NMR (300 MHz, Chloroform-d) δ 10.38 (v br s, 1H), 9.59 (s, 1H), 8.70 (d, J=1.9 Hz, 1H), 7.93 (s, 2H), 7.29 (d, J=3.6 Hz, 1H), 7.24 (br d, J=2.1 Hz, 1H), 7.20 (d, J=8.3 Hz, 1H), 6.55 (d, J=3.6 Hz, 1H), 3.69-3.66 (m, 4H), 2.99 (t, J=14.5 Hz, 2H), 2.91-2.87 (m, 4H), 2.63-2.60 (m, 4H), 1.88-1.81 (m, 4H), 1.71-1.64 (m, 2H); LRMS (M+H) m/z 486.40.

Example 168

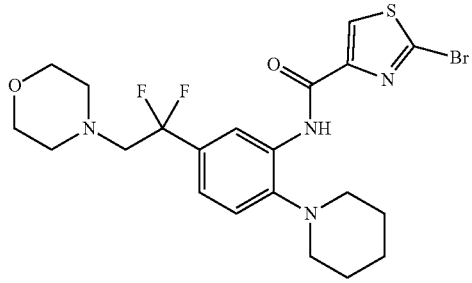 [SMILES: O=C(Nc1cc(C(F)(F)CN2CCOCC2)ccc1N1CCCCC1)c1csc(Br)n1]

2-bromo-N-(5-(1,1-difluoro-2-morpholinoethyl)-2-(piperidin-1-yl)phenyl)thiazole-4-carboxamide The compound was prepared according to general procedure (A): 1.0 mmol scale, >99% yield.

$^1$H NMR (300 MHz, Chloroform-d) δ 10.35 (s, 1H), 8.68 (d, J=2.0 Hz, 1H), 8.13 (s, 1H), 7.26 (dd, partially overlapped with CHCl$_3$, J=8.3, 2.0 Hz, 1H), 7.17 (d, J=8.3 Hz, 1H), 3.68-3.65 (m, 4H), 2.98 (t, J=14.4 Hz, 2H), 2.89-2.86 (m, 4H), 2.62-2.59 (m, 4H), 1.91-1.84 (m, 4H), 1.74-1.58 (m, 2H); LRMS (M+H) m/z 517.10.

Example 169

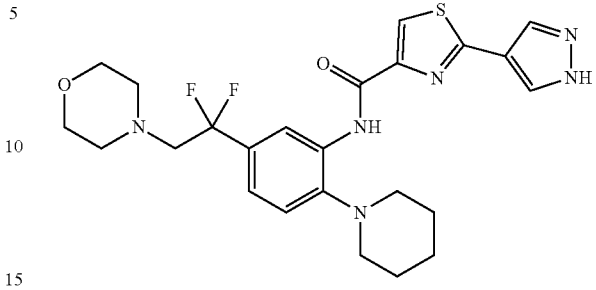

I-35: N-(5-(1,1-difluoro-2-morpholinoethyl)-2-(piperidin-1-yl)phenyl)-2-(1H-pyrazol-4-yl)thiazole-4-carboxamide The compound was prepared according to general procedure (B): 0.1 mmol scale, 68% yield.

$^1$H NMR (300 MHz, Chloroform-d) δ 10.50 (s, 1H), 10.22 (v br s, 1H), 8.75 (d, J=2.1 Hz, 1H), 8.11 (s, 1H), 8.10 (s, 2H), 7.28-7.25 (m, partially overlapped with CHCl$_3$, 1H), 7.18 (d, J=8.3 Hz, 1H), 3.69-3.66 (m, 4H), 3.00 (t, J=14.5 Hz, 2H), 2.92-2.88 (m, 4H), 2.64-2.61 (m, 4H), 1.92-1.85 (m, 4H), 1.71-1.64 (m, 2H); LRMS (M+H) m/z 503.37.

Example 170

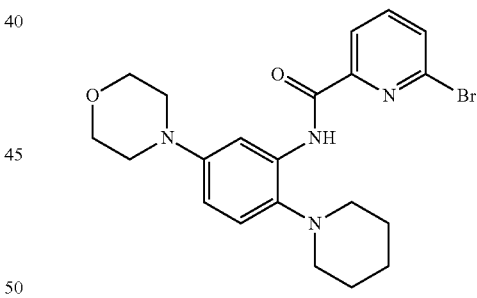

6-bromo-N-(5-morpholino-2-(piperidin-1-yl)phenyl) picolinamide

The compound was prepared according to general procedure (A): 1 mmol scale, 63% yield.

$^1$H NMR (300 MHz, Chloroform-d) δ 11.25 (s, 1H), 8.33 (d, J=2.8 Hz, 1H), 8.23 (dd, J=7.5, 1.0 Hz, 1H), 7.76 (dd, J=7.9, 7.5 Hz, 1H), 7.65 (dd, J=7.9, 1.0 Hz, 1H), 7.12 (d, J=8.6 Hz, 1H), 6.64 (dd, J=8.6, 2.8 Hz, 1H), 3.88-3.85 (m, 4H), 3.22-3.18 (m, 4H), 2.84-2.81 (m, 4H), 1.92-1.89 (m, 4H), 1.69-1.55 (m, 2H); LRMS (M+H) m/z 445.64, 447.87.

Example 171

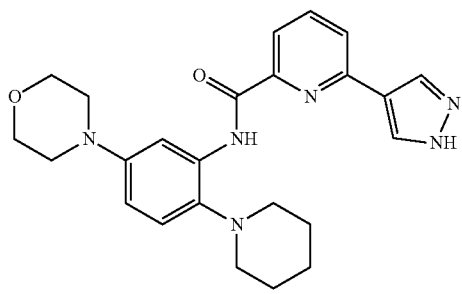 [SMILES: O=C(Nc1cc(N2CCOCC2)ccc1N1CCCCC1)c1cccc(-c2cn[nH]c2)n1]

I-75: N-(5-morpholino-2-(piperidin-1-yl)phenyl)-6-(1H-pyrazol-4-yl)picolinamide

The compound was prepared according to general procedure (B): 0.1 mmol scale, 47% yield.

$^1$H NMR (300 MHz, Chloroform-d) δ 11.12 (s, 1H), 10.39 (v br s, 1H), 8.39 (d, J=2.9 Hz, 1H), 8.29 (s, 1H), 8.289 (s, 1H), 8.16 (dd, J=7.8, 1.0 Hz, 1H), 7.90 (dd, J=7.8, 7.8 Hz, 1H), 7.66 (dd, J=7.8, 1.0 Hz, 1H), 7.12 (d, J=8.7 Hz, 1H), 6.66 (dd, J=8.7, 2.9 Hz, 1H), 3.88-3.85 (m, 4H), 3.22-3.19 (m, 4H), 2.85-2.82 (m, 4H), 1.83-1.76 (m, 4H), 1.63-1.54 (m, 2H); LRMS (M+H) m/z 433.64.

Example 172

LPS Induced IL23p19 in THP-1 Cells (with IFNγ Primed) Assay

Materials and Equipment

THP-1 Cells (ATCC, Cat # TIB-202), Dimethyl Sulfoxide (DMSO) (Sigma-Aldrich, Cat # D2650), RPMI 1640 (Cellgro, Cat #10-040-CM), Fetal Bovine Serum (Sigma, Cat # F4135), Albumin From Bovine Serum (BSA) (Sigma-Aldrich, Cat # A7906), LPS (Serotype K-235, Sigma, Product Number L 2143), IFNγ (Peprotech, Cat #300-02), Capture antibody: Human IL-23p19 ELISA (e-Bioscience, Cat. #14-7238-85), Detection antibody: Primary Mouse Biotinylated anti-human IL-12 (p40/p70) (e-Bioscience, Cat. #13-7129-85), Secondary HRP-conjugated Streptavidin (R&D Systems, Cat # DY998), 1×PBST Washing Buffer (PBS-Tween tablet) (VWR International, Cat #80058-558), ELISA Blocking Buffer (PBS with 1% BSA), ELISA Dilution Buffer (PBS with 1% BSA), 384 Well Flat-Bottom, MaxiSorp Black Immuno Plates (Thermo Scientific, Cat #12-565-346), 384 Well Flat-Bottom, White Tissue Culture Plates (Thermo Scientific, Cat #12-565-343), Super Signal ELISA Pico Chemiluminescent Substrate (Thermo Scientific, Cat #37070), Cell Titer Glo reagent (Promega, Cat # G7573), Positive control, IKK2VI inhibitor (Calbiochem, Cat #401483), AquaMax 4000 plate washer (Molecular Devices), Luminometer, Wallac Victor2 1420 Multilabel Counter.

Method

THP-1 Cells Stimulation:

On day 1, 50K/well THP-1 cells were seeded and primed with IFNγ (50 ng/mL) in 384-well plates for about 18 hours in RPMI media with 10% FBS. On day 2, the compound was serially diluted in DMSO from 5 mM in 3-fold dilutions, and then diluted 1:125 in RPMI media with 10% FBS. 50 μL/well 2× compound was added to 50 μL/well THP-1 cells (with IFNγ primed) in duplicate in 384 well tissue culture plates. The cells were pre-incubated with compound for 1 hour at 37° C., 5% $CO_2$ before addition of 10 μL/well 11×LPS to give a final concentration of 1 μg/mL LPS. Day 3, after stimulation for 18 hours at 37° C., 5% $CO_2$, the assay plate was centrifuged and 70 μL/well supernatant was harvested. IL-23p19 protein in 70 μL/well of supernatant was measured by sandwich ELISA, and 25 μl/well Cell Titer Glo reagent was added to the remaining cells to measure compound toxicity.

Human IL-23p19 Sandwich ELISA:

Maxisorp immuno ELISA plates were pre-coated with 25 μL/well of anti-IL-23p19 capture antibody (2.5 ug/mL) in PBS overnight at room temperature. After washing with 1×PBST, the plates were blocked using 100 μL/well of 1% BSA in PBS for 2 hours at room temperature. The plates were washed three times with 1×PBST and 70 μL/well supernatant were added. The plates were incubated at room temperature for 2 hours with shaking and washed three times with 1×PBST. 25 μL/well of biotin labeled anti-IL-12 (p40/p70) detection antibody (100 ng/mL) in PBS with 1% BSA was added and the plates were incubated at room temperature for 2 hours with shaking. After washing three times with 1×PBST, 25 μL/well of streptavidin-HRP (1:200) in PBS with 1% BSA was added and the plates were incubated at room temperature for 20 minutes with shaking. The plates were washed three times with 1×PBST and 25 μL/well of Super Signal ELISA Pico Chemiluminescent Substrate were added. The plates were read with a luminometer, and the chemiluminescence values were entered into Athena (Rigel) for curve fitting, $EC_{50}$ calculation, and database storage. The results are shown in Table 1.

Example 173

Compound Screening Using DC Cells

Materials

Human PBMC cells (All Cells, Cat No. PB002)
RPMI growth media containing 10% FBS
IFNγ (Peprotech, Cat No. 300-02)
GMCSF (Peprotech, Cat No. 300-03) and IL4 (Peprotech Cat No. 200-04)
White clear bottom 96 well plates (Fisher, Cat No. 07-200-587, Corning #3903)
LPS (Make 2.5 mg/ml Stock in PBS) from Sigma Aldrich (Cat No. L2018-5MG)
Cell Titer Glo reagent (Promega, Cat No. G7573)
Positive controls, IKK2VI inhibitor (Calbiochem, Cat No. 401483)

Protocol

1. Differentiation of PBMC's to DC Cells:

Human PBMC cells (400 million) obtained from the vendor were transferred into a T-175 flask containing 15 ml RPMI media (10% FBS) and incubate for 2 hours at 37° C. After 2 hours, the media including floating cells was aspirated out carefully and 12 ml of fresh RPMI media (10% FBS) containing GMCSF (100 ng/ml) and IL4 (20 ng/ml) was added, and the flask was kept in a 37° C. incubator for 7 days.

After 3 days, fresh GMCSF (100 ng/ml) and IL4 (20 ng/ml) were added to the flask and the incubation continued. After 7 days, the fully differentiated cells were harvested by spinning down (1200 rpm/5 min) and aspirating the media. The cells were suspended in fresh RPMI media (10% FBS) containing 50 ng/ml IFNγ (1000 U/ml) and then plated (50K/well in 100 μl) onto a white clear bottom 96 well plate and left in a 37° C. incubator for 24 hours.

2. Addition of Compounds:

After 24 hours incubation, 100 μl of RPMI media was added containing 2× concentrated test compound per well to the above cell-culture media (final concentration becomes 1×) and the plates were pre-incubated for 1 hour at 37° C. before stimulating with LPS.

After 1 hour compound pre-incubation, 10 μl per well of 20× concentrated LPS solution in RPMI media was added to give a final concentration of 1 μg/ml. The mixture was shaken and incubated the plates at 37° C. for an additional 18 hours.

155 μl of the supernatant was harvested from each well carefully (without the tip touching the bottom of the well) and to the remaining 50 μl/well of the cell culture plate was added 50 μl of Cell Titer Glo reagent. The mixture was incubated for 1-2 minutes on a shaker and the plate was read for luminescence intensity to determine the compound cytotoxicity. The cell culture supernatant collected above was used to carry out IL23 ELISA (65 μl-Supernatant) and IL10 ELISA (90 μl-Supernatant) as described below.

Example 174

Human IL-23 (p19/p40) ELISA Protocol (e-Biosciences)

Materials:
96-well high binding opaque white plates (from Pierce, Cat No. 15042);
1×PBS; 1×TBST washing buffer;
Blocking Solution: 0.5% Casein in PBS (from BDH, Cat No. 440203H);
Dilution Solution: 1% BSA in PBS (10% BSA from Fisher, Cat No. 37525);
Capture antibody: Rat anti-human IL-23 (p19) (e-Biosciences, Cat. No. 14-7238-85);
Detection antibody: Primary Mouse Biotinylated anti-human IL-12 (p40/p70) (e-biosciences, Cat No. 13-7129-85);
Secondary HRP-conjugated Streptavidin (R&D Systems, Cat No. DY998);
rHuman-IL-23 (e-biosciences, Cat No. 34-8239) (Suggested starting concentration=5 ng/ml in RPMI cell culture media);
Cell Culture Supernatant (65 μl from THP-1 cells primed with IFNγ (50 ng/ml-1000 U/ml) and stimulated with 0.01% SAC);
SuperSignal ELISA Pico Chemiluminescent substrate [Pierce, Cat No. 37069].
Coating Plates:

To 10.5 ml PBS add 50 μl of anti-IL23 (p19) was added capture antibody (2.5 μg/ml). The mixture was mixed well and 100 μl of the coating solution was added to each well of the 96 well white plates from Pierce. The wells were covered and incubated overnight at 4° C.

Blocking the Plates:

The anti-IL23 (p19)-antibody-coated plates were washed 2× using TBST (use plate washer) and blocked using 200 μl of 0.5% Casein for 1.5-2 hours at room temperature with shaking.

Addition of Supernatant and Detection:

The plates were washed 2× using TBST and the supernatant was transferred (65 μl/well) to the above pre-blocked/IL23 (p19)-antibody-coated 96 well plate, and incubated at room temperature for 1.5 hours with shaking.

The plates were washed 4× using TBST (plate washer) and 100 μl/well detection antibody solution prepared from 2 μl of biotin labeled anti-IL-12 (p40/p70) antibody in 11 ml 1% BSA/PBS solution (1-5000 dilution) was added. The plates were incubated for 1 hour with shaking at room temperature.

Again, the plates were washed 4× with TBST and 100 μl of HRP labeled Streptavidin (R&D Systems) solution (10 μl/10 ml 1% BSA solution) was added, and the plates were incubated at room temperature for another 45 minutes with shaking.

After 45 minutes, the plates were washed with TBST 4× and 100 ul/well Super Signal ELISA Pico Chemiluminescent Substrate from Pierce (3.5 ml A+3.5 ml B+3.5 ml MQ water) was added. The plates were shaken for 1-2 minutes then read on a plate reader.

The $EC_{50}$ results from the assays described in Examples 171 and 173 are shown in Table 1.

TABLE 1

| Compound code | IL23-p19 ELISA, Dendritic, LPS, 10 pt $EC_{50}$ (μM) | IL23-p19 ELISA, THP1-IFNγ, LPS, 10 pt $EC_{50}$ (μM) |
|---|---|---|
| I-1 | 0.843 | 0.3079 |
| I-2 | 0.1195 | 0.0368 |
| I-3 | 0.0712 | 0.0259 |
| I-4 | 3.598 | 0.3144 |
| I-5 | 0.1816 | 0.1449 |
| I-6 | 0.1141 | 0.0764 |
| I-7 | 0.6892 | 0.8802 |
| I-8 | 0.182 | 0.0637 |
| I-9 | 0.0672 | 0.036 |
| I-10 | 1.738 | 0.3032 |
| I-11 | 0.162 | 0.1336 |
| I-12 | 0.06 | 0.0841 |
| I-13 | 14.37 | 1.726 |
| I-14 | 1.915 | 0.1782 |
| I-15 | 0.4841 | 0.1726 |
| I-16 | 1.717 | 0.7405 |
| I-17 | 0.1658 | 0.2162 |
| I-18 | 0.1055 | 0.0951 |
| I-19 | ND* | 2.517 |
| I-20 | 1.116 | 2.328 |
| I-21 | 1.004 | 0.4652 |
| I-22 | 16.4 | 3.231 |
| I-23 | 2.267 | 2.862 |
| I-24 | 0.7939 | 0.8358 |
| I-25 | 0.5324 | 0.645 |
| I-26 | 0.8468 | 0.5543 |
| I-27 | 0.8574 | 2.989 |
| I-28 | 0.0638 | 0.1889 |
| I-29 | 0.0512 | 0.1047 |
| I-30 | ND* | ND* |
| I-31 | 0.0638 | 17.21 |
| I-32 | 0.3245 | 0.1731 |
| I-33 | ND* | 1670 |
| I-34 | 6.615 | 1.539 |
| I-35 | 2.603 | 1.076 |
| I-36 | 1.304 | 2.72 |
| I-37 | 0.1533 | 0.2618 |
| I-38 | 3.979 | 31.05 |
| I-39 | 3.229 | 6.594 |
| I-40 | ND* | 3.376 |
| I-41 | 9.225 | 3.921 |
| I-42 | 3.075 | 1.045 |
| I-43 | 3.453 | 2.692 |
| I-44 | 0.229 | 0.2217 |
| I-45 | 0.084 | 0.1172 |
| I-46 | 2.66 | 1.362 |
| I-47 | 2.456 | 0.1644 |
| I-48 | 0.4676 | 0.1774 |
| I-49 | 2.961 | 1.27 |
| I-50 | 0.0717 | 0.1299 |
| I-51 | 0.1536 | 0.0656 |
| I-52 | 3.168 | 1.057 |

TABLE 1-continued

| Compound code | IL23-p19 ELISA, Dendritic, LPS, 10 pt EC$_{50}$ (μM) | IL23-p19 ELISA, THP1-IFNy, LPS, 10 pt EC$_{50}$ (μM) |
| --- | --- | --- |
| I-53 | 0.4085 | 0.1674 |
| I-54 | 0.163 | 0.093 |
| I-55 | ND* | 9.777 |
| I-56 | 9.561 | 2.374 |
| I-57 | 1.15 | 0.4982 |
| I-58 | 5.596 | 1.499 |
| I-59 | 0.2943 | 0.2528 |
| I-60 | 0.1081 | 0.1088 |
| I-61 | 3.839 | 0.7674 |
| I-62 | 0.3113 | 0.3062 |
| I-63 | 0.1596 | 0.1505 |
| I-64 | 1.317 | 3.675 |
| I-65 | 0.1244 | 0.1952 |
| I-66 | 0.0418 | 0.0924 |
| I-67 | 0.4796 | 0.3071 |
| I-68 | 0.0476 | 0.0625 |
| I-69 | 2.824 | 2.634 |
| I-70 | 1.918 | 1.439 |
| I-71 | 2.275 | 19.28 |
| I-72 | 1.839 | 0.8702 |
| I-73 | 0.1749 | 0.0827 |
| I-74 | 0.1044 | 0.0514 |
| I-75 | ND* | 52.79 |

*ND indicates that an accurate inhibition curve may not have been produced due to compound insolubility, artifacts in the assay, and/or other factors.

In view of the many possible embodiments to which the principles of the invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, having a formula 1

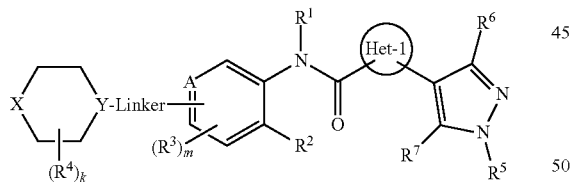

1 or a pharmaceutically acceptable salt, hydrate, N-oxide, or solvate thereof, wherein:

Het-1 is a 5- or 6-membered heteroaryl comprising at least one carbon atom and at least one heteroatom selected from N, O or S;

$R^1$ is H or alkyl;

$R^2$ is —N($R^c$)$_2$;

each $R^3$ independently is $C_{1-6}$alkyl, $C_{1-3}$haloalkyl, or halo;

m is 0, 1 or 2;

each $R^4$ independently is $C_{1-6}$alkyl;

k is 0, 1, 2, 3, 4, 5, 6, 7, 8, or 9;

A is N or CR$_h$;

$R^h$ is H, $R^3$ or the

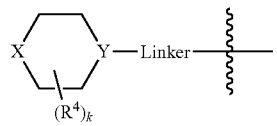

moiety;

$R^5$ is H, aliphatic, phosphonooxyalkyl, phosphonoalkyl, or acyl;

each of $R^6$ and $R^7$ independently is H, aliphatic, or halo;

X is O or NR$^9$;

$R^9$ is $R^a$, C(O)C$_{1-6}$aliphatic, C(O)N($R^c$)$_2$, or CO$_2R^a$;

Y is N or CH;

Linker is a bond, —(C(R$^{10}$)$_2$)$_n$—, —(C(R$^{10}$)$_2$)$_n$—O—, —C(O)—(C(R$^{10}$)$_2$)$_p$—, or —(C(R$^{10}$)$_2$)$_p$—N(R$^a$)—;

each R$^{10}$ independently is R$^a$ or R$^b$;

n is 1, 2, 3, 4, 5, or 6;

p is 0, 1, or 2;

$R^a$ is independently for each occurrence H, D, C$_{1-6}$ alkyl, or C$_{3-6}$cycloalkyl;

$R^b$ is independently for each occurrence —OH, —OR$^a$, or halo; and $R^c$ is independently for each occurrence R$^a$, or two R$^c$ groups together with the nitrogen bound thereto form a C$_{3-7}$heterocyclyl optionally substituted with 1, 2, 3 or 4 substituents selected from C$_{1-6}$ alkyl, C$_{1-3}$haloalkyl, —OH, or halo, and optionally interrupted with one or two additional heteroatoms selected from O, —N(R$^g$)—, or S, where R$^g$ is R$^a$, —C(O)R$^a$, —C(O)OR$^a$ or —C(O)N(R$^a$)$_2$; or the compound is selected from I-39: N-(2-methoxy-5-morpholinophenyl)-6-(1H-pyrazol-4-yl)picolinamide;

I-40: N-(2-methoxy-5-morpholinophenyl)-5-(1H-pyrazol-4-yl)furan-2-carboxamide; or I-41: N-(2-methoxy-5-morpholinophenyl)-2-(1H-pyrazol-4-yl)thiazole-4-carboxamide.

2. The compound of claim 1, wherein Het-1 is pyridinyl, furanyl or thiazolyl.

3. The compound of claim 2, wherein Het-1 is

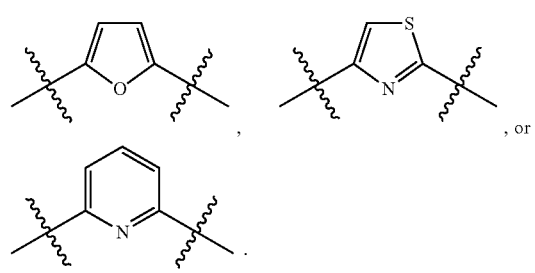

4. The compound of claim 1, wherein $R^1$ is H.

5. The compound of claim 1, wherein:

$R^2$ has a formula

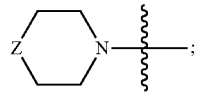

Z is a bond, O, —NR$^a$, —NC(O)R$^a$, or C(R$^8$)$_2$; and each $R^8$ independently is H, $C_{1-6}$alkyl, $C_{1-3}$haloalkyl, —OH, or halo.

6. The compound of claim 5, wherein each $R^8$ independently is H, —OH, $C_{1-3}$alkyl, or halo.

7. The compound of claim 5, wherein Z is a bond, O, or $C(R^8)_2$.

8. The compound of claim 5, wherein $R^2$ is

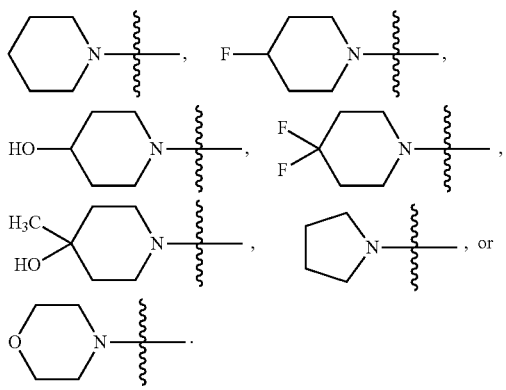

9. The compound of claim 1, wherein m is 1 or 2 and each $R^3$ independently is F, Cl, Br, or I.

10. The compound of claim 9, wherein m is 1 or 2 and each $R^3$ independently is F.

11. The compound of claim 1, wherein m is 1.

12. The compound of claim 1, wherein m is 0.

13. The compound of claim 1, wherein k is 0.

14. The compound of claim 1, wherein each of $R^6$ and $R^7$ independently is H, halo, or $C_{1-6}$ alkyl.

15. The compound of claim 1, wherein $R^5$ is H, $C_{1-6}$alkyl, —$CH_2OP(O)(R^d)_2$, —$CH_2P(O)(R^d)_2$, or acyl, where each $R^d$ is independently for each occurrence —$OR^a$, —$O^-M^+$ where each $M^+$ independently is an alkali metal ion selected from $K^+$, $Na^+$, $Li^+$ or an ammonium ion selected from $^+NH_4$ or $^+N(R^a)_4$, or —$O^-[M^{2+}]_{0.5}$ where $M^{2+}$ is an alkaline metal earth ion selected from $Mg^{2+}$, $Ca^{2+}$ or $Ba^{2+}$.

16. The compound of claim 15, wherein $R^5$ is H, $C_{1-6}$ alkyl, or —$CH_2OP(O)(R^d)_2$.

17. The compound of claim 16, wherein $R^5$ is H.

18. The compound of claim 1, wherein $R^6$ is H, $R^7$ is H, or both $R^6$ and $R^7$ are H.

19. The compound of claim 1, wherein $R^9$ is H or $C_{1-6}$alkyl.

20. The compound of claim 1, wherein the

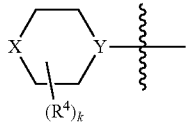

moiety is

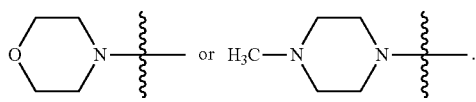

21. The compound of claim 1, wherein Linker is a bond, —$CH_2$—, —$C(O)$—, —$C(O)$—$CH_2$—, —$CH_2CH_2$—, —$CH_2CH_2N(CH_3)$—, —$CH_2CH_2N(H)$—, —$CH_2CH_2O$—, or —$CH_2CF_2$—.

22. The compound of claim 1, wherein the

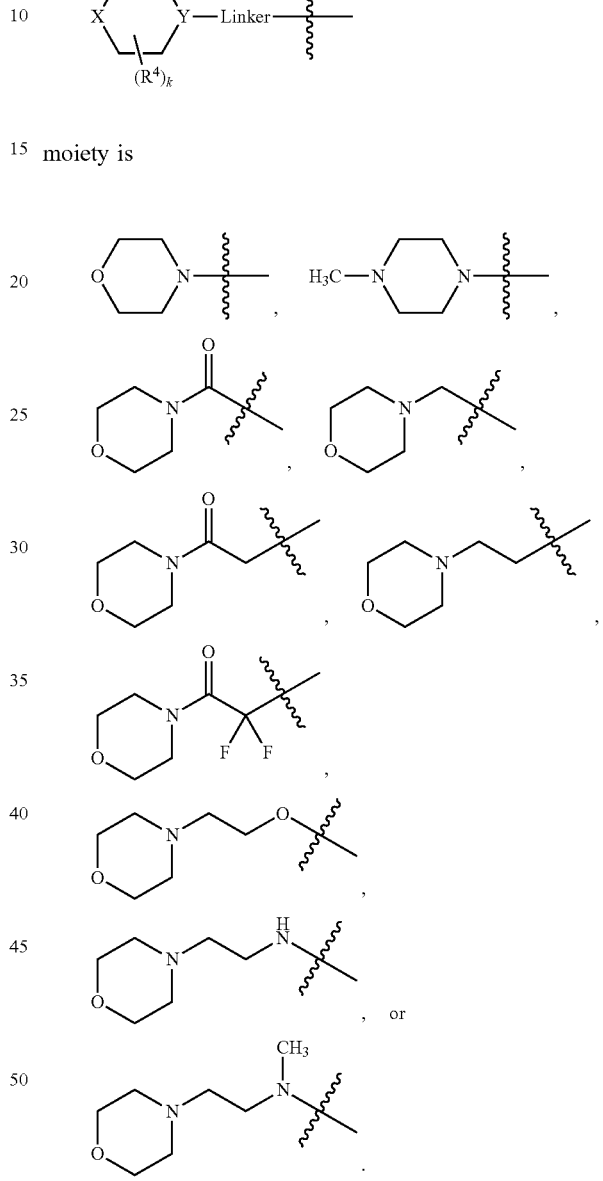

23. The compound of claim 1, wherein the compound has a formula

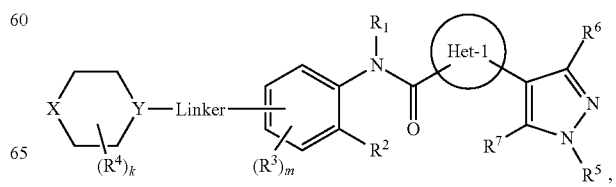

-continued

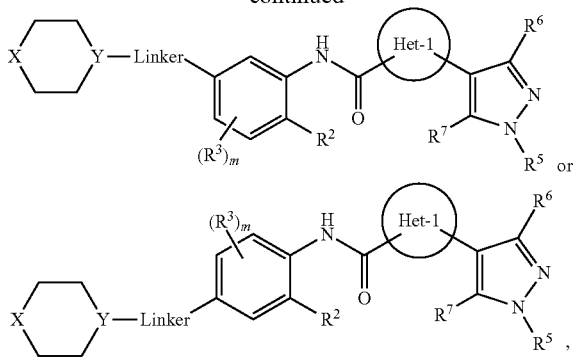

or or a pharmaceutically acceptable salt, hydrate, N-oxide, or solvate thereof.

24. The compound of claim 1, wherein the

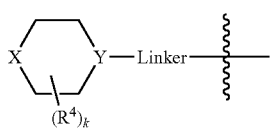

moiety is para to $R^2$.

25. The compound of claim 1, wherein the

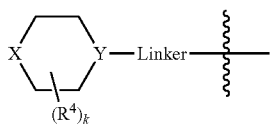

moiety is para to the amide.

26. The compound of claim 1, wherein m is 1 and $R^3$ is para to the amide.

27. The compound of claim 1, wherein m is 1 and $R^3$ is para to $R^2$.

28. The compound of claim 1, wherein the compound has a formula

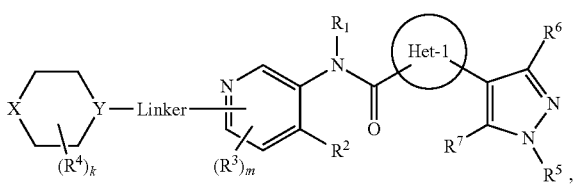

or a pharmaceutically acceptable salt, hydrate, N-oxide, or solvate thereof.

29. The compound of claim 28, wherein the

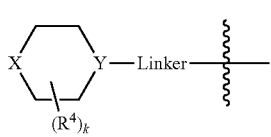

moiety is para to the amide.

30. The compound of claim 28, wherein the compound has a formula

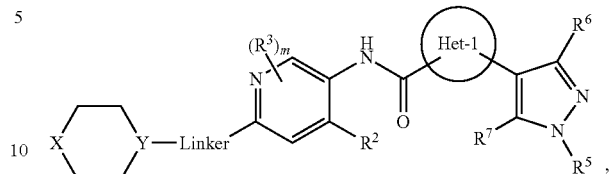

or a pharmaceutically acceptable salt, hydrate, N-oxide, or solvate thereof.

31. The compound of claim 1, wherein the

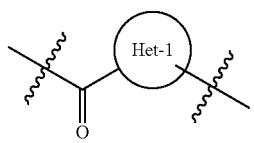

moiety is

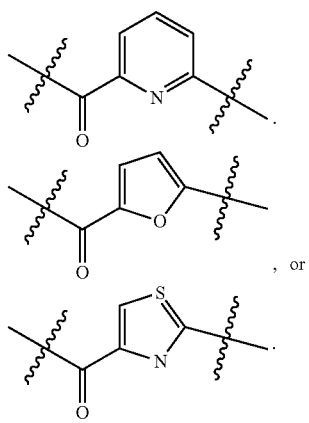

, or

32. The compound of claim 1, the compound having a structure according to formula 2

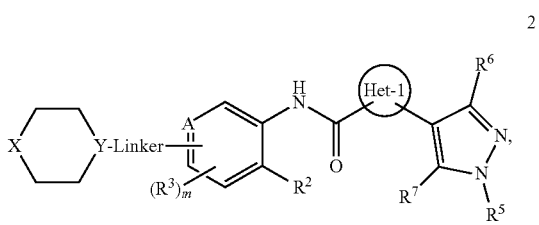

2 or a pharmaceutically acceptable salt, hydrate, N-oxide, or solvate thereof, wherein:
Het-1 is pyridinyl, furanyl or thiazolyl;
$R^2$ is $-N(R^c)_2$;
each $R^3$ independently is halo;
m is 0 or 1;
each of $R^5$, $R^6$ and $R^7$ is H;
A is N or $CR^h$;
$R^h$ is H, $R^3$ or the

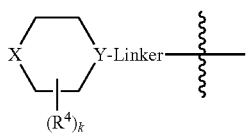

moiety;

X is O or NR⁹;
R⁹ is $R^a$;
Y is N or CH;
Linker is a bond, $-(C(R^{10})_2)_n-$, $-(C(R^{10})_2)_n-O-$, $-C(O)-(C(R^{10})_2)_p-$, or $-(C(R^{10})_2)_p-N(R^a)-$;
each $R^{10}$ independently is $R^a$ or $R^b$;
n is 1 or 2; and
p is 0 or 1.

33. The compound of claim 32, wherein the compound has a general formula selected from

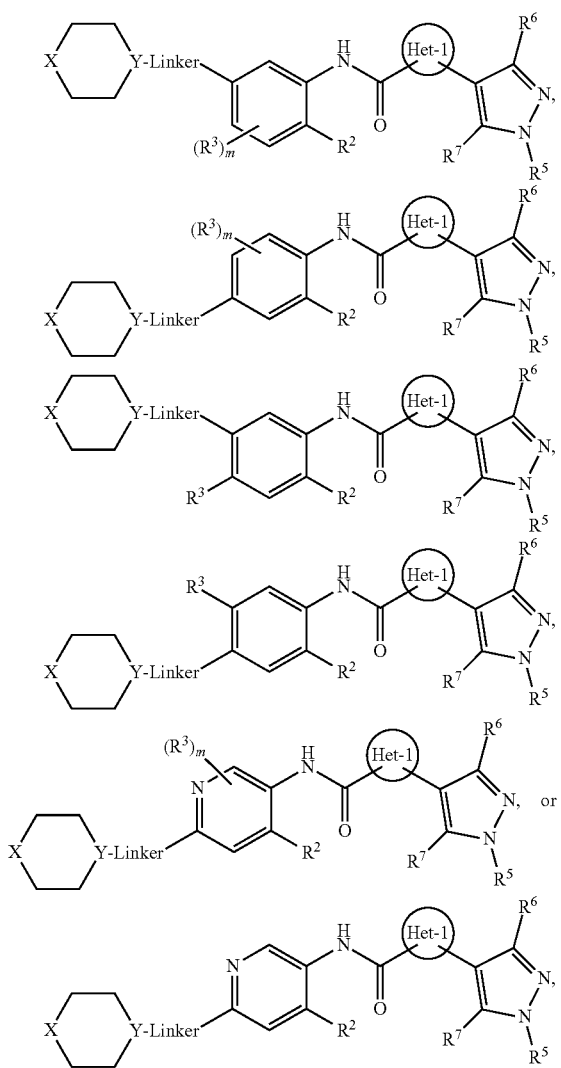

or a pharmaceutically acceptable salt, hydrate, N-oxide, or solvate thereof.

34. A compound selected from:
I-1: N-(4-(4-methylpiperazin-1-yl)-2-(piperidin-1-yl)phenyl)-6-(1H-pyrazol-4-yl)picolinamide;
I-2: N-(4-(4-methylpiperazin-1-yl)-2-(piperidin-1-yl)phenyl)-5-(1H-pyrazol-4-yl)furan-2-carboxamide;
I-3: N-(4-(4-methylpiperazin-1-yl)-2-(piperidin-1-yl)phenyl)-2-(1H-pyrazol-4-yl)thiazole-4-carboxamide;
I-4: N-(2-(4-fluoropiperidin-1-yl)-4-morpholinophenyl)-6-(1H-pyrazol-4-yl)picolinamide;
I-5: N-(2-(4-fluoropiperidin-1-yl)-4-morpholinophenyl)-5-(1H-pyrazol-4-yl)furan-2-carboxamide;
I-6: N-(2-(4-fluoropiperidin-1-yl)-4-morpholinophenyl)-2-(1H-pyrazol-4-yl)thiazole-4-carboxamide;
I-7: N-(2-(4-fluoropiperidin-1-yl)-4-(4-methylpiperazin-1-yl)phenyl)-6-(1H-pyrazol-4-yl)picolinamide;
I-8: N-(2-(4-fluoropiperidin-1-yl)-4-(4-methylpiperazin-1-yl)phenyl)-5-(1H-pyrazol-4-yl)furan-2-carboxamide;
I-9: N-(2-(4-fluoropiperidin-1-yl)-4-(4-methylpiperazin-1-yl)phenyl)-2-(1H-pyrazol-4-yl)thiazole-4-carboxamide;
I-10: N-(2-(4-hydroxypiperidin-1-yl)-4-morpholinophenyl)-6-(1H-pyrazol-4-yl)picolinamide;
I-11: N-(2-(4-hydroxypiperidin-1-yl)-4-morpholinophenyl)-5-(1H-pyrazol-4-yl)furan-2-carboxamide;
I-12: N-(2-(4-hydroxypiperidin-1-yl)-4-morpholinophenyl)-2-(1H-pyrazol-4-yl)thiazole-4-carboxamide;
I-13: N-(2,4-dimorpholinophenyl)-6-(1H-pyrazol-4-yl)picolinamide;
I-14: N-(2,4-dimorpholinophenyl)-5-(1H-pyrazol-4-yl)furan-2-carboxamide;
I-15: N-(2,4-dimorpholinophenyl)-2-(1H-pyrazol-4-yl)thiazole-4-carboxamide;
I-16: N-(2-(4-hydroxy-4-methylpiperidin-1-yl)-4-morpholinophenyl)-6-(1H-pyrazol-4-yl)picolinamide;
I-17: N-(2-(4-hydroxy-4-methylpiperidin-1-yl)-4-morpholinophenyl)-5-(1H-pyrazol-4-yl)furan-2-carboxamide;
I-18: N-(2-(4-hydroxy-4-methylpiperidin-1-yl)-4-morpholinophenyl)-2-(1H-pyrazol-4-yl)thiazole-4-carboxamide;
I-19: N-(2-(4,4-difluoropiperidin-1-yl)-4-morpholinophenyl)-6-(1H-pyrazol-4-yl)picolinamide;
I-20: N-(2-(4,4-difluoropiperidin-1-yl)-4-morpholinophenyl)-5-(1H-pyrazol-4-yl)furan-2-carboxamide;
I-21: N-(2-(4,4-difluoropiperidin-1-yl)-4-morpholinophenyl)-2-(1H-pyrazol-4-yl)thiazole-4-carboxamide;
I-22: N-(4-morpholino-2-(pyrrolidin-1-yl)phenyl)-6-(1H-pyrazol-4-yl)picolinamide;
I-23: N-(4-morpholino-2-(pyrrolidin-1-yl)phenyl)-5-(1H-pyrazol-4-yl)furan-2-carboxamide;
I-24: N-(4-morpholino-2-(pyrrolidin-1-yl)phenyl)-2-(1H-pyrazol-4-yl)thiazole-4-carboxamide;
I-25: N-(5-morpholino-2-(piperidin-1-yl)phenyl)-5-(1H-pyrazol-4-yl)furan-2-carboxamide;
I-26: N-(5-morpholino-2-(piperidin-1-yl)phenyl)-2-(1H-pyrazol-4-yl)thiazole-4-carboxamide;
I-27: N-(5-(2-morpholinoethoxy)-2-(piperidin-1-yl)phenyl)-6-(1H-pyrazol-4-yl)picolinamide;
I-28: N-(5-(2-morpholinoethoxy)-2-(piperidin-1-yl)phenyl)-5-(1H-pyrazol-4-yl)furan-2-carboxamide;
I-29: N-(5-(2-morpholinoethoxy)-2-(piperidin-1-yl)phenyl)-2-(1H-pyrazol-4-yl)thiazole-4-carboxamide;
I-30: N-(4-fluoro-5-(2-morpholinoethyl)-2-(piperidin-1-yl)phenyl)-6-(1H-pyrazol-4-yl)picolinamide;
I-31: N-(4-fluoro-5-(2-morpholinoethyl)-2-(piperidin-1-yl)phenyl)-5-(1H-pyrazol-4-yl)furan-2-carboxamide;
I-32: N-(4-fluoro-5-(2-morpholinoethyl)-2-(piperidin-1-yl)phenyl)-2-(1H-pyrazol-4-yl)thiazole-4-carboxamide;

I-33: N-(5-(1,1-difluoro-2-morpholinoethyl)-2-(piperidin-1-yl)phenyl)-6-(1H-pyrazol-4-yl)picolinamide;
I-34: N-(5-(1,1-difluoro-2-morpholinoethyl)-2-(piperidin-1-yl)phenyl)-5-(1H-pyrazol-4-yl)furan-2-carboxamide;
I-35: N-(5-(1,1-difluoro-2-morpholinoethyl)-2-(piperidin-1-yl)phenyl)-2-(1H-pyrazol-4-yl)thiazole-4-carboxamide;
I-36: N-(4-morpholino-2-(piperidin-1-yl)phenyl)-6-(1H-pyrazol-4-yl)picolinamide;
I-37: N-(4-morpholino-2-(piperidin-1-yl)phenyl)-5-(1H-pyrazol-4-yl)furan-2-carboxamide;
I-38: N-(4-morpholino-2-(piperidin-1-yl)phenyl)-2-(1H-pyrazol-4-yl)thiazole-4-carboxamide;
I-39: N-(2-methoxy-5-morpholinophenyl)-6-(1H-pyrazol-4-yl)picolinamide;
I-40: N-(2-methoxy-5-morpholinophenyl)-5-(1H-pyrazol-4-yl)furan-2-carboxamide;
I-41: N-(2-methoxy-5-morpholinophenyl)-2-(1H-pyrazol-4-yl)thiazole-4-carboxamide;
I-42: N-(6-morpholino-4-(piperidin-1-yl)pyridin-3-yl)-6-(1H-pyrazol-4-yl)picolinamide;
I-43: N-(6-morpholino-4-(piperidin-1-yl)pyridin-3-yl)-5-(1H-pyrazol-4-yl)furan-2-carboxamide;
I-44: N-(6-morpholino-4-(piperidin-1-yl)pyridin-3-yl)-2-(1H-pyrazol-4-yl)thiazole-4-carboxamide;
I-45: N-(4-(morpholine-4-carbonyl)-2-(piperidin-1-yl)phenyl)-6-(1H-pyrazol-4-yl)picolinamide;
I-46: N-(4-(morpholine-4-carbonyl)-2-(piperidin-1-yl)phenyl)-5-(1H-pyrazol-4-yl)furan-2-carboxamide;
I-47: N-(4-(morpholine-4-carbonyl)-2-(piperidin-1-yl)phenyl)-2-(1H-pyrazol-4-yl)thiazole-4-carboxamide;
I-48: N-(4-(morpholinomethyl)-2-(piperidin-1-yl)phenyl)-6-(1H-pyrazol-4-yl)picolinamide;
I-49: N-(4-(morpholinomethyl)-2-(piperidin-1-yl)phenyl)-5-(1H-pyrazol-4-yl)furan-2-carboxamide;
I-50: N-(4-(morpholinomethyl)-2-(piperidin-1-yl)phenyl)-2-(1H-pyrazol-4-yl)thiazole-4-carboxamide;
I-51: N-(4-(2-morpholino-2-oxoethyl)-2-(piperidin-1-yl)phenyl)-6-(1H-pyrazol-4-yl)picolinamide;
I-52: N-(4-(2-morpholino-2-oxoethyl)-2-(piperidin-1-yl)phenyl)-5-(1H-pyrazol-4-yl)furan-2-carboxamide;
I-53: N-(4-(2-morpholino-2-oxoethyl)-2-(piperidin-1-yl)phenyl)-2-(1H-pyrazol-4-yl)thiazole-4-carboxamide;
I-54: N-(4-(2-morpholinoethyl)-2-(piperidin-1-yl)phenyl)-6-(1H-pyrazol-4-yl)picolinamide;
I-55: N-(4-(2-morpholinoethyl)-2-(piperidin-1-yl)phenyl)-5-(1H-pyrazol-4-yl)furan-2-carboxamide;
I-56: N-(4-(2-morpholinoethyl)-2-(piperidin-1-yl)phenyl)-2-(1H-pyrazol-4-yl)thiazole-4-carboxamide;
I-57: N-(5-(morpholine-4-carbonyl)-2-(piperidin-1-yl)phenyl)-6-(1H-pyrazol-4-yl)picolinamide;
I-58: N-(5-(morpholine-4-carbonyl)-2-(piperidin-1-yl)phenyl)-5-(1H-pyrazol-4-yl)furan-2-carboxamide;
I-59: N-(5-(morpholine-4-carbonyl)-2-(piperidin-1-yl)phenyl)-2-(1H-pyrazol-4-yl)thiazole-4-carboxamide;
I-60: N-(5-(morpholinomethyl)-2-(piperidin-1-yl)phenyl)-6-(1H-pyrazol-4-yl)picolinamide;
I-61: N-(5-(morpholinomethyl)-2-(piperidin-1-yl)phenyl)-5-(1H-pyrazol-4-yl)furan-2-carboxamide;
I-62: N-(5-(morpholinomethyl)-2-(piperidin-1-yl)phenyl)-2-(1H-pyrazol-4-yl)thiazole-4-carboxamide;
I-63: N-(5-(2-morpholino-2-oxoethyl)-2-(piperidin-1-yl)phenyl)-6-(1H-pyrazol-4-yl)picolinamide;
I-64: N-(5-(2-morpholino-2-oxoethyl)-2-(piperidin-1-yl)phenyl)-5-(1H-pyrazol-4-yl)furan-2-carboxamide;
I-65: N-(5-(2-morpholino-2-oxoethyl)-2-(piperidin-1-yl)phenyl)-2-(1H-pyrazol-4-yl)thiazole-4-carboxamide;
I-66: N-(5-(2-morpholinoethyl)-2-(piperidin-1-yl)phenyl)-6-(1H-pyrazol-4-yl)picolinamide;
I-67: N-(5-(2-morpholinoethyl)-2-(piperidin-1-yl)phenyl)-5-(1H-pyrazol-4-yl)furan-2-carboxamide;
I-68: N-(5-(2-morpholinoethyl)-2-(piperidin-1-yl)phenyl)-2-(1H-pyrazol-4-yl)thiazole-4-carboxamide;
I-69: N-(4-(methyl(2-morpholinoethyl)amino)-2-(piperidin-1-yl)phenyl)-6-(1H-pyrazol-4-yl)picolinamide;
I-70: N-(4-(methyl(2-morpholinoethyl)amino)-2-(piperidin-1-yl)phenyl)-5-(1H-pyrazol-4-yl)furan-2-carboxamide;
I-71: N-(4-(methyl(2-morpholinoethyl)amino)-2-(piperidin-1-yl)phenyl)-2-(1H-pyrazol-4-yl)thiazole-4-carb oxamide;
I-72: N-(4-((2-morpholinoethyl)amino)-2-(piperidin-1-yl)phenyl)-6-(1H-pyrazol-4-yl)picolinamide;
I-73: N-(4-((2-morpholinoethyl)amino)-2-(piperidin-1-yl)phenyl)-5-(1H-pyrazol-4-yl)furan-2-carboxamide;
I-74: N-(4-((2-morpholinoethyl)amino)-2-(piperidin-1-yl)phenyl)-2-(1H-pyrazol-4-yl)thiazole-4-carboxamide; or
I-75: N-(5-morpholino-2-(piperidin-1-yl)phenyl)-6-(1H-pyrazol-4-yl)picolinamide.

35. A composition, comprising a compound of claim 1, and a pharmaceutically acceptable excipient.

36. The composition of claim 35, further comprising an additional therapeutic agent selected from an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof.

37. A method of inhibiting an IRAK protein in a subject with rheumatoid arthritis, comprising administering to the subject an effective amount of a compound according to claim 1.

* * * * *